US012435335B2

(12) United States Patent
Zhou

(10) Patent No.: US 12,435,335 B2
(45) Date of Patent: Oct. 7, 2025

(54) PROMOTING NUTRIENT ABSORPTION THROUGH THE COLON

(71) Applicant: Cornell University, Ithaca, NY (US)

(72) Inventor: Qiao Joe Zhou, Ardsley, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 17/935,492

(22) Filed: Sep. 26, 2022

(65) Prior Publication Data

US 2023/0392145 A1 Dec. 7, 2023

Related U.S. Application Data

(60) Provisional application No. 63/349,436, filed on Jun. 6, 2022.

(51) Int. Cl.

| | |
|---|---|
| ***C12N 15/113*** | (2010.01) |
| ***A61P 1/14*** | (2006.01) |
| ***C12N 9/22*** | (2006.01) |
| ***C12N 15/90*** | (2006.01) |

(52) U.S. Cl.

CPC .............. *C12N 15/113* (2013.01); *A61P 1/14* (2018.01); *C12N 9/22* (2013.01); *C12N 15/907* (2013.01); *C12N 2310/14* (2013.01); *C12N 2310/20* (2017.05); *C12N 2310/531* (2013.01); *C12N 2800/80* (2013.01)

(58) Field of Classification Search

CPC ...... C12N 15/113; C12N 9/22; C12N 15/907; C12N 2310/14; C12N 2310/20; C12N 2310/531; C12N 2800/80; A61P 1/14

See application file for complete search history.

(56) References Cited

U.S. PATENT DOCUMENTS

| | | | |
|---|---|---|---|
| 2011/0230547 A1 | 9/2011 | Kohwi-shigematsu et al. | |
| 2012/0270956 A1 | 10/2012 | Uhlen et al. | |
| 2018/0010195 A1 | 1/2018 | Shrivastava | |
| 2019/0367882 A1 | 12/2019 | Wells et al. | |
| 2021/0262041 A1 | 8/2021 | Galande et al. | |
| 2022/0176015 A1* | 6/2022 | Justin | A61L 27/58 |

FOREIGN PATENT DOCUMENTS

| | | |
|---|---|---|
| WO | 2016120853 | 8/2016 |
| WO | WO-2022/072553 A1 | 4/2022 |
| WO | 2023239609 | 12/2023 |

OTHER PUBLICATIONS

Zhou, Qiao, and Douglas A. Melton. "Extreme makeover: converting one cell into another." Cell stem cell 3.4 (2008): 382-388. (Year: 2008).*

Gu, Wei, et al. "SATB2 preserves colon stem cell identity and mediates ileum-colon conversion via enhancer remodeling." Cell Stem Cell 29.1 (2022): 101-115. (Year: 2022).*

Yu, Wei, et al. "SATB2/β-catenin/TCF-LEF pathway induces cellular transformation by generating cancer stem cells in colorectal cancer." Scientific Reports 7.1 (2017): 10939. (Year: 2017).*

Paldi, Andras. "Conceptual challenges of the systemic approach in understanding cell differentiation." Systems Biology (2018): 27-39. (Year: 2018).*

Zhou, Li-Quan, et al. "The AT-rich DNA-binding protein SATB2 promotes expression and physical association of human G[-and A[-globin genes." Journal of Biological Chemistry 287.36 (2012): 30641-30652. (Year: 2012).*

Liu, Guanqing, Yong Zhang, and Tao Zhang. "Computational approaches for effective CRISPR guide RNA design and evaluation." Computational and structural biotechnology journal 18 (2020): 35-44. (Year: 2020).*

GenBank2, *Homo sapiens* SATB homeobox 2 (SATB2), transcript variant 1, mRNA, https://www.ncbi.nlm.nih.gov/nuccore/1519316384?sat=49&satkey=78573105, retrieved May 31, 2021 (Year: 2021).*

GenBank3, DNA-binding protein SATB2 [Mus musculus], RefSeqGene on chromosome 2, https://www.ncbi.nlm.nih.gov/protein/1285032920?sat=49&satkey=61128199, Apr. 27, 2021 (Year: 2021).*

Gu, Jingfeng, et al., "SATB2 targeted by methylated miR-34c-5p suppresses proliferation and metastasis attenuating the epithelial-mesenchymal transition in colorectal cancer", *Cell Proliferation*, 51(4): e12455, (2018), 12 pgs.

Jiang, Guixing, et al., "miR-211 suppresses hepatocellular carcinoma by downregulating SATB2", *Oncotarget*, 6(11), (2015), 9457-9466.

Ramos, Benjamin D., et al., "A Comprehensive Evaluation of Special AT-rich Sequence-binding Protein 2 (SATB2) Immunohistochemical Staining in Mucinous Tumors From Gastrointestinal and Nongastrointestinal Sites", *Appl Immunohistochem Mol Morphol*, (2017), 8 pgs.

Roy, Sanjit K., et al., "SATB2 is a novel biomarker and therapeutic target for cancer", *J Cell Mol Med*, 24, (2020), 11064-11069.

Sun, Xiaohua, et al., "miR-449a inhibits colorectal cancer progression by targeting SATB2", *Oncotarget*, 8(60), (2017), 100975-100988.

Wang, Yun, et al., "microRNA-4270-5p inhibits cancer cell proliferation and metastasis in hepatocellular carcinoma by targeting SATB2", *Human Cell*, 33(4), (2020), 10 pgs.

Wu, Gang, et al., "miR-34a Inhibits Cell Proliferation by Targeting SATB2 in Hepatocellular Carcinoma", *BioMed Research International*, vol. 2018, Article ID 2863902, (2018), 1-7.

Yu, Wei, et al., "SATB2/β-catenin/TCF-LEF pathway induces cellular transformation by generating cancer stem cells in colorectal cancer", *Scientific Reports*, 7: 10939, (2017), 1-13.

"International Application Serial No. PCT US2023 024322, International Search Report mailed Sep. 21, 2023", 6 pgs.

"International Application Serial No. PCT US2023 024322, Written Opinion mailed Sep. 21, 2023", 4 pgs.

(Continued)

*Primary Examiner* — Ekaterina Poliakova-Georgantas
*Assistant Examiner* — John Charles McKillop
(74) *Attorney, Agent, or Firm* — Schwegman Lundberg & Woessner, P.A.

(57) ABSTRACT

A method for deleting or inactivating at least one Satb2 allele or inhibiting expression of a Satb2 gene in one or more starting cells of a subject, to thereby convert the starting cells into small intestine-like cells, and methods of using those cells, is provided.

20 Claims, 82 Drawing Sheets

Specification includes a Sequence Listing.

(56) References Cited

OTHER PUBLICATIONS

Gu, Wei, “SATB2 preserves colon stem cell identity and mediates ileum-colon conversion via enhancer remodeling”, Cell Stem Cell, Elsevier, Cell Press, Amsterdam, NL, vol. 29, No. 1, (Sep. 27, 2021), 101 pgs.

Munera, Jorge O, “Differentiation of Human Pluripotent Stem Cells into Colonic Organoids via Transient Activation of BMP Signaling”, Cell Stem Cell, Elsevier, Cell Press, Amsterdam, NL, vol. 21, No. 1, (Jun. 22, 2017), 51 pg.

Ni, Hengli, “SATB2 Defect Promotes Colitis and Colitis-associated Colorectal Cancer by Impairing C1-HC03-Exchange and Homeostasis of Gut Microbiota”, Journal of Crohn’s and Colitis, vol. 15, No. 12, (Dec. 18, 2021), 2088-2102.

Wei, Jyh-Ding, “SATB2 participates in regulation of menadione-induced apoptotic insults to osteoblasts : Roles of SATB2 in Osteoblast Apoptosis”, Journal of Orthopaedic Research, vol. 30, No. 7, (Jan. 3, 2012), 1058-1066.

Xu, Mu, “LncRNA SATB2-AS1 inhibits tumor metastasis and affects the tumor immune cell microenvironment in colorectal cancer by regulating SATB2”, Molecular Cancer, vol. 18, No. 1, [Online]. Retrieved from the Internet: http:link.springer.com article 10.1186 sl2943-019-1063-6 fulltext.html, (Sep. 6, 2019).

Zhang, Qiong, “Loss of Satb2 in the Cortex and Hippocampus Leads to Abnormal Behaviors in Mice”, Frontiers in Molecular Neuroscience, vol. 12, (Feb. 12, 2019), 12 pgs.

“International Application Serial No. PCT US2023 024322, International Preliminary Report on Patentability mailed Dec. 19, 2024”, 6 pgs.

* cited by examiner

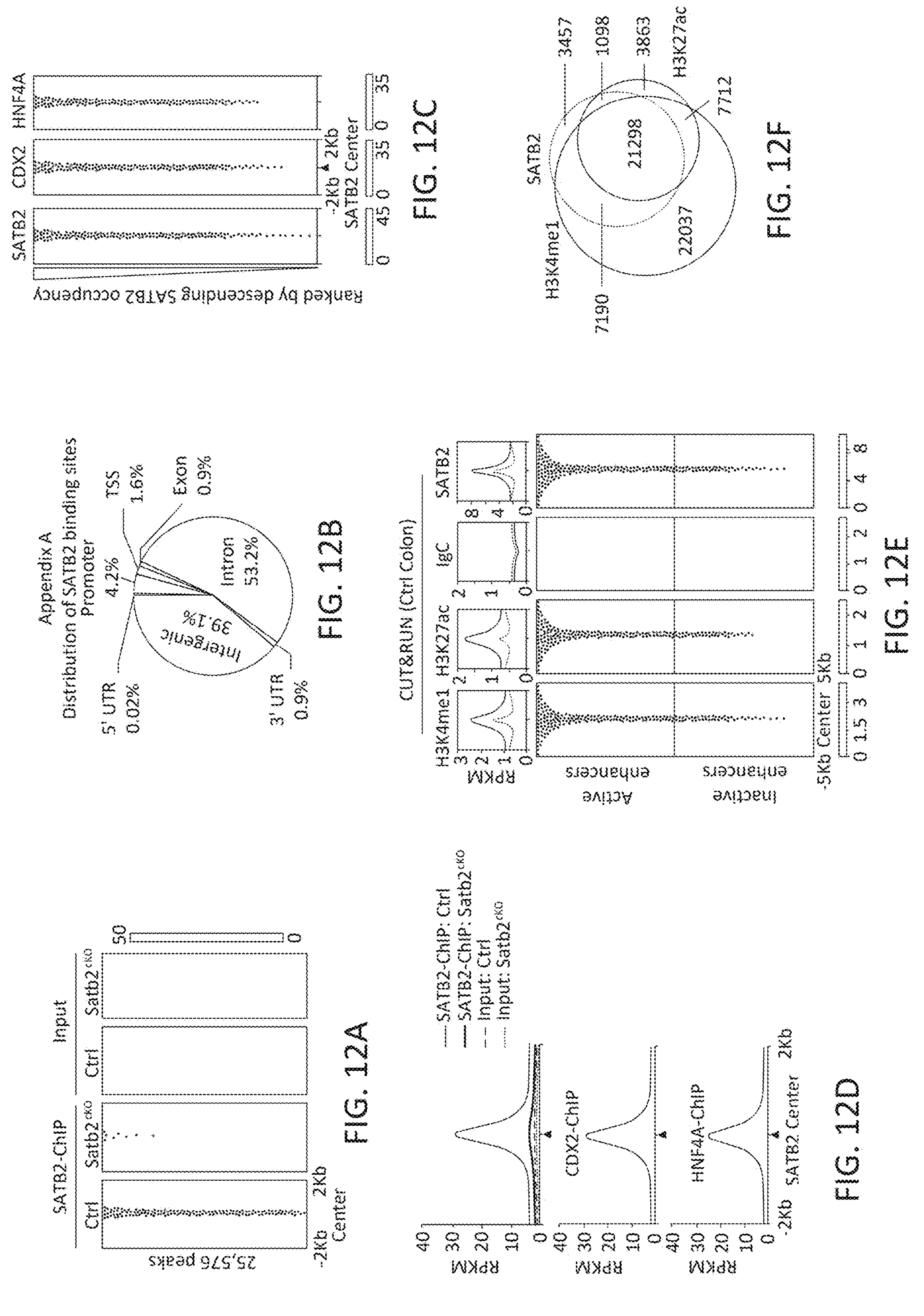
SATB2-ChIP
Input
Ctrl
Satb2cKO
25,576 peaks
-2Kb
Center
2Kb
50
0
FIG. 12A
Appendix A
Distribution of SATB2 binding sites
Promoter
4.2%
TSS
1.6%
Exon
0.9%
Intron
53.2%
Intergenic
39.1%
5' UTR
0.02%
3' UTR
0.9%
FIG. 12B
Ranked by descending SATB2 occupancy
SATB2
CDX2
HNF4A
-2Kb
SATB2 Center
2Kb
FIG. 12C
SATB2-ChIP: Ctrl
SATB2-ChIP: Satb2cKO
Input: Ctrl
Input: Satb2cKO
CDX2-ChIP
HNF4A-ChIP
RPKM
SATB2 Center
FIG. 12D
CUT&RUN (Ctrl Colon)
H3K4me1
H3K27ac
IgG
SATB2
RPKM
Active enhancers
Inactive enhancers
-5Kb Center 5Kb
FIG. 12E
SATB2
H3K4me1
H3K27ac
3457
1098
3863
7712
21298
22037
7190
FIG. 12F

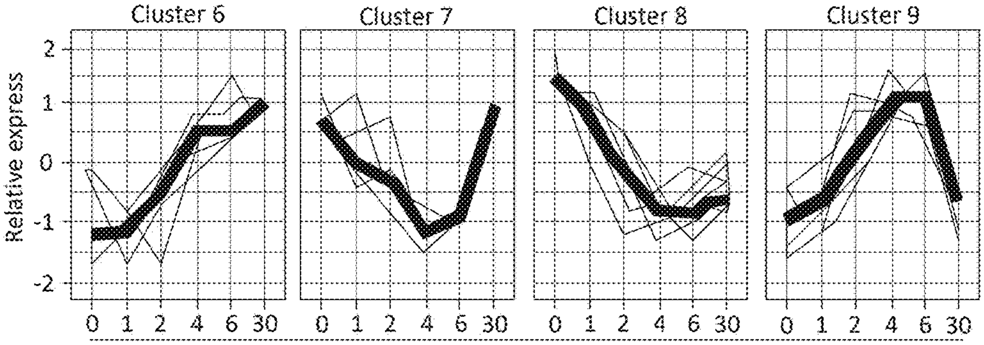

Enrichr GeneOntology

Cluster 6: (38 genes)
Cholesterol biosynthetic ($p = 2.010 \times 10^{3}$)
Secondary alcohol biosynthetic ($p = 2.125 \times 10^{3}$)
Sterol biosynthetic ($p = 2.620 \times 10^{3}$)

Cluster 7: (8 genes) Not applicable

Cluster 8: (26 genes)
Regulationof catecholamine secretion ($p = 7.776 \times 10^{3}$)
Intracellular pH elevation ($p = 7.776 \times 10^{3}$)
Mineralocortocoid biosynthetic ($p = 7.776 \times 10^{3}$)

Cluster 9: (26 genes)
Regulation of apoptotic cell clearance ($p = 3.399 \times 10^{3}$)
Negative regulation of keratinocyte differentiation ($p = 7.776 \times 10^{3}$)
Positive regulation of keratinocyte differentiation ($p = 9.066 \times 10^{3}$)

FIG. 17I

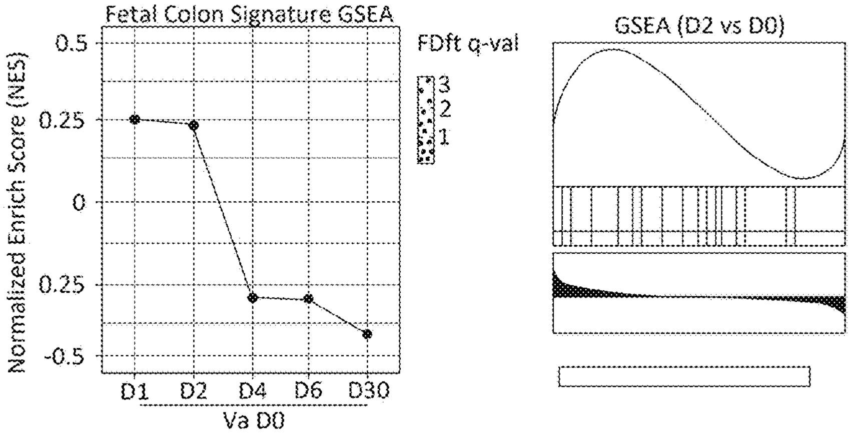

FIG. 17J

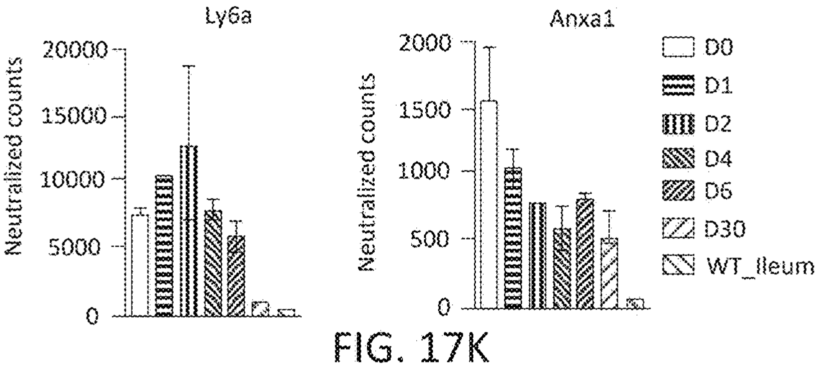

FIG. 17K

Large intestine signature genes

SEQUENCE LISTING

```
Sequence total quantity: 63
SEQ ID NO: 1            moltype = AA  length = 733
FEATURE                 Location/Qualifiers
source                  1..733
```

-continued mol_type = protein
organism = Homo sapiens
SEQUENCE: 1
MERRSESPCL RDSPDRRSGS PDVKGPPPVK VARLEQNGSP MGARGRPNGA VAKAVGGLMI 60
PVFCVVEQLD GSLEYDNREE HAEFVLVRKD VLFSQLVETA LLALGYSHSS AAQAQGIIKL 120
GRWNPLPLSY VTDAPDATVA DMLQDVYHVV TLKIQLQSCS KLEDLPAEQW NHATVRNALK 180
ELLKEMNQST LAKECPLSQS MISSIVNSTY YANVSATKCQ EFGRWYKKYK KIKVERVERE 240
NLSDYCVLGQ RPMHLPNMNQ LASLGKTNEQ SPHSQIHHST PIRNQVPALQ PIMSPGLLSP 300
QLSPQLVRQQ IAMAHLINQQ IAVSRLLAHQ HPQAINQQFL NHPPIPRAVK PEPTNSSVEV 360
SPDIYQQVRD ELKRASVSQA VFARVAFNRT QGLLSEILRK EEDPRTASQS LLVNLRAMQN 420
FLNLPEVERD RIYQDERERS MNPNVSMVSS ASSSPSSSRT PQAKTSTPTT DLPIKVDGAN 480
INITAAIYDE IQQEMKRAKV SQALFAKVAA NKSQGWLCEL LRWKENPSPE NRTLWENLCT 540
IRRFLNLPQH ERDVIYEEES RHHHSERMQH VVQLPPEPVQ VLHRQQSQPA KESSPPREEA 600
PPPPPPTEDS CAKKPRSRTK ISLEALGILQ SFIHDVGLYP DQEAIHTLSA QLDLPKHTII 660
KFFQNQRYHV KHHGKLKEHL GSAVDVAEYK DEELLTESEE NDSEEGSEEM YKVEAEEENA 720
DKSKAAPAEI DQR 733

SEQ ID NO: 2 moltype = DNA length = 5568
FEATURE Location/Qualifiers
source 1..5568
mol_type = other DNA
organism = Homo sapiens
SEQUENCE: 2
gagtccggct ctggctgctg gcagaggcgg ccgagagggg agaggctgga ggtgacagct 60
tgggcggccg ccgcgtttcc tcccgcgcgc ggtcccgggt ccctgcgtct tctcggctct 120
tggtgttacc ggtcccaccg ctctggccgc gcctcctcgc gagctagccg ccctgcgaac 180
cagcagcccc ggctcgccgc cgccgccgcc gcctccgggt tctcagccct ttctctccag 240
aacgggtctc cttcccgaag gtgtgaaaag gctctttcag cctccttctc ttccccccctc 300
ctccgccgtc ccctcccccg ctcgctcggg tgtccctttg gaggagtcct ttccctctcc 360
tcctcctccc cctcctccct ccccccatca tcatcataac aaccatctcc gcaccagaag 420
aagacaccct gacccaggac cttaaacatt aggacctggg gaagagggaa ggggaaggag 480
taaagaggaa gactaggaga acactgcaaa gccaagcacc agaaactttc caccctggat 540
tctctacttt tgctccatgg acagagcccc agtcagccaa gtttcagaca gaccgtgagc 600
agtccctgtg cgttttattg cgacctgccg gtgggaactt tgtctccgag tcggagcagc 660
atggagcggc ggagcgagag cccgtgtctg cgggacagcc ccgaccggcg gagcggcagc 720
ccggacgtca aggggcctcc cccagtgaag gtggcccggc tggagcagaa cggcagcccc 780
atgggagccc gcgggaggcc caacggcgcc gtggccaagg ccgtgggagg tttgatgatt 840
cctgtctttt gtgtcgtgga gcagttggac ggctctcttg aatatgacaa cagagaagaa 900
cacgccgagt ttgtcctggt gcggaaagat gtgcttttta gccagctggt ggagactgcg 960
ctcctggccc tggggtattc tcacagctct gcggcccagg cccaaggaat aatcaagctg 1020
ggaaggtgga accctctccc cctcagttat gtgacagatg cacccgacgc gacagtggcc 1080
gacatgctac aagatgtcta tcatgttgtg acgttgaaaa tccaattaca aagttgttca 1140
aagttggaag acttgcctgc ggagcagtgg aaccatgcca cagtccgcaa tgccttaaag 1200
gaactgctca aagagatgaa ccagagcaca ttagccaaag aatgccctct ctcccagagt 1260
atgatttcat ccattgtaaa tagcacatat tatgccaatg tgtcagcaac caagtgccag 1320
gagtttggga gatggtataa aaagtacaag aagattaaag tggaaagagt ggaacgagaa 1380
aacctttcag actattgtgt tctgggccag cgtccaatgc atttaccaaa tatgaaccag 1440
ctggcatccc tggggaaaac caacgaacag tctcctcaca gccaaattca ccacagtact 1500
ccaatccgaa accaagtgcc cgcattacag cccatcatga gccctggtct tctttctccc 1560
cagcttagtc cacaacttgt aaggcaacaa atagccatgg cccatctgat aaaccaacag 1620
attgccgtta gccggctcct ggctcaccag catcctcaag ccatcaacca gcagttcctg 1680
aaccatccac ccatccccag agcagttaag ccagagccaa ccaactcttc cgtggaagtc 1740
tctccagata tctaccagca agtcagagat gagctgaaga gggccagtgt gtcccaagct 1800
gtctttgcaa gagtggcatt caaccgcaca cagggattgt tgtctgagat tctgcgtaag 1860
gaagaagacc ctcggacagc ctctcagtct cttctagtaa acctgagggc catgcagaat 1920
ttcctcaatc tgccagaagt ggagcgagat cgcatctacc aggatgagag ggagcggagc 1980
atgaatccca atgtgagcat ggtctcctcg gcctccagca gtcccagctc ctcccgaacc 2040
cctcaggcca aaacctcgac accgacaaca gacctcccta ttaaggtgga cggcgccaac 2100
atcaacatca cagctgccat ttatgacgag atccaacagg agatgaaaag ggccaaggtg 2160
tctcaagccc tgtttgccaa agtggctgca aataaaagtc agggctggct gtgtgaactg 2220
ctccgctgga aggagaaccc aagcccagaa aaccgcaccc tctgggaaaa cctctgtacc 2280
atccgtcgct tcctgaacct tccccagcat gagagggatg tcatctatga ggaggagtca 2340
aggcatcacc acagcgaacg catgcaacac gtggtccagc ttccccctga gccggtgcag 2400
gtacttcata gacagcagtc tcagccagcc aaggagagtt cccctcccag agaagaagcg 2460
cctcccccac ctcctccgac tgaagacagt tgtgccaaaa agccccggtc tcgcacaaag 2520
atctccttag aagccctggg gatcctccaa agctttattc atgatgtagg cctgtaccca 2580
gaccaggaag ccatccacac tctttcggct cagctggatc tccccaaaca caccatcatc 2640
aagttcttcc agaaccagcg gtaccacgtg aagcaccacg ggaagctgaa agagcacctg 2700
ggctccgcgg tggacgtggc tgaatataag gacgaggagc tgctgaccga gtcagaggag 2760
aacgacagcg aggaaggctc cgaggagatg tacaaagtgg aggctgagga ggaaaatgct 2820
gacaaaagca aggcagcacc tgccgaaatt gaccagagat aatgtgaact tctactaggc 2880
aaagcaatac atcggtccaa ggattttctg ctttcatttc tttaaaagtt ttttgttagt 2940
ttgtttttttg tttttgtttt tgggtttttt tggctttatt tttgtctttt tatgtctgtt 3000
ttgtttttct taccctttttg gacatttctt tgttgcacag gatacaccta tagactgaat 3060
aagttcagta tttccgaatc agacatcgcc ttggcaaaga cactaaagcg ttacacttta 3120
tcccgtctct atgactggat catagtcatt ataatcacag gagactctgc cttcattatc 3180
cttgcactta acggaagtta catcaggcaa gtaccaggat gaaaagaact atgaaataaa 3240
tgaaggaagc tacaagtgtg tgtgtatatg tatatgtata tatctctata tttacatata 3300
tatattaaaa ttgcatggga cagagacttt gcaatccgaa agaatagact gtgaaatgag 3360

-continued

```
ttcttaaaga aaagacttgt ttatgtatta aaaaaaccac ttcacagtga gtcgctttgg  3420
ctttttgata aactgcggcc tgctctcagg gtggggtgac tatttttgaa ttcctattta  3480
ttttttgtgt ttgtccctga tttttttttt ttaattctat ggcttcctat ctggcagctt  3540
aatgggtaat ttttgaggta tgtatttaac aaaataaacg acactgccga aaaaaaaaaa  3600
agtgaagtga aaacaatcag ggcacattaa aatgatacaa gtcaaataaa tcttaaagac  3660
acaatgcaca cttaaaatga ctcaataaaa tgacttgcta cgttccgtta ttcaatttgt  3720
cattactgta gtgaacagat gcatttctgt ggaattccaa ataagtaaaa ctgaaattca  3780
gtgcagagaa aactttgtcc actagtgcaa gtcttgatca aatgacattt tgacattgga  3840
catatggaat tcatagtatg agccacattt tgttgtgaaa tttatttacc tgcttgtggc  3900
ttcaaatctg aaaattaata agcctgctcg tttaaaagtt gtttgttgtt gctgtttttt  3960
tgtctttttg ttttttacta gaaaatagtt cagtgtaata ttaagttaga aaagaagttg  4020
ctgcccagtt aaaggggctc cctctcaaat aaatctccat ccttccctct cccaaaagac  4080
atttctgatt tctgcttcac tttgggcttc ctcttcttcg tacacattcc atctacctaa  4140
tcaaacattt tcagtccctg atctctcctg tccctttcc tgggatgaca gccctaacaa  4200
gaactgtttt tgaatcgttg tgcagctcca ggcaatagag tatgtgaagc gatttcagta  4260
gaatcactta ctcatcctaa aagaaaacat tatcccagtt acctacatcg caattacctt  4320
atgtaaagca gaactaatgc tgactggatg tttaatggga tgagcattaa agctgcaatc  4380
tactatagta ctccagatct ctttcggctt cctatgagaa acaccagaag cattactttc  4440
cacttctact tacagtaatt gcaagaggag acctcacatt caggactggc ctagtgaacg  4500
taatccatgc tttaaactgg ccattaaaca gtcccacatg gttggatttt tttttttttt  4560
ttgagttgtg ctttcacaaa accttgtcaa agacctcatg caatatcact ttgaaagtta  4620
ttttctgttt actacacaaa cattgtaata taactgttaa tactatttat atatttgaaa  4680
ggtataaaag gtaggagtta aaaaaaaaac ctctatgtgt agatattaac tcagaactta  4740
caatatacag ggagaagaca tgttgcaata caagctaatt ctagctgctc agtaacctct  4800
ggagttttta aagggacatt ttcctgtact ttttcaaata atgatgttta aaaattatct  4860
tgacataagc gtcatatacc tttgcaaaag gatggttgtt tgcagttagc cctggcccca  4920
tccttcctat ttctgtagta tgctgcagct ttaatcagaa agtccatggt tgctgcttcc  4980
tgatctccga gttactcttt ccaaattgtc ttcttacact gttgctgaag gtcactctgt  5040
acacgtaatg gaaactgatt ttgccaagct cttacaaggt ggttcatcta tcgatggcat  5100
ccgcatttgg tatcttttac acttcaacca aaaatttatt aggtattttt caatgctaag  5160
tcttgccttt tatttttttaa tttcactgcc aagtttgcag tggttctaag tgaatctgtg  5220
ggcattttag cctgtggtct tgccagatct ttgcgaatta caatgcatat atgtctattt  5280
attcaatatc tgtcatataa tatctatttg gaagaagaaa ctttctcttg tagtgcctct  5340
tgacaaagca caatttcccg cctttttttt tttttgtgaa atgaaaaaaa caaattgtgt  5400
tttattgcgg tatcaacaat gtgaataagg attaacatat tgtaaatgtt ctttttttcca  5460
tgtaaatcaa ctatctttgt tatcactaag tgataattaa tttttaactt atgtgcattg  5520
ttaggctgtt agaatttttt ggttgttaaa ataaacgcat tcaataaa              5568

SEQ ID NO: 3           moltype = AA  length = 734
FEATURE                Location/Qualifiers
source                 1..734
                       mol_type = protein
                       organism = Homo sapiens
SEQUENCE: 3
MERRSESPCL RDSPDRRSGS PDVKGPPPVK VARLEQNGSP MGARGRPNGA VAKAVGGLMI  60
PVFCVVEQLD GSLEYDNREE HAEFVLVRKD VLFSQLVETA LLALGYSHSS AAQAQGIIKL  120
GRWNPLPLSY VTDAPDATVA DMLQDVYHVV TLKIQLQSCS KLEDLPAEQW NHATVRNALK  180
CELLKEMNQS TLAKECPLSQ SMISSIVNST YYANVSATKC QEFGRWYKKY KKIKVERVER  240
ENLSDYCVLG QRPMHLPNMN QLASLGKTNE QSPHSQIHHS TPIRNQVPAL QPIMSPGLLS  300
PQLSPQLVRQ QIAMAHLINQ QIAVSRLLAH QHPQAINQQF LNHPPIPRAV KPEPTNSSVE  360
VSPDIYQQVR DELKRASVSQ AVFARVAFNR TQGLLSEILR KEEDPRTASQ SLLVNLRAMQ  420
NFLNLPEVER DRIYQDERER SMNPNVSMVS SASSSPSSSR TPQAKTSTPT TDLPIKVDGA  480
NINITAAIYD EIQQEMKRAK VSQALFAKVA ANKSQGWLCE LLRWKENPSP ENRTLWENLC  540
TIRRFLNLPQ HERDVIYEEE SRHHHSERMQ HVVQLPPEPV QVLHRQQSQP AKESSPPREE  600
APPPPPPTED SCAKKPRSRT KISLEALGIL QSFIHDVGLY PDQEAIHTLS AQLDLPKHTI  660
IKFFQNQRYH VKHHGKLKEH LGSAVDVAEY KDEELLTESE ENDSEEGSEE MYKVEAEEEN  720
ADKSKAAPAE IDQR                                                    734

SEQ ID NO: 4           moltype = AA  length = 733
FEATURE                Location/Qualifiers
source                 1..733
                       mol_type = protein
                       organism = Homo sapiens
SEQUENCE: 4
MERRSESPCL RDSPDRRSGS PDVKGPPPVK VARLEQNGSP MGARGRPNGA VAKAVGGLMI  60
PVFCVVEQLD GSLEYDNREE HAEFVLVRKD VLFSQLVETA LLALGYSHSS AAQAQGIIKL  120
GRWNPLPLSY VTDAPDATVA DMLQDVYHVV TLKIQLQSCS KLEDLPAEQW NHATVRNALK  180
ELLKEMNQST LAKECPLSQS MISSIVNSTY YANVSATKCQ EFGRWYKKYK KIKVERVERE  240
NLSDYCVLGQ RPMHLPNMNQ LASLGKTNEQ SPHSQIHHST PIRNQVPALQ PIMSPGLLSP  300
QLSPQLVRQQ IAMAHLINQQ IAVSRLLAHQ HPQAINQQFL NHPPIPRAVK PEPTNSSVEV  360
SPDIYQQVRD ELKRASVSQA VFARVAFNRT QGLLSEILRK EEDPRTASQS LLVNLRAMQN  420
FLNLPEVERD RIYQDERERS MNPNVSMVSS ASSSPSSSRT PQAKTSTPTT DLPIKVDGAN  480
INITAAIYDE IQQEMKRAKV SQALFAKVAA NKSQGWLCEL LRWKENPSPE NRTLWENLCT  540
IRRFLNLPQH ERDVIYEEES RHHHSERMQH VVQLPPEPVQ VLHRQQSQPA KESSPPREEA  600
PPPPPPTEDS CAKKPRSRTK ISLEALGILQ SFIHDVGLYP DQEAIHTLSA QLDLPKHTII  660
KFFQNQRYHV KHHGKLKEHL GSAVDVAEYK DEELLTESEE NDSEEGSEEM YKVEAEEENA  720
DKSKAAPAEI DQR                                                     733

SEQ ID NO: 5           moltype = AA  length = 675
```

-continued

```
FEATURE                Location/Qualifiers
source                 1..675
                       mol_type = protein
                       organism = Homo sapiens
SEQUENCE: 5
MIPVFCVVEQ LDGSLEYDNR EEHAEFVLVR KDVLFSQLVE TALLALGYSH SSAAQAQGII  60
KLGRWNPLPL SYVTDAPDAT VADMLQDVYH VVTLKIQLQS CSKLEDLPAE QWNHATVRNA  120
LKELLKEMNQ STLAKECPLS QSMISSIVNS TYYANVSATK CQEFGRWYKK YKKIKVERVE  180
RENLSDYCVL GQRPMHLPNM NQLASLGKTN EQSPHSQIHH STPIRNQVPA LQPIMSPGLL  240
SPQLSPQLVR QQIAMAHLIN QQIAVSRLLA HQHPQAINQQ FLNHPPIPRA VKPEPTNSSV  300
EVSPDIYQQV RDELKRASVS QAVFARVAFN RTQGLLSEIL RKEEDPRTAS QSLLVNLRAM  360
QNFLNLPEVE RDRIYQDERE RSMNPNVSMV SSASSSPSSS RTPQAKTSTP TTDLPIKVDG  420
ANINITAAIY DEIQQEMKRA KVSQALFAKV AANKSQGWLC ELLRWKENPS PENRTLWENL  480
CTIRRFLNLP QHERDVIYEE ESRHHHSERM QHVVQLPPEP VQVLHRQQSQ PAKESSPPRE  540
EAPPPPPPTE DSCAKKPRSR TKISLEALGI LQSFIHDVGL YPDQEAIHTL SAQLDLPKHT  600
IIKFFQNQRY HVKHHGKLKE HLGSAVDVAE YKDEELLTES EENDSEEGSE EMYKVEAEEE  660
NADKSKAAPA EIDQR                                                 675

SEQ ID NO: 6           moltype = RNA  length = 20
FEATURE                Location/Qualifiers
source                 1..20
                       mol_type = other RNA
                       organism = synthetic construct
SEQUENCE: 6
tgctccacga cacaaaagac                                            20

SEQ ID NO: 7           moltype = RNA  length = 20
FEATURE                Location/Qualifiers
source                 1..20
                       mol_type = other RNA
                       organism = synthetic construct
SEQUENCE: 7
gattcctgtc ttttgtgtcg                                            20

SEQ ID NO: 8           moltype = RNA  length = 20
FEATURE                Location/Qualifiers
source                 1..20
                       mol_type = other RNA
                       organism = synthetic construct
SEQUENCE: 8
cttttgtgtc gtggagcagt                                            20

SEQ ID NO: 9           moltype = RNA  length = 20
FEATURE                Location/Qualifiers
source                 1..20
                       mol_type = other RNA
                       organism = synthetic construct
SEQUENCE: 9
tgtgtcgtgg agcagttgga                                            20

SEQ ID NO: 10          moltype = RNA  length = 20
FEATURE                Location/Qualifiers
source                 1..20
                       mol_type = other RNA
                       organism = synthetic construct
SEQUENCE: 10
actccagtct ttctagaaga                                            20

SEQ ID NO: 11          moltype = DNA  length = 25
FEATURE                Location/Qualifiers
source                 1..25
                       mol_type = other DNA
                       organism = synthetic construct
SEQUENCE: 11
ggcataagct ttgacttcca gtaac                                      25

SEQ ID NO: 12          moltype = DNA  length = 24
FEATURE                Location/Qualifiers
source                 1..24
                       mol_type = other DNA
                       organism = synthetic construct
SEQUENCE: 12
gtgatgaggg cgatgtacga ataa                                       24

SEQ ID NO: 13          moltype = RNA  length = 20
FEATURE                Location/Qualifiers
source                 1..20
                       mol_type = other RNA
                       organism = synthetic construct
```

```
SEQUENCE: 13
actccagtct ttctagaaga                                              20

SEQ ID NO: 14          moltype = DNA  length = 25
FEATURE                Location/Qualifiers
source                 1..25
                       mol_type = other DNA
                       organism = synthetic construct
SEQUENCE: 14
ggcataagct ttgacttcca gtaac                                        25

SEQ ID NO: 15          moltype = DNA  length = 24
FEATURE                Location/Qualifiers
source                 1..24
                       mol_type = other DNA
                       organism = synthetic construct
SEQUENCE: 15
gtgatgaggg cgatgtacga ataa                                         24

SEQ ID NO: 16          moltype = DNA  length = 21
FEATURE                Location/Qualifiers
source                 1..21
                       mol_type = other DNA
                       organism = synthetic construct
SEQUENCE: 16
gggtgtgaac cacgagaaat a                                            21

SEQ ID NO: 17          moltype = DNA  length = 20
FEATURE                Location/Qualifiers
source                 1..20
                       mol_type = other DNA
                       organism = synthetic construct
SEQUENCE: 17
gtcatgagcc cttccacaat                                              20

SEQ ID NO: 18          moltype = DNA  length = 20
FEATURE                Location/Qualifiers
source                 1..20
                       mol_type = other DNA
                       organism = synthetic construct
SEQUENCE: 18
ggggcgtctg tcacataact                                              20

SEQ ID NO: 19          moltype = DNA  length = 20
FEATURE                Location/Qualifiers
source                 1..20
                       mol_type = other DNA
                       organism = synthetic construct
SEQUENCE: 19
tttagccagc tggtggagac                                              20

SEQ ID NO: 20          moltype = DNA  length = 22
FEATURE                Location/Qualifiers
source                 1..22
                       mol_type = other DNA
                       organism = synthetic construct
SEQUENCE: 20
cagccacttt ccaatttcac tg                                           22

SEQ ID NO: 21          moltype = DNA  length = 23
FEATURE                Location/Qualifiers
source                 1..23
                       mol_type = other DNA
                       organism = synthetic construct
SEQUENCE: 21
gctggacata ctccttcacc tta                                          23

SEQ ID NO: 22          moltype = DNA  length = 21
FEATURE                Location/Qualifiers
source                 1..21
                       mol_type = other DNA
                       organism = synthetic construct
SEQUENCE: 22
ctgctaaccg gaacctatcg g                                            21

SEQ ID NO: 23          moltype = DNA  length = 21
FEATURE                Location/Qualifiers
source                 1..21
                       mol_type = other DNA
```

-continued

```
                      organism = synthetic construct
SEQUENCE: 23
tccagctctc cattgaactg a                                            21

SEQ ID NO: 24         moltype = DNA  length = 21
FEATURE               Location/Qualifiers
source                1..21
                      mol_type = other DNA
                      organism = synthetic construct
SEQUENCE: 24
cagagccagg agaactttga g                                            21

SEQ ID NO: 25         moltype = DNA  length = 22
FEATURE               Location/Qualifiers
source                1..22
                      mol_type = other DNA
                      organism = synthetic construct
SEQUENCE: 25
gtccataggt gatggtgagt tt                                           22

SEQ ID NO: 26         moltype = DNA  length = 21
FEATURE               Location/Qualifiers
source                1..21
                      mol_type = other DNA
                      organism = synthetic construct
SEQUENCE: 26
gttcaaggct accgtgaaga t                                            21

SEQ ID NO: 27         moltype = DNA  length = 20
FEATURE               Location/Qualifiers
source                1..20
                      mol_type = other DNA
                      organism = synthetic construct
SEQUENCE: 27
tcttgcttac gcgctcatag                                              20

SEQ ID NO: 28         moltype = DNA  length = 20
FEATURE               Location/Qualifiers
source                1..20
                      mol_type = other DNA
                      organism = synthetic construct
SEQUENCE: 28
atggctggca agaaagtctg                                              20

SEQ ID NO: 29         moltype = DNA  length = 21
FEATURE               Location/Qualifiers
source                1..21
                      mol_type = other DNA
                      organism = synthetic construct
SEQUENCE: 29
cgtgctgagt gttgatgatc t                                            21

SEQ ID NO: 30         moltype = DNA  length = 21
FEATURE               Location/Qualifiers
source                1..21
                      mol_type = other DNA
                      organism = synthetic construct
SEQUENCE: 30
aacatgaaac cagggatgtc c                                            21

SEQ ID NO: 31         moltype = DNA  length = 23
FEATURE               Location/Qualifiers
source                1..23
                      mol_type = other DNA
                      organism = synthetic construct
SEQUENCE: 31
cgagggttaa aatgcaggtt gag                                          23

SEQ ID NO: 32         moltype = DNA  length = 21
FEATURE               Location/Qualifiers
source                1..21
                      mol_type = other DNA
                      organism = synthetic construct
SEQUENCE: 32
caacatggag cccttgcgta a                                            21

SEQ ID NO: 33         moltype = DNA  length = 21
FEATURE               Location/Qualifiers
source                1..21
```

```
                        mol_type = other DNA
                        organism = synthetic construct
SEQUENCE: 33
atgagcacat catcaggcca g                                              21

SEQ ID NO: 34           moltype = DNA  length = 20
FEATURE                 Location/Qualifiers
source                  1..20
                        mol_type = other DNA
                        organism = synthetic construct
SEQUENCE: 34
ctcccatcaa agcagagcca                                                20

SEQ ID NO: 35           moltype = DNA  length = 20
FEATURE                 Location/Qualifiers
source                  1..20
                        mol_type = other DNA
                        organism = synthetic construct
SEQUENCE: 35
ccacgtggca tagagtctcc                                                20

SEQ ID NO: 36           moltype = DNA  length = 21
FEATURE                 Location/Qualifiers
source                  1..21
                        mol_type = other DNA
                        organism = synthetic construct
SEQUENCE: 36
gctatcgctc ttgttgtggt t                                              21

SEQ ID NO: 37           moltype = DNA  length = 21
FEATURE                 Location/Qualifiers
source                  1..21
                        mol_type = other DNA
                        organism = synthetic construct
SEQUENCE: 37
ttccaggact aggggttgaa g                                              21

SEQ ID NO: 38           moltype = DNA  length = 20
FEATURE                 Location/Qualifiers
source                  1..20
                        mol_type = other DNA
                        organism = synthetic construct
SEQUENCE: 38
aagccacctt tcggatgagg                                                20

SEQ ID NO: 39           moltype = DNA  length = 19
FEATURE                 Location/Qualifiers
source                  1..19
                        mol_type = other DNA
                        organism = synthetic construct
SEQUENCE: 39
cgcagcagtc gttgttctg                                                 19

SEQ ID NO: 40           moltype = DNA  length = 21
FEATURE                 Location/Qualifiers
source                  1..21
                        mol_type = other DNA
                        organism = synthetic construct
SEQUENCE: 40
aggctagttt acgcctccat t                                              21

SEQ ID NO: 41           moltype = DNA  length = 22
FEATURE                 Location/Qualifiers
source                  1..22
                        mol_type = other DNA
                        organism = synthetic construct
SEQUENCE: 41
aggaacttcc cgtgactttt ct                                             22

SEQ ID NO: 42           moltype = DNA  length = 18
FEATURE                 Location/Qualifiers
source                  1..18
                        mol_type = other DNA
                        organism = synthetic construct
SEQUENCE: 42
aacccaagcc tgcagaaa                                                  18

SEQ ID NO: 43           moltype = DNA  length = 23
FEATURE                 Location/Qualifiers
```

```
source                  1..23
                        mol_type = other DNA
                        organism = synthetic construct
SEQUENCE: 43
gagccaaagt aggtccagta atc                                              23

SEQ ID NO: 44           moltype = DNA  length = 20
FEATURE                 Location/Qualifiers
source                  1..20
                        mol_type = other DNA
                        organism = synthetic construct
SEQUENCE: 44
gaatgtgtga cctggatcgt                                                  20

SEQ ID NO: 45           moltype = DNA  length = 19
FEATURE                 Location/Qualifiers
source                  1..19
                        mol_type = other DNA
                        organism = synthetic construct
SEQUENCE: 45
tgtccaccat cgcttcttc                                                   19

SEQ ID NO: 46           moltype = DNA  length = 19
FEATURE                 Location/Qualifiers
source                  1..19
                        mol_type = other DNA
                        organism = synthetic construct
SEQUENCE: 46
aggcccatca tgtgagcag                                                   19

SEQ ID NO: 47           moltype = DNA  length = 21
FEATURE                 Location/Qualifiers
source                  1..21
                        mol_type = other DNA
                        organism = synthetic construct
SEQUENCE: 47
cacacggtac atcctcggaa t                                                21

SEQ ID NO: 48           moltype = DNA  length = 23
FEATURE                 Location/Qualifiers
source                  1..23
                        mol_type = other DNA
                        organism = synthetic construct
SEQUENCE: 48
atggctacaa aatgcacaaa gtg                                              23

SEQ ID NO: 49           moltype = DNA  length = 21
FEATURE                 Location/Qualifiers
source                  1..21
                        mol_type = other DNA
                        organism = synthetic construct
SEQUENCE: 49
cctgtgttcc ggtaaatgca g                                                21

SEQ ID NO: 50           moltype = DNA  length = 22
FEATURE                 Location/Qualifiers
source                  1..22
                        mol_type = other DNA
                        organism = synthetic construct
SEQUENCE: 50
gacagcttca tccgagaact tc                                               22

SEQ ID NO: 51           moltype = DNA  length = 20
FEATURE                 Location/Qualifiers
source                  1..20
                        mol_type = other DNA
                        organism = synthetic construct
SEQUENCE: 51
attgcccaat cccactgcat                                                  20

SEQ ID NO: 52           moltype = DNA  length = 21
FEATURE                 Location/Qualifiers
source                  1..21
                        mol_type = other DNA
                        organism = synthetic construct
SEQUENCE: 52
aacagtgcca acgaggtctt c                                                21

SEQ ID NO: 53           moltype = DNA  length = 21
```

-continued

```
FEATURE                Location/Qualifiers
source                 1..21
                       mol_type = other DNA
                       organism = synthetic construct
SEQUENCE: 53
cttgttgccg aggataggga a                                        21

SEQ ID NO: 54          moltype = DNA  length = 20
FEATURE                Location/Qualifiers
source                 1..20
                       mol_type = other DNA
                       organism = synthetic construct
SEQUENCE: 54
caggaataat caagctaggg                                          20

SEQ ID NO: 55          moltype = DNA  length = 20
FEATURE                Location/Qualifiers
source                 1..20
                       mol_type = other DNA
                       organism = synthetic construct
SEQUENCE: 55
tcacataact gagggggagg                                          20

SEQ ID NO: 56          moltype = DNA  length = 20
FEATURE                Location/Qualifiers
source                 1..20
                       mol_type = other DNA
                       organism = synthetic construct
SEQUENCE: 56
gggcgtctgt cacataactg                                          20

SEQ ID NO: 57          moltype = DNA  length = 20
FEATURE                Location/Qualifiers
source                 1..20
                       mol_type = other DNA
                       organism = synthetic construct
SEQUENCE: 57
ggcggcggca ccatgaccct                                          20

SEQ ID NO: 58          moltype = DNA  length = 20
FEATURE                Location/Qualifiers
source                 1..20
                       mol_type = other DNA
                       organism = synthetic construct
SEQUENCE: 58
ctcgcagcag cagctgccca                                          20

SEQ ID NO: 59          moltype = DNA  length = 20
FEATURE                Location/Qualifiers
source                 1..20
                       mol_type = other DNA
                       organism = synthetic construct
SEQUENCE: 59
cgcggccggg gagctctcgg                                          20

SEQ ID NO: 60          moltype = DNA  length = 20
FEATURE                Location/Qualifiers
source                 1..20
                       mol_type = other DNA
                       organism = synthetic construct
SEQUENCE: 60
tgctccacga cacaaaagac                                          20

SEQ ID NO: 61          moltype = DNA  length = 20
FEATURE                Location/Qualifiers
source                 1..20
                       mol_type = other DNA
                       organism = synthetic construct
SEQUENCE: 61
gattcctgtc ttttgtgtcg                                          20

SEQ ID NO: 62          moltype = DNA  length = 19
FEATURE                Location/Qualifiers
source                 1..19
                       mol_type = other DNA
                       organism = synthetic construct
SEQUENCE: 62
cttttgtgtc gggagcagt                                           19
```

-continued

```
SEQ ID NO: 63           moltype = DNA  length = 20
FEATURE                 Location/Qualifiers
source                  1..20
                        mol_type = other DNA
                        organism = synthetic construct
SEQUENCE: 63
tgtgtcgtgg agcagttgga                                        20
```

PROMOTING NUTRIENT ABSORPTION THROUGH THE COLON

CROSS-REFERENCE TO RELATED APPLICATIONS

This application claims the benefit of the filing date of U.S. application No. 63/349,436, filed on Jun. 6, 2022, the disclosure of which is incorporated by reference herein.

INCORPORATION BY REFERENCE OF SEQUENCE LISTING

A Sequence Listing is provided herewith as an xml file, "1676185US1.xml" created on Jan. 24, 2024, and having a size of 64,864 bytes. The content of the xml file is incorporated by reference herein in its entirety.

BACKGROUND

Several diseases and conditions can reduce nutrient absorption by the small intestine. In some cases, these diseases and conditions can lead to reduced survival. For example, approximately 15,000 patients in the United States have Short Bowel Syndrome (SBS) in which loss of a large portion of the small bowel is incapable of absorbing sufficient nutrients. SBS can be due to injuries or diseases such as Crohn's disease or necrotizing enterocolitis. The remaining remnant of small intestine can undergo structural and molecular adaptations to increase nutrient uptake, but such adaptations are often insufficient. There are few therapeutic options to treat severe SBS beyond long-term total parenteral nutrition (TPN), which can lead to complications such as infections and liver diseases. The prognosis for SBS is also poor. In patients with less than 50 cm of intestine, the expected 5-year survival is approximately 50%.

The GLP2 analog, Teduglutide, was recently developed for treatment of a subset of SBS patients by promoting mucosal growth (at a cost of up to $400,000 per year). New therapeutic approaches to treat SBS are urgently needed.

SUMMARY

As illustrated herein, Satb2 loss leads to stable conversion of colonic stem/progenitor cells into small intestine-like stem/progenitor cells and replacement of the colonic mucosa with those cells to provide a colonic mucosa that resembles the ileum. Methods and compositions are described herein that can delete or modify at least one Satb2 allele or inhibit expression of a Satb2 gene within in vivo or in vitro cells.

For example, at least one Satb2 allele can be inhibited or genetically modified in vivo by introduction of inhibitors and/or modifying agents through oral administration, direct injection, and other methods to thereby convert the starting cells into small intestine-like cells. Delivery vehicles such as AAV (Adeno Associated Virus) and nanoparticles can be used to introduce the inhibitors and/or modifying agents to a patient or subject.

Methods and compositions are also described herein that can disable at least one Satb2 allele or inhibit expression of a Satb2 gene in one or more isolated starting cells of a subject, to thereby convert the starting cells into small intestine-like cells. They can then be administered to a patient or subject.

The Satb2 allele(s) can be deleted or inactivated by genomic modification using, for example, one or more CRISPR, TALENS, ZFN, or base-editing reagents. Expression of the Satb2 gene can be inhibited by inhibitory nucleic acids such as antisense nucleic acids, siRNAs, small hairpin RNAs, expression systems that express such antisense nucleic acids, siRNAs, small hairpin RNAs, or combinations thereof.

The methods and compositions described herein can generate populations of engineered Satb2 cells, including Satb2-null cells, and cells having reduced Satb2 expression. Such populations of engineered Satb2 cells can be made in vivo. In some cases the engineered Satb2 cells can be made in vitro and then administered to a subject, for example, into the abdomen, into intestinal tissues. Such engineered Satb2 cells (e.g., SATB2-null organoids or SATB2-null stem/progenitor cells) can also be seeded onto a scaffold, for instance, a de-cellularized intestinal segment, or any biological or artificial scaffolds, to create transplantable gut segments. Such small intestine-like cells and/or scaffolds that include the engineered Satb2 cells can be administered to a subject in need thereof. Scaffold materials include but are not limited to fibrin, laminin, fibronectin, or combinations thereof, as well as gels made from partial or whole tissues (intestinal gel or other tissue gels). Scaffold materials may be supplemented with growth factors such WNT and EGF and others to enhance cell survival, proliferation, migration, and morphogenesis.

DESCRIPTION OF THE FIGURES

FIG. 1A is a schematic illustrating that SATB2 and FOXD2 were within the top 20 transcription factors enriched in both mouse and human, and the only common genes beside the posterior HOX genes between these two species. FIG. 1B shows a western blot and a graph quantifying mouse SATB2 protein levels in isolated epithelia of 4 different intestinal regions showed strong SATB2 expression in cecum and colon, weak expression in terminal ileum, and no expression in proximal ileum and jejunum. N=3 mice. *P<0.05, *P<0.001. Mean 1±S.D. Unpaired t-test. FIG. 1D shows that SATB2 is expressed in adult murine large intestine epithelial cells, including LGR$5^+$ stem cells, but absent in small intestine epithelium. ECAD, E-cadherin. FIG. 1) shows a western blot of isolated crypts or whole glands showing that SATB2 protein expression was not present in the duodenum (crypts and glands) or ileal crypts but detectable in whole ileal glands. N=4 mice. Mean±S.D. Unpaired t-test. FIG. 1E is a schematic diagram of the conditional knockout of SATB2 (Satb$2^{cKO}$) using VillinCre-ER and floxed Satb2. After deletion of Exons 4 and 5, multiple stop codons are created in the downstream exon. FIG. 1F shows characteristic images of colon from 2-month-old mice 30 days after intestinal deletion of Satb2 (in Vil-Cre$^{ER}$; Satb$2^{f/f}$; Satb$2^{cKO}$ mice) compared to characteristic images of colon from 2-month old mice that express wild type Satb2 (control). H&E staining showed that the characteristic flat colonic glands were replaced by elongated villus-like glands in the Satb$2^{cKO}$ mice, and many cells bearing Paneth morphology (pink-colored cells) appeared at the bottom of the glands. N=8 mice. Mean±SD. p value by Mann-Whitney U test. FIG. 1G graphically illustrates the mucosal depth and Paneth cells per crypt observed in ileum control, colon control, and colon Satb$2^{cKOc}$ sections. FIG. 1H graphically illustrates principal-component analysis (PCA) of RNA-seq data from intestinal epithelia of different tissues. FIG. 1**I graphically illustrates gene set enrichment analysis of RNA-seq data obtained from intestinal epithelia of $Satb2^{cKO}$ mice. FIG. 1D-1E show that RNA-seq of intestinal epithelia reveal a shift of the large intestine transcriptomes (cecum and colon) in $Satb2^{cKO}$ mice toward small intestine ileal transcriptomes by principal-component analysis (PCA) (FIG. 1D) and gene set enrichment analysis (FIG. 1E). NES, normalized enrichment score; FDR, false discovery rate. FIG. 1J shows immunofluorescence images illustrating the appearance of OLFM4+ small intestine stem cells, $LYZ1^+$ Paneth cells, and $FABP6^+$ and $FGF15^+$ ileal enterocytes in $Satb2^{cKO}$ colon and concomitant disappearance of $CA1^+$ and $AQP4^+$ colonocytes. FIG. 1K shows immunofluorescently stained images of control and $Satb2^{cKO}$ proximal colon sections obtained 6 months after tamoxifen (TAM) treatment, illustrating persistence of ileal-like mucosa in the mutant colon FIG. 1L shows histochemically stained images of control and $Satb2^{cKO}$ proximal and distal colon sections obtained 6 months after tamoxifen (TAM) treatment, illustrating absence of SATB2 and activation of FABP6 and RBP2 in both proximal and distal colon. FIG. 1M graphically illustrates SATB2, FABP6 and RBP2 expression in the control and $Satb2^{cKO}$ proximal and distal colon sections shown in FIG. 1L. n=5 areas quantified. *P<0.05, ***P<0.001. Mean±S.D. Unpaired t-test.

FIG. 2A illustrates scRNA-seq and post hoc annotation, showing that a majority of cells in $Satb2^{cKO}$ colon clustered with ileum (t-distributed stochastic neighbor embedding (t-SNE) plots, 3,912 cells from ileum, 3,627 cells from control colon, and 4,370 cells from Satb2cKO colon). The Satb2cKO colonic sample was harvested 30 days after tamoxifen (TAM) treatment, FIG. 2B shows dot plots of 30 representative genes of the major intestinal cell lineages. FIG. 2C graphically illustrates Uniform Manifold Approximation and Projection (UMAP) visualization of 594 $LGR5^+$ stem cells at G1/S phase. $Satb2^{cKO}$ colonic stem cells cluster with ileal rather than colonic stem cells. FIG. 2D shows images of control and $Satb2^{cKO}$ primary colonic glands grown in standard small intestine medium in 3D Matrigel. As illustrated, primary colonic glands from Satb2cKO mice yielded branching organoids at a similar efficiency as control ileal glands, which can be further propagated into secondary organoids. In contrast, control colonic glands generated few small spheroids. N=4, 5 mice. Mean±SD. p value by Mann-Whitney U test. FIG. 2E shows images illustrating that SAT1B2 deletion from colonic stem cells in $Lgr5^{CreERGFP}$; $Satb2^{f/f}$ mice led to progressive conversion of colonic epithelium to ileum. The deleted clones were marked by crypt GFP expression. 7 days after tamoxifen (TAM) treatment, SATB2 disappeared from the lower part of the glands, but OLFM4 was activated only in some of the $GFP^+$ colonic stem cells, indicating incomplete reprogramming at this stage. However, by day 36, the conversion of colonic stem cells appeared to be complete, with OLFM4 expression in most of the $GFP^+$ cells, presence of $LYZ1^+$ Paneth cells, and replacement of $CA1^+$ colonocytes with $FABP6^+$ enterocytes.

FIG. 3A shows a time course study of colonic mucosa gene expression after a single dose of tamoxifen (TAM) in $Satb2^{cKO}$ mice illustrating rapid activation of FABP6 and down-regulation of CA1 at day 2 and complete replacement of $CA1^+$ cells by $FABP6^+$ cells by day 6. OLFM4 and LYZ1 were not robustly activated until day 30. FIG. 3B shows principal-component analysis (PCA) of time-course RNA-seq data illustrating rapid activation of pathways typical of enterocytes and downregulation of pathways characteristic of colonocytes. FIG. 3C shows a heatmap representation of time-course RNA-seq data illustrating rapid activation of pathways typical of enterocytes and downregulation of pathways characteristic of colonocytes. Paneth and stem cell genes were only strongly activated at day 30.

FIG. 4A illustrates scRNA profiles of $Satb2^{cKO}$ colonic enterocytes closely resemble ileal enterocytes. The heatmap was plotted using the top 100 differentially expressed genes (DEGs) between ileal enterocytes and control colonocytes. The bar graph shows the top five differential Gene Ontology pathways between ileal enterocytes and control colonocytes. Some of the nutrient transporters are highlighted in the heatmap. FIG. 4B shows images of microvilli of $Satb2^{cKO}$ enterocytes were significantly longer than those of control colon and comparable with ileal enterocytes. n=10 randomly selected cells. Mean±SD. p value by Mann-Whitney U test. FIG. 4C is a schematic of the assay for measuring glucose and taurocholic acid absorption and trans-epithelial transport into portal circulation. A segment of the ileum or colon was tied on both ends to create a pouch; radiolabeled chemicals were injected into the pouch to allow absorption and transport. FIG. 4D graphically illustrates that the amount of glucose and taurocholic acid being transported in portal vein plasma or deposited in the liver tissue after infusion into the $Satb2^{cKO}$ colon is significantly higher compared with infusions into the control colon, indicating enhanced absorptive functions in the colon of SATB2-null mice. N=6-8 mice. Mean±SD. p value by Mann-Whitney U test.

FIG. 5A is a schematic diagram illustrating construction of a Satb2 transgenic mouse line ($CAG^{Satb2GFP}$), Co-expression of murine SATB2 (with a HA epitope tag) and GFP is activated in the adult intestine after tamoxifen (TAM) treatment of $Vil\text{-}Cre^{ER}$; $CAG^{Sat2GFP}$ ($Satb2^{OE}$) mice. FIG. 5B further illustrates construction of a Satb2 transgenic mouse line ($CAG^{Satb2GFP}$), showing immunostained ileal sections (30 days after TAM treatment of 2-month-old mice), confirming co-localization of the HA tag and GFP. FIG. 5C shows a representative FACS plot of GFP and EPCAM in purification of GFP+ and $GFP^-$ ileal epithelial cells. Ectopic expression of Satb2 activated colonic genes and suppressed ileal genes. FIG. 5D graphically illustrates quantified Satb2 transcript levels (measured by qPCR) in colon epithelial and GFP+ and $GFP^-$ ileal epithelial cells. N=3 mice. *p<0.001. Mean±SD. Unpaired t test. FIG. 5E shows GSEA of transcriptomes from GFP+ versus $GFP^-$ cells illustrating enrichment of colonic and depletion of ileal signature genes (P, nominal p value). N=3 mice. *p<0.001. Mean±SD. Unpaired t test. Ectopic expression of Satb2 activated colonic genes and suppressed ileal genes was observed. FIG. 5F illustrates ectopic SATB2 activated the colonic marker CA1 and suppressed OLFM4, LYZ1, and FABP6 in the ileum, in immunofluorescently stained ileum 30 days after TAM. White lines delineate villi and crypts. Dashed lines in magnified pictures outline crypts. FIG. 5G also illustrates that ectopic SATB2 activated the colonic marker CA1 and suppressed OLFM4, LYZ1, and FABP6 in the ileum, as graphically illustrated by quantified levels of $CA1^+$ and $FABP6^+$ cells among GFP+ or $GFP^-$ cells on the ileal villi. The numbers of OLFM4+ stem cells and LYZ1±Paneth cells were also quantified in GFP+ and $GFP^-$ crypts. N=5 mice. Mean±SD. p value by paired t test.

FIG. 6A illustrates binding motifs of top transcription factors enriched in SATB2 ChIP-seq sites (MACS $p<1\times10^{-9}$) by HOMER in control colonic epithelium. Motifs were ranked by $-\log_{10}$ (p value). FIG. 6B shows a Venn diagram illustrating the overlaps among $SATB2^{-}$, $CDX2^{-}$, and HNF4A-bound regions. Shown are two biological replicates for each of the factors. FIG. 6C illustrates that CDX2 and HNF4A antibodies can pull down SATB2 proteins from primary colonic tissues. FIGS. 6A-6C illustrate extensive genomic co-binding of SATB/2 with CDX2 and HNF4A in colonic epithelium. FIG. 6D shows Box-and-whisker plots representing relative gene expression changes. Genes adjacent to colonic enhancers (MAnorm p<0.01, distance<50 kb, 2,618 genes) were expressed at higher levels in control colon ($p<2\times10^{-16}$), whereas genes adjacent to ileal enhancers (MAnorm p<0.01, distance<50 kb, 2,837 genes) were expressed at higher levels in ileum and Satb2cKO colon ($p<2\times10^{-16}$). Each box represents the median and interquartile range; whiskers extend to 1.5 times the interquartile range. p value by unpaired, two-sided Wilcoxon rank-sum test; N:=3 mice. FIG. 6E illustrates that SATB2 ChIP-seq signals were enriched at colon-specific enhancers compared with ileum-specific enhancers in control colon ($p<2\times10^{-16}$). A plot is shown for a 20-kb window centered on each specific enhancer binding site. FIG. 6F illustrates inactivation of colon-specific enhancers and activation of ileum-specific enhancers in $Satb2^{cKO}$ colon. All plots are shown with a 20-kb window centered at colon-specific or ileum-specific enhancers for H3K4me1 and H3K27ac (CUT&RUN-seq), ATAC-seq, and CDX2 and HNF4A ChIP in ileum, colon, and $Satb2^{cKO}$ colon (N=2 biological replicates). FIG. 6G illustrates Genome Browser tracks of RNA-seq, histone modifications (CUT&RUN-seq), and transcription factor ChIP data at genomic loci of the colonic gene Carl and the ileal gene Bcl2115. Regions with significant enhancer and transcription factor binding changes among samples are highlighted. FIG. 6H shows a FACS plot of cell fractions enriched for stem cells (EPCAM±GFP+) or differentiated cells ($EPCAM+GFP^{-}$) isolated from $LGR5^{DTRGFP}$ murine colon. FIG. 6I illustrates a Pearson correlation of SATB2 binding signals in stem versus differentiated cells by CUT&RUN-seq shows concordant binding patterns. FIG. 6J illustrates SATB2 CUT&RUN binding profiles in a 10-kb window centered on SATB2 peaks identified by ChIP-seq. Together, FIG. 6H-6J illustrate that SATB2 bound similar genomic loci in colonic LGR5+ stem cells as non-stem cells.

FIG. 7A shows that SATB2 is expressed in $ECAD^{+}$ epithelial cells of the human colon but not in $ECAD^{+}$ epithelial cells of the human ileum. FIG. 7B is a diagram with images of the methods used for CRISPR-mediated genomic deletion of SATB2 in cultured human colonic organoids followed by differentiation. Representative images of organoids shown at different stages. FIG. 7C illustrates evaluation of four different guide RNAs for deletion efficiency of SATB2 in human cells. A Western blot is shown demonstrating that sgRNA1 efficiently disrupted SATB2 expression whereas the close homolog SATB1 was unaffected, n=3 independent experiments. Mean±S.D. FIG. 7D illustrates successful knockout of SATB2 expression in all five human organoid lines. Western blot images and quantifications shown. n=3 independent experiments. ***P<0.001. Unpaired t-test. FIG. 7E shows representative images of SATB2 expression in one of the primary human organoid lines (#87) and its absence after CRISPR-mediated deletion. sgRNA: single guide RNA, sgRNA1. FIG. 7F illustrates that RBP2, a marker of ileum, was detected in ileal human biopsy tissues. FIG. 7G illustrates that RBP2, a marker of ileum, was not detected in the colonic epithelium of human biopsy tissues. However, RBP2 was abundantly expressed in colonic organoids after SATB2 deletion, at levels comparable to that of control ileal organoids. n=6 samples (3 biological replicates each from 2 independent experiments). Mean±S.D. P value by Mann Whitney U-test. FIG. 7H shows that ileal makers SLC15A1 and FABP6 were activated in colonic organoids after SATB2 loss and that such markers are localized to the luminal epithelial side and the cytoplasm, respectively. Relative signal intensity was calculated by comparison with control ileal organoids. n=8 samples (4 biological replicates each in 2 independent experiments). Mean±SD. p value by Mann-Whitney U test. FIG. 7I illustrates that activities of small intestine disaccharidases and dipeptide peptidases were detected in knockout $SATB2^{hKO}$ colonic organoids. n=6 samples (3 biological replicates each in 2 independent experiments). Mean±SD. p value by Mann-Whitney U test.

FIG. 8A illustrates a comparison of our published RNA-seq data of FAGS-purified Lgr5-GFP stein cells ($Lgr5^{DTR-GFP}$ mice) from the duodenum and the colon identified the top 20 transcription factors (TFs) enriched in colonic stem cells. N=3 mice. FIG. 8B shows primary human duodenal and colonic organoids were cultured in Matrigel under high-Wnt conditions that favor stein and progenitor proliferation. RNA-seq comparison of the human organoids identified the top 20 colonic enriched TFs. N=4 biological replicates. FIG. 8C illustrates comparing the top 20 TFs enriched in both mouse and human, SATB2 and FOXD2 were the only common genes beside the posterior HOX genes. FIG. 8D provides three guide RNAs (sg1, 2, 3) for CRISPR-mediated disruption of murine Satb2. After Lentiviral delivery of guide RNA and CAS9 into murine colonic organoids and selection with puromycin (puromycin gene and CAS9 are co-expressed with the guide RNA), Western blot showed efficient deletion of SATB2 (85-95%), which was confirmed by immunostaining of SATB2 on control and SATB2 CRISPR organoids. *P<0.001. Mean±S.D. Unpaired t-test. FIG. 8E. Three guide RNAs were designed and used independently for CRISPR disruption of the Foxd2 gene in murine colonic organoids. Antibodies suitable for Western blot of FOXD2 were not apparently available, so an assay based on T7 endonuclease cutting of PCR-amplified Foxd2 genomic region targeted by CRISPR was used to quantify the Foxd2 genomic disruption efficiency at 57-74%, *P<0.001. Mean±S.D. Unpaired t-test.

FIG. 8H illustrates the up- and down-regulated genes were enriched for small intestine and large intestine respectively (FIG. 8I, tissue enrichment by Enrichr).

FIG. 9A shows Western blot and quantification of SATB2 protein levels in isolated epithelia of 5 different intestinal regions showed strong SATB2 expression in cecum and colon, weak expression in terminal ileum, and no expression in proximal ileum and jejunum. N=3 mice. *$P<0.05$, *$P<0.001$. Mean±S.D. Unpaired t-test FIG. 9B shows a diagram of the conditional knockout of SATB2 using Villin$^{Cre-ER}$ and floxed Satb2. After deletion of Exons 4 and 5, multiple stop codons are created in the downstream exon. FIG. 9C illustrates immunohistochemistry confirmed lack of SATB2 in Satb2$^{CKO}$ colon 30 days after tamoxifen treatment. FIG. 9D shows wide-view H&E histology pictures of control and Satb2cKO proximal colon 2 months after TAM. The mutant colon was covered by villi-like glands. The rugae structures remained. FIG. 9E shows Alcian blue stain showed the number of mature goblet cells in Satb2cKO colon decreased significantly compared with control colon, reaching a level comparable to ileum. N=3 mice. Mean±S.D. *$P<0.001$. Unpaired t-test. FIG. 9F shows there was no difference in the apoptosis rate, as assessed by activated caspase 3, among the 3 samples. N=3 mice. Mean±S.D. Unpaired t-test. G. 24-hour pulse-chase with Edu showed enhanced upward migration of epithelial cells in Satb2$^{cKO}$ colon versus control colon, at a rate comparable to that of ileum. N=3 mice. Mean±S.D. *$P<0.001$. Tukey's multiple comparison test. FIGS. 9H-K illustrate the transcriptome of Satb2$^{cKO}$ colonic epithelium resembles control ileum, as shown in the heatmap (FIG. 9H, (LFC>2, Padj<0.05, RPKM cut>0.5), volcano plots (FIG. 9I), and GeneOntology biological processes enriched in ileum vs control colon (FIG. 9J) and Satb2cKo colon vs control colon (FIG. 9K). FIG. 9**L illustrates wide-view immunofluorescence images of controls and Satb2cKo proximal colon 6 months after TAM showing persistence of ileal-like mucosa in the mutant colon.

FIG. 10A shows dot plots of some of the lineage-specific marker genes that were used to allocate all the epithelial cell transcriptomes (11,909) from control ileum, colon, and Satb2cKo into nine broadly defined groups. FIG. 10B illustrates quantitation of the lineage groups showed replacement of colonocytes by enterocytes and generation of Paneth cells in Satb2cKo colon, although a small number of colonocytes remain. FIG. 10C shows scRNA profiles of Satb2cKo colonic cells shifted toward ileum, based on scoring each annotated cell type with curated ileal signature genes (ileal identity score). Violin plots of the distribution of ileal identity score.*$P<1\times10^{-12}$. Mann Whitney U-test. FIGS. 10D-10G illustrate identification of intestinal stem cells from the scRNA profiles. Lgr5$^+$ and Lgr5$^-$ cells were extracted from the "Progenitor group" of the integrated Sc-Seq dataset (FIG. 101)). Lgr5$^+$ cells expressed higher levels of the stem cell marker genes Ascl2 and Axin2 (violin plots, FIG. 10D) and scored significantly higher than Lgr5$^-$ cells using a published list of small intestine stem cell genes (Munoz et al. 2012) (FIG. 10E). y axis represents relative expression value. The cell cycle status of the stem cell clusters was marked in FIG. 10F. The top five differential GeneOntology biological processes enriched in LGR5$^+$ stem cell populations of Satb2$^{cKO}$ colon vs control colon were plotted in FIG. 10**G.

FIG. 11A illustrates when cultured in large intestine medium that contains extra Wnt3a, isolated crypts from ileum, control colon, and Satb2$^{cKO}$ colon all produced spheroids in Matrigel (lower panel). The same batch of control colonic crypts, when cultured in small intestine medium without Wnt3a, yielded only a few small spheroids whereas ileal and Satb2$^{cKO}$ colonic crypts produced many branching organoids (tipper panel). FIG. 11A illustrates time lapse images show the growth and branching morphogenesis of one representative ileal organoid and one Satb2$^{cKO}$ colonic organoid grown in small intestine medium over the course of 4 days. FIG. 11C illustrates heatmap of the top 75 DEGs (average LogFC) among the three Lgr5$^+$ stem cell single-cell transcriptomes. MHCII genes (highlighted in red) were among the most differentially expressed genes between ileal and Satb2$^{cKO}$ stem cells. FIG. 11D illustrates principal component analysis (PCA) of RNA-seq data from primary epithelia and cultured organoids showed a closer resemblance between ileal and Satb2$^{cKO}$ colonic transcriptomes after culturing in identical medium, suggesting environmental factors likely influenced differential gene expression between ileal mucosa and ileal-like mucosa in Satb2$^{cKO}$ colon. FIG. 11E illustrates Pearson correlation of ileal vs Satb2$^{cKO}$ colonic transcriptome from primary epithelia or cultured organoids (r, Pearson correlation coefficient). FIGS. 11F-11G illustrate querying our Sc-Seq data, mature enterocytes in Satb2$^{cKO}$ colon express a myriad of transporters for lipids, bile salts, vitamins, amino acids, and carbohydrates, similar to ileal enterocytes. Shown are dot plots of the transporters from the scRNA profiles of identified mature ileal enterocytes, mature Satb2$^{cKO}$ colonic enterocytes, and mature colonic colonocytes (FIG. 11F). Scores were calculated using the selected genes (FIG. 11G). FIG. 11H illustrates immunohistochemistry of HA-tag and GFP in jejunum showed that they were co-expressed in Satb2$^{cKO}$ adult mice4 weeks after TAM. The expression of SATB2/GFP is mosaic, with about 79% jejunal glands marked by GFP. I. qRT-PCR of Satb2 mRNA from FAGS-purified GFP$^+$ and GFP$^-$ cells from jejunum and ileum showed the level of ectopic Satb2 expression in GFP+ cells is comparable to that of control colon. N=4 mice. Mean±S.D. FIGS. 11J and 11K. qRT-PCR of a basket of signature genes for the large and small intestine showed that SATB2 can strongly suppress small intestine genes in both ileum and jejunum whereas the activation of colonic genes was much weaker in jejunum than ileum. N=4 mice. Mean±S.D. *$P<0.05$, $P<0.01$, *P<00001 Unpaired t-test.

FIGS. 12A-12H illustrate SATB2 regulates enhancer dynamics and transcription factor binding in the colon to ileum plasticity. Related to FIG. 5. FIGS. 12A-12B illustrate SATB2 genomic binding sites in colonic tissues were identified by ChIP-seq using both input and Satb2$^{cKO}$ colonic tissues as controls, yielding 25,576 peaks (peak call by MACS2, duplicate biological samples) (FIG. 12A). The genomic binding sites were predominantly localized to introns and intergenic regions (FIG. 12B). FIGS. 12C-12D illustrate aligned genomic binding profiles of SATB2, CDX2 and HNF4a in control Colon showed extensive co-localization. FIGS. 12E-12F illustrate enrichments of H3K4me1, H3k27ac and IgG controls determined by CUT&RUN in control colon was aligned with SATB2 binding sites (FIG. 12E) and quantified (FIG. 12F). Enhancers were partitioned into active and inactive based on H3K27ac enrichments. FIG. 12G illustrates signals of histone marks, TFs, and ATAC around colon- and ileum-specific enhancers (identified by comparing the signal strength between all H3K4me1$^+$ enhancers in control colon and ileum) in controls and Satb2$^{cKO}$ colon (KO), indicating activation of ileal enhancers and inactivation of colonic enhancers in SATB2 mutant colon. FIG. 12H shows Western blots and quantification of HNF4A and CDX2 co-IP from control and $Satb2^{cKO}$ colonic tissues.

FIG. 13A illustrates a diagram of the experimental setup for human colonic organoid culture, CRISPR, and differentiation analysis. Representative images of organoids shown at different stages. FIG. 13B illustrates Western blot and quantification of SATB2 protein expression in the five organoid lines. N=3 independent experiments. Mean±S.D. FIG. 13C illustrates four different guide RNAs were evaluated for deletion efficiency of SATB2. Western blot showed sgRNA1 efficiently disrupted SATB2 expression whereas the close homolog SATB1 was unaffected. N=3 independent experiments. Mean±S.D. FIG. 13D illustrates successful knockout of SATB2 expression in all 5 organoid lines. Western blot images and quantifications shown. N=3 independent experiments. *P<0.001, Unpaired t-test. FIG. 13E illustrates heatmap of differential expressed genes (Padj<0.1) between control and SATB2 knockout ($SATB2^{hKO}$) organoids. Some of the known colonic and small intestine genes are highlighted in red and green, respectively. FIG. 13F illustrates RBP2, a marker of ileum, was detected in ileal but not colonic epithelium of human biopsy tissues. RBP2 was abundantly expressed in colonic organoids after SATB2 deletion, at levels comparable to that of control ileal organoids. N=6 samples (3 biological replicates each from 2 independent experiments). Mean±S.D. P value by Mann Whitney U-test. FIG. 13G illustrates SLC15A1 was detected in the brush border (white arrows) of human ileal epithelium and the luminal side of human ileal organoids. FABP6 was detected in the cytoplasm of the ileal epithelium and organoids. Both markers were not detected in colonic epithelium. FIG. 13H illustrates diagrams showing the chemical reactions mediated by dipeptide peptidase (OPP) and disaccharidase, two small intestinal digestive enzymes, and the corresponding assays to quantify their activities. FIG. 13I. Staining and quantification of the colonic enriched CEACAM1 in primary tissue sections (N=5 randomly selected epithelial areas) and organoids (N=6 samples (3 biological replicates each from 2 independent experiments)). Mean±S.D. *P<0.001. Unpaired t-test. FIG. 13J. Staining of the colonic enriched goblet cell marker MUC2 in primary tissue sections and colonic control and STAB2 KO organoids.

FIG. 14A illustrates a comparison of published RNA-seq data of FACS-purified Lgr5-GFP stem cells (Lgr5DTRGFP mice) from the duodenum and the colon identified the top 20 transcription factors (TFs) enriched in colonic stein cells. N=3 mice. FIG. 14B illustrates primary human duodenal and colonic organoids were cultured in Matrigel under high-Wnt conditions that favor stem and progenitor proliferation. RNA-seq comparison of the human organoids identified the top 20 colonic enriched TFs. N=4 biological replicates. FIG. 14C illustrates comparing the top 20 TFs enriched in both mouse and human, SATB2 and FOXD2 were the only common genes beside the posterior HOX genes. FIG. 14D illustrates three guide RNAs (sg1, 2, 3) for CRISPR-mediated disruption of murine Satb2. After Lentiviral delivery of guide RNA and CAS9 into murine colonic organoids and selection with puromycin (puromycin gene and CAS9 are co-expressed with the guide RNA), Western blot showed efficient deletion of SATB2 (85-95%), which was confirmed by immunostaining of SATB2 on control and SATB2 CRISPR organoids. *P<0.001. Mean±S.D. Unpaired t-test. FIG. 14E illustrates three guide RNAs used independently for CRISPR disruption of the Foxd2 gene in murine colonic organoids. An assay based on T7 endonuclease cutting of PCR-amplified Foxd2 genomic region targeted by CRISPR was used to quantify the Foxd2 genomic disruption efficiency at 57-74%. *P<0.001. Mean±S.D. Unpaired t-test. FIGS. 14F-14I. show that RNA-seq of murine colonic organoids revealed significant transcriptomic changes in Satb2 CRISPR organoids (Satb2 KO), but not Foxd2 KO organoids. FIG. 14F illustrates principal component analysis. 229 genes were up-regulated and 86 genes down-regulated in SATB2 CRISPR organoids vs control colonic organoids (LFC>2, Padj<0.05) as shown in the heatmap (FIG. 14G) and the volcano plots (FIG. 14H). The up- and down-regulated genes were enriched for small intestine and large intestine respectively (FIG. 14I, tissue enrichment by Enrichr).

FIG. 15A illustrates Western blot and quantification of SATB2 protein levels in isolated epithelia of 4 different intestinal regions showed strong SATB2 expression in cecum and colon, weak expression in terminal ileum, and no expression in proximal ileum and jejunum. N=3 mice. *P<0.05, *P<0.001. Mean±S.D. Unpaired t-test. FIG. 15B illustrates Western blot using isolated crypts or whole glands showed SATB2 protein expression was not present in the duodenum (crypts and glands) or ileal crypts but detectable in whole ileal glands. N=4 mice. Mean±S.D. Unpaired t-test. FIG. 15C illustrates purification of EPCAM+GFP+ stem cells from LGR5CreERGFP mice and qRT-PCR showed Satb2 mRNA was present at high levels only in colonic stem cells but not in any of the small intestinal stem cell populations. N=4 mice. Mean±S.D. Unpaired t-test. FIG. 15D illustrates a diagram of the conditional knockout of SATB2 using VillinCre-ER and floxed Satb2. After deletion of Exons 4 and 5, multiple stop codons are created in the downstream exon. FIG. 15E illustrates immunohistochemistry confirmed lack of SATB2 in Satb2cKO colon 30 days after tamoxifen treatment. FIG. 15F illustrates a wide-view H&E histology pictures of control and Satb2cKO proximal colon 2 months after TAM. The mutant colon was covered by villi-like glands. The rugae structures remained. FIG. 15G illustrates Alcian blue stain showed the number of mature goblet cells in Satb2cKO colon decreased significantly compared with control colon, reaching a level comparable to ileum. N=3 mice. Mean±S.D. *P<0.001. Unpaired t-test. FIG. 15H illustrates that there was no difference in the apoptosis rate, as assessed by activated caspase 3, among the 3 samples. N=3 mice. Mean±S.D. Unpaired t-test. FIG. 15I illustrates that a 24-hour pulse-chase with Edu showed enhanced upward migration of epithelial cells in Satb2cKO colon versus control colon, at a rate comparable to that of ileum. N=3 mice. Mean±SD *P<0.001. Tukey's multiple comparison test. FIGS. 15J-15M provides a transcriptome of Satb2cKO colonic epithelium that resembles control ileum, as shown in the heatmap (FIG. 15J, (LFC>2, Padj<0.05, RPKM cut>0.5), volcano plots (FIG. 15K), and GeneOntology biological processes enriched in ileum vs control colon (FIG. 15L) and Satb2cKO colon vs control colon (FIG. 15**M).

FIG. 16A illustrates a wide-view immunofluorescence images of controls and Satb2cKO proximal colon 6 months after TAM showing persistence of ileal-like mucosa in the mutant colon. FIG. 16B-16C illustrate histochemistry on Swiss roles of the entire colon showed absence of SATB2 and activation of FABP6 and RBP2 in both proximal and distal colon. n=5 areas quantified. *P<0.05, ***P<0.001. Mean±S.D. Unpaired t-test.

FIGS. 17A-17K illustrate single cell RNA sequencing reveals stem cell conversion and rerouting of cell lineage differentiation in Satb2cKO colon to ileum. FIG. 17A illustrates dot plots of some of the lineage-specific marker genes that were used to allocate all the epithelial cell transcriptomes (11,909) from control ileum, colon, and Satb2cKO into nine broadly defined groups. FIG. 17B illustrates quantitation of the lineage groups showed replacement of colonocytes by enterocytes andgeneration of Paneth cells in Satb2cKO colon, although a small number of colonocytes remain. FIG. 17C illustrates scRNA profiles of Satb2cKO colonic cells shifted toward ileum, based on scoring each annotated cell type with curated ileal signature genes (ileal identity score). Violin plots of the distribution of ileal identity score. *P<1×10−12. Mann Whitney U-test. FIGS. 17D-17G illustrate dentification of intestinal stem cells from the scRNA profiles. Lgr5+ and Lgr5− cells were extracted from the "Progenitor group" of the integrated Sc-Seq dataset (FIG. 17D). Lgr5+ cells expressed higher levels of the stem cell marker genes Ascl2 and Axin2 (violin plots, FIG. 17D) and scored significantly higher than Lgr5− cells using a published list of small intestine stem cell genes (FIG. 17E). y axis represents relative expression value. The cell cycle status of the stem cell clusters was marked in FIG. 17F. The top five differential GeneOntology biological processes enriched in LGR5+ stem cell populations of Satb2cKO colon vs control colon were plotted in FIG. 17G. FIG. 17H illustrates 7 days after TAM treatment of Lgr5CreERGFP; Satb2f/f mice, epithelial renewal in the GFPmarked colonic glands were incomplete. Nevertheless, all FABP6+ cells had lost SATB2 expression while FABP6 and CA1 were expressed in distinct cells, indicating cell autonomous regulation of the two markers by SATB2. FIG. 17I provides RNA-seq profiles and GeneOntology analysis of clusters 6-9 in SATB2 timed deletion study. FIGS. 17J and 17K illustrate GSEA analysis showed no significant enrichment of fetal gene set in colonic transcriptomes from day 1 to 6 after TAM treatment of Satb2cKO mice (FIG. 17**J). The fetal markers Ly6a and Anxa1 also showed limited or no up-regulation in colonic mucosa after Satb2 deletion (RNA-seq data).

FIG. 18A shows that when cultured in large intestine medium that contains extra Wnt3a, isolated crypts from ileum, control colon, and Satb2cKO colon all produced spheroids in Matrigel (lower panel). The same batch of control colonic crypts, when cultured in small intestine medium without Wnt3a, yielded only a few small spheroids whereas ileal and Satb2cKO colonic crypts produced many branching organoids (upper panel). FIG. 18B shows time lapse images show the growth and branching morphogenesis of one representative ileal organoid and one Satb2cKO colonic organoid grown in small intestine medium over the course of 4 days. FIGS. 18C and 18D show a heatmap of the top 75 DEGs (average LogFC) among the three Lgr5+ stem cell singlecell transcriptomes. MHCII genes (highlighted in FIG. 18C and shown separately in FIG. 18D) were among the most differentially expressed genes between ileal and Satb2cKO stem cells. FIG. 18E shows images of Matrigel cultures of ileum, control colon, and Satb2cKO colon in WENR medium followed by differentiation. FIG. 18F and FIG. 18G illustrate a Pearson correlation and PCA of ileal vs Satb2cKO colonic transcriptome from primary epithelia or cultured organoids showed a closer resemblance between ileal and Satb2cKO colonic transcriptomes after culturing in identical medium. FIGS. 18H and 18I show querying the scRNA data, mature enterocytes in Satb2cKO colon express a myriad of transporters for lipids, bile salts, vitamins, amino acids, and carbohydrates, similar to ileal enterocytes. Shown are dot plots of the transporters from the scRNA profiles of identified mature ileal enterocytes, mature Satb2cKO colonic enterocytes, and mature colonic colonocytes (FIG. 18H). Scores were calculated using the selected genes (FIG. 18I). FIG. 18J illustrates immunohistochemistry of HA-tag and GFP in jejunum showed that they were co-expressed in Satb2cKO adult mice4 weeks after TAM. The expression of SATB2/GFP is mosaic, with about 79% jejunal glands marked by GFP. FIG. 18K shows qRT-PCR of Satb2 mRNA from FACS-purified GFP+ and GFP− cells from duodenum, jejunum, and ileum of Satb2OE mice showed the levels of ectopic Satb2 expression in GFP+ cells were comparable to that of control colon. N=4 mice. Mean±S.D. *p<0.001, unpaired t-test. FIG. 18L and FIG. 18**M show qRT-PCR of a basket of signature genes for the large and small intestine showed that SATB2 strongly suppressed small intestine genes in all small intestinal regions whereas the activation of colonic genes was much weaker in jejunum and minimal in duodenum, compared with ileum. N=4 mice. Mean±S.D. *P<0.05, P<0.01, *P<0.001. Unpaired t-test.

FIG. 19A and FIG. 19B show SATB2 genomic binding sites in colonic tissues were identified by ChIP-seq using both input and Satb2cKO colonic tissues as controls, yielding 25,576 peaks (peak call by MACS2, duplicate biological samples) (FIG. 19A). The genomic binding sites were predominantly localized to introns and intergenic regions (FIG. 19B). FIG. 19P shows SATB2 CUT&RUTN profiles centered on SATB2 ChIP peaks showed high concordance, indicating that these two methods identified similar binding events. The profiles from stem cells and differentiated cells were also similar, indicating similar binding patterns in stem and differentiated cells.

FIG. 20A illustrates a diagram of the experimental setup for human colonic organoid culture, CRISPR, and differentiation analysis. Representative images of organoids shown at different stages. FIG. 20B illustrates Western blot and quantification of SATB2 protein expression in the five organoid lines. n=3 independent experiments. Mean±S.D. FIG. 20C illustrates four different guide RNAs were evaluated for deletion efficiency of SATB2. Western blot showed sgRNA1 efficiently disrupted SATB2 expression whereas the close homolog SATB1 was unaffected. n=3 independent experiments. Mean±S.D. FIG. 20D illustrates successful knockout of SATB2 expression in all 5 organoid lines. Western blot images and quantifications shown. n=3 independent experiments. *P<0.001. Unpaired t-test. FIG. 20E illustrates a heatmap of differential expressed genes (Padj<0.1) between control and SATB2 knockout (SATB2hKO) organoids. Some of the known colonic and small intestine genes are highlighted in red and green, respectively. FIG. 20F illustrates that RBJP2, a marker of ileum, was detected in ileal but not colonic epithelium of human biopsy tissues. RBP2 was abundantly expressed in colonic organoids after SATB2 deletion, at levels comparable to that of control ileal organoids. n=6 samples (3 biological replicates each from 2 independent experiments). Mean±S.D. P value by Mann Whitney U-test. FIG. 20G illustrates SLC15A1 was detected in the brush border (white arrows) of human ileal epithelium and the luminal side of human ileal organoids. FABP6 was detected in the cytoplasm of the ileal epithelium and organoids. Both markers were not detected in colonic epithelium. FIG. 20H illustrates diagrams showing the chemical reactions mediated by dipeptide peptidase (DPP) and disaccharidase, two small intestinal digestive enzymes, and the corresponding assays to quantify their activities. FIG. 20I illustrates staining and quantification of the colonic enriched CEACAM1 in primary tissue sections (n=5 randomly selected epithelial areas) and organoids (n=6 samples (3 biological replicates each from 2 independent experiments)). Mean±S.D. *P<0.001. Unpaired t-test. FIG. 20J illustrates staining of the colonic enriched goblet cell marker MUC2 in primary tissue sections and colonic control and STAB2 KO organoids.

DETAILED DESCRIPTION

Figure 1A:
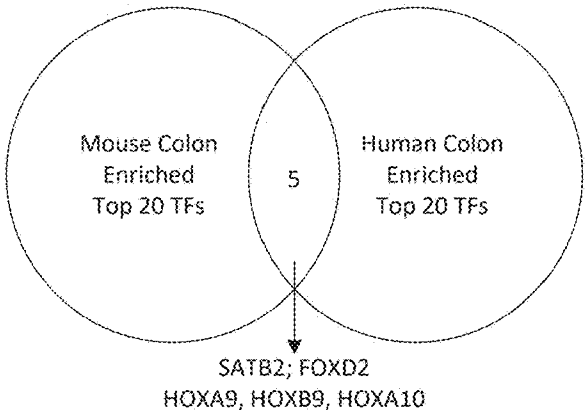
FIGS. 1A-1M illustrate conversion of large intestine mucosa to one that resembles ileal small intestine in knockout Satb2 (Satb$2^{cKO}$) mice.

Methods and compositions are described herein that can delete or modify at least one Satb2 allele or inhibit expression of a Satb2 gene in one or more starting cells of a subject, to thereby convert the starting cells into small intestine-like cells. As illustrated herein, engineered SATB2-null organoids and/or SATB2-null stem cells can stably convert into small intestine-like tissues useful for replacing colonic mucosa with tissues that function as small intestine.

There are fundamental differences between the colon and the small intestine in structure, cell types, physiological function and disease susceptibility. Devastating and prevalent intestinal diseases, including ulcerative colitis and colorectal cancers, arise in the colon but not necessarily in the small intestine. Colon absorbs water but cannot uptake most nutrients. Consequently, a significant loss of the small intestine leads to digestive failure in Short Bowel Syndrome (SBS) that cannot be compensated for by the colon. Although some progress has been made in studies of stein cells and pathways that regulate small intestine development and regeneration, our understanding of colon ontogeny is currently limited. A number of factors and pathways, including CDX2, HNF4α, GATA6, YAP, HOPX, WNT and BMP, are known to influence colonic development and homeostasis. However, their expression is not restricted to colon nor is their function colon-specific. Thus, molecular determinants that distinguish the colon from the small intestine and confer colon-specific differentiation, gene expression and function, has remained largely uncharacterized, hindering a deeper understanding of regionalized intestinal diseases and therapeutic development.

As described herein, SATB2 (Special AT-rich sequence-binding Protein 2) is a conserved colon-enriched chromatin factor. Genetic deletion of Satb2 from adult mouse intestine revealed a striking phenotype: the colonic epithelium undergoes a homeotic-like transformation to resemble that of small intestine, with the appearance of villi-like structures, Paneth cells, and enterocytes expressing abundant nutrient transporters. Colonic transcriptome also shifts in adult Satb2-null mice towards ileum and the Satb2-null colon can absorb nutrients. These results show that SATB2 plays a crucial role in maintaining large intestine gene expression, differentiation, and function while suppressing the small intestine fate. Therefore, SATB2 is a "master regulator" of colonic identity.

SATB2

Colonic SATB2 expression has been noted and used as a diagnostic marker for colorectal cancers. However, the normal function of SATB2 in mature colon has previously not been identified. Experiments described herein show that SATB2 is a "master regulator" of colonic identity. Moreover, the work described herein shows that deletion of SATB2 in murine and human colonic cell types can convert those cell types into small intestinal type cells.

The SATB2 gene in humans resides on chromosome 2 (location 2q33.1; NC_000002.12 (199269500..199471266, complement; NC_060926.1 (199753552.. 199955035, complement)). A sequence for the human SATB2 protein is available from the NCBI database as accession no. NP_001165980.1, and shown below as SEQ ID NO:1.

```
  1 MERRSESPCL RDSPDRRSGS PDVKGPPPVK VARLEQNGSP
 41 MGARGRPNGA VAKAVGGLMI PVFCVVEQLD GSLEYDNREE
 81 HAEFVLVRKD VLFSQLVETA LLALGYSHSS AAQAQGIIKL
121 GRWNPLPLSY VIDAPDATVA DMLQDVYHVV TLKIQLQSCS
161 KLEDLPAEQW NHATVRNALK ELLKEMNQST LAKECPLSQS
201 MISSIVNSTY YANVSATKCQ EFGRWYKKYK KIKVERVERE
241 NLSDYCVLGQ RPMHLPNMNQ LASLGKTNEQ SPHSQIHHST
281 PIRNQVPALQ PIMSPGLLSP QLSPQLVRQQ IAMAHLINQQ
```

-continued

```
321 IAVSRLLAHQ HPQAINQQFL NHPPIPRAVK PEPTNSSVEV
361 SPDIYQQVRD ELKRASVSQA VFARVAFNRT QGLLSEILRK
401 EEDPRTASQS LLVNLRAMQN FLNLPEVERD RIYQDERERS
441 MNPNVSMVSS ASSSPSSSRT PQAKTSTPTT DLPIKVDGAN
481 INITAAIYDE IQQEMKRAKV SQALFAKVAA NKSQGWLCEL
521 LRWKENPSPE NRILWENLCT IRRFLNLPQH ERDVIYEEES
561 RHHHSERMQH VVQLPPEPVQ VLHRQQSQPA KESSPPREEA
601 PPPPPPTEDS CAKKPRSRTK ISLEALGILQ SFIHDVGLYP
641 DQEAIHTLSA QLDLPKHTII KFFQNQRYHV KHHGKLKEHL
681 GSAVDVAEYK DEELLTESEE NDSEEGSEEM YKVEAEEENA
721 DKSKAAPAEI DQR
```

A cDNA encoding the SEQ ID NO:1 SATB2 protein is available from the NCBI database as accession no. NM_001172509.2, and shown below as SEQ ID NO:2.

```
   1 GAGTCCGGCT CTGGCTGCTG GCAGAGGCGG CCGAGAGGGG
  41 AGAGGCTGGA GGTGACAGCT TGGGGGGCCG CCGCGTTTCC
  81 TCCCGCGCGC GGTCCCGGGT CCCTGCGTCT TCTCGGCTCT
 121 TGGTGTTACC GGTCCCACCG CTCTGGCCGC GCCTCCTCGC
 161 GAGCTAGCCG CCCTGCGAAC CAGCAGCCCC GGCTCGCCGC
 201 CGCCGCCGCC GCCTCCGGGT TCTCAGCCCT TTCTCTCCAG
 241 AACGGGTCTC CTTCCCGAAG GTGTGAAAAG GCTCTTTCAG
 281 CCTCCTTCTC TTCCCCCCTC CTCCGCCGTC CCCTCCCCCG
 321 CTCGCTCGGG TGTCCCTTTG GAGGAGTCCT TTCCCTCTCC
 361 TCCTCCTCCC CCTCCTCCCT CCCCCCATCA TCATCATAAC
 401 AACCATCTCC GCACCAGAAG AAGACACCCT GACCCAGGAC
 441 CTTAAACATT AGGACCTGGG GAAGAGGGAA GGGGAAGGAG
 481 TAAAGAGGAA GACTAGGAGA ACACTGCAAA GCCAAGCACC
 521 AGAAACTTTC CACCCTGGAT TCTCTACTTT TGCTCCATGG
 561 ACAGAGCCCC AGTCAGCCAA GTTTCAGACA GACCGTGAGC
 601 AGTCCCTGTG CGTTTTATTG CGACCTGCCG GTGGGAACTT
 641 TGTCTCCGAG TCGGAGCAGC ATGGAGCGGC GGAGCGAGAG
 681 CCCGTGTCTG CGGGACAGCC CCGACCGGCG GAGCGGCAGC
 721 CCGGACGTCA AGGGGCCTCC CCCAGTGAAG GTGGCCCGGC
 761 TGGAGCAGAA CGGCAGCCCC ATGGGAGCCC GCGGGAGGCC
 801 CAACGGCGCC GTGGCCAAGG CCGTGGGAGG TTTGATGATT
 841 CCTGTCTTTT GTGTCGTGGA GCAGTTGGAC GGCTCTCTTG
 881 AATATGACAA CAGAGAAGAA CACGCCGAGT TTGTCCTGGT
 921 GCGGAAAGAT GTGCTTTTTA GCCAGCTGGT GGAGACTGCG
 961 CTCCTGGCCC TGGGGTATTC TCACAGCTCT GCGGCCCAGG
1001 CCCAAGGAAT AATCAAGCTG GGAAGGTGGA ACCCTCTCCC
1041 CCTCAGTTAT GTGACAGATG CACCCGACGC GACAGTGGCC
```

-continued

```
1081 GACATGCTAC AAGATGTCTA TCATGTIGTG ACGTTGAAAA
1121 TCCAATTACA AAGTIGTTCA AAGTTGGAAG ACTIGCCTGC
1161 GGAGCAGTGG AACCATGCCA CAGTCCGCAA TGCCTTAAAG
1201 GAACTGCTCA AAGAGATGAA CCAGAGCACA TTAGCCAAAG
1241 AATGCCCTCT CTCCCAGAGT ATGATTTCAT CCATTGTAAA
1281 TAGCACATAT TATGCCAATG TGTCAGCAAC CAAGTGCCAG
1321 GAGTTTGGGA GATGGTATAA AAAGTACAAG AAGATTAAAG
1361 TGGAAAGAGT GGAACGAGAA AACCTTTCAG ACTATTGTGT
1401 TCTGGGCCAG CGTCCAATGC ATTTACCAAA TATGAACCAG
1441 CTGGCATCCC TGGGGAAAAC CAACGAACAG TCTCCTCACA
1481 GCCAAATTCA CCACAGTACT CCAATCCGAA ACCAAGTGCC
1521 CGCATTACAG CCCATCATGA GCCCIGGICT TCTTTCTCCC
1561 CAGCTTAGTC CACAACTTGT AAGGCAACAA ATAGCCATGG
1601 CCCATCTGAT AAACCAACAG ATTGCCGTTA GCCGGCTCCT
1641 GGCTCACCAG CATCCTCAAG CCATCAACCA GCAGTTCCTG
1681 AACCATCCAC CCATCCCCAG AGCAGTTAAG CCAGAGCCAA
1721 CCAACTCTTC CGTGGAAGTC TCTCCAGATA TCTACCAGCA
1761 AGTCAGAGAT GAGCTGAAGA GGGCCAGTGT GTCCCAAGCT
1801 GTCTTTGCAA GAGTGGCATT CAACCGCACA CAGGGATTGT
1841 TGTCTGAGAT TCTGCGTAAG GAAGAAGACC CTCGGACAGC
1881 CTCTCAGTCT CTTCTAGTAA ACCTGAGGGC CATGCAGAAT
1921 TTCCTCAATC TGCCAGAAGT GGAGCGAGAT CGCATCTACC
1961 AGGATGAGAG GGAGCGGAGC ATGAATCCCA ATGTGAGCAT
2001 GGTCTCCTCG GCCTCCAGCA GTCCCAGCTC CTCCCGAACC
2041 CCTCAGGCCA AAACCTCGAC ACCGACAACA GACCTCCCTA
2081 TTAAGGTGGA CGGCGCCAAC ATCAACATCA CAGCTGCCAT
2121 TTATGACGAG ATCCAACAGG AGATGAAAAG GGCCAAGGTG
2161 TCTCAAGCCC TGTTTGCCAA AGTGGCTGCA AATAAAAGTC
2201 AGGGCTGGCT GTGTGAACTG CTCCGCTGGA AGGAGAACCC
2241 AAGCCCAGAA AACCGCACCC TCTGGGAAAA CCTCTGTACC
2281 ATCCGTCGCT TCCTGAACCT TCCCCAGCAT GAGAGGGATG
2321 TCATCTATGA GGAGGAGICA AGGCATCACC ACAGCGAACG
2361 CATGCAACAC GTGGTCCAGC TTCCCCCTGA GCCGGTGCAG
2401 GTACTTCATA GACAGCAGTC TCAGCCAGCC AAGGAGAGTT
2441 CCCCTCCCAG AGAAGAAGCG CCTCCCCCAC CTCCTCCGAC
2481 TGAAGACAGT TGTGCCAAAA AGCCCCGGTC TCGCACAAAG
2521 ATCTCCTTAG AAGCCCTGGG GATCCTCCAA AGCITTATTC
2561 ATGATGTAGG CCTGTACCCA GACCAGGAAG CCATCCACAC
2601 TCTTTCGGCT CAGCTGGATC TCCCCAAACA CACCATCATC
2641 AAGTTCTTCC AGAACCAGCG GIACCACGTG AAGCACCACG
```

-continued

```
2681 GGAAGCTGAA AGAGCACCTG GGCTCCGCGG TGGACGTGGC
2721 TGAATATAAG GACGAGGAGC TGCTGACCGA GTCAGAGGAG
2761 AACGACAGCG AGGAAGGCTC CGAGGAGATG TACAAAGTGG
2801 AGGCTGAGGA GGAAAATGCT GACAAAAGCA AGGCAGCACC
2841 TGCCGAAATT GACCAGAGAT AATGTGAACT TCTACTAGGC
2881 AAAGCAATAC ATCGGTCCAA GGATTTTCTG CTTTCATTTC
2921 TTTAAAAGTT TTTTGTTAGT TTGTTTTTTG TTTTTGTTTT
2961 TGGGTTTTTT TGGCTTTATT TTTGTCTTTT TATGTCTGTT
3001 TTGTTTTTCT TACCCTTTTG GACATTTCTT TGTTGCACAG
3041 GATACACCIA TAGACTGAAT AAGTTCAGTA TTTCCGAATC
3081 AGACATCGCC TTGGCAAAGA CACTAAAGCG TTACACTTTA
3121 TCCCGTCICT ATGACTGGAT CATAGTCATT ATAATCACAG
3161 GAGACTCTGC CTTCATTATC CTTGCACTTA ACGGAAGTTA
3201 CATCAGGCAA GTACCAGGAT GAAAAGAACT ATGAAATAAA
3241 TGAAGGAAGC TACAAGTGTG TGTGTATATG TATATGTATA
3281 TATCTCTATA TTTACATATA TATATTAAAA TTGCATGGGA
3321 CAGAGACTTT GCAATCCGAA AGAATAGACT GTGAAATGAG
3361 TTCTTAAAGA AAAGACTIGT TTATGTATTA AAAAAACCAC
3401 TTCACAGTGA GTCGCTTTGG CTTTTTGATA AACTGCGGCC
3441 TGCTCTCAGG GTGGGGTGAC TATTTTTGAA TTCCTATTTA
3481 TTTTTTGTGT TTGTCCCTGA TTTTTTTTTT TTAATTCTAT
3521 GGCTTCCTAT CTGGCAGCTT AATGGGTAAT TTTTGAGGTA
3561 TGTATTTAAC AAAATAAACG ACACTGCCGA AAAAAAAAAA
3601 AGTGAAGTGA AAACAATCAG GGCACATTAA AATGATACAA
3641 GTCAAATAAA TCTTAAAGAC ACAATGCACA CTTAAAATGA
3681 CTCAATAAAA TGACTTGCTA CGTTCCGTTA TTCAATTTGT
3721 CATTACTGTA GTGAACAGAT GCATTTCTGT GGAATTCCAA
3761 ATAAGTAAAA CTGAAATTCA GTGCAGAGAA AACTTIGTCC
3801 ACTAGTGCAA GTCTTGATCA AATGACATTT TGACATTGGA
3841 CATATGGAAT TCATAGTATG AGCCACATTT TGTTGTGAAA
3881 TTTATTTACC TGCTTGTGGC TICAAATCTG AAAATTAATA
3921 AGCCTGCTCG TTTAAAAGTT GTTTGTTGTT GCTGTTTTTT
3961 TGTCTTTTTG TTTTTTACTA GAAAATAGTT CAGTGTAATA
4001 TTAAGTTAGA AAAGAAGTTG CTGCCCAGTT AAAGGGGCTC
4041 CCTCTCAAAT AAATCTCCAT CCTTCCCTCT CCCAAAAGAC
4081 ATTTCTGATT TCTGCTTCAC TTTGGGCTTC CTCTTCTTCG
4121 TACACATTCC ATCTACCTAA TCAAACATTT TCAGTCCCTG
4161 ATCTCTCCTG TCCCTTTTCC TGGGATGACA GCCCTAACAA
4201 GAACTGTTTT TGAATCGTTG TGCAGCTCCA GGCAATAGAG
4241 TATGTGAAGC GATTTCAGTA GAATCACTTA CTCATCCTAA
4281 AAGAAAACAT TATCCCAGTT ACCTACATCG CAATTACCTT
```

-continued

```
4321 ATGTAAAGCA GAACTAATGC TGACTGGATG TTTAATGGGA
4361 TGAGCATTAA AGCTGCAATC TACTATAGTA CTCCAGATCT
4401 CTTTCGGCTT CCTATGAGAA ACACCAGAAG CATTACTITC
4441 CACTTCTACT TACAGTAATT GCAAGAGGAG ACCTCACATT
4481 CAGGACTGGC CTAGTGAACG TAATCCATGC TTTAAACTGG
4521 CCATTAAACA GTCCCACATG GITGGATTTT TTTTTTTTTT
4561 TTGAGTIGTG CTTTCACAAA ACCTTGTCAA AGACCTCATG
4601 CAATATCACT TTGAAAGTTA TTTTCTGTTT ACTACACAAA
4641 CATTGTAATA TAACTGTTAA TACTATTTAT ATATTTGAAA
4681 GGIATAAAAG GTAGGAGITA AAAAAAAAAC CTCTATGTGT
4721 AGATATTAAC TCAGAACTTA CAATATACAG GGAGAAGACA
4761 TGTTGCAATA CAAGCTAATT CTAGCTGCTC AGTAACCTCT
4801 GGAGTTTTTA AAGGGACATT TTCCTGTACT TTTTCAAATA
4841 ATGATGTTTA AAAATTATCT TGACATAAGC GTCATATACC
4881 TTTGCAAAAG GATGGITGTT TGCAGTTAGC CCTGGCCCCA
4921 TCCTTCCTAT TTCTGTAGTA TGCTGCAGCT TTAATCAGAA
4961 AGTCCATGGT TGCTGCTTCC TGATCTCCGA GTTACTCTTT
5001 CCAAATTGTC TTCTTACACT GITGCTGAAG GTCACTCTGT
5041 ACACGTAATG GAAACTGATT TIGCCAAGCT CTTACAAGGT
5081 GGTTCATCTA TCGATGGCAT CCGCATTTGG TATCTTTTAC
5121 ACTTCAACCA AAAATTTATT AGGTATTTTT CAATGCTAAG
5161 TCTTGCCTTT TATTTTTTAA TTTCACTGCC AAGTTTGCAG
5201 TGGTTCTAAG TGAATCTGTG GGCATTTTAG CCTGTGGTCT
5241 TGCCAGATCT TTGCGAATTA CAATGCATAT ATGTCTATTT
5281 ATTCAATATC TGTCATATAA TATCTATTTG GAAGAAGAAA
5321 CTTTCTCTTG TAGTGCCTCT TGACAAAGCA CAATTTCCCG
5361 CCTTTTTTTT TTTTTGTGAA ATGAAAAAAA CAAATTGTGT
5401 TTTATTGCGG TATCAACAAT GTGAATAAGG ATTAACATAT
5421 TGTAAATGTT CTTTTTTCCA TGTAAATCAA CTATCTTIGT
5461 TATCACTAAG TGATAATTAA TTTTTAACTT ATGTGCATTG
5521 TTAGGCTGTT AGAATTTTTT GGTTGTTAAA ATAAACGCAT
5561 TCAATAAA
```

Another example of a human SATB2 amino acid sequence is available from the NCBI database as accession no. NP_056080.1, and shown below as SEQ ID NO:3.

```
  1 MERRSESPCL RDSPDRRSGS PDVKGPPPVK VARLEQNGSP
 41 MGARGRPNGA VAKAVGGIMI PVECVVEQLD GSLEYDNREE
 81 HAEFVLVRKD VLFSQLVETA LLALGYSHSS AAQAQGIIKL
121 GRWNPLPLSY VIDAPDATVA DMLQDVYHVV TLKIQLQSCS
161 KLEDLPAEQW NHATVRNALKCELLKEMNQST LAKECPLSQS
```

-continued

```
201 MISSIVNSTY YANVSATKCQ EFGRWYKKYK KIKVERVERE

241 NLSDYCVLGQ RPMHLPNMNQ LASLGKINEQ SPHSQIHHST

281 PIRNQVPALQ PIMSPGLLSP QLSPQLVRQQ IAMAHLINQQ

321 IAVSRLLAHQ HPQAINQQFL NHPPIPRAVK PEPTNSSVEV

361 SPDIYQQVRD ELKRASVSQA VFARVAENRT QGLLSEILRK

401 EEDPRTASQS LLVNLRAMQN FLNLPEVERD RIYQDERERS

441 MNPNVSMVSS ASSSPSSSRT PQAKTSTPTT DLPIKVDGAN

481 INITAAIYDE IQQEMKRAKV SQALFAKVAA NKSQGWLCEL

521 LRWKENPSPE NRTLWENLCT IRRELNLPQH ERDVIYEEES

561 RHHHSERMQH VVQLPPEPVQ VLHRQQSQPA KESSPPREEA

601 PPPPPPTEDS CAKKPRSRIK ISLEALGILQ SFIHDVGLYP

641 DQEAIHTLSA QLDLPKHTII KFFQNQRYHV KHHGKLKEHL

681 GSAVDVAEYK DEELLTESEE NDSEEGSEEM YKVEAEEENA

721 DKSKAAPAEI DQR
```

A cDNA encoding the SEQ ID NO:3 human SATB2 protein is available from the NCBI database as accession no. NM_015265.4.

Another example of a human SATB2 amino acid sequence is available from the NCBI database as accession no. NP_001165988.1, and shown below as SEQ ID NO:4.

```
  1 MERRSESPCL RDSPDRRSGS PDVKGPPPVK VARLEQNGSP

 41 MGARGRPNGA VAKAVGGLMI PVFCVVEQLD GSLEYDNREE

 81 HAEFVLVRKD VLFSQLVETA LLALGYSHSS AAQAQGIIKL

121 GRWNPLPLSY VIDAPDATVA DMLQDVYHVV TLKIQLQSCS

161 KLEDLPAEQW NHATVRNALK ELLKEMNQST LAKECPLSQS

201 MISSIVNSTY YANVSATKCQ EFGRWYKKYK KIKVERVERE

241 NLSDYCVIGQ RPMHLPNMNQ LASIGKTNEQ SPHSQIHHST

281 PIRNQVPALQ PIMSPGLLSP QLSPQLVRQQ IAMAHLINQQ

321 IAVSRLLAHQ HPQAINQQFL NHPPIPRAVK PEPTNSSVEV

361 SPDIYQQVRD ELKRASVSQA VFARVAFNRT QGLLSEILRK

401 EEDPRTASQS LLVNLRAMQN FLNLPEVERD RIYQDERERS

441 MNPNVSMVSS ASSSPSSSRT PQAKTSTPTT DLPIKVDGAN

481 INITAAIYDE IQQEMKRAKV SQALFAKVAA NKSQGWICEL

521 LRWKENPSPE NRTLWENLCT IRRELNLPQH ERDVIYEEES

561 RHHHSERMQH VVQLPPEPVQ VLHRQQSQPA KESSPPREEA

601 PPPPPPTEDS CAKKPRSRTK ISLEALGILQ SFIHDVGLYP

641 DQEAIHILSA QLDLPKHTII KFFQNQRYHV KHHGKLKEHL

681 GSAVDVAEYK DEELLTESEE NDSEEGSEEM YKVEAEEENA

721 DKSKAAPAEI DQR
```

A cDNA encoding the SEQ ID NO:4 human SATB2 protein is available from the NCBI database as accession no. NM_001172517.1.

Another example of a human SATB2 amino acid sequence is available from the NCBI database as accession no. XP_005246453.1, and shown below as SEQ ID NO:5.

```
  1 MIPVECVVEQ LDGSLEYDNR EEHAEFVLVR KDVLFSQLVE

 41 TALLALGYSH SSAAQAQGII KLGRWNPLPL SYVTDAPDAT

 81 VADMLQDVYH VVILKIQLQS CSKLEDLPAE QWNHATVRNA

121 LKELLKEMNQ STLAKECPLS QSMISSIVNS TYYANVSATK

161 CQEFGRWYKK YKKIKVERVE RENLSDYCVL GQRPMHLPNM

201 NQLASLGKTN EQSPHSQIHH STPIRNQVPA LQPIMSPGLL

241 SPQLSPQLVR QQIAMAHLIN QQIAVSRLLA HQHPQAINQQ

281 FLNHPPIPRA VKPEPINSSV EVSPDIYQQV RDELKRASVS

321 QAVFARVAFN RTQGLLSEIL RKEEDPRTAS QSLLVNLRAM

361 QNFLNLPEVE RDRIYQDERE RSMNPNVSMV SSASSSPSSS

401 RTPQAKTSTP TTDLPIKVDG ANINITAAIY DEIQQEMKRA

441 KVSQALFAKV AANKSQGWLC ELLRWKENPS PENRTLWENL

481 CTIRRELNLP QHERDVIYEE ESRHHHSERM QHVVQLPPEP

521 VQVLHRQQSQ PAKESSPPRE EAPPPPPPTE DSCAKKPRSR

561 TKISLEALGI LQSFIHDVGL YPDQEAIHTL SAQLDLPKHT

601 IIKFFQNQRY HVKHHGKLKE HLGSAVDVAE YKDEELLTES

641 EENDSEEGSE EMYKVEAEEE NADKSKAAPA EIDQR
```

A cDNA encoding the SEQ ID NO:5 human SATB2 protein is available from the NCBI database as accession no. XM_005246396.4.

Various isoforms and variants of the SATB2 proteins and nucleic acids can be present in populations of subjects. Any such isoforms and variants can also be engineered pursuant to the methods described herein. Such isoforms and variants of the SATB2 proteins and nucleic acids can have sequences with between 55-100% sequence identity to a reference sequence, for example to any of the SATB2 sequences described herein. For example, the isoforms and variants of the SATB2 proteins and nucleic acids can have at least 55% sequence identity, at least 60%, at least 70%, at least 80%, at least 90%, at least 95%, at least 96%, at least 97% sequence, at least 98%, at least 99% identity to any of the sequences described herein. The sequence comparisons can be over a specified comparison window. Optimal alignment may be ascertained or conducted, for example, using the homology alignment algorithm of Needleman and Wunsch, J. Mol. Biol. 48:443-53 (1970).

Engineered SATB2-Null Cells & Organoids

As illustrated herein, loss of Satb2 in intestinal cells can transform the colonic epithelium into ileal small intestine, with the appearance of villi-like structures, Paneth cells, and enterocytes expressing abundant nutrient transporters. The colonic transcriptome also shifts towards the ileum so that the Satb2-null colon can absorb nutrients. Hence, methods are described herein for engineering cells to generate Satb2-null cells and organoids.

A variety of cell types can serve as starting cells to be engineered to generate Satb2-null cells and organoids. Examples of starting cells that can be used include colonic organoids, colonic stein cells, embryonic stem cells (ESCs), induced pluripotent stem cells (iPSCs), or combinations thereof. The cells can be autologous or allogeneic to a subject who maybe in need of treatment for an intestinal disease or condition. For example, in some cases a small biopsy of a subject's colon can be obtained by colonoscopy, colonic stem and/or progenitor cells can be isolated from such a sample (or another sample or source), and the stem and/or progenitor cells can be modified as described herein.

A variety of engineering methods can be used to modify the starting cells and generate Satb2-null cells and organoids. Examples include clustered regularly interspaced short palindromic repeats (CRISPR)-associated methods, cre-lox methods, TALEN-associated methods, base editing methods, insertion mutagenesis, and other methods for in vitro mutagenesis. Non-limiting examples of methods of introducing a modification into the genome of a cell can include use of microinjection, viral delivery, recombinase technologies, homologous recombination, cre-lox, CRISPR, TALENS, CRISPR, base-editing, and/or ZFN methods, see, e.g. Clark and Whitelaw Nature Reviews Genetics 4:825-833 (2003); which is incorporated by reference herein in its entirety. Such methods can reduce the expression or functioning of gene products of the SATB2.

In some cases, clustered regularly interspaced short palindromic repeats (CRISPR)-associated Cas-guide RNA systems can be used to create one or more modifications in genomic alleles encoding SATB2. However, other methods can use nucleases, such as zinc finger nucleases (ZFNs), transcription activator like effector nucleases (TALENs), and/or meganucleases with a guide nucleic acid that allows the nuclease to target the genomic Satb2 site(s).

The starting cells can in some cases be modified by microinjection or transfection with one or more expression cassettes or expression vectors that can express the components of the gene editing machineries. In some cases, a targeting vector can be used to introduce a deletion or modification of one or more genomic Satb2 site(s).

A "targeting vector" is a vector generally has a 5' flanking region and a 3 flanking region homologous to segments of the gene of interest. The 5' flanking region and a 3' flanking region can surround a DNA sequence comprising a modification and/or a donor (foreign) DNA sequence to be inserted into the gene. In some cases, the donor or foreign DNA sequence may encode a selectable marker. In some cases, the targeting vector does not comprise a selectable marker, but such a selectable marker can facilitate identification and selection of cells with desirable mutations. Examples of suitable selectable markers include antibiotics resistance genes such as chloramphenicol resistance, gentamycin resistance, kanamycin resistance, spectinomycin resistance (SpecR), neomycin resistance gene (NEO), and/or the hygromycin β-phosphotransferase genes. The 5' flanking region and the 3' flanking region can be homologous to regions within the gene, or to regions flanking the gene to be deleted, modified, or replaced with the unrelated DNA sequence. The targeting vector is contacted with the native (endogenous) gene of interest within the cell under conditions that favor homologous recombination. For example, the cell can be contacted with the targeting vector under conditions that result in transformation of the cell(s) with the targeting vector.

A typical targeting vector contains nucleic acid fragments of not less than about 0.1 kb nor more than about 10.0 kb from one or both the 5' and the 3' ends of the genomic locus which encodes the gene to be modified (e.g. the genomic Satb2 site(s)). In some cases nucleic acid fragments from both the 5' and the 3' ends of the Satb2 genomic locus are used. These two fragments are separated by an intervening fragment of nucleic acid which encodes the modification to be introduced. When the resulting construct recombines homologously with the chromosome at the Satb2 locus, it results in the introduction of the modification, e.g. a deletion of a portion of the genomic Satb2 site(s), replacement of the genomic Satb2 promoter or coding region site(s), or the insertion of non-conserved codon or a stop codon.

In some cases, a Cas nuclease/CRISPR system can be used to create a modification in genomic Satb2 that reduces the expression or functioning of the Satb2 gene products. Clustered regularly interspaced short palindromic repeats (CRISPR)/CRISPR-associated (Cas) systems are useful for, e.g. RNA-programmable genome editing (see e.g., Marraffini and Sontheimer. Nature Reviews Genetics 11: 181-190 (2010); Sorek et al. Nature Reviews Microbiology 2008 6: 181-6; Karginov and Hannon. Mol Cell 2010 1:7-19; Hale et al. Mol Cell 2010:45:292-302; Jinek et al. Science 2012 337:815-820; Bikard and Marraffini Curr Opin Immunol 2012 24:15-20; Bikard et al. Cell Host & Microbe 2012 12: 177-186; all of which are incorporated by reference herein in their entireties). A CRISPR guide RNA can be used that can target a Cas enzyme to the desired location in the genome, where it generates a double strand break. This technique is described, for example, by Mali et al. (Science 2013 339:823-6), which is incorporated by reference herein in its entirety. Kits for the design and use of CRISPR-mediated genome editing are commercially available, e.g. the PRECISION X CAS9 SMART NUCLEASE™ System (Cat No. CAS900A-1) from System Biosciences, Mountain View, CA.

CRISPR/Cas systems are useful, for example, for RNA-programmable genome editing (see e.g., Marraffini and Sontheimer. Nature Reviews Genetics 11: 181-190 (2010); Sorek et al. Nature Reviews Microbiology 2008 6: 181-6; Karginov and Hannon. Mol Cell 2010 1:7-19; Hale et al. Mol Cell 2010:45:292-302; Jinek et al. Science 2012 337: 815-820; Bikard and Marraffini Curr Opin Immunol 2012 24:15-20; Bikard et al. Cell Host & Microbe 2012 12: 177-186; all of which are incorporated by reference herein in their entireties).

A CRISPR guide RNA can be used that can target a Cas enzyme to the desired location in the genome, where it can cleave the genomic DNA for generation of a genomic modification. This technique is described, for example, by Mali et al. Science 2013 339:823-6; which is incorporated by reference herein in its entirety. Kits for the design and use of CRISPR-mediated genome editing are commercially available, e.g. the PRECISION X CAS9 SMART NUCLEASE™ System (Cat No. CAS900A-1) from System Biosciences, Mountain View, CA.

Several guide RNAs were evaluated for knock-out of human Satb2, including guide RNAs that included one of the following sequences:

```
1:
                                  (SEQ ID NO: 6)
TGCTCCACGACACAAAAGAC;

2:
                                  (SEQ ID NO: 7)
GATTCCTGTCTTTTGTGTCG;

3:
                                  (SEQ ID NO: 8)
CTTTTGTGTCGTGGAGCAGT;

4:
                                  (SEQ ID NO: 9)
TGTGTCGTGGAGCAGTTGGA
```

While each of these successfully modified the Satb2 gene, the first guide (SEQ ID NO:6) provided the highest modification frequency.

In other cases, a cre-lox recombination system of bacteriophage P1, described by Abrernski et al. 1983. *Cell* 32:1301 (1983), Sternberg et al., *Cold Spring Harbor Symposia on Quantitative Biology*, Vol. XLV 297 (1981) and others, can be used to promote recombination and alteration of the SATB2 genomic site(s). The cre-lox system utilizes the cre recombinase isolated from bacteriophage P1 in conjunction with the DNA sequences that the recombinase recognizes (termed lox sites).

The genomic mutations so incorporated can alter one or more amino acids in the encoded SATB2gene products. For example, genomic sites modified so that one or more of the encoded SATB2 gene products are non-functional, is more prone to degradation, is less stable so that the half-life of such gene products(s) is reduced, or a combination thereof. In another example, genomic sites can be modified so that at least one amino acid of a polypeptide for SATB2 is deleted or mutated to alter its activity. For example, a conserved amino acid or a conserved domain can be modified to improve or reduce of the activity of the SATB2. For example, a conserved amino acid or several amino acids in a conserved domain of the SATB2 can be replaced with one or more amino acids having physical and/or chemical properties that are different from the conserved amino acid(s).

To change the physical and/or chemical properties of a selected conserved amino acid(s), the conserved amino acid(s) can be deleted or replaced by amino acid(s) of another class, where the classes are identified in the following table.

| Classification | Genetically Encoded |
|---|---|
| Hydrophobic | A, G, F, I, L, M, P, V, W |
| Aromatic | F, Y, W |
| Apolar | M, G, P |
| Aliphatic | A, V, L, I |
| Hydrophilic | C, D, E, H, K, N, Q, R, S, T, Y |
| Acidic | D, E |
| Basic | H, K, R |
| Polar | Q, N, S, T, Y |
| Cysteine-Like | C |

The guide RNAs and nuclease can be introduced via one or more vehicles such as by one or more expression vectors (e.g., viral vectors), virus like particles, ribonucleoproteins (RNPs), via nanoparticles, liposomes, or a combination thereof. The vehicles can include components or agents that can target particular cell types (e.g., antibodies that recognize cell-surface markers), facilitate cell penetration, reduce degradation, or a combination thereof.

Such genomic modifications can reduce the expression or functioning of Satb2 gene products by at least 10%, or at least 15%, or at least 20%, or at least 25%, or at least 30%, or at least 35%, or at least 40%, or at least 45%, or at least 50% compared to the unmodified Satb2 gene product expression or functioning.

The engineered SATB2-null organoids or cells can also be seeded onto a scaffold, for instance, one or more decellularized intestinal segments, biological scaffolds, artificial scaffolds, or combinations thereof to create transplantable gut segments.

Several methods can be for forming structures such as tubes. Such methods can include formation of self-assembled cell sheets, which are rolled into tubes; natural polymeric scaffolds (e.g. collagen, elastin, fibrin); synthetic polymeric scaffolds (e.g. polyglycolide (PGA), polylactic acid (PLA), polycaprolactone (PCL)); and decellularized scaffolds, in which similar tissue (allogenic, xenogenic) is stripped of cells and reseeded with a subject's own cells. The use of collagen as a scaffold material has been overlooked due to the weak mechanical properties of standard collagen gel, but it can be used to grow various cell types and the density of collagen can be increased to facilitate formation of sheets and tube, thereby providing improved tissue-equivalent structures. Methods for "plastic compression" of collagen involve placing a collagen gel on a nylon (hydrophilic) membrane and paper blot. By loading the gel from above, the water is forced from the gel, which aligns the collagen fibers and makes the collagen denser. Such plastic compression provides a dense collagen sheet, which can be rolled to form a tube. Another method wraps a nylon membrane and paper towels around a collagen gel, followed by suspension to allow water extraction. Another method involves slowly rotating a standard collagen gel to expel water and thus form a thin-walled, densified collagen tube. Other methods are described in WO/2020/208094.

A range of SATB2 null cells can be seeded into scaffold tubes. For example, about $1\times10^5$ cells to about $1\times10^{10}$ cells per tube can be incubated with scaffold tubes. The cell-seeded scaffolds can be perfused with media to support the growth and attachment of the cells.

Inhibitory Nucleic Acids

The expression of Satb2 can be inhibited, for example by use of an inhibitory nucleic acid that specifically recognizes and binds to a nucleic acid that encodes the SATB2 protein. Such binding can inhibit the expression or translation of the Satb2 nucleic acid so that little or no SATB2 protein is generated.

An inhibitory nucleic acid can have at least one segment that will hybridize to a Satb2 nucleic acid under intracellular or stringent conditions. The inhibitory nucleic acid can reduce expression of a nucleic acid encoding SATB2. A nucleic acid may hybridize to a Satb2 genomic DNA, a messenger RNA, or a combination thereof. An inhibitory nucleic acid may be incorporated into a plasmid vector or viral DNA. It may be single stranded or double stranded, circular or linear.

An inhibitory nucleic acid is a polymer of ribose nucleotides or deoxyribose nucleotides having more than 13 nucleotides in length. An inhibitory nucleic acid may include naturally occurring nucleotides; synthetic, modified, or pseudo-nucleotides such as phosphorothiolates; as well as nucleotides having a detectable label such as $P^{32}$, biotin or digoxigenin. An inhibitory nucleic acid can reduce the expression and/or activity of a Satb2 nucleic acid. Such an inhibitory nucleic acid may be completely complementary to a segment of an endogenous Satb2 nucleic acid (e.g., an RNA). Alternatively, some variability is permitted in the inhibitory nucleic acid sequences relative to Sab sequences. An inhibitory nucleic acid can hybridize to a Satb2 nucleic acid under intracellular conditions or under stringent hybridization conditions and is sufficiently complementary to inhibit expression of the endogenous Satb2 nucleic acid. Intracellular conditions refer to conditions such as temperature, pH and salt concentrations typically found inside a cell, e.g. an animal or mammalian cell. One example of such an animal or mammalian cell is a stem cell or an intestinal progenitor cell. Another example of such an animal or mammalian cell is a more differentiated cell derived from a stem cell or progenitor cell. Generally, stringent hybridization conditions are selected to be about 5° C. lower than the thermal melting point ($T_m$) for the specific sequence at a defined ionic strength and pH. However, stringent conditions encompass temperatures in the range of about 1° C. to about 20° C. lower than the thermal melting point of the selected sequence, depending upon the desired degree of stringency as otherwise qualified herein. Inhibitory oligonucleotides that comprise, for example, 2, 3, 4, or 5 or more stretches of contiguous nucleotides that are precisely complementary to a Satb2 coding sequence that can be separated by a stretch of contiguous nucleotides that are not complementary to the adjacent coding sequences, and that can inhibit the function of a Satb2 nucleic acid. In general, each stretch of contiguous nucleotides is at least 4, 5, 6, 7, or 8 or more nucleotides in length. Non-complementary intervening sequences may be 1, 2, 3, or 4 nucleotides in length. One skilled in the art can easily use the calculated melting point of an inhibitory nucleic acid hybridized to a sense nucleic acid to estimate the degree of mismatching that will be tolerated for inhibiting expression of a particular target nucleic acid.

Inhibitory nucleic acids of the invention include, for example, a short hairpin RNA, a small interfering RNA, a ribozyme or an antisense nucleic acid molecule.

The inhibitory nucleic acid molecule may be single or double stranded (e.g. a small interfering RNA (siRNA)) and may function in an enzyme-dependent manner or by steric blocking. Inhibitory nucleic acid molecules that function in an enzyme-dependent manner include forms dependent on RNase H activity to degrade target mRNA. These include single-stranded DNA, RNA, and phosphorothioate molecules, as well as the double-stranded RNAi/siRNA system that involves target mRNA recognition through sense-antisense strand pairing followed by degradation of the target mRNA by the RNA-induced silencing complex. Steric blocking inhibitory nucleic acids, which are RNase-H independent, interfere with gene expression or other mRNA-dependent cellular processes by binding to a target mRNA and getting in the way of other processes. Steric blocking inhibitory nucleic acids include 2'-O alkyl (usually in chimeras with RNase-H dependent antisense), peptide nucleic acid (PNA), locked nucleic acid (LNA) and morpholino antisense.

Small interfering RNAs, for example, may be used to specifically reduce translation of SATB2 such that translation of the encoded SATB2 is reduced. SiRNAs mediate post-transcriptional gene silencing in a sequence-specific manner. See, for example, website at invitrogen.com/site/us/en/home/Products-and-Services/Applications/rnai.html. Once incorporated into an RNA-induced silencing complex, siRNA mediate cleavage of the homologous endogenous mRNA transcript by guiding the complex to the homologous mRNA transcript, which is then cleaved by the complex. The siRNA may be homologous and/or complementary to any region of the Satb2 transcript. The region of homology may be 100 nucleotides or less in length, 50 nucleotides or less in length, 40 nucleotides or less in length, 30 nucleotides or less in length, 25 nucleotides or less in length, and in some cases about 21 to 23 nucleotides in length. SiRNA is typically double stranded and may have two-nucleotide 3' overhangs, for example, 3' overhanging UU dinucleotides. Methods for designing siRNAs are known to those skilled in the art. See, for example, Elbashir et al. *Nature* 411: 494-498 (2001); Harborth et al. *Antisense Nucleic Acid Drug Dev.* 13: 83-106 (2003).

The pSuppressorNeo vector for expressing hairpin siRNA, commercially available from IMGENEX (San Diego, California), can be used to generate siRNA for inhibiting expression of Satb2. The construction of the siRNA expression plasmid involves the selection of the target region of the mRNA, which can be a trial-and-error process. However, Elbashir et al. have provided guidelines that appear to work ~80% of the time. Elbashir, S M., et al., *Analysis of gene function in somatic mammalian cells using small interfering RNAs.* Methods, 2002. 26(2): p. 199-213. Accordingly, for synthesis of synthetic siRNA, a target region may be selected preferably 50 to 100 nucleotides downstream of the start codon. The 5' and 3' untranslated regions and regions close to the start codon should be avoided as these may be richer in regulatory protein binding sites. As siRNA can begin with AA, have 3' UU overhangs for both the sense and antisense siRNA strands, and have an approximate 50% G/C content. An example of a sequence for a synthetic siRNA is 5'-AA(N19)UU), where N is any nucleotide in the mRNA sequence and should be approximately 50% G-C content. The selected sequence(s) can be compared to others in the human genome database to minimize homology to other known coding sequences (e.g., by Blast search, for example, through the NCBI website).

SiRNAs may be chemically synthesized, created by in vitro transcription, or expressed from an siRNA expression vector or a PCR expression cassette. See, e.g., website at invitrogen.com/site/us/en/home/Products-and-Services/Applications/rnai.html. When an siRNA is expressed from an expression vector or a PCR expression cassette, the insert encoding the siRNA may be expressed as an RNA transcript that folds into an siRNA hairpin. Thus, the RNA transcript may include a sense siRNA sequence that is linked to its reverse complementary antisense siRNA sequence by a spacer sequence that forms the loop of the hairpin as well as a string of U's at the 3' end. The loop of the hairpin may be of any appropriate lengths, for example, 3 to 30 nucleotides in length, preferably, 3 to 23 nucleotides in length, and may be of various nucleotide sequences including, AUG, CCC, UUCG, CCACC, CTCGAG, AAGCUU, CCACACC and UUCAAGAGA (SEQ ID NO:30). SiRNAs also may be produced in vivo by cleavage of double-stranded RNA introduced directly or via a transgene or virus. Amplification by an RNA-dependent RNA polymerase may occur in some organisms.

An inhibitory nucleic acid such as a short hairpin RNA siRNA or an antisense oligonucleotide may be prepared using methods such as by expression from an expression vector or expression cassette that includes the sequence of the inhibitory nucleic acid. Alternatively, it may be prepared by chemical synthesis using naturally occurring nucleotides, modified nucleotides or any combinations thereof. In some embodiments, the inhibitory nucleic acids are made from modified nucleotides or non-phosphodiester bonds, for example, that are designed to increase biological stability of the inhibitory nucleic acid or to increase intracellular stability of the duplex formed between the inhibitory nucleic acid and the target Satb2 nucleic acid.

An inhibitory nucleic acid may be prepared using available methods, for example, by expression from an expression vector encoding a complementarity sequence of the Satb2 nucleic acid. Alternatively, it may be prepared by chemical synthesis using naturally occurring nucleotides, modified nucleotides or any mixture of combination thereof. In some embodiments, the Satb2 nucleic acids are made from modified nucleotides or non-phosphodiester bonds, for example, that are designed to increase biological stability of the nucleic acids or to increase intracellular stability of the duplex formed between the inhibitory nucleic acids and other (e.g., endogenous) nucleic acids.

For example, the Satb2 inhibitory nucleic acids can be peptide nucleic acids that have peptide bonds rather than phosphodiester bonds.

Naturally occurring nucleotides that can be employed in the Satb2 inhibitory nucleic acids include the ribose or deoxyribose nucleotides adenosine, guanine, cytosine, thymine and uracil. Examples of modified nucleotides that can be employed in the Satb2 nucleic acids include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine.

Thus, inhibitory nucleic acids of the Satb2 described herein may include modified nucleotides, as well as natural nucleotides such as combinations of ribose and deoxyribose nucleotides. The inhibitory nucleic acids and may be of same length as wild type Satb2 described herein. The inhibitory nucleic acids of the Satb2 described herein can also be longer and include other useful sequences. In some embodiments, the inhibitory nucleic acids of the Satb2 are somewhat shorter. For example, inhibitory nucleic acids of the Satb2 can include a segment that has a nucleic acid sequence that can be missing up to 5 nucleotides, or missing up to 10 nucleotides, or missing up to 20 nucleotides, or missing up to 30 nucleotides, or missing up to 50 nucleotides, or missing up to 100 nucleotides from the 5' or 3' end.

The inhibitory nucleic acids can be introduced via one or more vehicles such as via expression vectors (e.g., viral vectors), via virus like particles, via ribonucleoproteins (RNPs), via nanoparticles, via liposomes, or a combination thereof. The vehicles can include components or agents that can target particular cell types, facilitate cell penetration, reduce degradation, or a combination thereof.

Therapies

In some cases, subjects can be administered compositions that include genomic editing components such as expression cassettes or expression vectors that can express the machinery for intracellular editing of one or both endogenous Satb2 alleles. In other cases, cells can be modified in vitro and then administered to a subject either as a population of Satb2-null cells, as a tubular scaffold/implant that is populated by the Satb2-null cells, or a combination thereof.

As described above, cells can be contacted and/or treated with any of the mutating agents (e.g., CRISPR guide RNAs, ribonucleoprotein complexes, cre-lox systems) described herein for targeting and modifying Satb2 to produce Satb2-null cells. This method can be performed in vitro or in vivo. The cells to be modified can be autologous or allogeneic to the subject to be treated.

The cells to be modified can, for example, be colonic organoids, colonic stem cells, embryonic stem cells (ESCs), induced pluripotent stem cells (iPSCs), or combinations thereof.

For example, for in vitro modification, cells can be obtained from a subject, and these cells can be contacted and/or treated with any of mutating agents (e.g., guide RNAs, ribonucleoprotein complexes, cre-lox systems) described herein for SATB2 to generate modified cells. The modified cells can be expanded in culture to form a population of modified cells and the population of cells can be administered to a subject, e.g. a mammal such as a human. The amount or number of cells administered can vary but amounts in the range of about $10^6$ to about $10^9$ cells can be used. The cells are generally delivered in a physiological solution such as saline or buffered saline. The cells can also be delivered in a device or a vehicle so that a population of liposomes, exosomes or microvesicles.

Modified Satb2-null cells generated as described herein can be employed for regeneration and engraftment in a human patient or other subjects in need of such treatment. The cells are administered in a manner that permits them to graft and reconstitute or regenerate within a subject or recipient. Scaffolds and implants that are populated with Satb2-null cells can also be administered. Cells and/or scaffolds are administered to patients at various time points, for example, as therapy for a subject having or suspected of having an intestinal disease or condition. Examples of diseases and/or conditions that may be treated with the methods, cells and/or scaffolds described herein include short bowel disease, congenital short bowel syndrome, irritable bowel syndrome, digestive failure, intestinal injury, intestinal atresia, intussusception, meconium ileus, midgut volvulus, omphalocele, reduced nutritional absorption, fistula, Crohn's disease, necrotizing enterocolitis ulcerative colitis, or colorectal cancer. Administration of cells should improve intestinal functions and health of the patient, increase nutrient absorption, and reduce their risk of infections and other pathophysiologies associated with malnutrition.

Many cell types are capable of migrating to an appropriate site for regeneration and differentiation within a subject. Expanded Satb2-null cells can thus in some cases be administered to by systemic injection. For example, the cells can be administered intravascularly. In some embodiments, the cells can be administered parenterally by injection into a blood vessel or into a convenient cavity.

To determine the suitability of cell compositions for therapeutic administration, the Satb2-null cells can first be tested in a suitable animal model (e.g., a mouse, rat or other animal as described herein). For example, the expanded Satb2-null cells can be assessed for their ability to survive and maintain their phenotype in vivo. Cells can also be assessed to ascertain whether they populate a substantial percentage of the colon in viva, or to determine an appropriate number of cells to be administered. Cell compositions can be administered to immunodeficient animals (such as nude mice, or animals rendered immunodeficient chemically or by irradiation).

Satb2-null cells can be introduced by injection, catheter, implantable device, or the like. A population of expanded cells can be administered in any physiologically acceptable excipient or carrier that does not adversely affect the cells.

Satb2-null cells can be supplied in the form of a pharmaceutical composition. Such a composition can include an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. The choice of the cellular excipient and any accompanying constituents of the composition that includes a population of expanded cells can be adapted to optimize administration by the route and/or device employed.

A composition that includes a population of Satb2-null cells can also include or be accompanied by one or more other ingredients that facilitate engraftment or functional mobilization of the expanded cells.

The Satb2-null cells generated by the methods described herein can include some percentage of non-intestinal, non-stem cells or non-progenitor cells. For example, a population of expanded cells for use in compositions and for administration to subjects can contain endothelial cells. The presence of such endothelial cells has no adverse effects, and in some cases can actually be helpful.

However, a population of Satb2-null cells for use in compositions and for administration to subjects can have less than about 20% Satb2-expressing cells, less than 15% Satb2-expressing cells, less than 10% Satb2-expressing cells, less than about 5% Satb2-expressing cells, less than about 3% Satb2-expressing cells, less than about 2% Satb2-expressing cells, or less than about 1% Satb2-expressing cells of the total cells in the cell population.

The number of cells administered to a subject or a patient can vary. For example, subjects with different diseases and/or conditions can need different amounts of Satb2-null cells. In some cases, number of Satb2-null cells in the cell compositions described herein can be packaged for ready administration to a subject or patient. For example, the cells can be packaged to contain at least 1 million cells, or at least 5 million cells, at least 10 million cells, or at least 25 million cells, at least 50 million cells, or at least 70 million cells, at least 100 million cells, or at least 200 million cells, at least 300 million cells, at least 400 million cells, at least 500 million cells, or at least 600 million cells, at least 700 million cells, at least 800 million cells, at least 1000 million cells, or at least 2000 million cells, at least 5000 million cells, at least 7000 million cells, at least 10,000 million cells, or at least 30,000 million cells, at least 50,000 million cells, or at least 100,000 million cells.

Treatment may include administering the cells and/or cell-scaffold alone or the treatment can include administering Satb2 modifying/mutating agents (e.g., guide RNAs or ribonucleoprotein complexes) described herein for modifying Satb2, with or without the Satb2-null cells. Such agents can be administered separately from or with the modified cells/scaffold. For example, the modified cells may be administered prior to, during, or after administering any of the mutating agents (e.g., guide RNAs or ribonucleoprotein complexes) described herein for engineering Satb2 alleles.

Mutating/modifying agents that can be administered to a subject can include expression vectors and/or targeting vectors for modifying endogenous Satb2 alleles. The expression vectors and/or targeting vectors can encode and express nucleases (e.g., cas nucleases), guide RNAs, donor DNAs, and/or any other components for genomic editing.

For example, mutating agents can be administered via a viral vector. Suitable viral vectors include, for example, retroviral vectors, herpes simplex virus (HSV)-based vectors, parvovirus-based vectors, e.g., adeno-associated virus (AAV)-based vectors, AAV-adenoviral chimeric vectors, and adenovirus-based vectors. These viral vectors can be prepared using standard recombinant DNA techniques described in, for example, Sambrook et al., *Molecular Cloning, a Laboratory Manual,* 3rd edition, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994).

For example, gene modifying vector, e.g., a viral gene modifying vector, can be used that is useful for delivering genomic engineering components to the gastrointestinal tract. A "gene transfer vector" is any molecule or composition that has the ability to carry a heterologous nucleic acid sequence into a suitable host cell where synthesis of the encoded gene product, nucleic acid or protein takes place. Typically, a gene transfer vector is a nucleic acid molecule that has been engineered, using recombinant DNA techniques, to include nucleic acid sequences for the genomic engineering components. The gene transfer vector can be comprised of DNA. Examples of suitable DNA-based gene transfer vectors include plasmids and viral vectors. The gene transfer vector can be integrated into the host cell genome or can be present in the host cell in the form of an episome.

In one embodiment, the AAV vector is generated using an AAV that infects humans (e.g., AAV2). Alternatively, the AAV vector is generated using an AAV that infects non-human animals (e.g., rodents) or primates (e.g., chimpanzees).

The AAV vector may comprise expression control sequences, such as promoters, enhancers, polyadenylation signals, transcription terminators, internal ribosome entry sites (IRES), and the like, that provide for the expression of the genomic editing components in a host cell. Exemplary expression control sequences are available and described in, for example, Goeddel, Gene Expression Technology: Methods in Enzymology, Vol. 185, Academic Press, San Diego, CA. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, and the RSV promoter. Inducible promoters include, for example, the Tet system (U.S. Pat. Nos. 5,464,758 and 5,814,618), the Ecdysone inducible system (No et al., *Proc. Natl. Acad. Sci.,* 93:3346 (1996)), the T-REX™ system (Invitrogen, Carlsbad, CA), LACSWITCH™ System (Stratagene, San Diego, CA), and the Cre-ERT tamoxifen inducible recombinase system (Indra et al., *Nuc. Acid. Res.,* 27:4324 (1999); *Nuc. Acid. Res.,* 28:e99 (2000); U.S. Pat. No. 7,112,715; and Kramer & Fussenegger, *Methods Mol. Biol.,* 308:123 (2005)).

Typically AAV vectors are produced using well characterized plasmids. For example, human embryonic kidney 293T cells are transfected with one of the transgene specific plasmids and another plasmid containing the adenovirus helper and AAV rep and cap genes (specific to AAVrh.10, 8 or 9 as required). After 72 hours, the cells are harvested and the vector is released from the cells by five freeze/thaw cycles. Subsequent centrifugation and benzonase treatment removes cellular debris and unencapsidated DNA. Iodixanol gradients and ion exchange columns may be used to further purify each AAV vector. Next, the purified vector is concentrated by a size exclusion centrifuge spin column to the required concentration. Finally, the buffer is exchanged to create the final vector products formulated (for example) in 1× phosphate buffered saline. The viral titers may be measured by TaqMan® real-time PCR and the viral purity may be assessed by SDS-PAGE.

Definitions

The term "about" as used herein when referring to a measurable value such as an amount, a length, and the like, is meant to encompass variations of ±20% or ±10%, more preferably ±5%, even more preferably ±1%, and still more preferably ±0.1% from the specified value.

As used herein, a "cell" refers to any type of cell isolated from a prokaryotic, eukaryotic, or archaeon organism, including bacteria, archaea, fungi, protists, plants, and animals, including cells from tissues, organs, and biopsies, as well as recombinant cells, cells from cell lines cultured in vitro, and cellular fragments, cell components, or organelles comprising nucleic acids. The term also encompasses artificial cells, such as nanoparticles, liposomes, polymersomes, or microcapsules encapsulating nucleic acids. The methods described herein can be performed, for example, on a sample comprising a single cell or a population of cells. The term also includes genetically modified cells.

A "coding region" or a sequence which "encodes" a selected polypeptide or a selected RNA, is a nucleic acid molecule which is transcribed (in the case of DNA templates) into RNA and/or translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, ncRNAs, tracrRNAs, ncRNAs modified to include heterologous sequences, cDNA from viral, prokarvotic or eukaryotic ncRNA, mRNA, viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

"Operably linked" refers to an arrangement of elements wherein the components so described are configured so as to perform their usual function. Thus, a given promoter operably linked to a coding region is capable of effecting the expression of the encoded sequence when the proper polymerases are present. The promoter need not be contiguous with the coding region, so long as it functions to direct the expression thereof. Thus, for example, intervening untranslated yet transcribed sequences can be present between the promoter sequence and the coding region and the promoter sequence can still be considered "operably linked" to the coding region.

"Encoded by" refers to a nucleic acid sequence that codes for a polypeptide or RNA. For example, a polypeptide sequence or a portion thereof is encoded by the nucleic acid sequence. The RNA sequence or a portion thereof contains a nucleotide sequence that is encoded by a DNA (or other nucleic acid) sequence.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein, DNA, or RNA or cause other adverse consequences. That is, a nucleic acid or peptide can be purified if it is substantially free of cellular material, viral material, or culture medium when obtained from nature or when produced by recombinant DNA techniques, or free from chemical precursors or other chemicals when chemically synthesized. Purity and homogeneity are typically determined using analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

"Substantially purified" generally refers to isolation of a substance (nucleic acid, compound, polynucleotide, protein, polypeptide, peptide composition) such that the substance comprises the majority percent of the sample in which it resides. Typically, in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

"Expression" refers to detectable production of a gene product by a cell. The gene product may be a transcription product (i.e., RNA), which may be referred to as "gene expression", or the gene product may be a translation product of the transcription product (i.e., a protein), depending on the context.

"Mammalian cell" refers to any cell derived from a mammalian subject suitable for transfection with vector systems comprising, as described herein. The cell may be xenogeneic, autologous, or allogeneic. The cell can be a primary cell obtained directly from a mammalian subject. The cell may also be a cell derived from the culture and expansion of a cell obtained from a mammalian subject. Immortalized cells are also included within this definition. In some embodiments, the cell has been genetically engineered to express a recombinant protein and/or nucleic acid.

The term "subject" includes animals, including both vertebrates and invertebrates, including, without limitation, invertebrates such as arthropods, mollusks, annelids, and cnidarians; and vertebrates such as amphibians, including frogs, salamanders, and caecillians; reptiles, including lizards, snakes, turtles, crocodiles, and alligators; fish; mammals, including human and non-human mammals such as non-human primates, including chimpanzees and other apes and monkey species; laboratory animals such as mice, rats, rabbits, hamsters, guinea pigs, and chinchillas; domestic animals such as dogs and cats; farm animals such as sheep, goats, pigs, horses and cows; and birds such as domestic, wild and game birds, including chickens, turkeys and other gallinaceous birds, ducks, geese, and the like. In some cases, the disclosed methods find use in experimental animals, in veterinary application, and in the development of animal models for disease, including, but not limited to, rodents including mice, rats, and hamsters; primates, and transgenic animals. In some cases, the subject is a human.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses.

The term "derived from" is used herein to identify the original source of a molecule but is not meant to limit the method by which the molecule is made which can be, for example, by chemical synthesis or recombinant means.

A polynucleotide or nucleic acid "derived from" a designated sequence refers to a polynucleotide or nucleic acid that includes a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

The terms "hybridize" and "hybridization" refer to the formation of complexes between nucleotide sequences which are sufficiently complementary to forn complexes via Watson-Crick base pairing.

The term "homologous region" refers to a region of a nucleic acid with homology to another nucleic acid region Thus, whether a "homologous region" is present in a nucleic acid molecule is determined with reference to another nucleic acid region in the same or a different molecule. Further, since a nucleic acid is often double-stranded, the term "homologous, region," as used herein, refers to the ability of nucleic acid molecules to hybridize to each other. For example, a single-stranded nucleic acid molecule can have two homologous regions which are capable of hybridizing to each other. Thus, the term "homologous region" includes nucleic acid segments with complementary sequences. Homologous regions may vary in length but will typically be between 4 and 500 nucleotides (e.g., from about 4 to about 40, from about 40 to about 80, from about 80 to about 120, from about 120 to about 160, from about 160 to about 200, from about 200 to about 240, from about 240 to about 280, from about 280 to about 320, from about 320 to about 360, from about 360 to about 400, from about 400 to about 440, etc.).

As used herein, the terms "complementary" or "complementarity" refers to polynucleotides that are able to form base pairs with one another. Base pairs are typically formed by hydrogen bonds between nucleotide units in an antiparallel orientation between polynucleotide strands. Complementary polynucleotide strands can base pair in a Watson-Crick manner (e.g., A to T, A to U, C to G), or in any other manner that allows for the formation of duplexes. As persons skilled in the art are aware, when using RNA as opposed to DNA, uracil (U) rather than thymine (T) is the base that is considered to be complementary to adenosine. However, when uracil is denoted in the context of the present invention, the ability to substitute a thymine is implied, unless otherwise stated. "Complementarity" may exist between two RNA strands, two DNA strands, or between an RNA strand and a DNA strand. It is generally understood that two or more polynucleotides may be "complementary" and able to form a duplex despite having less than perfect or less than 100% complementarity. Two sequences are "perfectly complementary" or "100% complementary" if at least a contiguous portion of each polynucleotide sequence, comprising a region of complementarity, perfectly base pairs with the other polynucleotide without any mismatches or interruptions within such region. Two or more sequences are considered "perfectly complementary" or "100% complementary" even if either or both polynucleotides contain additional non-complementary sequences as long as the contiguous region of complementarity within each polynucleotide is able to perfectly hybridize with the other. "Less than perfect" complementarity refers to situations where less than all of the contiguous nucleotides within such region of complementarity are able to base pair with each other. Determining the percentage of complementarity between two polynucleotide sequences is a matter of ordinary skill in the art.

In general, "a CRISPR system" refers collectively to transcripts and other elements involved in the expression of or directing the activity of CRISPR-associated ("Cas") genes, including sequences encoding a Cas gene, and a CRISPR array nucleic acid sequence including a leader sequence and at least one repeat sequence. In some embodiments, one or more elements of a CRISPR system are derived from a type I, type II, or type III CRISPR system. Cas1 and Cas2 are found in all three types of CRISPR-Cas systems, and they are involved in spacer acquisition. In the I-E system of *E. coli*, Cas1 and Cas2 form a complex where a Cas2 dimer bridges two Cas1 dimers. In this complex Cas2 performs a non-enzymatic scaffolding role, binding double-stranded fragments of invading DNA, while Cas1 binds the single-stranded flanks of the DNA and catalyzes their integration into CRISPR arrays.

In some embodiments, one or more elements of a CRISPR system are derived from a particular organism comprising an endogenous CRISPR system, such as *Streptococcus pyogenes*. In general, a CRISPR system can be characterized by elements that promote the formation of a CRISPR complex at the site of a target sequence (also referred to as a protospacer in the context of an endogenous CRISPR system).

The term "donor polynucleotide" or "donor DNA" refers to a nucleic acid or polynucleotide that provides a nucleotide sequence of an intended edit to be integrated into the genome at a target locus by HDR or recombineering.

A "target site" or "target sequence" is the nucleic acid sequence recognized (i.e., sufficiently complementary for hybridization) by a guide RNA (gRNA) or a homology arm of a donor polynucleotide (donor DNA). The target site may be allele-specific (e.g., a major or minor allele). For example, a target site can be a genomic site that is intended to be modified such as by insertion of one or more nucleotides, replacement of one or more nucleotides, deletion of one or more nucleotides, or a combination thereof.

In certain embodiments, the disclosure provides protospacers that are adjacent to short (3-5 bp) DNA sequences termed protospacer adjacent motifs (PAM). The PAMs are important for type I and type II systems during acquisition. In type I and type II systems, protospacers are excised at positions adjacent to a PAM sequence, with the other end of the spacer is cut using a ruler mechanism, thus maintaining the regularity of the spacer size in the CRISPR array. The conservation of the PAM sequence differs between CRISPR-Cas systems and may be evolutionarily linked to Cas1 and the leader sequence.

In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al, J. BacterioL, 169:5429-5433 (1987); and Nakata et al., J. BacterioL, 171:3553-3556 (1989)), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 (1993); Hoe et al., Emerg. Infect. Dis., 5:254-263 (1999); Masepohl et al, Biochim. Biophys. Acta 1307:26-30 (1996); and Mojica et al, Mol. Microbiol, 17:85-93 (1995)). The CRISPR loci typically differ from other SSRs by the structure of the repeats, which have been termed short regularly spaced repeats (SRSRs) (Janssen et al, OMICS J. Integ. Biol., 6:23-33 (2002); and Mojica et al, Mot. Microbiol., 36:244-246 (2000)). In general, the repeats are short elements that occur in clusters that are regularly spaced by unique intervening sequences with a substantially constant length (Mojica et al., (2000), supra). Although the repeat sequences are highly conserved between strains, the number of interspersed repeats and the sequences of the spacer regions typically differ from strain to strain (van Embden et al., J. Bacteriol., 182:2393-2401 (2000)). CRISPR loci have been identified in more than 40 prokaryotes (See e.g., Jansen et al, Mol Microbiol., 43:1565-1575 (2002); and Mojiica et al, (2005)) including, but not limited to *Aeropyrum, Pyrobaculum, Sulfolobus, Archaeoglobus, Halocarcula, Methanobacteriumn, Methanococcus*, M*ethanosarcina, Methanopyrus, Pyrococcus, Picrophilus, Thernioplasnia, Corynebacterium, Mycobacterium, Streptomyces, Aquifrx, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myrococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga.*

In some embodiments, an enzyme coding sequence encoding a CRISPR enzyme (e.g., cas9) is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about one or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

A guide RNA is a single-stranded ribonucleic acid, although in some cases it may form some double-stranded regions by folding onto itself. In some cases, the guide RNA is about 10, 20, 30, 40, 50, 60, 70, 80, 90, 100 or more nucleic acid residues in length. In some cases, the guide RNA is from about 10 to about 30 nucleic acid residues in length. In some cases, the guide RNA is about 20 nucleic acid residues in length. For example, the length of the guide RNA can be at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides or residues in length. In some cases, the guide RNA is from 5 to 50, 10 to 50, 15 to 50, 20 to 50, 25 to 50, 30 to 50, 35 to 50, 40 to 50, 45 to 50, 5 to 75, 10 to 75, 15 to 75, 20 to 75, 25 to 75, 30 to 75, 35 to 75, 40 to 75, 45 to 75, 50 to 75, 55 to 75, 60 to 75, 65 to 75, 70 to 75, 5 to 100, 10 to 100, 15 to 100, 20 to 100, 25 to 100, 30 to 100, 35 to 100, 40 to 100, 45 to 100, 50 to 100, 55 to 100, 60 to 100, 65 to 100, 70 to 100, 75 to 100, 80 to 100, 85 to 100, 90 to 100, 95 to 100, or more nucleotides or residues in length. In some cases, the guide RNA is from 10 to 15, 10 to 20, 10 to 30, 10 to 40, or 10 to 50 residues in length.

"Administering" a nucleic acid, such as an expression cassette, comprises transducing, transfecting, electroporating, translocating, fusing, phagocytosing, shooting or ballistic methods, etc., i.e., any means by which a nucleic acid can be transported across a cell membrane.

The subject matter disclosed herein is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosed subject matter. The upper and lower limits of these smaller ranges may independently be included in the smaller ranges, and are also encompassed within the disclosed subject matter, subject to any specifically excluded limit in the stated range. Where the stated range includes one or both of the limits, ranges excluding either or both of those included limits are also included in the disclosed subject matter.

Unless defined otherwise, all technical and scientific terms used herein have the same meaning as commonly understood by one of ordinary skill in the art to which the disclosed subject matter belongs. Although any methods and materials similar or equivalent to those described herein can also be used in the practice or testing of the disclosed subject matter, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cell" includes a plurality of such cells and reference to "the nucleic acid" includes reference to one or more nucleic acids and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of any features or elements described herein, which includes use of a "negative" limitation.

The invention will be further described by the following non-limiting examples.

Example 1: Materials and Methods

This Example describes some of the experimental procedures and results obtained in the develop of the invention. Appendix A may provide further information and figures.

Mouse Strains

All mouse experiments were conducted under the IACUC protocol 2018-0050 at Weill Cornell Medical College or protocol 03-132 at Dana-Farber Cancer Institute. Mice were housed in a temperature- and humidity-controlled environment with 12 hr light/dark cycle and food/water ad libitum. All mouse experiments were performed with both males and females at 2 months of age. The Satb2loxp/loxp (Satb2f/f) strain (Dobreva et al., 2006) was a gift from Dr. Jeff Macklis of Harvard University. The Vil-CreERT2 strain (el Marjou et al.,b2004) was a gift from Sylvie Robine (Institute Pasteur). Vil-CreERT2; Eedloxp/loxp (Eedf/f) mice were derived as described by Jadhav et al., 2016 and Xie et al., 2014. The Lgr5DTRGFP strain was from Genentech Inc. (Tian et al., 2011), the Lgr5GFPCreER strain (Barker et al., 2007) was purchased from Jackson Lab. The CAGSATB2GFP strain was generated in this study (details of generation in Method Details section). To confer conditional deletion of floxed alleles, 4 mg per 25 g of body weight of tamoxifen (TAM, 10 mg per ml in corn oil) was intraperitoneally injected once every 2 days for a total of 3 times.

Data and Code Availability

The high-through sequencing raw and processed data in this paper have been deposited to Gene Expression Omnibus (CEO) (ATACSeq:GSE148690 and GSE180037. ScRNA-Seq: GSE148693. ChIP-Seq: GSE167287. CUT&RUNT: GSE180029 and GSE167289. Bulk RNA-Seq: GSE148692, GSE167284, GSE180023, GSE167281, GSE167282, GSE167283, GSE167285, GSE16728 and GSE180013). The following public GEO datasets were also analyzed: GSE115541, GSE71713 and GSE130822 (Banerjee et al., 2018; Jadhav et al., 2016; Murata et al., 2020).

Mouse Primary Intestinal Organoids

Mouse primary intestinal organoid culture was performed as previously described (Sugimoto and Sato, 2017). Organoid derivation was performed on ice or at 4° C. unless specified. Briefly, intestinal tissues were cut into approximately 0.5 cm size pieces and incubated in 2.5 mM EDTA for 45 minutes (mins) (small intestine) or in 10 mM EDTA for 60 mins (large intestine). After vigorous pipetting with 1% BSA pre-coated 10 mL serological pipettes, epithelium cell clumps were collected by centrifugation at 300 g for 5 minutes. Crypts were further isolated by filtering through a 70 mm cell strainer. 50-200 Crypts per 25 μl Matrigel™ droplet were cultured in either ENR (small intestine) or WENR (large intestine) medium (Table 1A) in humidified chambers containing 5% CO2 at 37° C. The formation efficiency of primary organoids was determined by dividing the number of organoids at Day 5 by the initial Crypt numbers. To assay secondary organoids, primary organoids were dissociated with TrypLE Express (3 minutes at 37° C.), resuspended in cold DMEM with 2% FBS, and centrifuged at 300 g for 3 mins. The cell pellets were embedded in Matrigel™ in a 1:5 ratio. The formation efficiency of secondary organoids was determined by dividing the number of organoids at Day 5 by the initial crypt number.

TABLE 1A

ENR (small intestine) or WENR (large intestine) medium

| Ingredient | Supplier | Cat | Final conc | WME | ADF | ADF-ENR | ADF-WENR |
|---|---|---|---|---|---|---|---|
| GlutaMax | Gibco | 35,050 | 2 mM | + | + | + | + |
| d-Glucose | Sigma | G8769 | 25 mM | + | + | + | + |
| EGF | Gibco | PMG8041 | 50 ng/ml | | | + | + |
| Noggin | — | | 10% (v/v) | | | + | + |
| R-spondin1 | — | | 10% (v/v) | | | + | + |
| Wnt3a | — | | 50% (v/v) | | | | + |
| N2 | Gibco | 17,502 | 1× | | | + | + |
| B27 | Gibco | 17,504 | 1× | | | + | + |
| HEPES | Gibco | 15,630 | 10 mM | | | + | + |
| Gentamycin | Gibco | 15,750 | 50 μg/mL | + | + | + | + |
| Amphotericin B | Gibco | 15,290 | 2.5 μg/mL | + | + | + | + |

WME, William's medium E; ADF, advanced DMEM/F-12; EGF, epithelial growth factor.

WME, William's medium E; ADF, advanced DMEM/F-12; EGF, epithelial growth factor.

Human Primary Intestinal Organoids and Intestinal Biopsy Samples

Human organoids were generated from biopsy samples collected at Weill Cornell Medicine or obtained from the In Vivo Animal and Human Studies Core at University of Michigan Center for Gastrointestinal Research. To generate organoids, human colon or ileum biopsy samples were cut into pieces (approximate 1 mm in size) and washed with cold DPBS by pipetting 2-3 times. Samples were treated with collagenase type IV (Worthington, 2 mg/ml in F12K medium) at 37° C. for 30 mins with pipetting every 10 mins. Digestion was terminated by adding F12K with 10% FBS, followed by filtration with a 100 mm cell strainer (VWR). Pelleted crypts were resuspended in human 31) Organoid Culture Medium (HCM; Table 1B) and Matrigel™ with a 1:5 volume ratio and embedded with 10-20 crypts per 10 μl droplet. Human organoids were expanded in HCM and differentiated in Human 3D Organoid Differentiation Medium (HDM; Table 1B) for 72 hours.

Mouse and human colonic tissues used for experimentation were generally taken from proximal colon unless indicated otherwise.

TABLE 1B

Media for Human Organoid Culture & Differentiation

| Human 3D Organoid Culture Medium (HCM) | | Human 3D Organoid Differentiation Medium (HDM) | |
|---|---|---|---|
| Reagents | Final Conc. | Reagents | Final Conc. |
| Glutamax | 2 mM | Glutamax | 2 mM |
| HEPES | 10 mM | HEPES | 10 mM |
| Primocin | 100 μg/ml | Primocin | 100 μg/ml |
| EGF | 50 ng/ml | Y-27632 | 10 μM |
| N2 supplement | 1X | A83-01 | 500 nM |
| B27 supplement | 1X | B27 supplement | 1X |
| N-acetyl-L-cysteine | 1 mM | N-acetyl-L-cysteine | 1 mM |
| L-WRN Condition Medium & | 50% V/V | L-WRN Condition Medium & | 25% V/V |
| SB202190 | 100 μM | Gastrin | 10 nM |
| A83-01 | 500 nM | FGF-2 | 50 ng/ml |
| Y-27632 * | 10 μM | IGF-1 | 100 ng/ml |
| Gastrin | 10 nM | DAPT # | 5 μM |
| Nicotinamide | 10 mM | In Advanced DMEM/F12 | |
| CHIR99021 | 2.5 μM | # DAPT was added for secretion cells niche differentiation (Goblet cells et, al.) | |
| In Advanced DMEM/F12 | | | |

Generation of the CAGSATB2GFP Transgenic Mouse Line

The knock-in construct, modified from pR26CAG/GFP Dest (Addgene #74281) (Chu et al., 2016), carries a CAG promoter followed by a Neomycin-transcription stop cassette flanked by Loxp sites, HA epitope-tagged murine Satb2, an IRES element, and GFP. Donor DNA consists of a 1,083 kb left arm and a 4,341 bp G/GFP right arm. The construct was targeted to the ROSA26 locus by pro-nuclear injection paired with purified CAS9 protein (purchased from IDT) and a validated gRNTA targeting ROSA26 (ACUCCAGUCUUUCUAGAAGA; SEQ ID NO:10). The transgenic progenies were genotyped for cassette integration into the genomic locus of ROSA26. A total of 5 double transgenic lines were established by crossing with the Vil-CreERT2 mouse line. Transgene expression in adult mice was analyzed by immunohistochemistry for GFP, the HA epitope tag, and SATB2 after tamoxifen (TAM) injection at 2 months of age. This analysis yielded very similar results from all 5 transgenic lines.

CRISPR-Mediated Gene Knockout in Colonic Organoids and Genomic Targeting Efficiency Calculation Satb2 and Foxd2 sgRNAs were designed with either Broad Institute online software or the Synthego CRISPR design tool and cloned into a LentiCRISPRv2 vector (Addgene plasmid #52961) (Sanjana et al., 2014). The lentiviruses were packaged with second-generation helper plasmids by transfection with lipofectamine 3000 (Thermo Fisher Scientific, L3000015) and titrated by counting puromycin resistant clones in HEK293T cells 5 days after infection.

To generate the colonic organoids with gene ablation, single cell suspensions of 105 murine or human colonic organoids were mixed with 20 μl of $10^8$ $TCID_{50}$/ml of virus in 200 μl medium (either WENR for murine or HCM for human) in one well of a non-tissue culture treated 24 well plate and centrifuged at 1,100 g at 37° C. for 30 mins to facilitate infection. After centrifugation, 200 ml of culture medium was added and the plate was further incubated for 4 hours at 37° C. Cells were then resuspended, pelleted, and embedded in Matrigel™. Puromycin selection (1.0-2.5 μg/ml) was initiated 4 days post infection and lasted for 4 days. After puromycin selection, colonic organoids were seeded into new Matrigel drops and cultured in differentiation medium (DEM) (WENR medium without WRN conditioned medium and with the addition of 1 μg/ml RSpondin and 10 μML-161,982). Three days after differentiation, the organoids were either directly lysed in RLT buffer (QIAGEN) for RNA exaction, or incubated with cell recovery solution on ice, to remove Matrigel, for immunofluorescence and immunoblotting analyses.

The CRISPR-mediated deletion efficiency of Satb2 was analyzed with immunofluorescence and immunoblotting, using a rabbit monoclonal anti-Satb2 antibody (Key resource table). For Foxd2, multiple commercially available antibodies were tested, but none was found suitable for immunofluorescence or Western Blot. Instead, the disruption efficiency at the Foxd2 genomic locus was evaluated, using a DNA mismatch detection assay with T7 endonuclease1 (NEB). Genomic DNA was extracted with an E.Z.N.A tissue DNA kit (OMEGA). Foxd2 target regions were PCR amplified with Phusion High-Fidelity DNA polymerase (NEB) plus Kapa Hifi GC buffer (ThermoFisher), according to the manufacturer's protocol. PCR products were pre-amplified with forward primer: GGCATAAGCTTTGACTTCCAGTAAC (SEQ ID NO:11) and reverse primer: GTGATGAGGGCGATGTACGAATAA (SEQ ID NO: 12), at high annealing temperature (68° C.) for 10 cycles, followed by 60° C. for 30 cycles. The heteroduplexed PCR products from Foxd2 CRISPR KO and homogeneous PCR products from the control group were incubated individually or mixed at a 1:1 ratio with T7 endonuclease 1 at 37° C. for 15 mins. The reaction was stopped by adding 1 mM EDTA (final concentration) and purified with the ZYMO DNA purification Kit. DNA fragment concentration was visualized by agarose gel electrophoresis and quantified with an Agilent TapeStation (A.02.02).

The gene modification percentage was calculated using the following formula:

$$\% \text{ gene modification} = 100 \times (1 - (1 - \text{fraction cleaved})1/2)$$

For the group mixed 1:1 with the control DNA fragment, the formula used is as below:

$$\% \text{ gene modification} = 200 \times (1 - (1 - \text{fraction cleaved})1/2)$$

Bulk RNA Sequencing Analysis

Bulk RNA-seq was performed as previously described with the exception of mapping to the mouse reference genome mm10 instead of mm9 (Banerjee et al., 2018). Briefly, reads alignment was performed by STAR package (Dobin et al., 2013). The raw count tables were generated by featureCounts (Liao et al., 2014). The DEseq2 package was used for differential expression analysis (Love et al., 2014). The Limma package (Ritchie et al., 2015) was used to remove donor-donor variance and batch-effect. Differentially expressed genes were generally determined using parameters of adjusted p value<0.05 and LFC>2 or <−2 unless specified. The heatmaps were plotted using the R package, pheatmap. GO enrichment analysis and GSEA analysis were conducted with the clusterProfiler package (Yu et al., 2012)(Wu, 2021) and GSEA desktop software (Subramanian et al., 2005).

In Vivo Time Course SATB2 Deletion

Satb2$^{cKO}$ mice were injected once with tamoxifen at 2 mg per 25 g body weight. The proximal ⅓ of the colon was collected at days 1, 2, 4, and 6 post-injection. Non-injected Satb2$^{cKO}$ mice (day 0) and injected Satb2$^{f/f}$ littermates served as controls. For RNA-seq, epithelial cells were isolated by three subsequent incubations with 10 mM EDTA and 1 mM DL-Dithiothreitol (DTT) in cold DMEM (GIBCO) for 10 min on a rotator, vigorous shaking, and collection of supernatants. All three supernatants were combined, centrifuged for 2 min at 400 g and lysed in TRIZOL (Life Technologies). RNA was extracted with TRIZOL Plus RNA purification kit (Life Technologies) according to manufacturer's instructions combined with on-column DNase-treatment (QIAGEN) and sent out to Novogene Corp. inc. (CA, USA) for quality control, library preparation, and sequencing. The DEseq2 R package was used to normalize the raw feature counts. The likelihood Ratio Test (LRT) was used to identify Differentially Expressed Genes (DEGs) across time-points with the threshold adjusted p value<0.01. The normalized counts of DEGs were transformed by varianceStabilizingTransformation (VST) function and scaled by scale function. The distance of DEGs was calculated by the dist function. Gene expression patterns across time points were then clustered by hierarchical clustering. The tree was then cut by the cutree function with the parameter k=9. The mean values were used in the data visualization.

ATAC-Seq

ATAC experiments were performed following the Omni-ATAC protocol (Buenrostro et al., 2015) as previously described (Banerjee et al., 2018). Briefly, 50K intestinal epithelial cells were purified by FACS and pelleted by centrifugation at 500 g at 4° C. for 5 mins. Nuclei were exacted in ATAC-Resuspension Buffer (RSB, 10 mM Tris-HCl pH 7.4, 10 mM NaCl, 3 mM $MgCl_2$) with 0.1% NP40, 0.1% Tween-20, and 0.01% Digitonin. DNA was fragmented by Nextera Tn5 Transposase (Illumina, 2003419) and immediately purified with a MiniElute PCR Purification Kit (QIAGEN). For ATAC-seq library building, NEBNext 2× MasterMix (New England Biolabs) was used to pre-Amplify for 5 cycles and determine the required number of additional cycles by qPCR amplification. The final libraries were size selected (200 bp to 800 bp, including index) with AMPure XP beads (Beckman), purified, and loaded for sequencing.

The purified libraries were sequenced by Novogene on Illumina HiSeq-2000, to obtain paired-end 150 bp reads. Alignment BAM files for the ATAC-seq were generated with the mm10 reference genome using nf-core pipelines. Narrow peaks were called using standard MACS2 (Feng et al., 2012). ATAC-seq peak files that had regions of less than 1 kb from transcriptional start site (TSS) were removed using bedtools (Quinlan and Hall, 2010). Biological replicates were concatenated and sorted, and peaks merged within a maximum distance of 500 bp.

Cell Sorting and 10× Genomic Sample Preparation for Single Cell RNA Sequencing

To purify intestinal cells for scRNA-seq, a protocol described by Haber et al. (2017) was used. Briefly, murine proximal colon from TAM injected Vil-Cre$^{ER}$; Satb2$^{f/f}$ (Satb2$^{cKO}$) mice, or proximal colon and entire ileum from TAM injected Satb2$^{f/f}$ (Controls) mice were harvested and rinsed in cold PBS. The tissues were incubated in 20 mM EDTA-PBS while rocking in a cold room for 90 mins. Every 30 mins, the tubes containing intestinal tissues were shaken vigorously for one minute, and dissociated epithelial fractions were collected. After 90 mins, the 3 collections from each tissue were combined and dissociated into single cells with TrypLE (one minute at 37° C.). The single cell suspensions in FACS buffer (1% glucose, 10 mM HEPES, 10 mM Y-27632, 1 mM N-acetyl-l-cysteine and 2% FBS in DPBS) were passed through a 40 mm filter and stained with anti-mouse CD326 (Epcam), anti-mouse CD31 and anti-mouse CD45 (Key resources table), Live Epcam$^+$, CD45$^-$, and CD31$^-$ epithelial cells, sorted by SONY MA900 in FACS buffer, were washed with 0.4% BSA in PBS and processed with 10× genomics single cell droplet sample preparation workflow at the Genomics Core facility at Weill Cornell Medicine.

Ten thousand (10,000) cells in Master Mix were loaded into each channel of the Chromium Controller cartridge to produce droplets. Beads-in-Emulsion (GEMs) were transferred, and GEMs-RT was undertaken in droplets by PCR incubation. After purification of first-strand cDNA from the post GEM-RT reaction mixture, barcoded and full-length cDNAs were amplified via PCR for library construction.

Enzymatic fragmentation and size selection were used to optimize the cDNA amplicon size. TruSeq Read 1 (read 1 primer sequence) was added during GEM incubation. A sample index and TruSeq Read 2 (read 2 primer sequence) were added via end-repair, A-tailing, adaptor ligation, and PCR. The final libraries were assessed by an Agilent Technology 2100 Bioanalyzer and sequenced on an Illumina NovaSeq sequencer.

scRNA-Seq Analysis with Seurat

Sequencing data from the Illumina NovaSeq were aligned to mouse mm10 in CellRanger 3.1.0. Seurat version 3.2.0 was used to perform quality control, count normalization, and clustering on the single cell transcriptomic data using standard methods as follows: unique molecular identifiers (UMIs) which barcode each individual mRNA molecule within a cell during reverse transcription were used to remove PCR duplicates. Cells expressing fewer than 300, or greater than 5,000 genes were removed to exclude non-cells or cell aggregates. Cells expressing greater than 18 percent mitochondrial related genes were also removed.

After quality control, the objects of wild-type (WT) ileum, colon and Satb2$^{cKO}$ colon were merged (hereafter named "the combined object") and the CellCycleScoring function was used to calculate a cell cycle score and assign a cell cycle status for each cell. Normalization of the combined object was conducted by SCTransform method in Seurat with regression out of confounding sources including mitochondrial mapping percentage and cell cycle scores (S score and G2M score). To perform linear dimensional reduction, RunPCA function was implemented with default parameters. To construct a K-nearest neighbor (KNN) graph, the Finder-Neighbors function was used and took first 22 principal components as input. The FinderClusters function with default parameters a resolution of 1.5 implements modularity optimization technique to iteratively group cells together in order to cluster the cells. Nonlinear dimensional reduction techniques FIt-SNE and UMAP were used to visualize the results.

The enriched transcripts in each cell cluster or groups of clusters were identified by the FindAllMarkers function using the following parameters: only.pos=TRUE, min.pct=0.3, logfc.threshold=0.3, and referred to as "global markers." Each cluster was then annotated based on the markers. To refine the annotation, wild-type colon object was additionally subseted and re-normalization performed. The cells from colonic object were re-clustered using first 30 PCs and a resolution of 1. The markers of WT colonic clusters were identified by the FindAllMarkers with the same parameters mentioned above. Each colonic cell cluster was annotated and re-assigned back to the combined object to refine cluster annotation.

For integrated analysis, per best practice suggestions in the Seurat package (Butler et al., 2018), the SelectIntegrationFeatures function was used to select the genes that were taken as input in the anchors identification procedure by the PrepSCTIntegration and the FindIntegrationAnchors functions using the merged control colon and ileum object as reference and the knockout object as query. The integration of the KO and WT objects were implemented by the IntegratedData function with the anchors identified previously. Dimension reduction, clustering and visualization were performed using the same methods mentioned above.

For ileal cell type scoring, the control wild-type objects were merged and SCTransformed using the same parameters mentioned above with the annotation retained. The scoring gene list for each cell type consists of the top 20 (avg_logFC) global cluster markers and all the differentially expressed genes between each ileal cell type and its colonic counterpart (e.g., enterocytes versus colonocytes) identified by the FindAllMarkers function and the FindMarkers function respectively with the following parameters: only.pos=TRUE, min.pct=0.3, logfc.threshold 0.3. The MH C genes were among the most differentially expressed between small intestine and colon. Their expression is strongly influenced by the microbiome and they do not constitute an intrinsic feature of the ileum. MHCII genes were removed from the gene lists. The gene lists were then applied as inputs in the AddModuleScore function with default parameters, which calculates module scores for feature expression programs on single cell level.

In order to identify stein cells in the samples, the combined object for the progenitor group was first identified as a subset and divided into two groups based on detection of Lgr5 gene expression. The stem cell gene list was taken as input for the AddModuleScore with default parameters to calculate stem cell signature score between these two groups. Eventually, the combined object was subset for the Lgr5 positive "Progenitor" in the G1 or S cell cycle. The subset went through the standard analysis procedure as mentioned above for normalization, clustering and visualization with the first 20 PCs and a resolution of 0.8. Four clusters were identified, and their makers were found by the FindAllMarkers function. According to the markers, cluster 1 appeared to be Goblet progenitors and thus was removed.

Dual Cross-Linking ChIP-Seq and Cut & Run Enhancer-Seq

ChIP for Transcription Factors (TFs) SATB2, HNF4A, and CDX2, was performed as described (Saxena et al., 2017). EDTA stripped primary intestinal glands were cross-linked with 2 mM disuccinimidyl glutarate (DSG, Thermo Fisher Scientific, 20593) at room temperature (RT) for 45 mins, followed by 1% formaldehyde (Sigma, F8775) fixation for 10 mins. For each experiment, 50 µl of pelleted cross-linked cells were resuspended in 350 µl sarkosyl lysis buffer (0.25% sarkosyl, 1 mM DTT and protease inhibitor in RIPA buffer (0.1% SDS, 1% Triton X-100, 10 mM Tris HCl, 1 mM EDTA, 0.1% sodium deoxycholate, 0.3 M sodium chloride, pH 7.5)) and sonicated at 15% amplification by a tip sonicator (Qsonica, Q125) to obtain 200 bp to 800 bp chromatin fragments. Lysates were spun down at 20,000 g at 4° C. to remove insoluble fractions, then diluted in RIPA buffer with protease inhibitor in a final 2 mL volume. Diluted lysates were incubated with anti-transcription factor anti bodies at 4° C. overnight and were additionally incubated with 30 µl protein A/G magnetic beads (Thermo Fisher Scientific, 88803) for 90 mins the next day. This was followed by 6 washes with cold RIPA buffer beads. Cross-links were reversed overnight by incubating at 65° C. in 1% SDS and 0.1 M $NaHCO_3$. Any remaining proteins were digested by Proteinase K (Thermo Fisher Scientific, 26160) for 1 hour at 37° C. DNA was purified with a MinElute purification kit (QIAGEN, 28004). Libraries were prepared using the ThruPLEX DNA-Seq Kit (Takara bio, R400428 and R400427).

Cut & Run was performed by the Center for Epigenetics Research (CER) in Memorial Sloan Kettering Cancer Center. Briefly, single cell suspensions were collected as described in the single cell RNA sequencing section. Dead cells were removed using a Dead Cell Removal Kit (Miltenyi Biotec). Cells ($10^5$) were attached to Concanavalin A conjugated magnetic beads, permeabilized, and incubated with histone enhancer maker antibodies at room temperature for 20 mins. pAG-MNase (1:1000) was added in digitonin buffer (5% digitonin, 60 mM HEPES, 0.5 M sodium chloride, 1.5 mM spermidine hydrochloride, protease inhibitor, pH 7.5) to bind with antibodies. Finally, targeted chromatins were digested and released into the supernatant. DNA was purified with a MinElute purification kit. Libraries were prepared using the ThruPLEX DNA-Seq Kit (Takara bio, R400665). All the libraries were size selected (200-800 bp) by AMPure XP beads and loaded for sequencing.

SATB2 Cut & Run experiment with FACS purified $LGR5^+$ stem cells was performed with the same method as Cut & Run described above, using polyclonal anti-SATB2 or control Rabbit IgG antibodies incubated overnight at 4° C.

ChIP-Seq Analyses for Transcription Factors

All reads (CDX2, HNF4A and SATB2) were trimmed with trim_galore (see website bioinformatics.babraham.ac.uk/projects/trim_galore/), and subject to quality control with FastQC before and after adaptor trimming. For ChIP-Seq, Bowtie2 (Langmead and Salzberg, 2012) was used to align the two independent ChIP-Seq analyses to the mouse (mm10) genome with default parameters. Aligned ChIP-Seq data in SAM format were transformed to DAM files and non-uniquely mapped reads were filtered-out. Duplicate alignments were then marked and removed using Sambamba (Tarasov et al., 2015). The merge function in samtools (Li et al., 2009) was used to merge the BAM files of different replicates and filter out non-uniquely mapped reads. Deeptools (Ramírez et al., 2014) bamCoverage (duplicate reads ignored, RPKM normalized) was used to generate bigWig files from BAM files. Reads that overlapped with the Broad Institute sequencing blacklist (ENCODE Project Consortium; see website at mitra.stanford.edu/kundaje/akundaje/release/blacklists/mm10-mouse/mm10.blacklist. bed.gz) were discarded. The mapped reads from the biological replicates were combined for each factor and then peak calling was performed using the ChIP-Seq (macs2) (Feng et al., 2012) peak caller (v2.2.7) with parameters callpeak-f BAMPE-g mm -p 0.0000000001, and was controlled by KO/input. Heatmaps of ChIP-Seq were created by quantile normalized bigWigs using computeMatrix, plotHeatmap, and plotProfile from deeptools.

MAnorm (Shao et al., 2012), software designed for quantitative comparisons of ChIP-Seq datasets, was applied to compare ChIPSeq signal intensities between samples. The window size was 1 kb, which matched the average width of the identified ChIP-Seq peaks. Tissue specific peaks were defined using the following criteria: (1) defined as 'unique' by the MAnorm algorithm, (2) P value<0.01, (3) raw counts of unique reads 10. Peaks common to two samples were defined using the following criteria: (1) defined as 'common' by the MAnorm algorithm and (2) raw read counts of both samples>10.

The annotatePeaks function in HOMER (Heinz et al., 2010) was used to annotate the peaks. To identify the distribution of the binding sites of ChIP-Seq data, peak sites were mapped to TSS (transcription start site), TTS (transcription termination site), Exon (Coding), 5' UTR Exon, 3' UTR Exon, Intronic, or Intergenic, which are common annotations defined by HOMER. A promoter region was defined as a region within ±2 Kb from the TSS. Enriched motifs were identified within 200 bp regions centered on SATB2 ChIP-seq peak summits using findMotifsGenome.p1 with options '-length-len "8, 10, 12"' and '-size 200' on the repeat-masked mouse genome (mm10r) from HOMER.

Cut & Run Analyses for Histone Modifications

Reads (H3K4me1 and H3K27ac) were trimmed with trim_galore. Paired-end reads were then mapped to the mm10 genome using Bowtie2, with parameters as described by Skene et al. (2018) using-local-very-sensitive-local-no-unal-no-mixed-no-discordant-phred33-I 10-X 700. Only uniquely mapped reads were retained with samtools. Peaks were called from macs2 with pooled reads and with both replicate samples by merge broad and narrow peak files. For the enhancer analysis, only peaks±2 Kb outside TSSs were permitted, using 'distal peaks' as enhancer peaks. Tissue specific enhancers were identified between ileum and colon using MAnorm.

Immunohistochemistry, Edu Labeling, and Western Blot

Intestinal tissues were processed as described by Ariyachet et al. (2016). Organoids were removed from Matrigel with Cell Recovery Solution (Corning 354253), fixed with 4% paraformaldehyde in PBS on ice for 30 mins, and then processed with the same procedure as the intestinal tissues. Immunohistochemistry was performed using a standard procedure, incubating with primary antibodies at 4° C. overnight, followed with secondary antibodies at room temperature for 45 mins. A Click-iT™ EDU Cell Proliferation Kit with Alexa Fluor® 555 (C10338) was used to evaluate proliferation. The images were captured using either a confocal microscope (710 Meta) or a Nikon fluorescence microscope. For western blot analysis, a monoclonal rabbit anti-SATB2 antibody was used to bind SATB2 protein, followed by an incubation with a secondary anti-Rabbit Peroxidase (HRP). Protein bands were visualized using enhanced chemiluminescent substrate (Pico from Thermo fisher) and recorded by a Li-COR C-Digit or li-COR odyssey clx blot scanner. The relative signal intensity was quantified by ImageJ (v1.51 (100)).

For immunohistochemistry, samples were processed through heat mediated antigen retrieval in Citric Acid buffer (pH 6.0) except for the samples that stained for monoclonal anti-SATB2 antibodies, which were processed in Tris-EDTA (pH 9.0). Samples were then stained with primary rabbit antibodies, followed by Goat anti-Rabbit HRP polymer (Vector Laboratories, MP-7451) incubation, and finally, developed with AP (Magenta color, Vector Laboratories, MP-7724) or DAB (Brown color, Vector Laboratories, SK-4103) HRP Substrate. The images of swiss rolled colon were taken by a confocal digital slide scanner in MSKCC image core and processed by Caseviewer (v2.4). An Alcian Blue Stain Kit (Vector Laboratories, H-3501) was used to stain goblet cells.

Quantitative Analysis of Histological Staining and Fluorescence in ImageJ

All sections were evaluated by multiple people, including a clinical pathologist. All image quantifications were done in ImageJ (Fiji, Version: 2.1.0/1.53c) as previously described (Fuhrich et al., 2013; Jensen, 2013). Briefly, immunofluorescence images were split into individual channel by click image>color>split channel. Relative signal intensity was calculated by comparison to the average density of the controls.

For immunohistochemistry images, the hematoxylin and specific antibody staining were separated into three different panels with the function of color deconvolution for PAS (AP development) or H-DAB (DAB development). Next, epithelial area was overlaid on the AP/DAB signal channel image. The final epithelial AP/DAB intensity (f) was calculated according the formula: f=255−mean intensity (obtained from the software analysis, range from 0-255, zero=deep brown, highest expression, 255=total white), Relative signal intensity was calculated by comparison to the average density of the controls.

Immunoprecipitation

EDTA stripped colonic grand epithelium cells from control and $Satb2^{cKO}$ mice were cross-linked with DSP (Thermo Fisher Scientific, PG82081) at room temperature for 45 minutes. Pellets of epithelial cells were incubated with RIPA buffer and sonicated at 15% amplification for 20 seconds. After 10 minutes (maximum speed down), supernatants were incubated with anti-CDX2 and anti-HNF4A antibodies overnight in a cold room with a rotation speed of 10 RPM. After adding 30 μl protein A/G magnetic beads for 90 minutes on the next day, the protein and beads complex was pulled down by a magnetic stander. Next, six cold RIPA buffer washes were performed. Then cross-links were cleaved by 50 mM DTT with boiling for 5 mins. Immunoblots were used to visualize the interaction between target proteins.

$[^{14}C]$-Taurocholic Acid and $[^{3}H]$-Glucose In Vivo Absorption Study $^{14}C$-Taurocholic acid and $^{3}H$-Glucose were purchased from American Radiolabeled Chemicals, Inc. To perform the absorption study, mice were fasted overnight for about 16 hours. Following deep anesthetization, a 2 cm section of the distal ileum or proximal colon was cleaned of luminal content by repeated flushing with saline and was tied on both ends with sutures to create a sealed pouch. Two microcuries (ρCi) $^{3}H$-glucose and 0.6 μCi $^{14}C$-Taurocholic acid dissolved in 100 μl 10% dextrose solution were injected into the pouch. After 5 or 20 mins, blood was collected from the hepatic portal vein with a 27-gauge needle, Plasma was harvested after centrifugation at 12,000 rpm for 4 mins at 4° C. Plasma protein was precipitated with the addition of $Ba(OH)_2$ and $ZnSO_4$ to 20 μl plasma. The supernatant was dissolved in Ultima Gold Scintillation fluid (PerkinElmer). A liquid scintillation counter with dual channels for $^{3}H$ and $^{14}C$ was used to measure radioactivity in all samples.

For liver sampling, the right upper lobe from each mouse was removed and stored at −20° C. Frozen tissues were homogenized in $dH_2O$ (50 mg of tissue in 500 μl of $dH_2O$) with a Dounce homogenizer. Following homogenization, the glass tubes were placed in a heat block for 10 mins at 100° C., vortexed, and cooled to room temperature. The homogenized samples were centrifuged at 16,000 g for 5 minutes. Supernatants were collected. 500 μl of supernatant per sample was added to scintillation vials containing the scintillation cocktail for counting.

Disaccharidase and Dipeptidyl Peptidase IV (DPP4) Assay

After Matrigel removal, differentiated human organoids were transferred to BSA-pre-coated 1.5 mL Eppendorf tubes and washed three times in PBS. For the disaccharidase enzyme activity assay, 5 mg of an organoid pellet was incubated with 100 µL of 56 mM sucrose in PBS or PBS only at 37° C. for 45 mins. Aliquots of the supernatant were sampled for glucose detection using the Glucose Colorimetric Assay Kit (Cayman), according to the manufacturer's protocol. Briefly, the samples were diluted with PBS in a 1:1 and 1:2 ratio to ensure glucose concentration levels in the standard range (0-25 mg/dl). The enzyme and samples mixtures were incubated at 37° C. for 10 mins. The absorbance (510 nm) was measured with a plate reader (SpectraMax M2). Glucose concentration was determined by comparison to a glucose standard curve. For the DPP4 assay, Gly-Pro-p-nitroanilide hydrochloride (Sigma, G0513) in PBS was added to an organoid pellet at a final concentration of 1.5 mM. The organoid tubes were incubated at 37° C. in a tissue culture incubator with the lip open for 30 mins and were mixed every 10 mins. The supernatants were collected and absorbance was measured at 410 nm with a plate reader (SpectraMax M2). Released nitroanilide concentration was determined by comparison to a 4-nitroanilide (Sigma, 185310) standard curve (0-200 µg/ml). The concentration was finally normalized to a total cell lysate protein amount of 1 mg.

Quantification and Statistical Analysis

Quantification methods and statistical analysis are described in the figure legends. The exact biological or technical replicates are indicated within individual figure legends. The statistical results were presented as the means, individual values and error bars represent SD. GraphPad Prism 9 or R was used to determine statistical significance by unpaired/paired Student t test or Mann-Whitney U test if the data do not meet t test requirements (Normal distribution and similar variance). The exact p values are reported in each figure or indicated as *, p % 0.001; , p %) 0.01; *, p % 0.05, ns=not significant.

Example 2: SATB2 is Enriched and Required in Colonic Epithelium

To identify genes involved in maintaining colonic identity in adult mice and humans, the inventors interrogated their published RNA sequencing (RNA-seq) data of purified murine LGR5$^+$ intestinal stem cells (ISCs) from the duodenum and colon for colon-enriched transcription factors (TFs; Jadhav et al., 2016; Murata et al., 2020). In addition, duodenal and colonic organoids from human biopsy samples were cultured under high-WNT conditions (WNT3A-EGF-Noggin-Rspondin1 (WENR) medium), which favors intestinal stem cell growth (VanDussen et al., 2019), and RNA-seq was used to identify transcription factors (TFs) enriched in human colonic organoids.

Besides posterior Hox genes, two transcription factors, SATB2 and FOXD2, were enriched in murine and human colon (FIG. 1A). Immunoblots and immunohistochemistry (FIG. 1B, 1C) revealed prominent SATB2 expression in adult mouse cecal and colonic epithelia, including in LGR5$^+$ intestinal stem cells at the crypt base.

To assess any requirements SATB2 and FOXD2 may have in regulating colonic identity, CRISPR (clustered regularly interspaced short palindromic repeats), Cas9, and different guide RNAs were used to disrupt Satb2 or Foxd2 in murine colonic organoids. Several guide RNAs were evaluated for knock-out of Satb2, including guide RNAs that included one of the following sequences:

```
1:
                              (SEQ ID NO: 6)
TGCTCCACGACACAAAAGAC;

2:
                              (SEQ ID NO: 7)
GATTCCTGTCTTTTGTGTCG;

3:
                              (SEQ ID NO: 8)
CTTTTGTGTCGTGGAGCAGT;

4:
                              (SEQ ID NO: 9)
TGTGTCGTGGAGCAGTTGGA
```

While each of these successfully modified the Satb2 gene, the first guide (SEQ ID NO:6) provided the highest modification frequency.

Experiments indicated that disrupting Foxd2 had little effect on the colonic transcriptome.

Figure 1B:
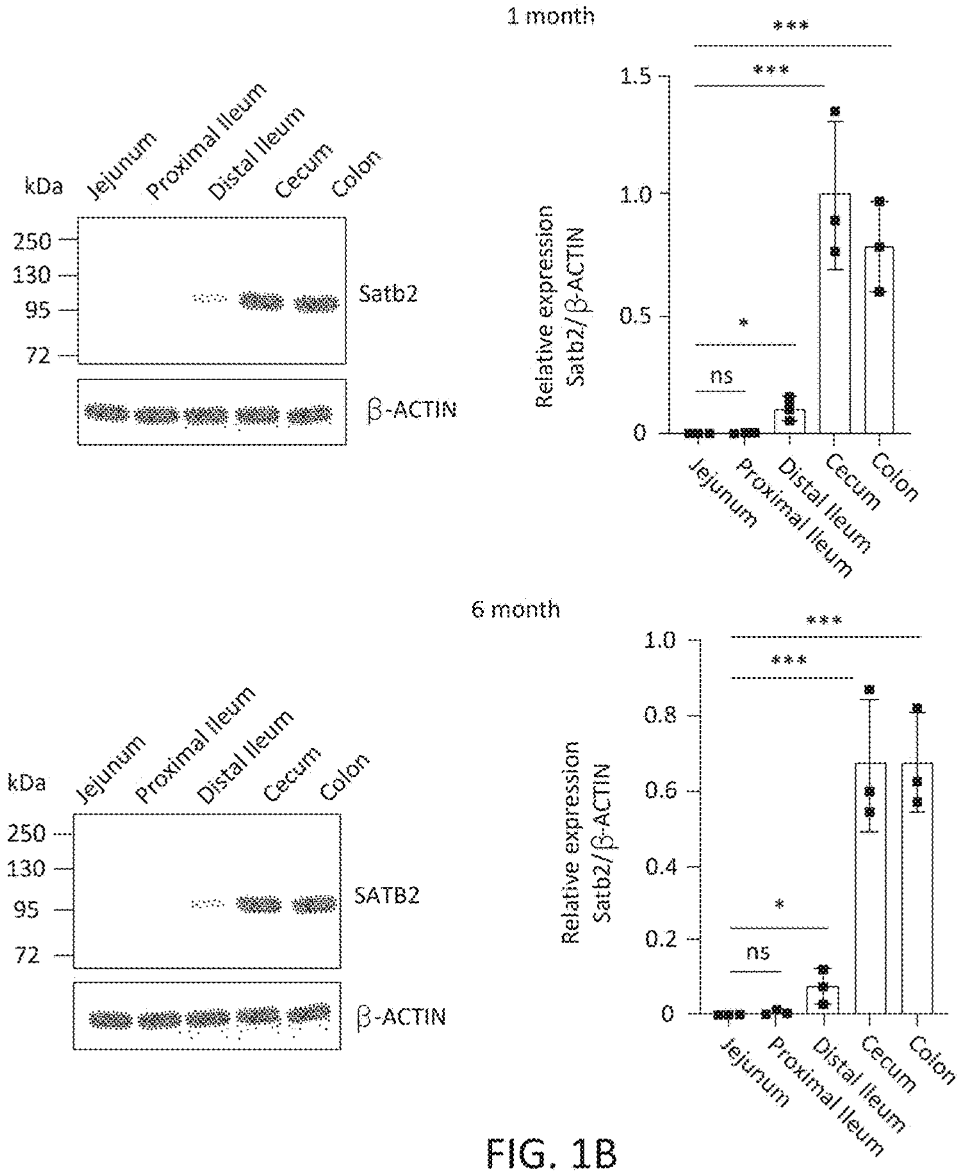
Figure 1C:
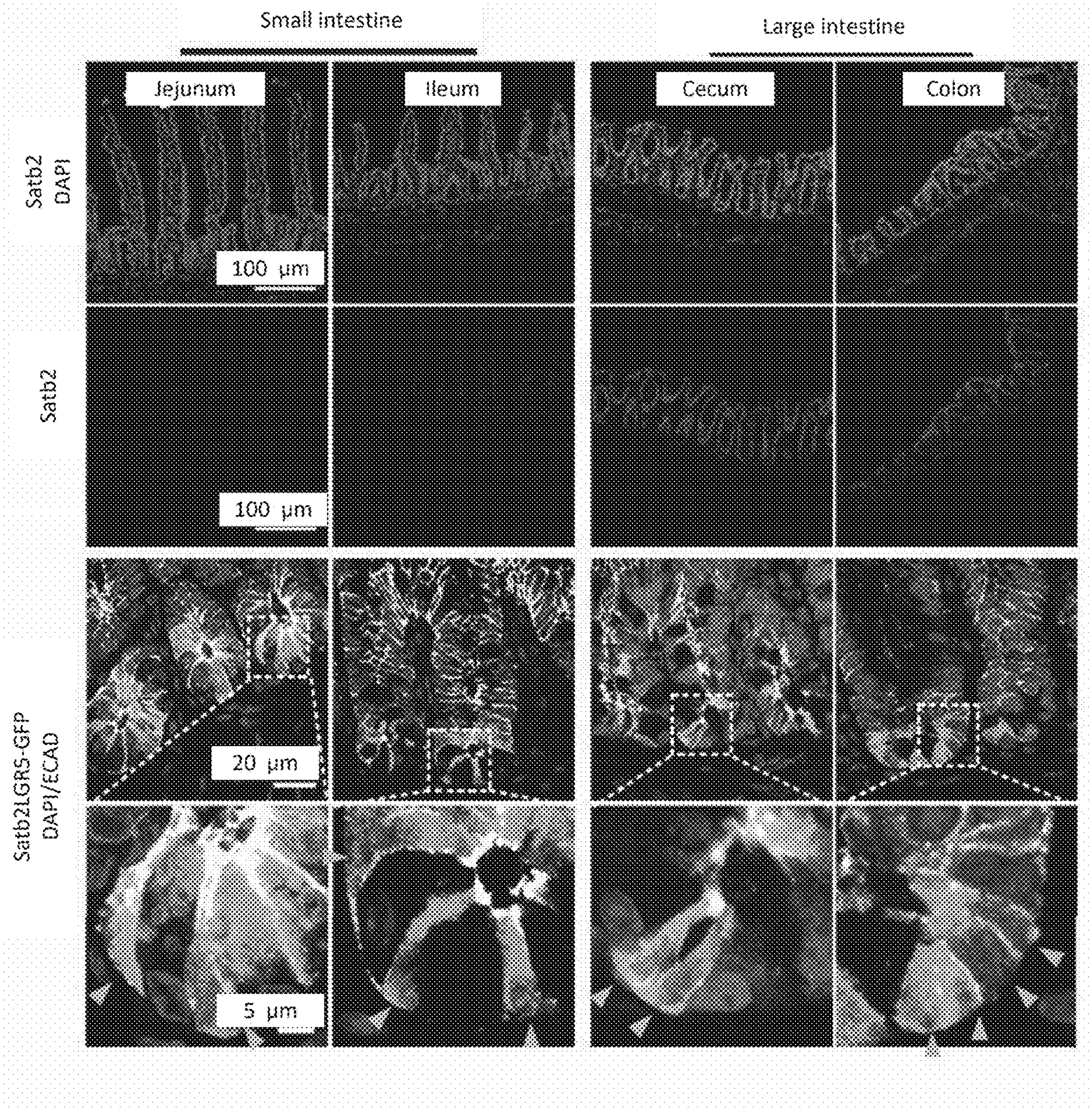
Figure 1D:
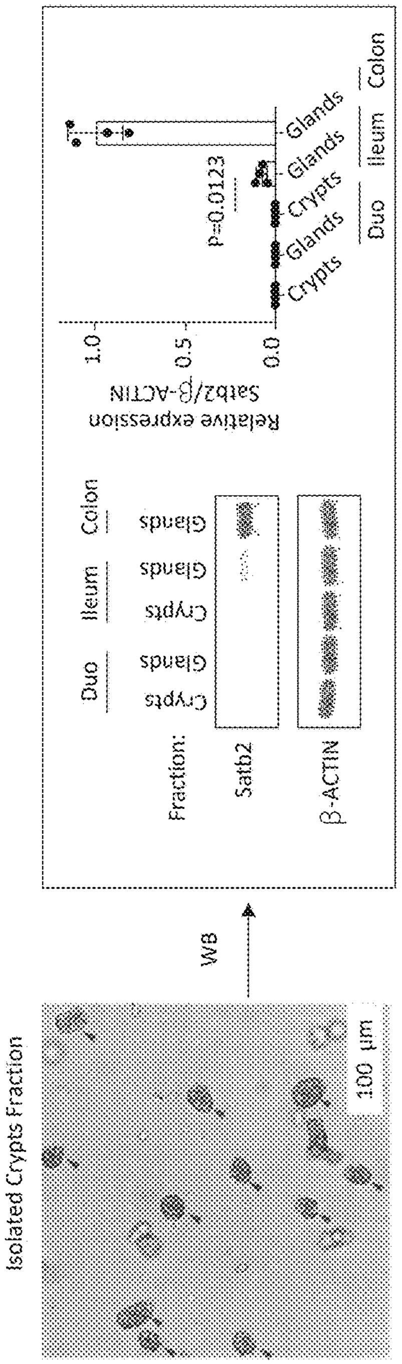
Figure 1E:
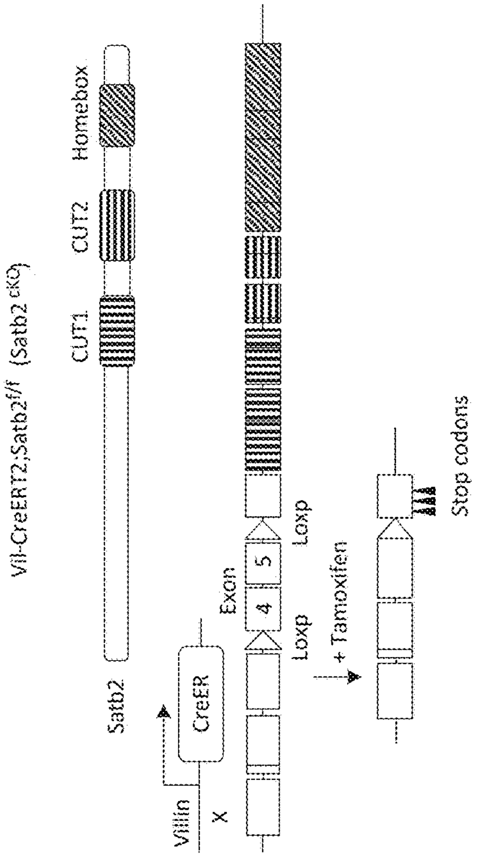
Figure 1F:
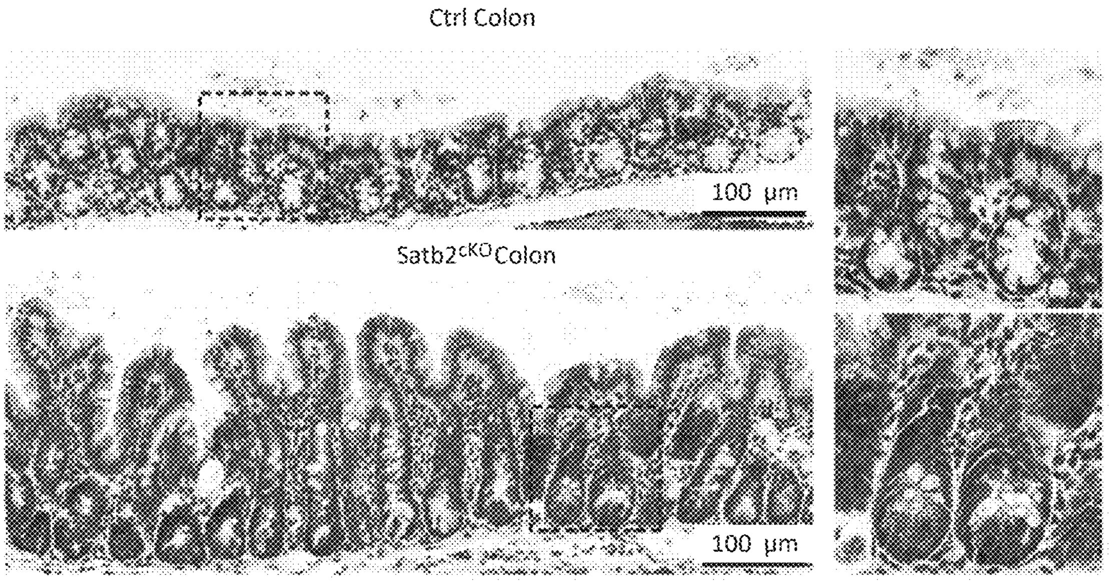

However, Satb2 loss significantly altered the mRNA profile, reducing colonic genes and increasing small intestine genes, indicating a requirement for Satb2 in maintaining adult colonic identity. Satb2 deletion efficiencies of 55%-95% were obtained in independent experiments (FIG. 1E-1F).

Example 3: Replacement of Colonic Mucosa with Ileum-Like Mucosa in Adult Mice after SATB2 Loss SATB2 is a homeodomain-containing chromatin factor expressed in developing craniofacial tissues and cortical neurons (Alcamo et al., 2008; Britanova et al., 2006, 2008; Dobreva et al., 2006). Human SATB2 mutations cause craniofacial anomalies and cognitive impairment (Zarate and Fish, 2017). SATB2 is also expressed in the fetal and adult murine and human hindgut and may be used as a diagnostic marker for colorectal cancer (Munera and Wells, 2017; Perez Montiel et al., 2015), but its intestinal functions are largely unknown.

Immunoblots and immunohistochemistry (FIG. 1B-1C) revealed prominent SATB2 expression in adult mouse cecal and colonic epithelia, including in LGR5$^+$ intestinal stein cells at the crypt base. Ileal villus cells showed weak nuclear SATB2 staining, but the small intestine was otherwise devoid of SATB2 (FIG. 1B). Immunoblotting confirmed lack of SATB2 expression in ileal crypts (FIG. 1D). qRT-PCR of LGR5$^+$ intestinal stein cells isolated by fluorescence-activated cell sorting (FACS) from different gut segments of Lgr5$^{CreERGFP}$ reporter mice showed high-level Satb2 mRNA in colonic but not in small intestine intestinal stein cells.

Figure 1G:
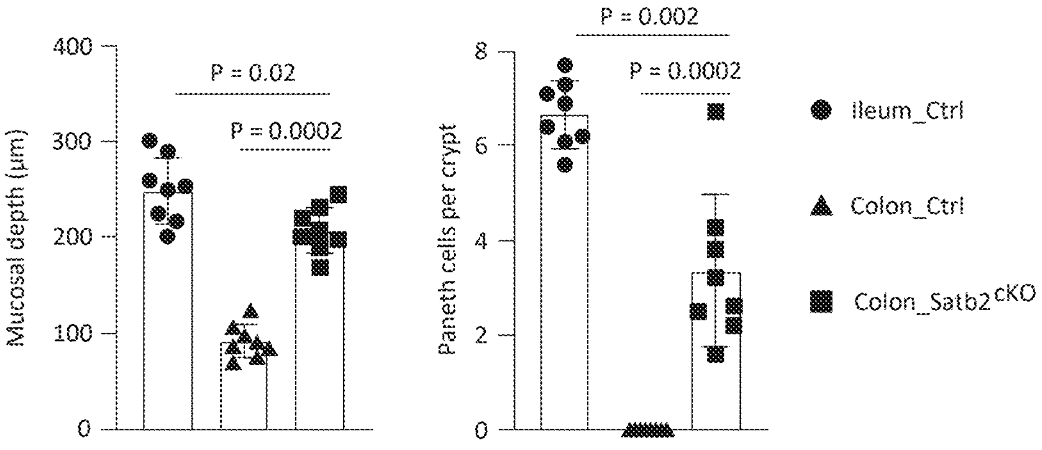

To evaluate intestinal Satb2 function in vivo, Satb2 was deleted in the intestinal mucosa within 2-month old Satb2$^{f/f}$ mice by crossing with the Villin-Cre$^{ER(T2)}$ strain (FIG. 1E), leading to nearly complete absence of SATB2. One month after tamoxifen (TAM) treatment, the colonic mucosa of Vil-Cre$^{ER}$; Satb2$^{f/f}$ mice (hereafter referred to as Satb2$^{cKO}$) was remodeled significantly, with the characteristic flat epithelium replaced by villus structures (mucosal depth, 208±24 µm versus 92±18 µm in Satb2$^{f/f}$ controls) and the presence of Paneth cells at the crypt base (FIG. 1F-1G), resembling the small intestine. Goblet cells stained with Alcian blue were decreased significantly (9%±2% of all epithelial cells) to levels comparable with the ileum (8%±1%) rather than the colon (15%±1.5%). Apoptosis rates were similar in mutant and control colon. 5-ethynyl-2-deoxyuridine (EdU) pulse-chase revealed accelerated movement of epithelial cells away from the crypt base (mutant versus control colon, $p<0.0001$, Tukey's multiple comparison test), similar to normal ileum (mutant colon versus control ileum, $p>0.99$, Tukey's multiple comparison test), which may account for the architectural remodeling in Satb2$^{cKO}$ colon.

Figure 1H:
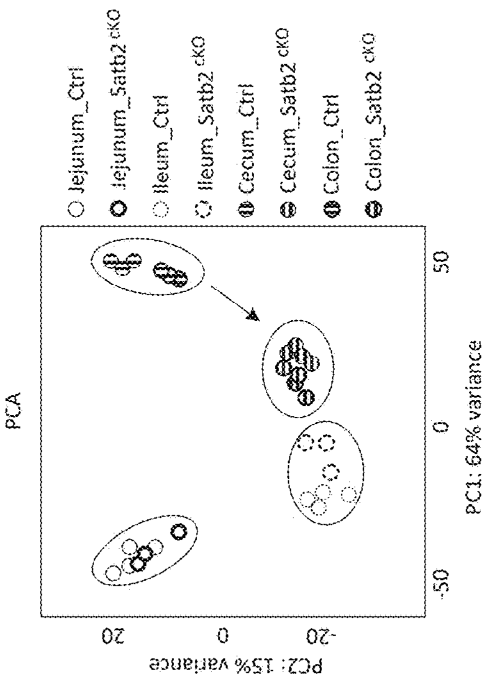
Figure 1I:
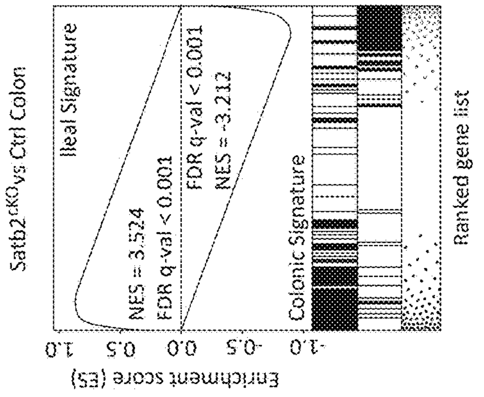

Whole-epithelium RNA-seq revealed little difference between Satb2-null and control jejunum or ileum, whereas the mutant cecal and colonic transcriptomes resembled that of normal ileum (FIG. 1H). Of the 362 ileal enriched genes (control ileal versus colonic transcriptome, log 2 fold change [LFC]>2, adjusted p [Padj]<0.05), 309 (85.4%) were upregulated in Satb2$^{cKO}$ colon, whereas 238 of 302 colon-enriched genes (78.8%) were downregulated (FIG. 1). Accordingly, molecular pathways that control digestion, absorption, and solute transport, reflecting ileal functions, were activated at the expense of colonic functions such as fatty acid and xenobiotic metabolism.

Figure 1J:
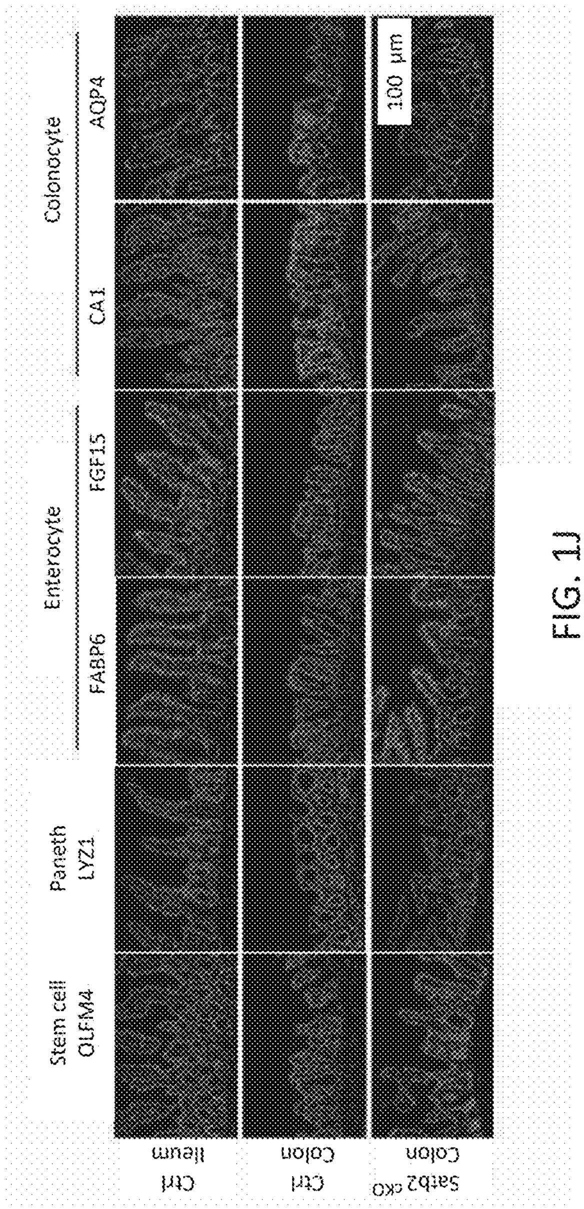

Immunohistochemistry revealed loss of colonic markers such as CA1 and AQP4 and gain of ileal markers such as OLFM4 (stein cells), FABP6, and FGF15 (enterocytes) and the Paneth cell product Lysozyme 1 (LYZ1) (FIG. 1J).

Figure 1K:
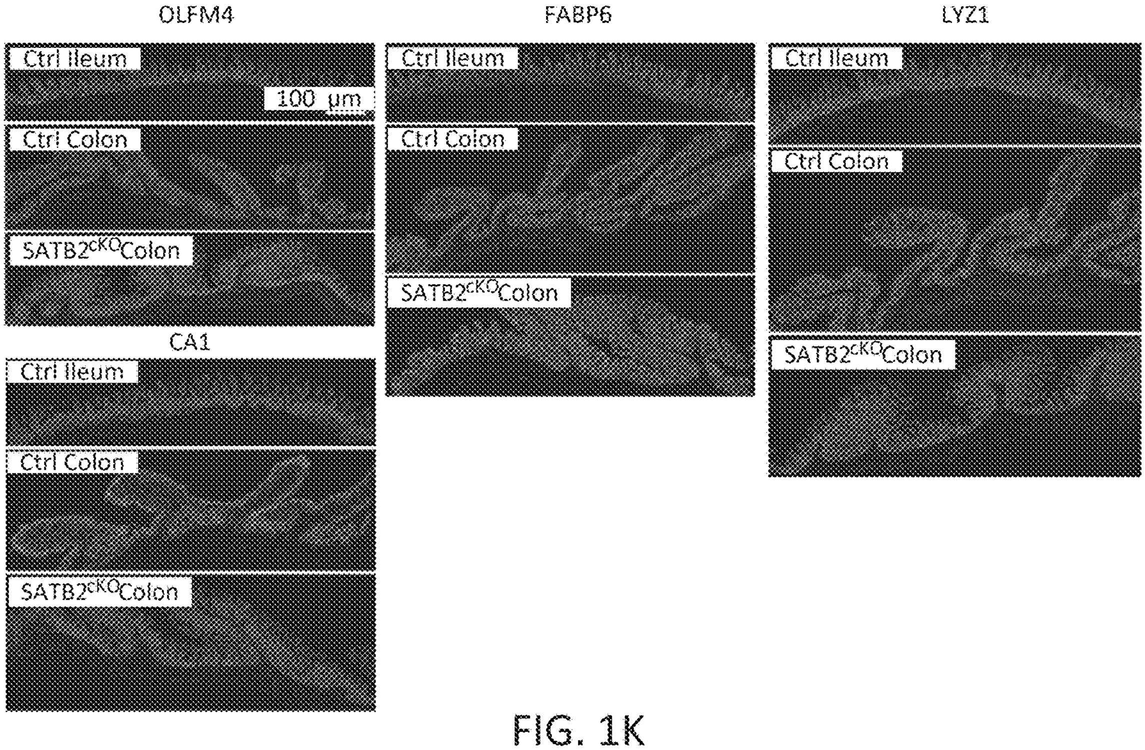
Figure 1L:
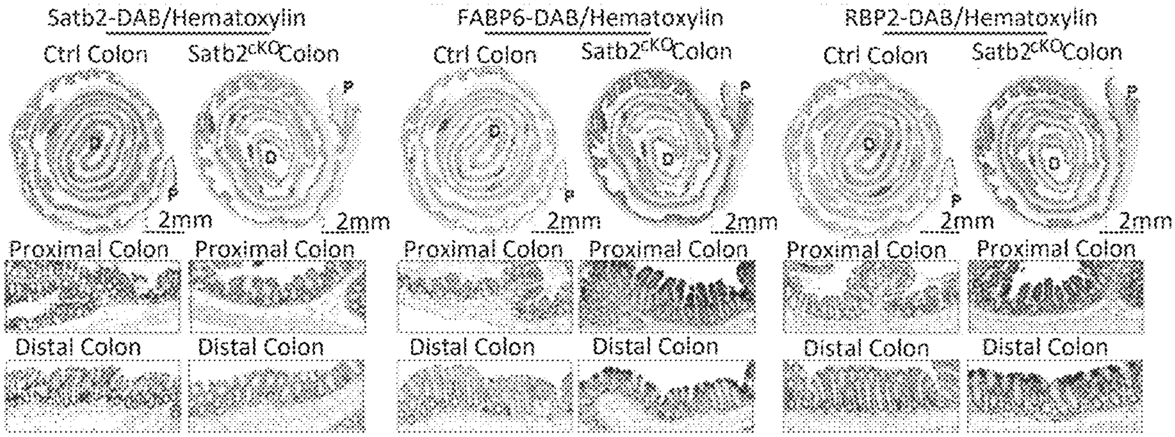
Figure 1M:
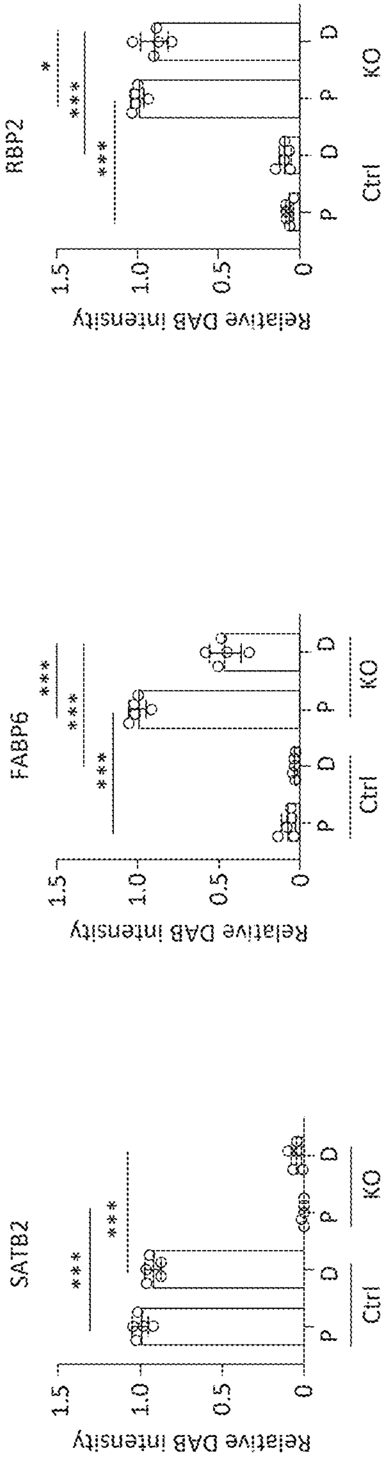

Tissue remodeling in Satb2$^{cKO}$ colon was accompanied by elevated immune cell presence. Six months after TAM treatment, Satb2-null colon was still wholly lined by an ileum-like mucosa with widespread expression of ileal genes in the proximal and distal colon, with the proximal colon displaying more prominent villi (FIGS. 1K-1M). These data indicate stable colonic-to-ileal conversion after SATB2 loss.

Example 4: Conversion of LGR5+ Colonic Stem Cells to Ileum-Like Stem Cells

Given the stable colonic remodeling after SATB2 loss, the inventors hypothesized that colonic intestinal stem cells may have converted into ileum-like intestinal stem cells. To evaluate this hypothesis, three different approaches were used: single-cell transcriptome profiling of LGR5$^+$ stem cells, organoid cultures, and Satb2 deletion from LGR5$^+$ intestinal stem cells.

Figure 2A:
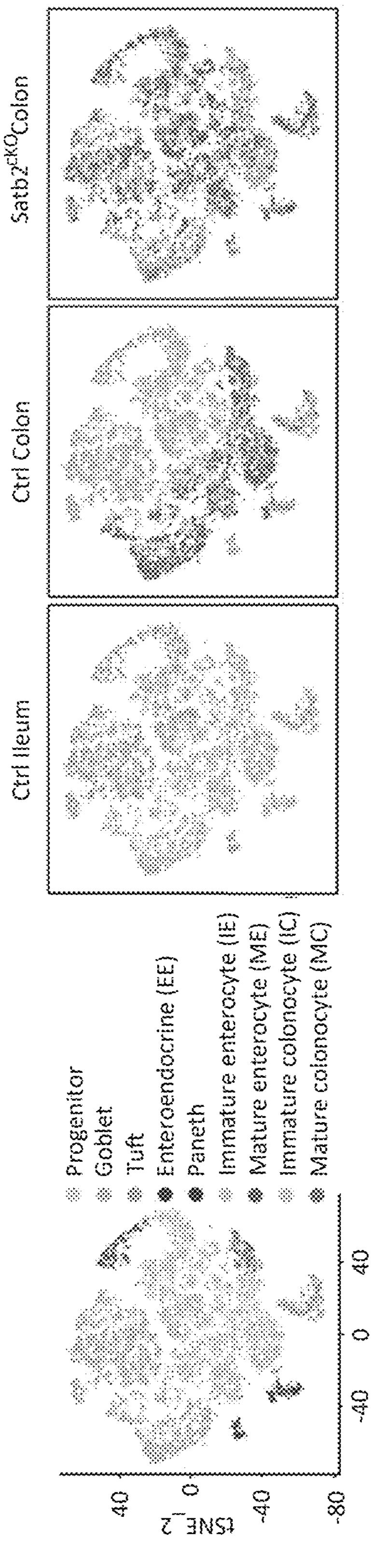
FIGS. 2A-2E illustrate conversion of $LGR5^+$ colonic stem cells to ileum-like stem cells after SATB2 loss.
Figure 2B:
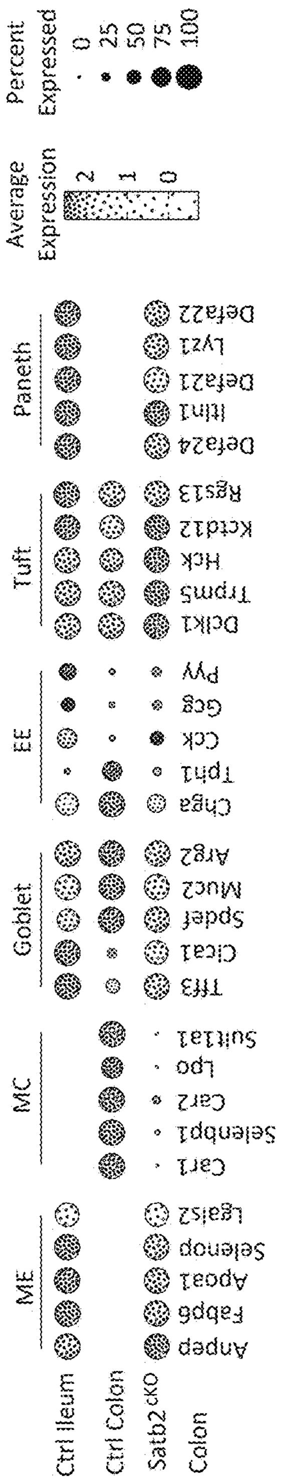

First epithelial cells were profiled using single-cell RNA-seq (scRNA-seq), where the epithelial cells were FACS-purified Epithelial Cell Adhesion Molecule (EPCAM)$^+$ CD45$^-$ CD3$^-$ cells obtained thirty days after tamoxifen (TAM) treatment. Transcriptomes from 3,912 control ileal, 3,627 control colonic, and 4,370 Satb2$^{cKO}$ colonic cells were integrated and partitioned into seven populations, including goblet, enterocyte, colonocyte, Paneth, tuft, and enteroendocrine (EE) cells, annotated with lineage-specific markers (Haber et al., 2017; FIG. 2A). Cells bearing low lineage markers but high proliferating genes (Mki67 or Mcm3/6) were classified as progenitors, which include LGR5$^+$ intestinal stem cells as a subset (FIG. 2A). A majority of differentiated cells from the Satb2$^{cKO}$ colon clustered with ileal cells (FIG. 2A) and expressed canonical ileal markers (FIG. 2B).

The similarity between control ileal and Satb2$^{cKO}$ colonic transcriptomes was further assessed using cohorts of genes enriched in each ileal cell type (ileal identity scores), which similarly showed broad adoption of ileal identity by Satb2$^{cKO}$ colonic cells. For example, colonocytes, representing 22.4% of the control colon, were replaced by enterocytes in Satb2$^{cKO}$ mice (21.5% of the total population).

Figure 2C:
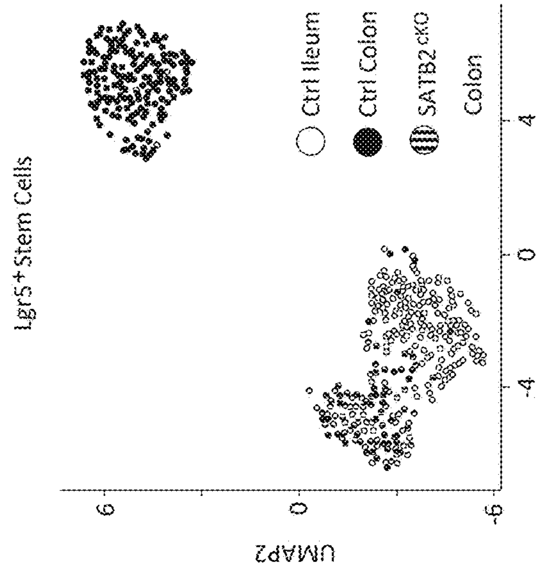

Lgr5$^+$ stem cells within the "progenitor" groups expressed high levels of the ISC markers Ascl2 and Axin2 and scored significantly higher than Lgr5$^-$ progenitors on a stem cell scorecard (Munoz et al., 2012) (Wilcoxon rank-sum test continuity correction $p<2.2\ e^{-16}$). Focusing on intestinal stem cell subsets at the G1/S cell cycle phase (control ileum, 209 cells; control colon, 230 cells; mutant colon, 155 cells), which have been proposed as basal stem cells (Biton et al., 2018), Satb2$^{cKO}$ colonic cells clustered with ileal and not with colonic intestinal stem cells (FIG. 2C). Compared with control colon, the ileum-like intestinal stem cells in Satb2$^{cKO}$ colon were enriched for Gene Ontology pathways of antimicrobial and innate immune responses and depleted of sulfur and phospholipid metabolism pathways.

Figure 2D:
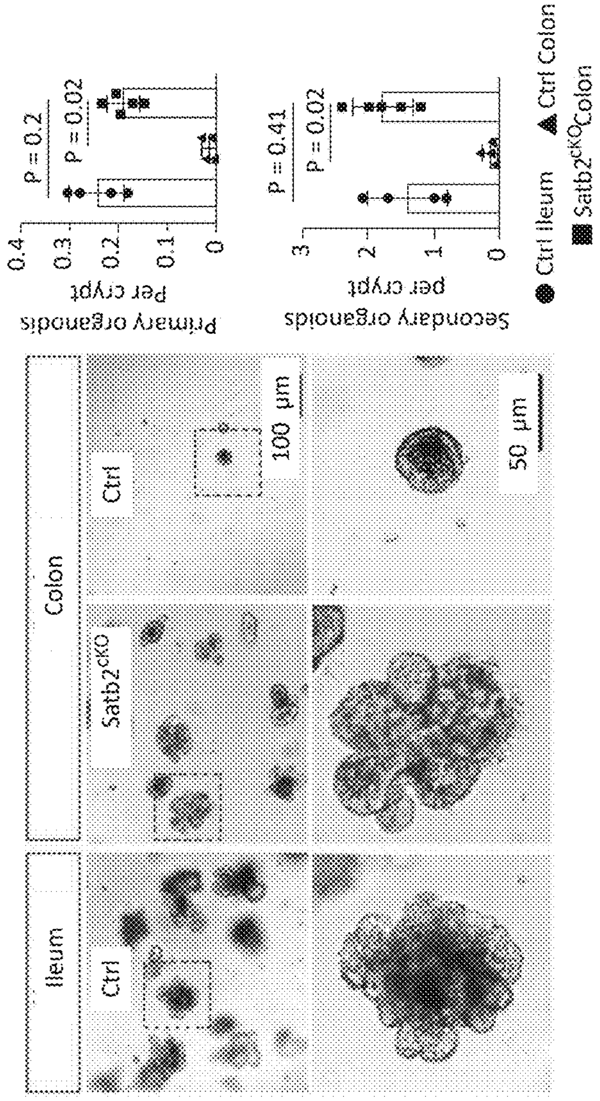

Next stem cells were evaluated in organoid cultures. Large and small intestine intestinal stem cells differ in their ability to form organoids in 3D Matrigel cultures. Colonic crypts fail to generate organoids in standard EGF-Noggin-Rspondin1 (ENR) small intestine medium lacking WNT3A (Sato et al., 2011). Crypts isolated from control ileum, control colon, and Satb2$^{cKO}$ colon produced spheroids in WENR medium containing high WNT3A. However, in ENR medium, control colonic crypts yielded only few non-branching spheroids (0.015±0.013 structures per crypt), and most of these could not be passaged, whereas control ileal (0.25±0.06 primary and 1.4±0.6 secondary structures per crypt) and Satb2-null colonic crypts (0.19±0.03 primary and 1.8±0.5 secondary structures per crypt) formed branching organoids that could be propagated (FIG. 2D).

Figure 2E:
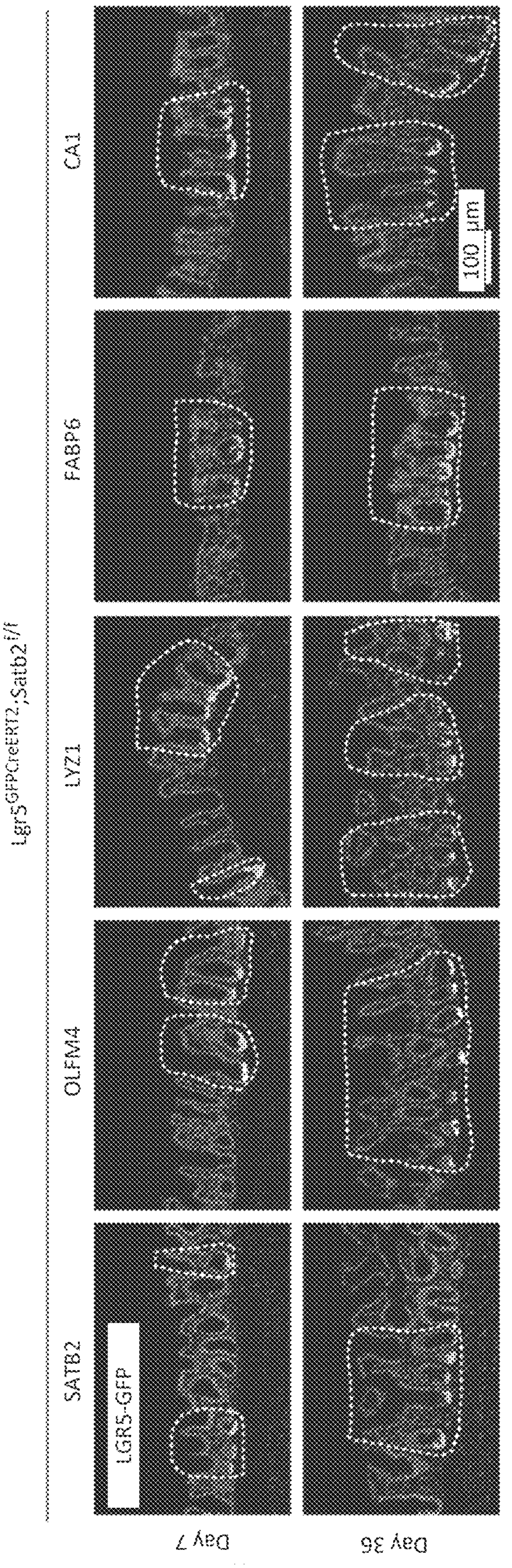

Last, Satb2 was directly deleted from LGR5$^+$ intestinal stem cells in Lgr5$^{GFP\text{-}Cre(ER)}$; Satb2$^{f/f}$ mice. Lgr5$^{GFP\text{-}Cre(ER)}$ (expression is mosaic and restricted to the ISC compartment. TAM injection into Lgr5$^{GFP\text{-}Cre(ER)}$; Satb2$^{f/f}$ mice accordingly yielded mosaic Satb2-null colonic crypts carrying GFP$^+$ intestinal stem cells (FIG. 2E). One week after treatment, SATB2 disappeared from the lower parts of GFP$^+$ crypts, where new cells reside, but persisted in higher cell tiers, which house older cells with intact Satb2. Activation of the ileal markers OLFM4 and FABP6 and suppression of the colonic marker CA1 were partial in GFP$^+$ glands, and LYZ1$^+$ cells were absent (FIG. 2E), suggesting incomplete epithelial remodeling at this early time. Importantly, all FABP6$^+$ cells lost SATB2, whereas FABP6 and CA1 mark distinct cells, indicating cell-autonomous regulation of these marker genes by SATB2. Intestinal stem cell and epithelial remodeling were complete by 36 days, with OLFM4 present in most GFP$^+$ cells, LYZ1$^+$ cells present in GFP$^+$ glands, and replacement of CA1$^+$ colonocytes by FABP6$^+$ enterocytes (FIG. 2E). These observations indicate time-dependent conversion of colonic stem cells and resetting of the differentiation pattern. The findings from single-cell profiling, organoid culture, and ISC-specific gene deletion are consistent with a fundamental conversion of colonic into ileum-like stem cells in the absence of SATB2.

Example 5: SATB2 Safeguards Colonocyte Identity

Given that SATB2 is expressed in stem and differentiated colonic cells, the inventors hypothesized that SATB2 may directly regulate differentiated cell identity.

To address this hypothesis, a single dose of TAM was administered to Satb2$^{cKO}$ mice to reduce SAT32 expression, and colonic gene expression was examined 1, 2, 4, or 6 days later.

Figure 3A:
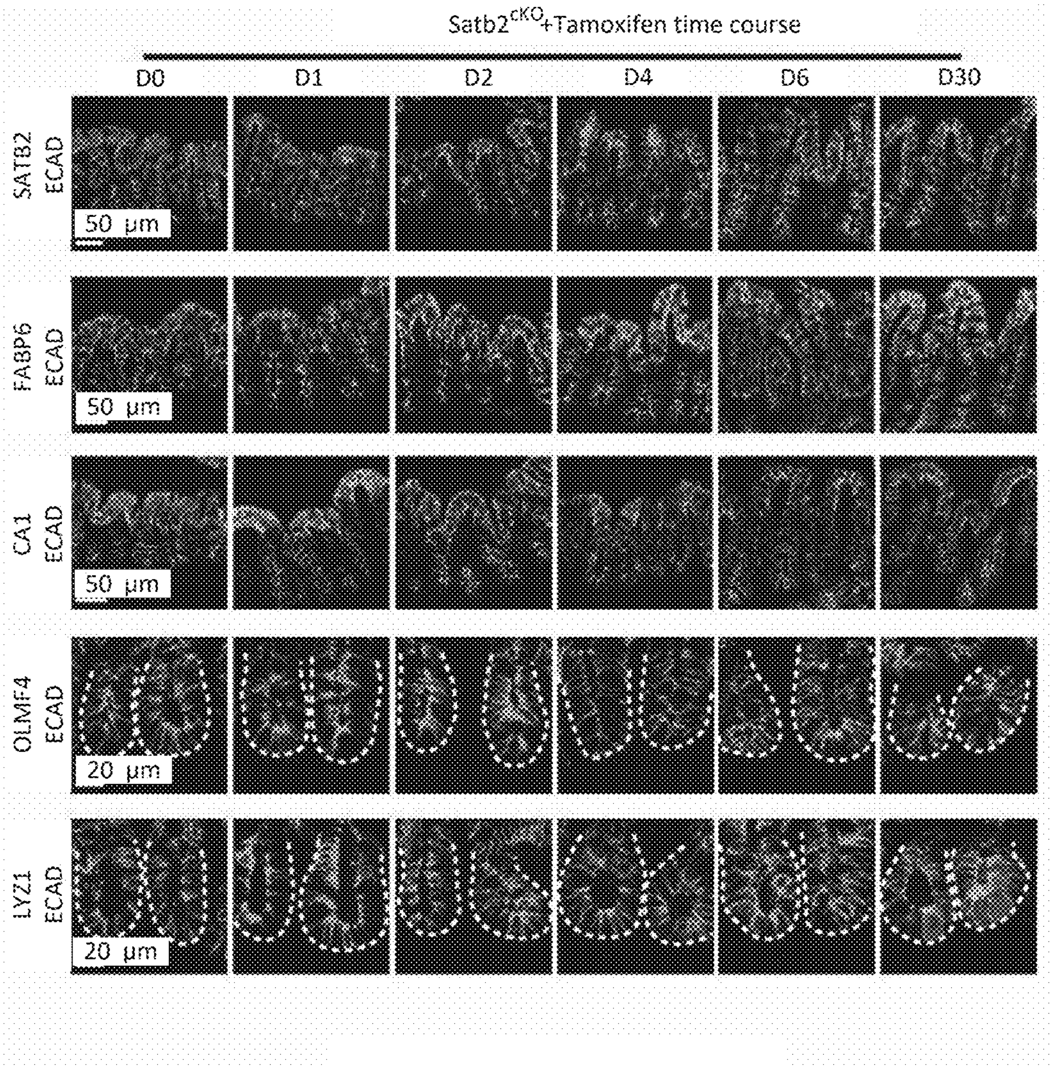
FIGS. 3A-3C illustrate rapid conversion of colonocytes to enterocytes after SATB2 loss.

As shown in FIG. 3, SATB12 signals disappeared by day 2, with concomitant FABP6 activation and CA1 suppression in a subset of colonic cells located in the upper glands (FIG. 3A). At this early time, epithelial self-renewal has not reached the upper glands, so these cells were pre-existing mature colonocytes. By day 4, most glandular cells had activated FABP6 and lost CA1 (FIG. 3A). In contrast, OLFM4 and LYZ expression in the crypts only became prominent in day 30 samples (FIG. 3A).

These data indicate that a rapid identity switch from colonocytes to enterocytes occurs after SATB2 loss, which is independent of stem cell conversion.

Figure 3B:
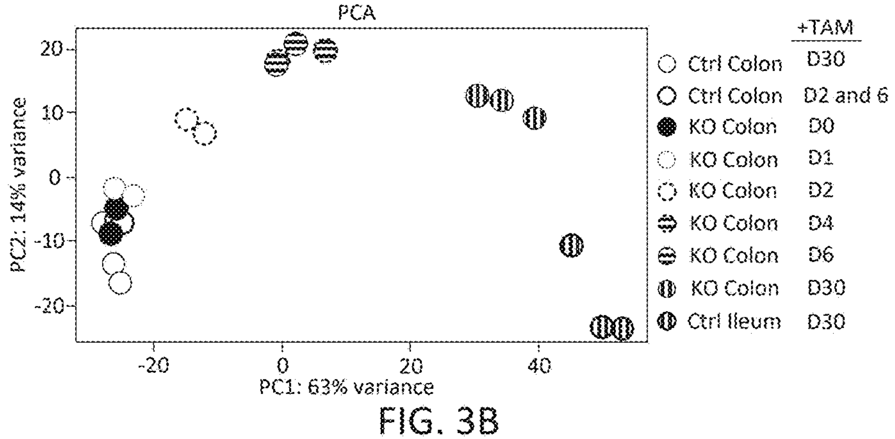
Figure 3C:
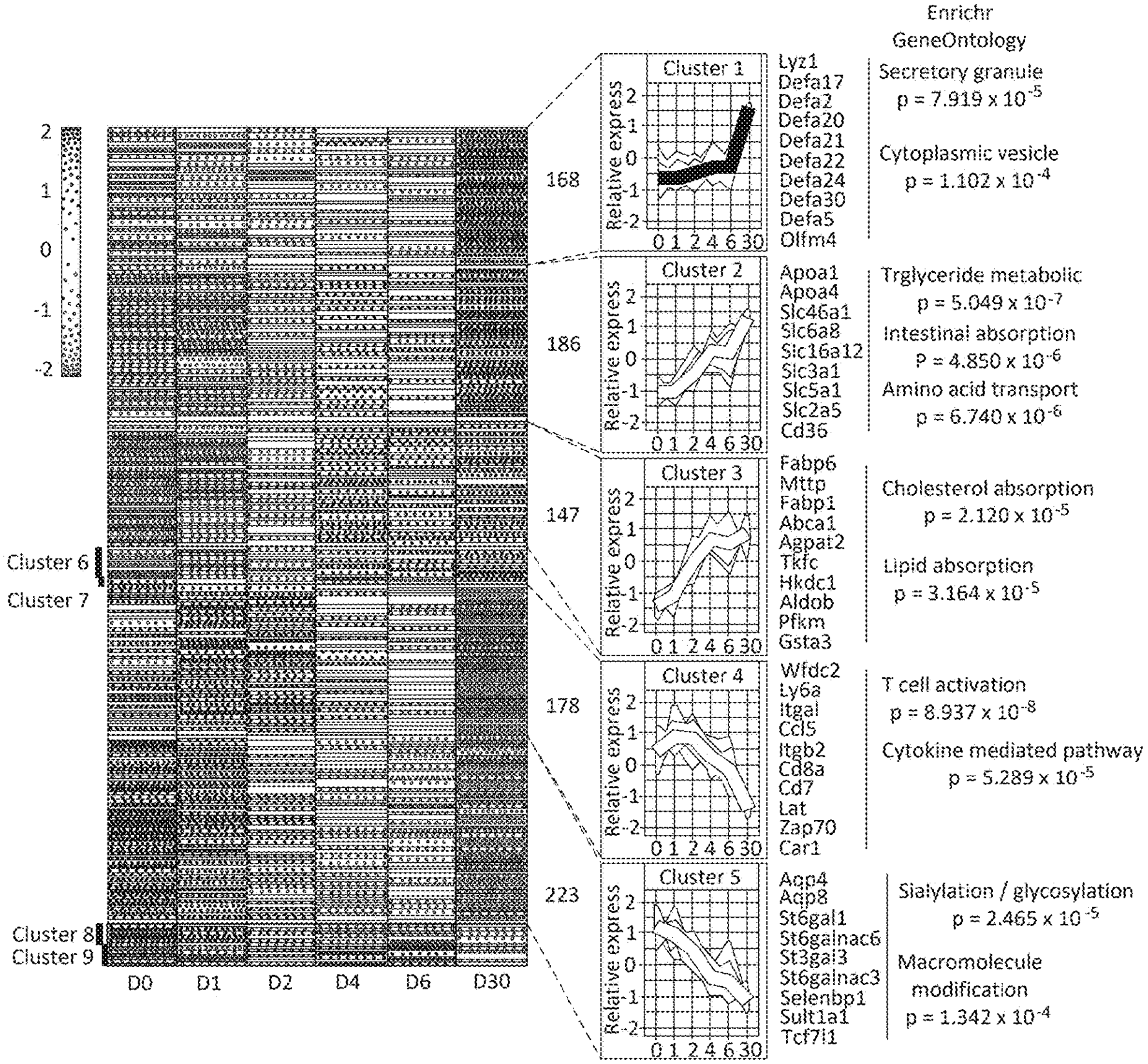

Consistent with the immunohistochemistry data, RNA-seq showed activation of hundreds of genes (FIG. 3B). FIG. 3C shows a heatmap representation of time-course RNA-seq data illustrating rapid activation of pathways typical of enterocytes and downregulation of pathways characteristic of colonocytes. Paneth and stem cell genes were only strongly activated at day 30. involved in nutrient absorption and transport by day 4. Clusters 2 and 3 include genes involved in metabolism and absorption, which were strongly activated as early as by day 4 or day 6. Cluster 6 relates to Cholesterol biosynthetic pathways ($p=2.010\times10^{-3}$, Secondary alcohol biosynthetic pathways ($p=2.126\times10^{-3}$), Sterol biosynthetic pathways ($p=2.620\times10^{-3}$)). Clusters 4 and 5 relate to colon-specific pathways in immune modulation and glycosylation that were downregulated after just a few days (FIG. 3C). Significant activation of Defensin genes and Olfm4 was only achieved at day 30 (cluster 1, FIG. 3C).

Notably, gene set enrichment analysis revealed no enrichment of fetal signature genes (Fordham et al., 2013) in Satb2$^{cKO}$ colonic transcriptomes between day 1 and 6. Examination of two fetal markers showed a modest and transient increase in Ly6a (Sca1) but not Anxa1. Significant fetal gene activation was thus not associated with colonic-to-ileal transformation.

These data indicate that SATB2 safeguards the identity of mature colonocytes in addition to its critical role in maintaining stem cell identity.

Example 6: Environmental Factors Influence Colonic-to-Ileal Conversion

A minority of Satb2$^{cKO}$ colonic cells retained colonic identity, including 9.2% of mature absorptive cells and 3.8% of goblet cells. The inventors postulated that the colonic milieu may influence differentiation of the ileum-like mucosa in Satb2$^{cKO}$ colon. Some studies illustrate the importance of microbial and niche signals in regulating intestinal gene expression and transcription factor activity (Chen et al., 2019; Davison et al., 2017; Nichols and Davenport, 2021; Thaiss et al., 2016). For example, the microbiota is necessary and sufficient to induce expression of major histocompatibility complex (MHC) class II genes in small intestine (but not colon) intestinal stem cells (Biton et al., 2018; Umesaki et al., 1995). Consistently, MIHC class II genes were high in ileal and low in control colonic and ileum-like Satb2$^{cKO}$ colonic intestinal stem cells. To mitigate environmental influences, ileal and Satb2$^{cKO}$ colonic organoids were cultured in identical WENR medium for one passage, differentiated the organoids, and performed RNA-seq. Principal-component analysis (PCA) and Pearson correlation showed that the transcriptomes of ileal and Satb2$^{cKO}$ colonic organoids resembled each other (Pearson r=0.983) more closely than the two samples harvested in vivo (r=0.954). Nevertheless, significant differences remained. This indicates that environmental factors contributed to, but were not the main cause of, the incomplete conversion of a subset of colonic cells to ileal identity in Satb2-null colon.

Figure 4A:
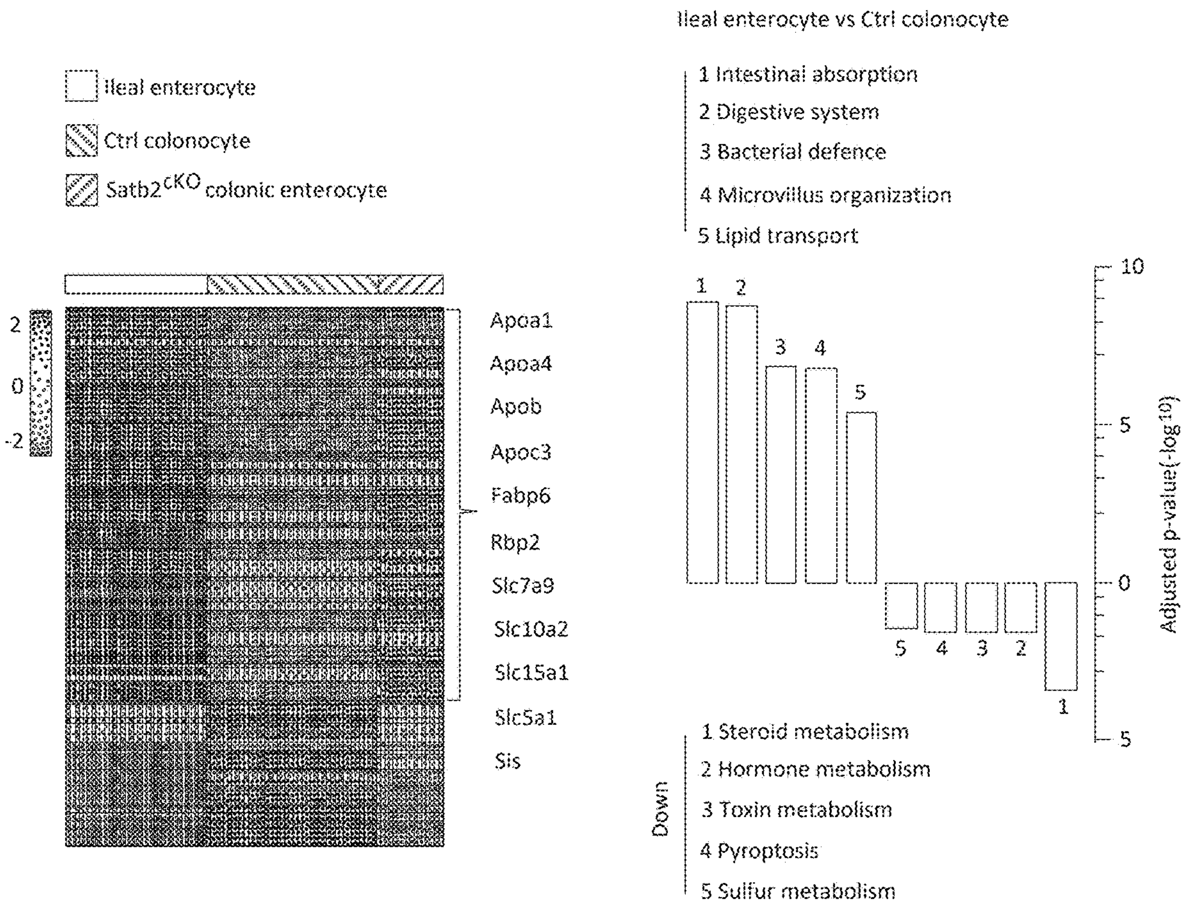
FIGS. 4A-4D illustrate generation of bona fide nutrient-absorbing enterocytes in $Satb2^{cKO}$ colon.
Figure 4B:
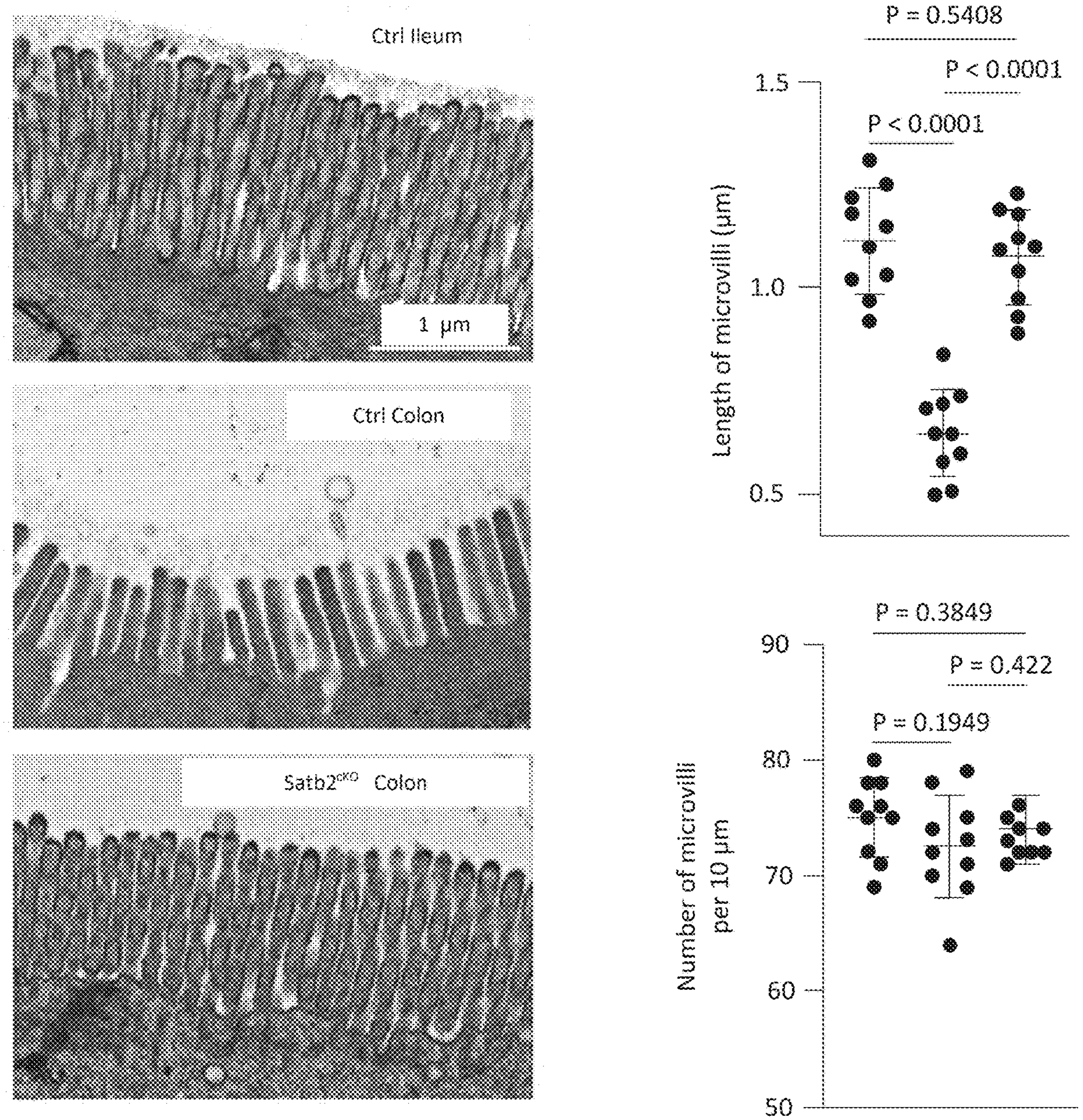

Example 7: Generation of Bona Fide Nutrient-Absorbing Enterocytes in the Ileum-Like Colon Ileal enterocytes absorb nutrients as well as bile salts and vitamins. Ileal and Satb2$^{cKO}$ colonic enterocytes expressed many transporters for lipids, carbohydrates, amino acids, bile salts, and vitamins that were absent or low in colonocytes (FIG. 4A). Satb2$^{cKO}$ colonic enterocytes were enriched for functional pathways in nutrient absorption and digestion and, notably, in genes relating to microvillus organization (FIG. 4A). Enterocytes are well known to sprout longer microvilli than colonocytes to increase their absorptive surface. Electron microscopy revealed substantially longer microvilli in Satb2$^{cKO}$ colonic enterocytes than in control colonocytes, comparable with those of ileal enterocytes (FIG. 4B).

Figure 4C:
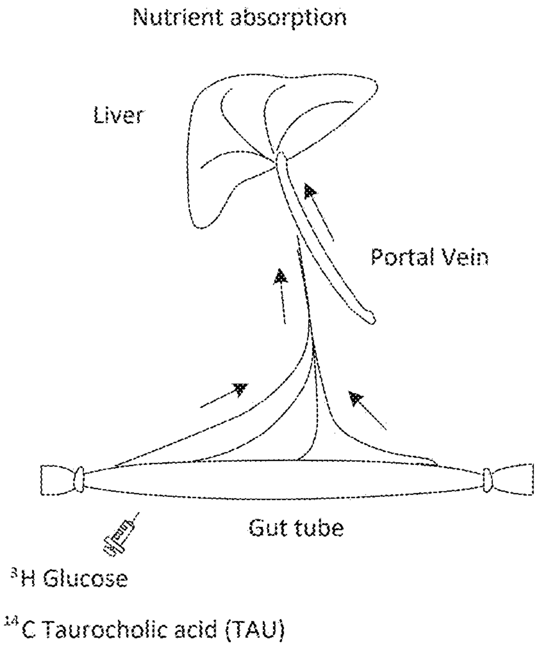
Figure 4D:
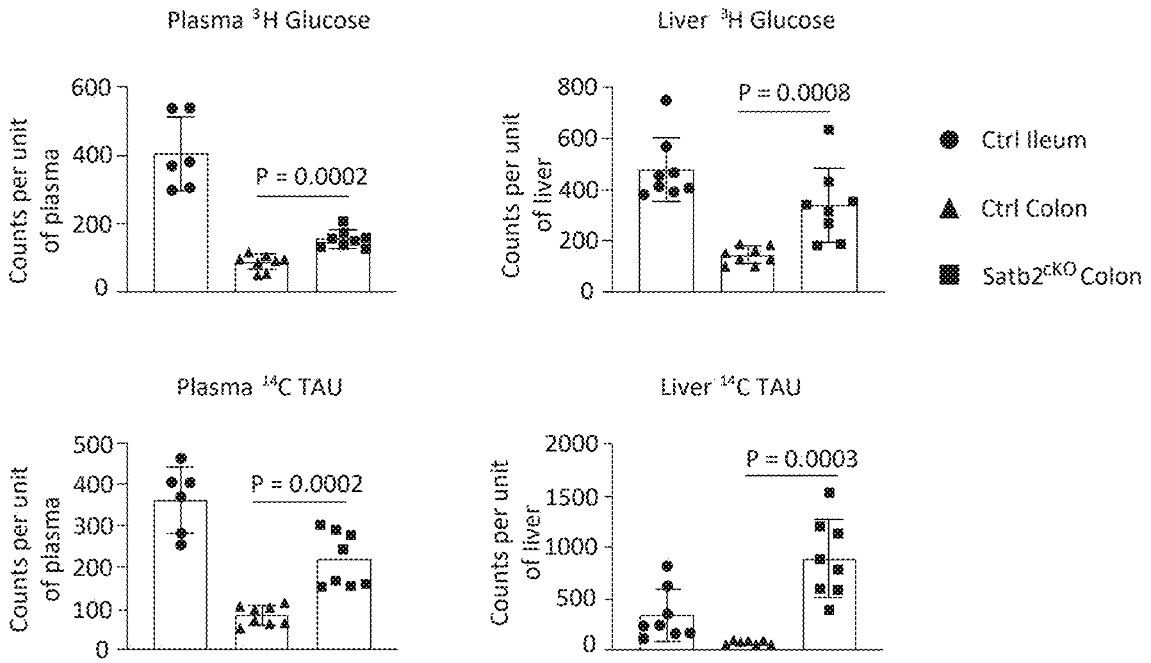

To evaluate whether the ileum-like mucosa in Satb2$^{cKO}$ colon can more readily absorb nutrients and bile salts, an in vivo absorption assay was employed that involved tying both ends of a segment of the ileum or colon to create a pouch, followed by injection of [$^3$H]glucose and [$^{14}$C] taurocholic acid into this pouch, enabling detection of trans-epithelial transport of radiolabeled materials into the portal circulation and its incorporation in the liver tissue (FIG. 4C). Portal plasma and liver parenchyma from Satb2$^{cKO}$ mice showed significantly higher radiotracer levels compared with controls (FIG. 4D). These findings indicate that bona fide enterocytes were generated in the Satb2$^{cKO}$ colon.

Example 8: SATB2 Confers Colonic Characteristics on the Mature Ileum

Figure 5A:
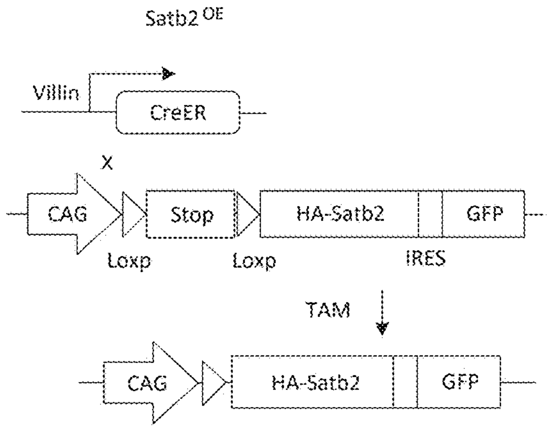
FIGS. 5A-5G illustrate that SATB2 confers colonic characteristics to adult ileum.

To evaluate whether SATB2 can confer a colonic fate to the small intestine mucosa, a transgenic mouse line, CAG$^{SATB2\text{-}GFP}$, was generated in which CRE excision of a stop cassette activated hemagglutinin (HA) epitope-tagged SATB2 and GFP (FIG. 5A).

Figure 5B:
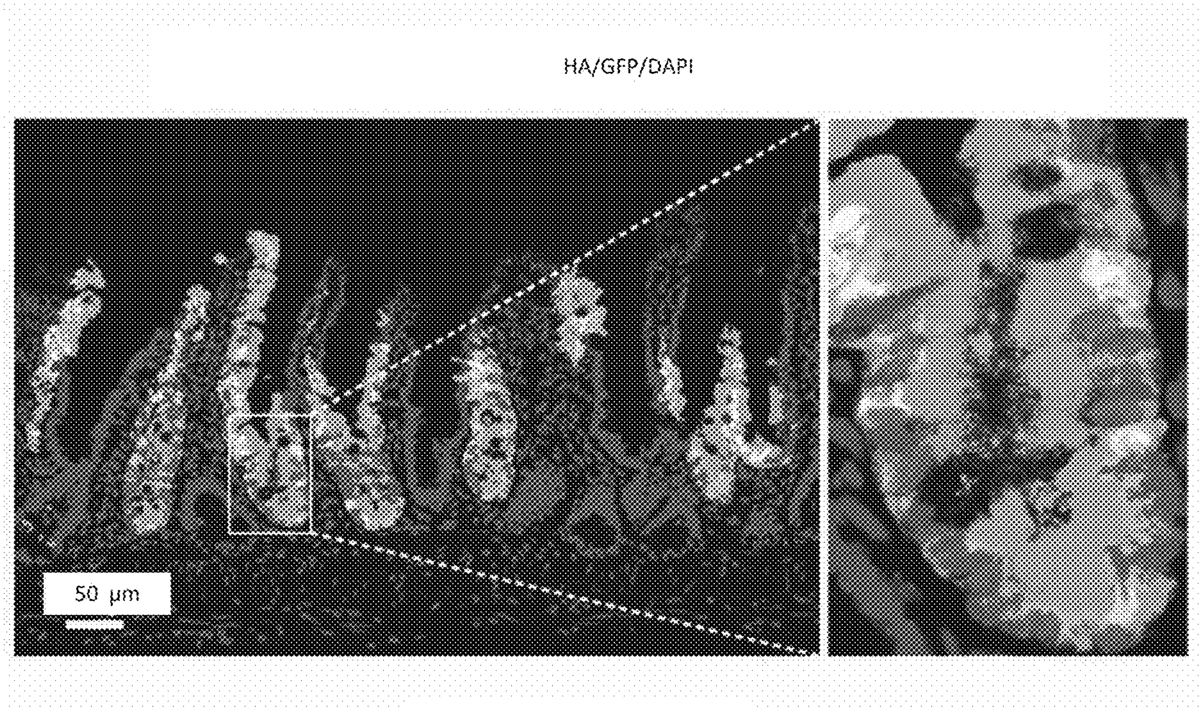

TAM treatment of 2-month-old Vil-Cre$^{ER}$; CAG$^{SATB2\text{-}GFP}$ mice (referred to as Satb2$^{OE}$) led to mosaic expression of HA-tagged SATB2 and GFP throughout the intestine. Relatively low numbers of cells expressed HA-tagged SATB2 and GFP in the ileum (approximately 10%-15% of the glands; FIG. 5B) but higher numbers were expressed in the jejunum and duodenum (2>50% of the glands).

Figure 5C:
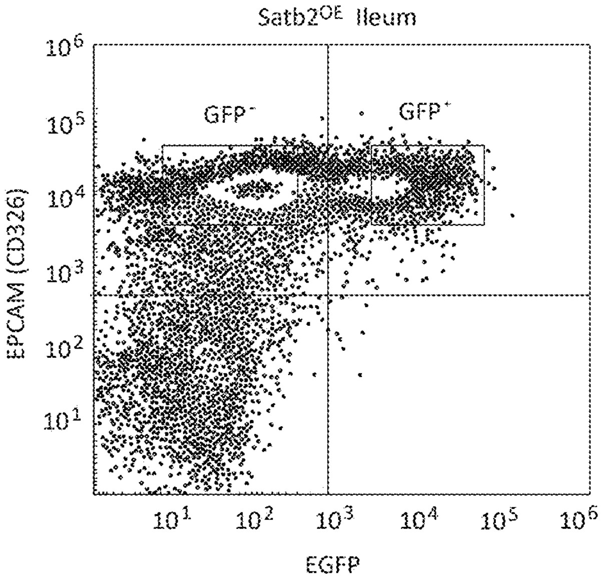
Figure 5D:
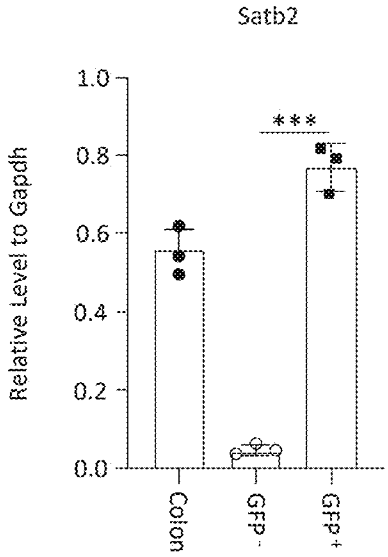
Figure 5E:
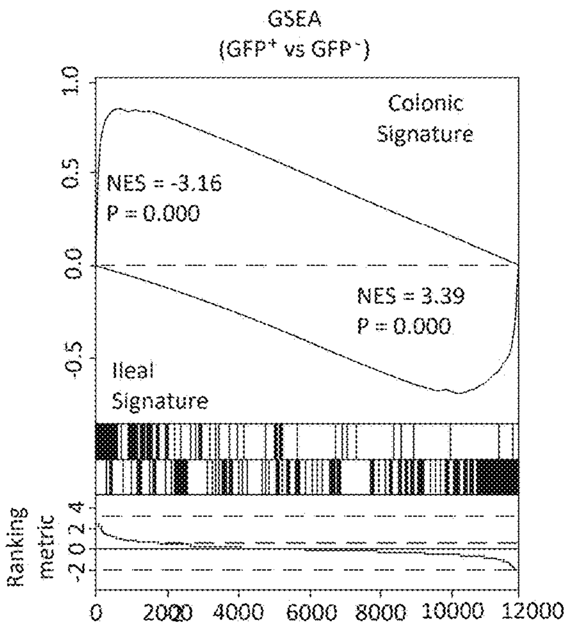

RNA-seq of FACS-purified GFP$^+$ cells from the ileum and jejunum showed Satb2 mRNA levels comparable with those in the colon (FIG. 5C-5D). Compared with GFP ileal cells, 225 genes were downregulated and 131 genes were upregulated in ileal GFP cells (LFC>1.5, Padj<0.1); these genes were enriched for colonic and ileal tissue signatures, respectively (FIG. 5E). Among the downregulated genes were large numbers of enterocyte nutrient transporters and Defensins characteristic of Paneth cells.

Figure 5F:
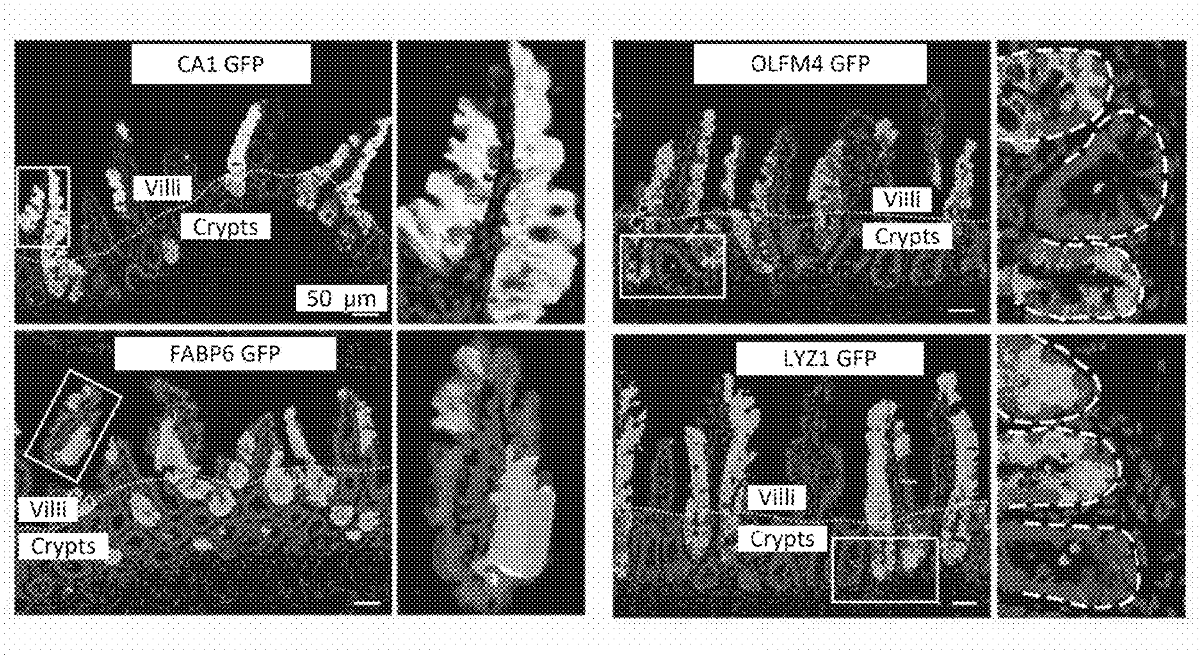
Figure 5G:
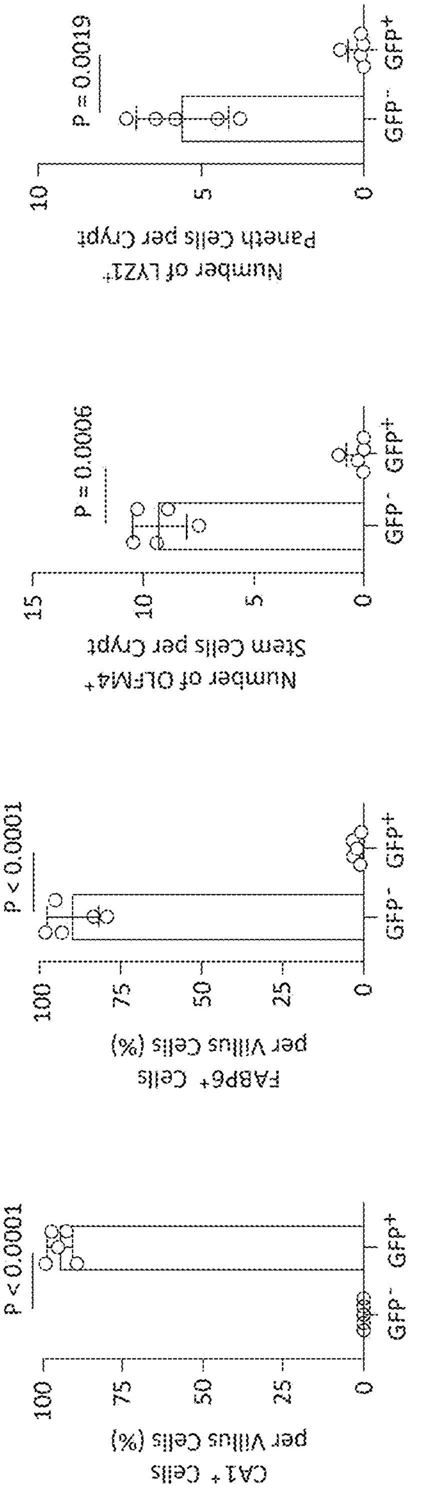

Colonic epithelium absorbs electrocytes and synthesizes many glycoproteins, including specific mucins for anti-microbial defense. GFP$^+$ ileal cells expressed an array of key electrolyte transporters and principal glycosylation enzymes. Thus, they acquired molecular machineries necessary for colonic functions. In ileal villi marked with GFP, immunohistochemistry 30 days after TAM administration showed suppression of the ileal marker FABP6 and activation of the colonic marker CA1 (FIG. 5F-5G) OLFM4 and LYZ1 also disappeared from $GFP^+$ crypts (FIG. 5G), consistent with the transcriptomics data. In contrast to $Satb2^{OE}$ ileum, qRT-PCR analysis indicated that jejunal and duodenal $GFP^+$ cells downregulated small intestine genes but failed to activate most colonic genes, with the duodenum being the least responsive.

SATB2 is therefore sufficient to confer colon-like characteristics on the adult ileum.

Figure 6A:
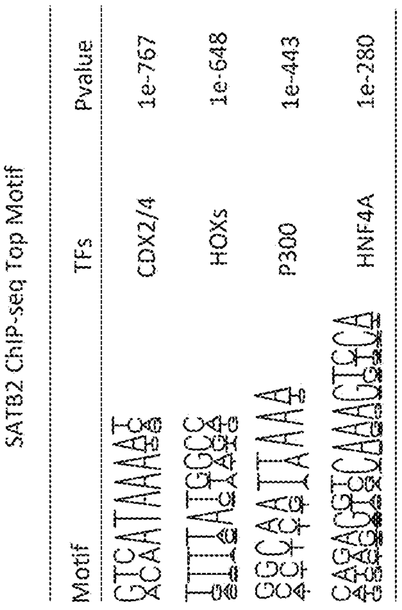
FIGS. 6A-6J illustrate that SAT32 regulates enhancer dynamics and binding of intestinal transcription factors CDX2 and HNF4A.
Figure 6B:
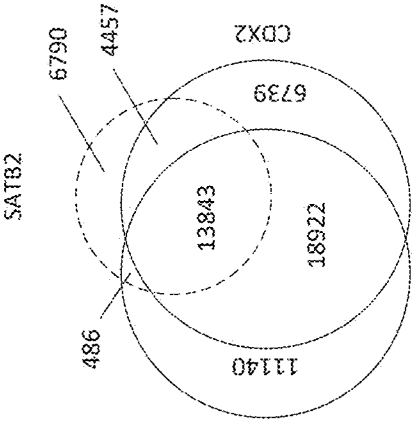
Figure 6C:
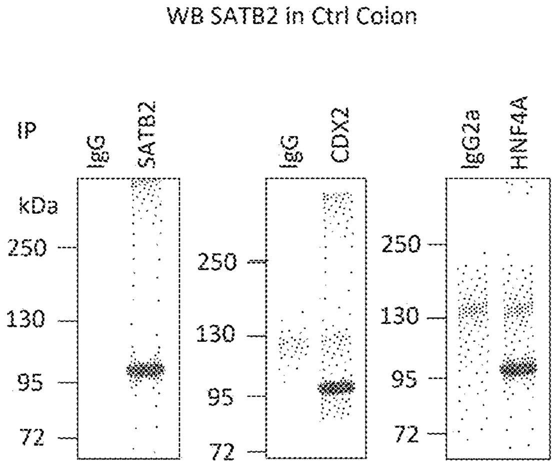

Example 9: SATB2 Regulates Enhancer Dynamics and Transcription Factor Binding in the Colon To investigate how SATB2 might control colonic fate and tissue plasticity, the inventors mapped genome-wide SATB2 binding using chromatin immunoprecipitation sequencing (ChIP-seq). Duplicate SATB2 ChIP data from control colonic epithelia yielded highly concordant data with 25,576 high-quality peaks ($p<1\times10^{-9}$, using input DNA and SATB2cKO ChIP as controls). These peaks were enriched for AT-rich sequences, consistent with SAT32 binding preference (Szemes et al, 2006; FIG. 6A). Among the top enriched DNA-binding motifs identified by HOMER were those for the intestinal transcription factors CDX2 and HNF4A, indicating co-localization of the two transcription factors with SATB2 (FIG. 6A). Indeed, ChIP-seq for CDX2 and FHNF4A revealed extensive co-localization, with 54.1% (13,843 of 25,576) of SATB2 peaks co-bound by both TFs (FIG. 6B). Moreover, CDX2 and HNF4A antibodies co-precipitated SAT132 from colonic tissue (FIG. 6C), indicating physical interactions of SATB2 with CDX2/HNF4A.

Figure 6D:
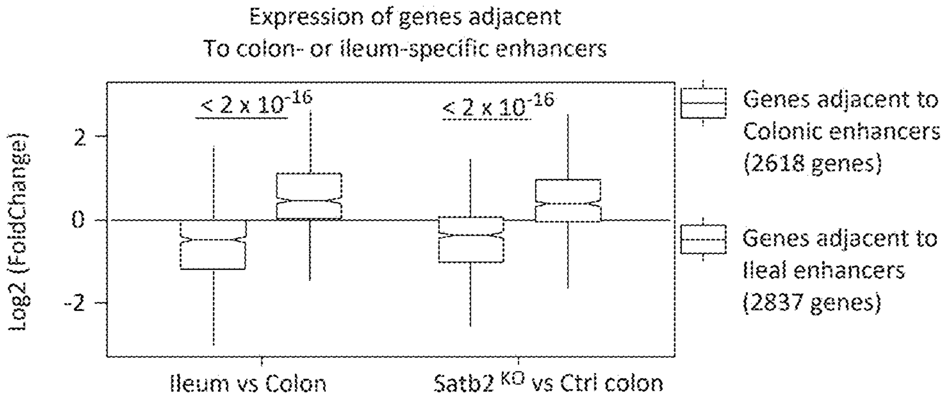
Figure 6E:
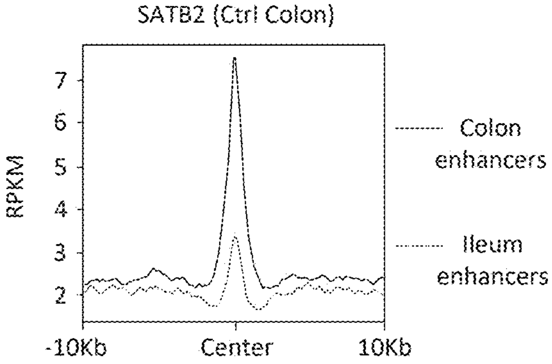

Colonic SATB2 binding occurred predominantly in intergenic regions and introns (39.1% and 53.2% of peaks, respectively) and enriched for the motif of P300, the histone H3K27 acetyltransferase and a hallmark of active enhancers (FIG. 6A; $p<1\times10^{-443}$). The inventors used cleavage under targets and release using nuclease (CUT&RUN) to map putative (H3K4me1) and active (H3K27ac) enhancers in control ileum, colon, and SATB2cKO colon epithelia. Peaks were called with Model-based Analysis of ChIP-Seq 2 (MACS2) using duplicate samples. Tissue-specific enhancers (H3K4me1, transcriptional start site [TSS]-distal regions) were identified by MAnorm. Assay for Transposase Accessible Chromatin with high-throughput sequencing(AT AC-seq) was employed to further chart the chromatin landscapes in these tissues. Analysis of all $H3K4me1^+$ enhancers defined 7,375 colon-specific and 5,784 ileum-specific sites (MAnorm, $p<0.01$), with nearby genes (<50 kb) enriched for colonic or ileal expression, respectively (FIG. 6D). In normal colon, a majority of SAT132 binding (59.5%) occurred within $H3K27ac^+$ active enhancers (FIG. 6E), and 67% of SATB2/CDX2/HNF4A co-bound sites overlapped with active enhancers.

Figure 6F:
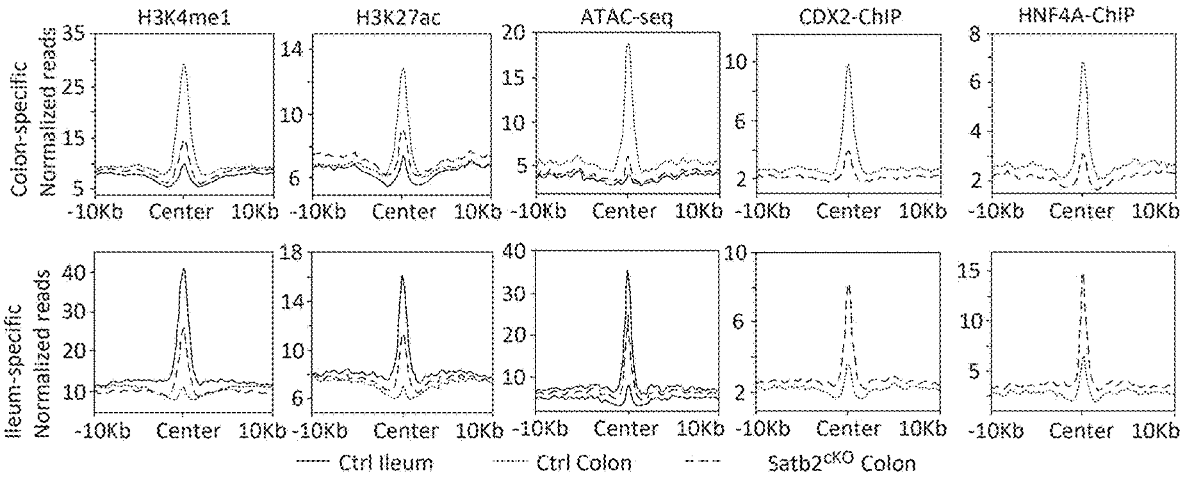
Figure 6G:
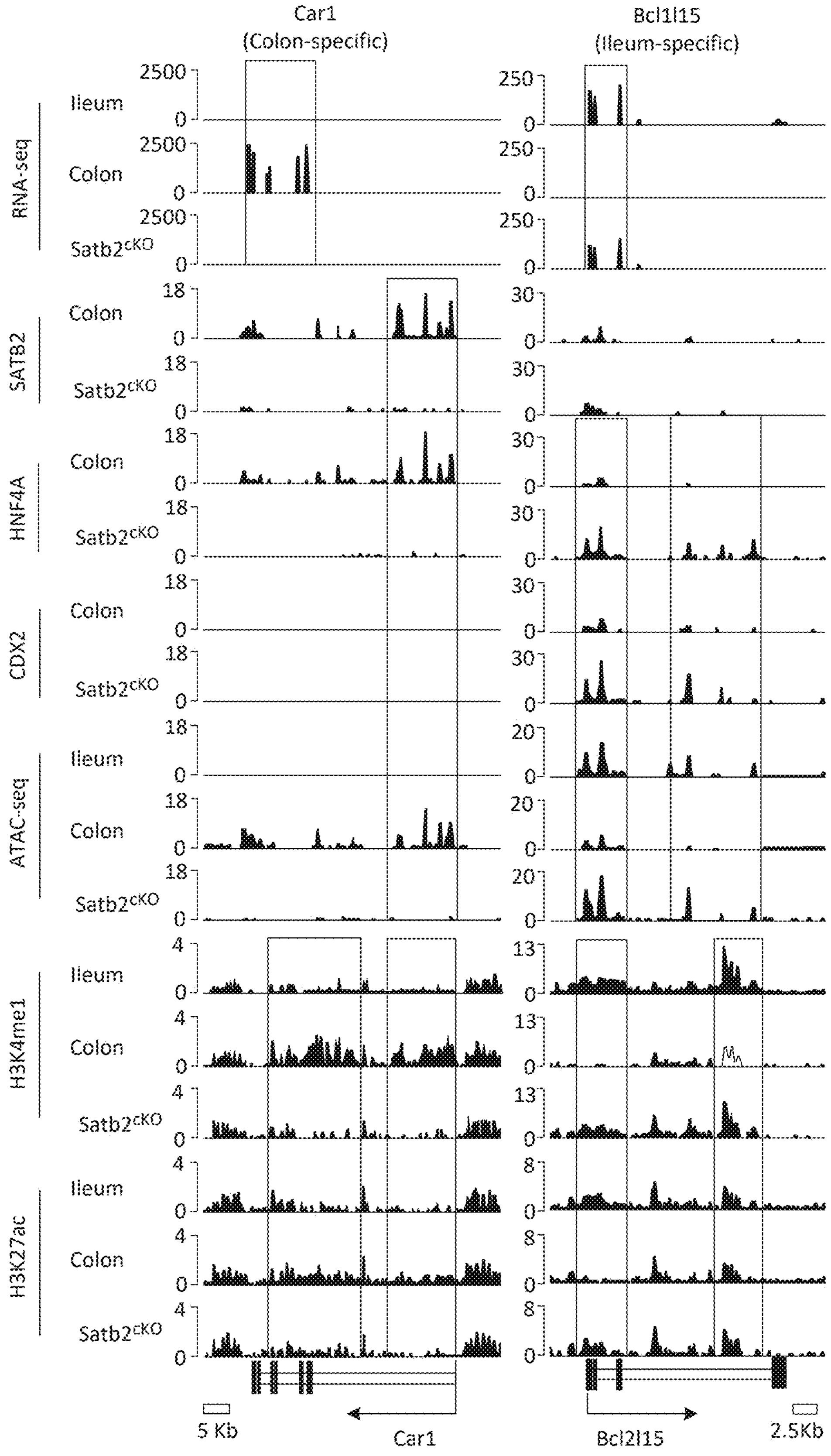

In control colon, the colon-specific enhancers had high levels of H3K4me1 and H3K27ac, strong ATAC signals, and robust binding by CDX2 and HNF4A, all hallmarks of active enhancers (FIG. 6F-6G). These enhancers were deactivated in the $Satb2^{cKO}$ colon. The $Satb2^{cKO}$ colon also displayed low levels of H3K4me1, H3K27ac, open chromatin, and CDX2 or HNF4A occupancy. These results indicate that SATB2 has a role in maintaining active colonic enhancers. Notably, ileum-specific enhancers in normal colon retained low but detectable signals of ATAC, H3K4me1, H3K27ac, CDX2, and HNF4A; after SATB2 loss, each of these signals was enhanced significantly (FIG. 6F-6G). Thus, ileal enhancers are not constitutively silent at baseline in mature colon but retain weak enhancer features. These "primed" enhancers likely provide the necessary chromatin substrate for ileal gene activation and tissue fate plasticity.

Many developmental enhancers active in embryos and decommissioned in adult intestines retain low H3K4me1 and are reactivated after prolonged loss of polycomb repressive complex 2 (PRC2) (Jadhav et al., 2019). The inventors sought information to ascertain whether the "primed" ileal enhancers in adult colon were erstwhile active developmental enhancers. Analysis of published midgut ATAC profiles (Banerjee et al., 2018) and new hindgut ATAC profiles from developing (embryonic days 12, 14, and 16) and newborn mice revealed no evidence that ileal enhancers had been active in developing hindgut or colonic enhancers active in developing midgut. Moreover, genetic deletion of Eed in adult intestine ($Villin^{CreER}$; $Eed^{f/f}$), which inactivated PRC2, did not result in colonic-to-ileal conversion. Combined removal of Eed and Satb2 ($Villin^{CreER}$; $Eed^{f/f}$; $Satb2^{f/f}$) also did not enhance the transcriptomic shift toward ileum. Thus, the primed ileal enhancers in adult colon are not decommissioned fetal enhancers, and PRC2 is not overtly involved in SATB2-dependent colonic identity maintenance.

In adult intestine, CDX2 and HNF4A function primarily as transcriptional activators (Verzi et al., 2011, 2013). After Satb2 loss, CDX2 levels decreased approximately 1-fold, whereas HNF4A increased by 1-fold. Nevertheless, the two transcription factors associate with each other in normal and $Satb2^{CKO}$ colon (FIG. 6C), and their co-binding switched from colonic to ileal enhancers after SATB2 loss (FIG. 6F-6G), correlating closely with downregulation of colonic and activation of ileal genes (FIG. 6D).

These data indicate that SATB2 regulates colonic gene expression and tissue plasticity in part by modulating enhancer interactions with crucial intestinal transcription factors.

Figure 6H:
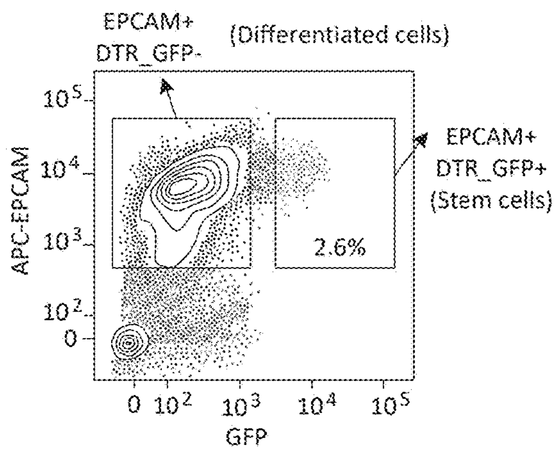
Figure 6I:
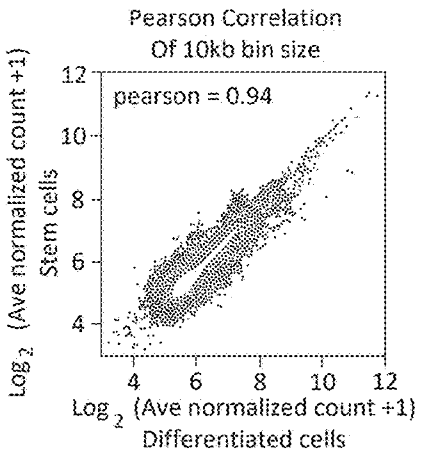
Figure 6J:
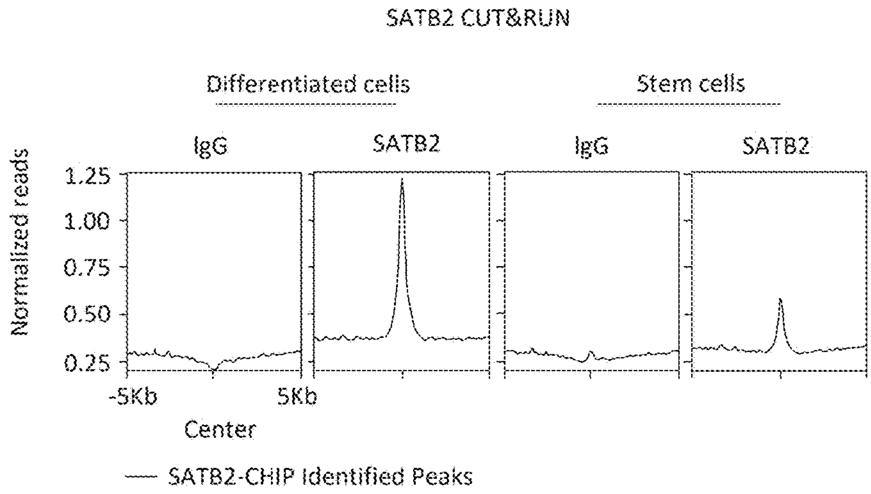

SATB2 binding was then evaluated in $LGR5^+$ colonic intestinal stem cells versus differentiated cells, isolated respectively, by FACS from $LGR5^{DTRGFP}$ reporter mice (FIG. 6H). SATB2 CUT&RUN with approximately $2\times10^5$ cells each yielded 7,523 peaks in $LGR5^+$ cells and 15,757 peaks in $LGR5^-$ cells. Although the average signal strength of SATB2 binding events in intestinal stem cells was lower than in differentiated cells, their binding patterns on the whole-genome level were highly concordant (FIG. 6I; Pearson r=0.94) and aligned well with the SATB2 binding peaks identified by ChIPseq. FIG. 6J illustrates SATB2 CUT&RUN binding profiles in a 10-kb window centered on SATB2 peaks identified by ChIP-seq. Together, FIG. 6H-6J illustrate that SATB2 bound similar genomic loci in colonic LGR5+ stem cells as non-stem cells.

Taken together, these results indicate that SATB2 binds the same genomic sites in stem cells as in differentiated cells, indicating that SATB2 can "prime" the stem cells for a differentiation path to colonic progenies.

Figure 7A:
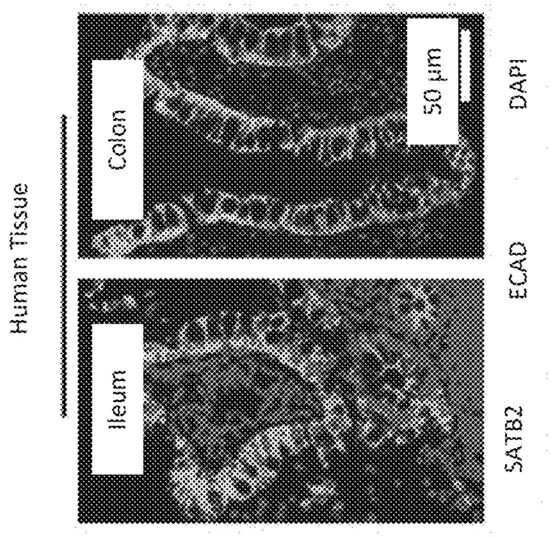
FIGS. 7A-7I illustrate colonic-to-ileal plasticity after SATB2 loss in human colonic organoids.
Figure 7B:
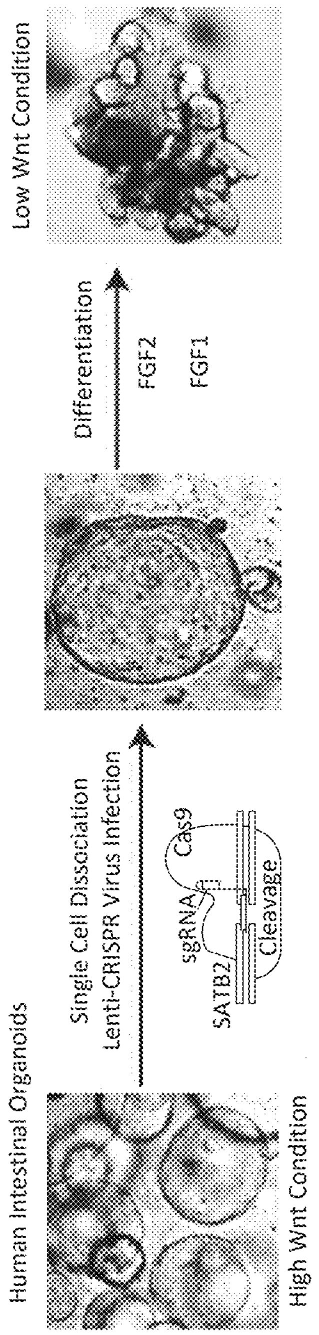
Figure 7C:
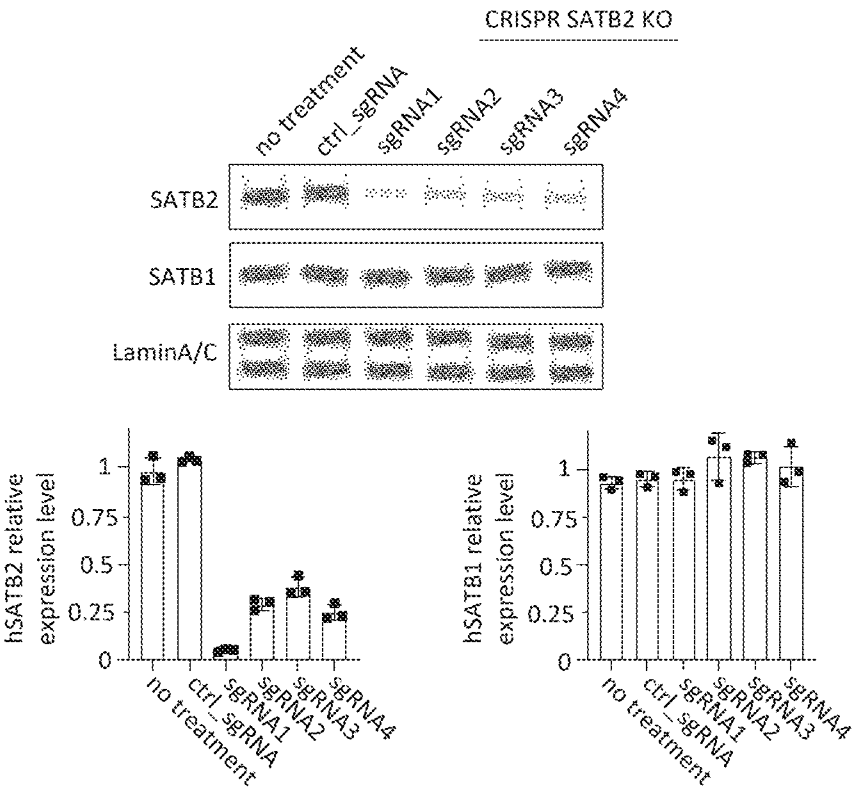
Figure 7D:
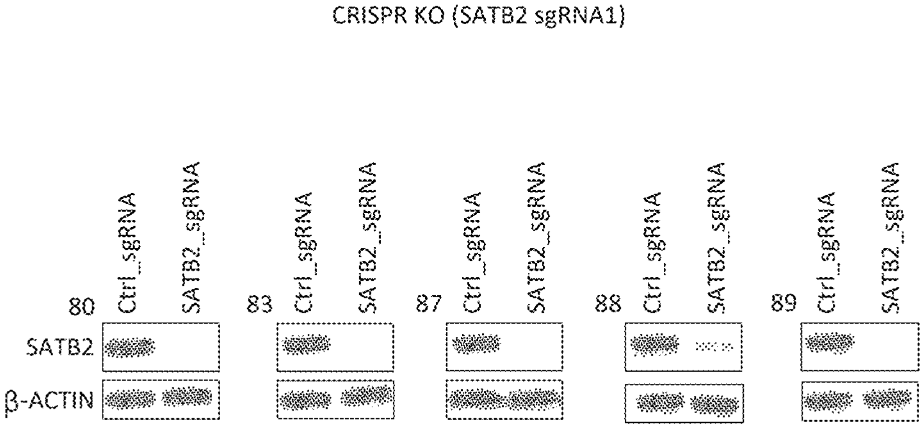
Figure 7E:
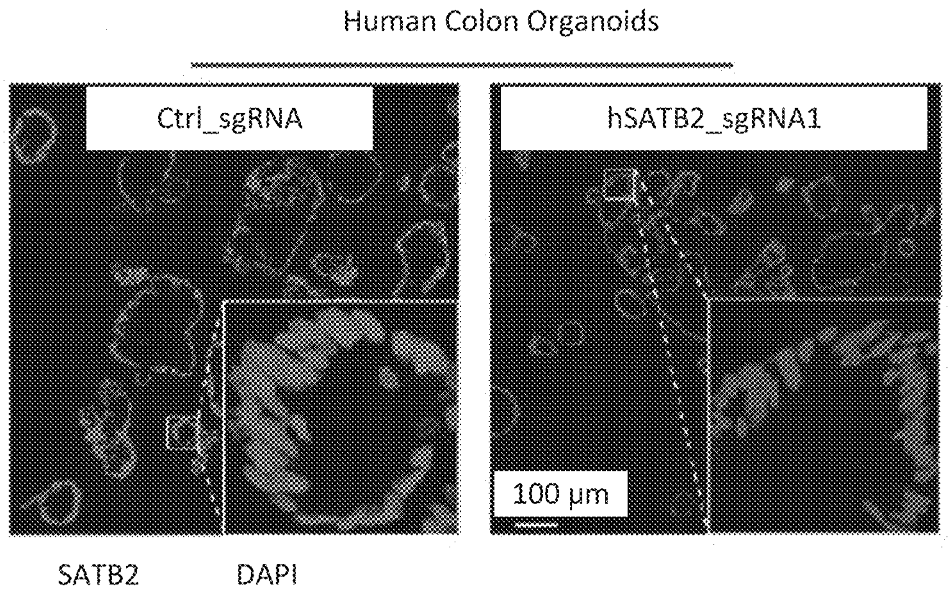

Example 10: Human Colonic Organoids Adopt Ileal Characteristics after SATB2 Loss SATB2 expression is restricted to the colonic mucosa in adult human intestine (FIG. 7A). To evaluate SATB2 function in humans, CRISPR-Cas9 was used to delete SATB2 from five normal human colonic organoid lines that expressed SATB2 at comparable levels (FIG. 7B). Of the four guide RNAs (gRNAs) assessed, one efficiently reduced SATB2 expression by 95%-98% (FIG. 7B-7C). RNA-seq analysis of the five isogenic control (Cas9 alone) and SATB2 knockout ($SATB2^{hKO}$) organoid lines showed significant suppression of colonic genes and activation of small intestinal genes (FIG. 7C-7D). FIG. 7E shows representative images of SATB2 expression in one of the primary human organoid lines (#87) and its absence after CRISPR-mediated deletion using sgRNA1.

Figure 7F:
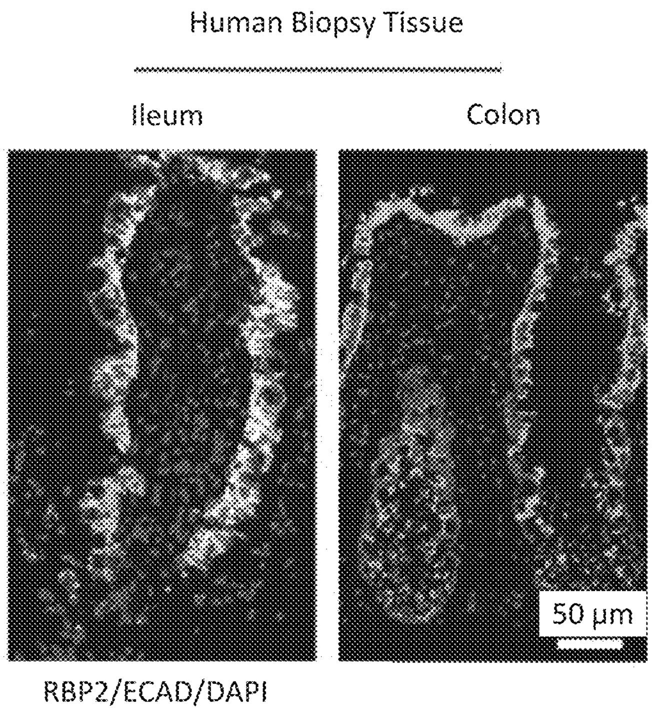
Figure 7G:
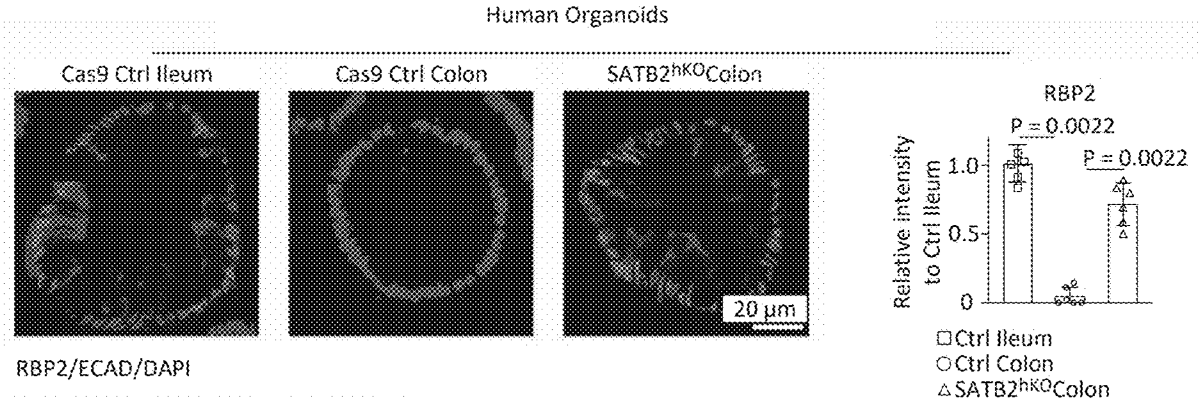
Figure 7H:
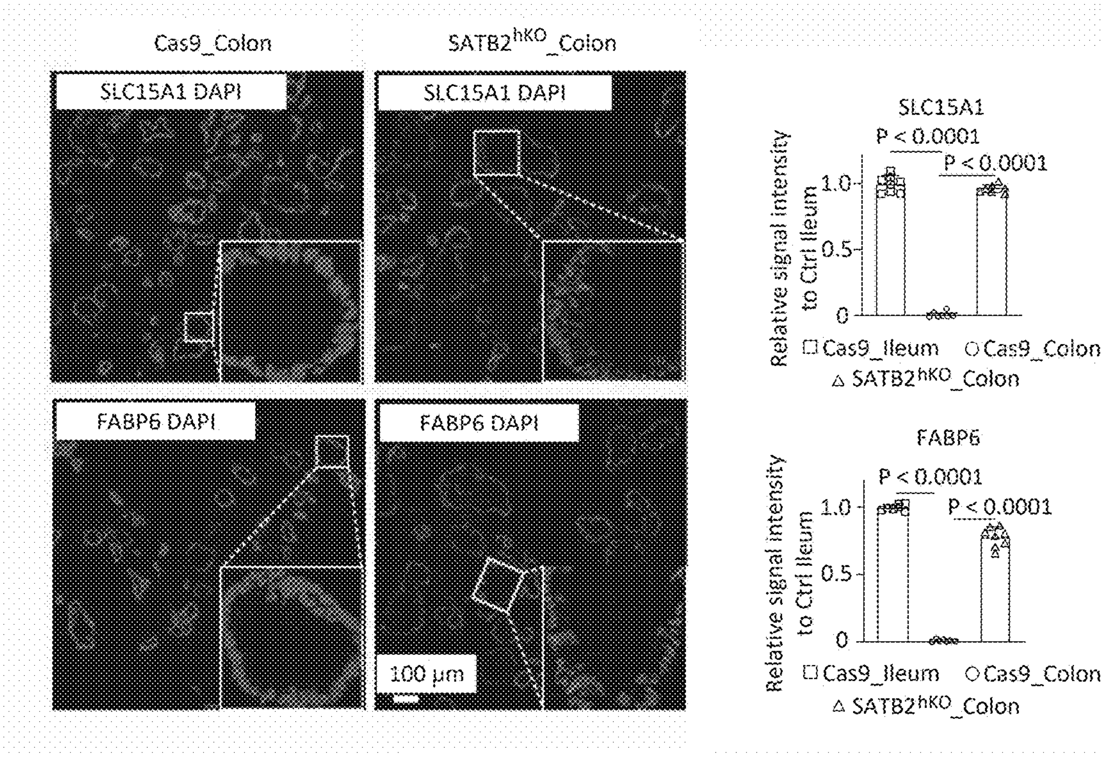

Kyoto Encyclopedia of Genes and Genomes (KEGG) pathways were identified and the top activated included nutrient and vitamin absorption and retinol metabolism. Immunohistochemistry of SATB2$^{hKO}$ colonic organoids confirmed expression of the ileal enterocyte markers FABP6 and RBP2 and the small intestine brush-border peptide transporter SLC15A1 (FIG. 7F-7G). FIG. 7F illustrates that RBP2, a marker of ileum, was detected in ileal human biopsy tissues. However, FIG. 7G illustrates that RBP2 was not detected in the colonic epithelium of human biopsy tissues. Instead, RBP2 was abundantly expressed in colonic organoids after SATB2 deletion, at levels comparable to that of control ileal organoids (FIG. 7G). FIG. 7H shows that ileal makers SLC15A1 and FABP6 were activated in colonic organoids after SATB2 loss and that such markers are localized to the luminal epithelial side and the cytoplasm, respectively.

Figure 7I:
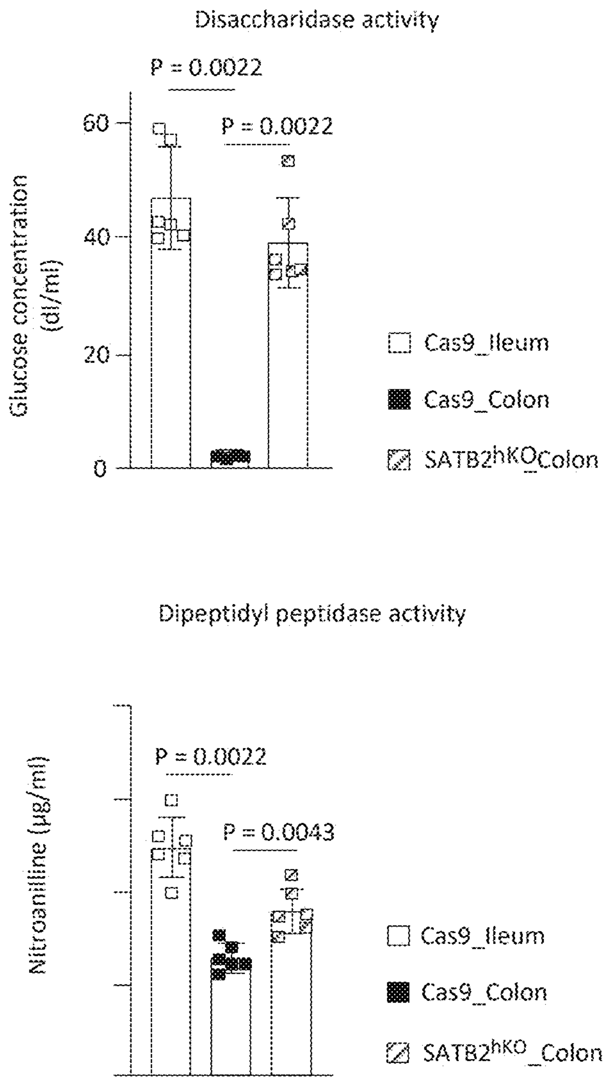

Digestive enzyme activities of the small intestine, disaccharidase and dipeptidyl peptidase, were also elevated significantly in SATB2$^{hKO}$ colonic organoids (FIG. 7I). These enzymatic activities are shown below. Absorbance and a colorimetric assay was used to detect 4-nitroanilide generated by dipeptidyl peptidase and the sugars produced by disaccharidase.

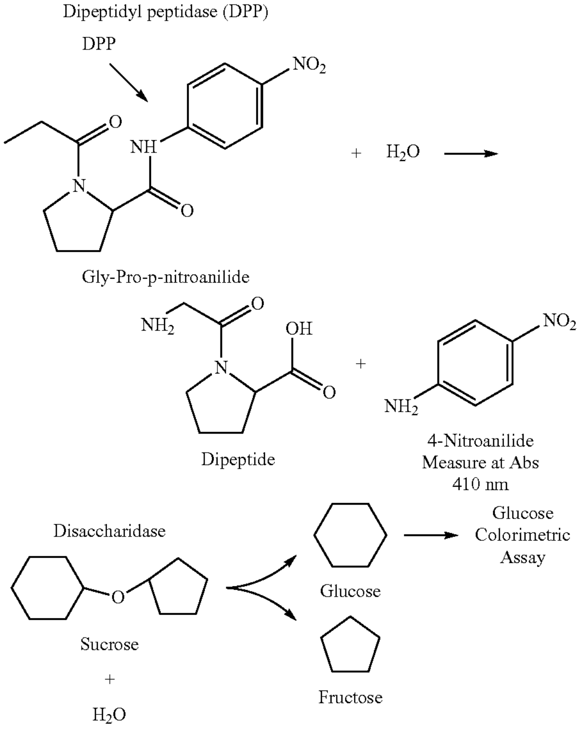

In contrast to the detected small intestine enzyme activities, human colon markers CEACAM1 and MUC2 were downregulated in the SATB2$^{hKO}$ colonic organoids.

These data indicate that SATB2 has a conserved function in preserving human colonic epithelial identity and mediating colonic-to-ileal plasticity.

The results provided herein show that a tissue-restricted chromatin factor, SATB2, uniquely maintains mouse and human colonic stem cell and tissue identity. As illustrated herein. SATB2 regulates colonic transcription and cell fate in part by modulating enhancer dynamics and targeting intestinal transcription factors such as CDX2 and HNF4A. SATB2 binds the same genomic sites in stem and differentiated cells and directly maintains the colonic identity of stem and non-stein cells. Thus, there is a fundamental similarity of SATB2 mechanisms of function in stem versus non-stem cells.

The results provided herein also reveal a surprising degree of inherent plasticity between adult ileal and colonic mucosa, likely enabled by the presence of primed ileal enhancers in the colon and vice versa. Unlike many quiescent enhancers in the adult gut (Jadhav et al., 2019), the ileal enhancers activated by Satb2 loss are not decommissioned developmental enhancers, and they are not overtly subject to PRC2 regulation.

Low levels of SATB2 are present in the ileum but not the jejunum or duodenum, and exogenous SATB2 expression elicits a gradient of responses along the proximal-distal axis, with the ileum being the most responsive and the duodenum the least. This correlation suggests a potential role of endogenous ileal SATB2 in regulating this plasticity by "priming" colonic enhancers, analogous to its role in the colon.

Example 11: Materials and Methods

This Example describes some of the experimental procedures and results obtained in the development of the invention.

Mouse Strains and Tamoxifen Administration

All mouse experiments were conducted under the IACUC protocol 2018-0050 at Weill Cornell Medical College. The Satb2$^{loxp/loxp}$ (Satb2$^{f/f}$) strain was a gift from Dr. Jeff Macklis of Harvard University. The Vil-Cre$^{ERT2}$ and Lgr5$^{GFPcreER}$ strains were gifts from Dr. Ramesh Shivdasani of Dana-Farber Cancer Institute. To confer conditional deletion of flexed alleles, 2 mg per 25 g of body weight of tamoxifen (TAM, 10 mg per ml in corn oil) was intraperitoneally injected once every 2 days for a total of 3 times.

Generation of the CAG$^{SATB2GFP}$ Transgenic Mouse Line

The knock-in construct, modified from pR26CAG/GFP Dest (Addgene #74281), carries a GAG promoter followed by a Neomycin-transcription stop cassette flanked by Loxp sites, HA epitope-tagged murine Satb2, an IRES element, and GFP. Donor DNA consists of a 1,083 kb left arm and a 4,341 bp right arm. The construct was targeted to the ROSA26 locus by pro-nuclear injection paired with purified CAS9 protein (purchased from IDT) and a validated gRNA targeting ROSA26 (ACUCCAGUCUUUCUACAAGA; SEQ ID NO: 13). The transgenic progenies were genotyped for cassette integration into the genomic locus of ROSA26. A total of 5 double transgenic lines were established by crossing with the Vil-Cre$^{ERT2}$ mouse line. Transgene expression in adult mice was analyzed by immunohistochemistry for GFP, the HA epitope tag, and SATB2 after TAM injection at 2 months of age. This analysis yielded very similar results from all 5 transgenic lines.

Intestinal Crypt Isolation and Organoid Culture

Intestinal organoid culture was performed as previously described (Sugimoto and Sato, 2017). Briefly, mouse intestinal crypts were isolated by incubating small intestine in 2.5 mM EDTA for 30 minutes (mins) or large intestine in 10 mM EDTA for 60 minutes. 50-200 Crypts per 25 μl Matrigel™ droplet were cultured in either ENR (small intestine) or WENR (large intestine) medium (Key Resource Table) in humidified chambers containing 5% $CO_2$ at 37° C. The formation efficiency of primary organoids was determined by dividing the number of organoids at Day 5 by the initial Crypt numbers. To assay secondary organoids, primary organoids were dissociated with TrypLE Express (3 minutes at 37° C.), resuspended in cold DMEM with 2% FBS, and centrifuged at 300 g for 3 minutes. The cell pellets were embedded in Matrigel™ in a 1:5 ratio. The formation efficiency of secondary organoids was determined by dividing the number of organoids at Day 5 by the initial crypt number.

Human organoids were generated from biopsy samples collected at Weill Cornell Medicine or obtained from the In Vivo Animal and Human Studies Core at University of Michigan Center for Gastrointestinal Research (Key Resource Table). To generate organoids, human colon or ileum biopsy samples were cut into about 1 mm piece and washed with cold DPBS by pipetting 2-3 times. Samples were treated with collagenase type IV (Worthington, 2 mg/ml in F12K medium) at 37° C. for 30 minutes with pipetting every 10 minutes. Digestion was terminated by adding F12K with 10% FBS, followed by filtration with a 100 μm cell strainer (Falcon). Pelleted crypts were resuspended in human 3D Organoid Culture Medium (HCM, Key Resource Table) and Matrigel™ with a 1:5 volume ratio and embedded with 10-20 crypts per 10 μl droplet. Human organoids were expanded in HCM and differentiated in Human 3D Organoid Differentiation Medium (HDM, Key Resource Table) for 72 hours.

CRISPR-Mediated Gene Knockout in Colonic Organoids and Genomic Targeting Efficiency Calculation Satb2 and Foxd2 sgRNAs were designed with either Broad Institute online software or the Synthego CRISPR design tool (Key Resource Table) and cloned into a LentiCRISPRv2 vector (Addgene plasmid #52961). The lentiviruses were packaged with second-generation helper plasmids by transfection with lipofectamine 3000 (Thermo Fisher Scientific, L3000015) and titrated by counting puromycin resistant clones in HEK293T cells 5 days after infection.

To generate the colonic organoids with gene ablation, single cell suspensions of $10^5$ murine or human colonic organoids were mixed with 20 μL of $10^8$ TCIDso/ml of virus in 200 μl medium (either WENR for murine or HCM for human) in one well of a non-tissue culture treated 24 well plate, and centrifuged at 1,100 g at 37° C. for 30 minutes to facilitate infection. After centrifugation, 200 μl of culture medium was added and the plate was further incubated for 4 hours at 37° C. Cells were then resuspended, pelleted, and embedded in Matrigel™ Puromycin selection (1.0-2.5 μg/ml) was initiated 4 days post infection and lasted for 4 days. After puromycin selection, colonic organoids were seeded into new Matrigel drops and cultured in differentiation medium (WENR medium without WRN conditioned medium and with the addition of 1 μg/ml RSpondin and 10 μM L-161982). 3 days after differentiation, the organoids were either directly lysed in RLT buffer (Qiagen) for RNA exaction, or incubated with cell recovery solution on ice, to remove Matrigel, for immunofluorescence and immunoblotting analyses.

The CRISPR-mediated deletion efficiency of Satb2 was analyzed with immunofluorescence and immunoblotting, using a rabbit monoclonal anti-Satb2 antibody (Key Resource Table). For Foxd2, multiple commercially available antibodies were tested, but none was found suitable for immunofluorescence or Western Blot. Instead, the disruption efficiency at the Foxd2 genomic locus was evaluated, using a DNA mismatch detection assay with T7 endonuclease1 (NEB). Genomic DNA was extracted with an E.Z.N.A tissue DNA kit (OMEGA). Foxd2 target regions were PCR amplified with Phusion High-Fidelity DNA polymerase (NEB) plus Kapa Hifi GC buffer (ThermoFisher), according to the manufacturer's protocol. PCR products were pre-amplified with forward primer: GCCATAAGCTTTGAC TTCCAGTAAC (SEQ ID NO:14) and reverse primer: GTGATGAGGGCGATGTACGAATAA (SEQ ID NO:15), at high annealing temperature (68° C.) for 10 cycles, followed by 60° C. for 30 cycles. The hetero-duplexed PCR products from Foxd2 CRISPR KO and homogeneous PCR products from the control group were incubated individually or mixed at a 1:1 ratio with T7 endonuclease 1 at 37° C. for 15 minutes. The reaction was stopped by adding 1 mM EDTA (final concentration) and purified with the ZYMO DNA purification Kit. DNA fragment concentration was visualized by agarose gel electrophoresis and quantified with an Agilent Bioanalyzer. The gene modification percentage was calculated using the following formula: % gene modification=100×(1− (1−fraction cleaved)1/2). For the group mixed 1:1 with the control DNA fragment, the formula used is as below: % gene modification=200×(1−(1−fraction cleaved)1/2).

Bulk RNA Sequencing Analysis

Bulk RNA-seq was performed as previously described (Banerjee et al., 2018). The DEseq2 package was used for differential expression analysis. The Limma package was used to remove donor-donor variance and batch-effect (Ritchie et al., 2015). Differentially expressed genes were generally determined using parameters of adjusted p-value<0.05 and LFC>2 or <−2 unless specified. The heatmaps were plotted using the R package, pheatmap. GO enrichment analysis and GSEA analysis were conducted with the clusterProfiler package and GSEA desktop software (Yu et al., 2012).

ATAC-Seq

The ATAC experiments were performed as previously described.(Kim et al., 2014) Briefly, 50K intestinal epithelial cells were purified by FACS and pelleted by centrifugation at 500 g at 4° C. for 5 minutes. Nuclei were exacted in ATAC-Resuspension Buffer (RSB, 10 mM Tris-HCl pH 7.4, 10 mM NaCl, 3 mM MgCl2) with 0.1% NP40, 0.1%) Tween-20, and 0.01% Digitonin. DNA was fragmented by Nextera Tn5 Transposase (Illumina) and immediately purified with a MiniElute PCR Purification Kit (Qiagen). For ATAC-seq library building, NEBNext 2× MasterMix was used to pre-Amplify for 5 cycles and determine the required number of additional cycles by qPCR amplification. The final libraries were size selected (200 bp to 800 bp, including index) with AMpure beads, purified, and loaded for sequencing.

The purified libraries were sequenced by Novagene on Illumina HiSeq-2000, to obtain paired-end 150 bp reads. Alignment BALM files for the ATAC-seq were generated with the mm10 reference genome using nf-core pipelines. Narrow peaks were called using standard MACS2. ATAC-seq peak files that had regions of less than 1 kb from transcriptional start site (TSS) were removed using bedtool. Biological replicates were concatenated and sorted, and peaks merged within a maximum distance of 500 bp.

Cell Sorting and 10× Genomic Sample Preparation for Single Cell RNA Sequencing

To purify intestinal cells for scRNA-seq, a published protocol was followed (Haber et al., 2017). Briefly, murine proximal colon from TAM injected Vil-$Cre^{ER}$; $Satb2^{f/f}$ ($Satb2^{cKO}$) mice, or proximal colon and entire ileum from TAM injected $Satb2^{f/f}$(Controls) mice were harvested and rinsed in cold PBS. The tissues were incubated in 20 mM EDTA-PBS while rocking in a cold room for 90 minutes, Every 30 minutes, the tubes containing intestinal tissues were shaken vigorously for one minute, and dissociated epithelial fractions were collected. After 90 minutes, the 3 collections from each tissue were combined and dissociated into single cells with TrypLE (one minute at 37° C.). The single cell suspensions in FACS buffer (1% glucose, 10 mM HEPES, 10 μM Rock inhibitor, 1 mM N-acetyl-l-cysteine and 2% FBS in DPBS) were passed through a 40 μm filter and stained with anti-mouse CD326 (Epcam), anti-mouse CD31 and anti-mouse CD45 (Key Resource Table). Live $Epcam^+$, $CD45^-$, and $CD3^-$ epithelial cells, sorted by SONY MA900 in FACS buffer, were washed with 0.4% BSA in PBS and processed with 10× genomics single cell droplet sample preparation workflow at the Genomics Core facility at Weill Cornell Medicine.

10,000 cells in Master Mix were loaded into each channel of the Chromium Controller cartridge to produce droplets. Beads-in-Emulsion (GEMs) were transferred, and GEMs-RT was undertaken in droplets by PCR incubation After purification of first-strand cDNA from the post GEM-RT reaction mixture, barcoded and full-length cDNAs were amplified via PCR for library construction. Enzymatic fragmentation and size selection were used to optimize the cDNA amplicon size. TruSeq Read 1 (read 1 primer sequence) was added during GEM incubation. A sample index and TruSeq Read 2 (read 2 primer sequence) were added via end-repair, A-tailing, adaptor ligation, and PCR. The final libraries were assessed by an Agilent Technology 2100 Bioanalyzer and sequenced on an Illumina Novaseq sequencer.

scRNA-Seq Analysis with Seurat

Sequencing data from the Illumina NovaSeq were aligned to mouse mm10 in Cell Ranger 3.1.0. Seurat version 3.2.0 was used to perform quality control, count normalization, and clustering on the single cell transcriptomic data using standard methods as follows: unique molecular identifiers (UMIs) which barcode each individual mRNA molecule within a cell during reverse transcription were used to remove PCR duplicates. Cells expressing fewer than 300, or greater than 5,000 genes were removed to exclude non-cells or cell aggregates. Cells expressing greater than 18 percent mitochondrial related genes were also removed.

After quality control, the objects of wild-type (WT) ileum, colon and $Satb2^{cKO}$ colon were merged (hereafter named "the combined object") and the CellCycleScoring function was used to calculate a cell cycle score and assign a cell cycle status for each cell. Normalization of the combined object was conducted by SCTransform method in Seurat with regression out of confounding sources including mitochondrial mapping percentage and cell cycle scores (S score and G2M score). To perform linear dimensional reduction, RunPCA function was implemented with default parameters. To construct a K-nearest neighbor (KNN) graph, the FinderNeighbours function was used and took first 22 principal components as input. The FinderClusters function with default parameters a resolution of 1.5 implements modularity optimization technique to iteratively group cells together in order to cluster the cells. Non-linear dimensional reduction techniques Flt-SNE and UMAP were used to visualize the results.

The enriched transcripts in each cell cluster or groups of clusters were identified by the FindAllMarkers function using the following parameters: only.pos=TRUE, min.pct=0.3, logfc.threshold=0.3, and referred to as "global markers". Each cluster was then annotated based on the markers. To refine the annotation, wild-type colon object was additionally subseted and re-normalization performed. The cells from colonic object were re-clustered using first 30 PCs and a resolution of 1. The markers of WT colonic clusters were identified by the FindAllMarkers with the same parameters mentioned above. Each colonic cell cluster was annotated and re-assigned back to the combined object to refine cluster annotation.

For integrated analysis, per best practice suggestions in the Seurat package, the SelectlntegrationFeatures function was used to select the genes that were taken as input in the anchors identification procedure by the PrepSCTlntegration and the FindlntegrationAnchors functions using the merged control colon and ileum object as reference and the knockout object as query. The integration of the KO and WIT objects were implemented by the Integrated Data function with the anchors identified previously. Dimension reduction, clustering and visualization were performed using the same methods mentioned above.

For ileal cell type scoring, the control wild type objects were merged and SCTransformed using the same parameters mentioned above with the annotation retained. The scoring gene list for each cell type consists of the top 20 (avg_logFC) global cluster markers and all the differentially expressed genes between each ileal cell type and its colonic counterpart (e.g. enterocytes vs colonocytes) identified by the FindAllMarkers function and the FindMarkers function respectively with the following parameters: only.pos=TRUE, min.pct=0.3, logfc.threshold=0.3. The MIC genes were among the most differentially expressed between small intestine and colon. Their expression is strongly influenced by the microbiome and they do not constitute an intrinsic feature of the ileum. MHCII genes were removed from the gene lists. The gene lists were then applied as inputs in the AddModuleScore function with default parameters, which calculates module scores for feature expression programs on single cell level.

In order to identify stem cells in the samples, the combined object for the progenitor group subset was divided into two groups based on the detection of Lgr5 gene expression. The stem cell gene list was taken as input for the AddModuleScore with default parameters to calculate stem cell signature score between these two groups. Eventually, the combined object was subset for the Lgr5 positive "Progenitor" in the G1 or S cell cycle. The subset went through the standard analysis procedure as mentioned above for normalization, clustering and visualization with the first 20 PCs and a resolution of 0.8. Four clusters were identified, and their makers were found by the FindAllMarkers function. According to the markers, cluster 1 appeared to be Goblet progenitors and thus was removed.

Dual Cross-Linking ChIP-Seq and Cut & Run Enhancer-Seq

ChIP for Transcription Factors (TFs) SATB2, HNF4A, and CDX2, was performed as described (Saxena et al., 2017). EDTA stripped primary intestinal glands were cross-linked with 2 mM disuccinimidyl glutarate (DSG, Thermo Fisher Scientific. 20593) at room temperature (RT) for 45 minutes, followed by 1% formaldehyde (Sigma, F8775) fixation for 10 minutes. For each experiment, 50 μl of pelleted cross-linked cells were resuspended in 350 μl sarkosyl lysis buffer (0.25% sarkosyl, 1 mM DTT and protease inhibitor in RIPA buffer (0.1% SDS, 1% Triton X-100, 10 mM Tris HCl, 1 mM EDTA, 0.1% sodium deoxycholate, 0.3 M sodium chloride, PH 7.5)) and sonicated at 15% amplification by a tip sonicator (Qsonica, 0125) to obtain 200 bp to 800 bp chromatin fragments. Lysates were spun down at 20,000 g at 4° C. to remove insoluble fractions, then diluted in RIPA buffer with protease inhibitor in a final 2 ml volume. Diluted lysates were incubated with TFs antibodies (Key Resource Table) at 4° C. overnight and were additionally incubated with 30 μl protein A/G magnetic beads (Thermo Fisher Scientific, 88803) for 90 minutes the next day. This was followed by 6 washes with cold RIPA buffer beads. Cross-links were reversed overnight by incubating at 65° C. in 1% SDS and 0.1 M NaHCO3. Any remaining proteins were digested by Proteinase K (Thermo Fisher Scientific, 26160) for 1 hour at 37° C. DNA was purified with a MinElute purification kit (Qiagen, 28004). Libraries were prepared using the ThruPLEX DNA-Seq Kit (Takara bio, R400428 and R400427).

Cut & Run was performed by the Center for Epigenetics Research (GER) in Memorial Sloan Kettering Cancer Center. Briefly. Single cell suspensions were collected as described in the single cell RNA sequencing section. Dead cells were removed using a Dead Cell Removal Kit (Miltenyi Biotec). 105 cells were attached to Concanavalin A conjugated magnetic beads, permeabilized, and incubated with histone enhancer maker antibodies (Key Resource Table) at RT for 20 minutes. pAG-MNase (1:1000) was added in digitonin buffer (5% digitonin, 60 mM HEPES, 0.5 M sodium chloride, 1.5 mM spermidine hydrochloride, protease inhibitor, PH 7.5) to bind with antibodies. Finally, targeted chromatins were digested and released into the supernatant. DNA was purified with a MinElute purification kit. Libraries were prepared using the ThruPLEX DNA-Seq Kit (Takara bio, R400665). All the libraries were size selected (200-800 bp) by AMPure XP beads (Beckman, A63880) and loaded for sequencing.

ChIP-Seq Analyses for Transcription Factors

All reads (CDX2, HNF4A and SATB2) were trimmed with trim_galore (https://www.bioinformatics.babraham.ac.uk/projects/trim_galore/), and subject to quality control with FastQC before and after adapter trimming. For ChIP-Seq, Bowtie2 (Langmead and Salzberg, 2012) was used to align the two independent ChIP-Seq analyses to the mouse (mm10) genome with default parameters. Aligned ChIP-Seq data in SAM format were transformed to BAM files and non-uniquely mapped reads were filtered-out. Duplicate alignments were then marked and removed using Sambamba (Tarasov et al., 2015). The merge function in samtools (Li et al., 2009) was used to merge the BAM files of different replicates and filter out non-uniquely mapped reads. Deeptools (Ramirez et al., 2014) bamCoverage (duplicate reads ignored, RPKM normalized) was used to generate bigWig files from BAM files. Reads that overlapped with the Broad Institute sequencing blacklist (ENCODE Project Consortium, http://mitra.stanford.edu/kundaje/akundaje/release/blacklists/mm1 Omouse/mm10.blacklist.bed.gz) were discarded. The mapped reads from the biological replicates were combined for each factor and then peak calling was performed using the ChIP-Seq (macs2) (Feng et al., 2012) peak caller (v2.2.7) with parameters callpeak-f BAMPE-g mm-p 0.0000000001, and was controlled by KO/input. Heat maps of ChIP-Seq were created by quantile normalized bigWigs using computeMatrix, plotHeatmap, and plotProfile from deeptools.

MAnorm(Shao et al., 2012), software designed for quantitative comparisons of ChIP-Seq datasets, was applied to compare ChIP-Seq signal intensities between samples. The window size was 1 kb, which matched the average width of the identified ChIP-Seq peaks. Tissue specific peaks were defined using the following criteria: (1) defined as 'unique' by the MAnorm algorithm, (2) P value<0.01, (3) raw counts of unique reads>10. Peaks common to two samples were defined using the following criteria: (1) defined as 'common' by the MAnorm algorithm and (2) raw read counts of both samples>10. The annotatePeaks function in HOMER (Heinz et al., 2010) was used to annotate the peaks. To identify the distribution of the binding sites of ChIP-Seq data, peak sites were mapped to TSS (transcription start site), TTS (transcription termination site), Exon (Coding), 5' UTR Exon, 3' UTR Exon, lntronic, or Intergenic, which are common annotations defined by HOMER. A promoter region was defined as a region within ±2 Kb from the TSS. For analysis of enriched transcription factor DNA motifs in the peaks from the ChIP-Seq data, the findMotifsGenome function in HOMER was employed, using mm10 MotifOutput/-size given-mask.

Cut & Run Analyses for Histone Modifications

Reads (H3K4me1 and H3K27ac) were trimmed with trim_galore. Paired-end reads were then mapped to the mm10 genome using Bowtie2, with parameters as previously detailed, (Skene et al., 2018) using --local--very-sensitive-local--no-unal-no-mixed--no-discordant--phred33-I10-X 700. Only uniquely mapped reads were retained with samtools. Peaks were called from macs2 with pooled reads and with both replicate samples by merge broad and narrow peak files. For the enhancer analysis, only peaks±2 Kb outside TSSs were permitted, using 'distal peaks' as enhancer peaks. Tissue specific enhancers were identified between ileum and colon using MAnorm.

Immunohistochemistry, Edu Labeling, and Western Blot

Intestinal tissues were processed as previously described. (Ariyachet et al., 2016) Organoids were removed from Matrigel with Cell Recovery Solution (Corning 354253), fixed with 4% paraformaldehyde in PBS on ice for 30 minutes, and then processed with the same procedure as the intestinal tissues. Immunohistochemistry was performed using a standard procedure, incubating with primary antibodies (Key Resource Table) at 4° C. overnight, followed with secondary antibodies (Key Resource Table) at room temperature for 45 minutes. A Click-iT™ EDU Cell Proliferation Kit with Alexa Fluor®555 (C10338) was used to evaluate proliferation. The images were captured using either a confocal microscope (710 Meta) or a Nikon fluorescence microscope. For Western blot analysis, a monoclonal rabbit anti-SATB2 antibody was used to bind SATB2 protein, followed by an incubation with a secondary anti-Rabbit Peroxidase (HRP). Protein bands were visualized using enhanced chemiluminescent substrate (Pico from Thermo fisher) and recorded by a Li-COR C-Digit blot scanner.

For immunohistochemistry, samples were processed through heat mediated antigen retrieval in Citric Acid buffer (PH 6.0). Samples were then stained with primary rabbit antibodies (Key Resource Table), followed by Goat anti-Rabbit HRP polymer (Vector Laboratories, MP-7451) incubation, and finally, developed with AP (Magenta color, Vector Laboratories, MP-7724) HRP Substrate. An Alcian Blue Stain Kit (Vector Laboratories, H-3501) was used to stain goblet cells.

Quantitative Analysis of Histological Staining and Fluorescence in ImageJ

All sections were evaluated by multiple people, including a clinical pathologist. All image quantifications were done in ImageJ (Fiji, Version: 2.1.0/1.53c) as previously described (Fuhrich et al., 2013; Jensen, 2013). Briefly, immunofluorescence images were split into individual channel by click image>color>split channel. Relative signal intensity was calculated by comparison to the average density of the controls.

For immunohistochemistry images, the hematoxylin and specific antibody staining were separated into 3 different panels with the function of color deconvolution for PAS (AP development). Next, epithelial area was overlaid on the AP signal channel image. The final epithelial AP intensity (f) was calculated according the formula: f=255—mean intensity (obtained from the software analysis, range from 0-255, zero=deep brown, highest expression, 255=total white). Relative signal intensity was calculated by comparison to the average density of the controls.

Immunoprecipitation

EDTA stripped colonic grand epithelium cells from control and Satb2$^{cKO}$ mice were cross-linked with DSP (Thermo Fisher Scientific, PG82081) at RT for 45 minutes. Pellets of epithelial cells were incubated with RIPA buffer and sonicated at 15% amplification for 20 seconds. After 10 minutes (maximum speed down), supernatants were incubated with anti-CDX2 and anti-HNF4A (Key Resource Table) overnight in a cold room with a rotation speed of 10 RPM. After adding 30 μl protein A/G magnetic beads for 90 minutes on the next day, the protein and beads complex was pulled down by a magnetic stander. Next, 6 cold RIPA buffer washes were performed. Then cross-links were cleaved by 50 mM DTT boiling for 5 minutes. Immunoblots were used to visualize the interaction between target proteins.

[$^{14}$C]-Taurocholic acid and [$^{3}$H-]-Glucose In vivo absorption study 14C-Taurocholic acid and $^{3}$H-Glucose were purchased from American Radiolabeled Chemicals, Inc. To perform the absorption study, mice were fasted overnight for about 16 hours. Following deep anesthetization, a 2 cm section of the distal ileum or proximal colon was cleaned of luminal content by repeated flushing with saline and was tied on both ends with sutures to create a sealed pouch. 2 μCi $^{3}$H-glucose and 0.6 μCi $^{14}$C-Taurocholic acid dissolved in 100 μl 10% dextrose solution were injected into the pouch. After 5 or 20 minutes, blood was collected from the hepatic portal vein with a 27-gauge needle. Plasma was harvested after centrifugation at 12,000 rpm for 4 minutes at 4° C. Plasma protein was precipitated with the addition of $Ba(OH)_2$ and $ZnSO_4$ to 20 μl plasma. The supernatant was dissolved in Ultima Gold Scintillation fluid (PerkinElmer). A liquid scintillation counter with dual channels for $^{3}$H and $^{14}$C was used to measure radioactivity in all samples.

For liver sampling, the right upper lobe from each mouse was removed and stored at −20° C. Frozen tissues were homogenized in $dH_2O$ (50 mg of tissue in 500 μl of $dH_2O$) with a Dounce homogenizer. Following homogenization, the glass tubes were placed in a heat block for 10 minutes at 100° C., vortexed, and cooled to room temperature. The homogenized samples were centrifuged at 16,000 g for 5 minutes. Supernatants were collected. 500 μl of supernatant per sample was added to scintillation vials containing the scintillation cocktail for counting.

Disaccharidase and Dipeptidyl Peptidase IV (DPP4) Assay

After Matrigel removal, differentiated human organoids were transferred to BSA-pre-coated 1.5 ml Eppendorf tubes and washed three times in PBS. For the disaccharidase enzyme activity assay, 5 mg of an organoid pellet was incubated with 100 μl of 56 mM sucrose in PBS or PBS only at 37° C. for 45 minutes. Aliquots of the supernatant were sampled for glucose detection using the Glucose Colorimetric Assay Kit (Cayman), according to the manufacturer's protocol. Briefly, the samples were diluted with PBS in a 1:1 and 1:2 ratio to ensure glucose concentration levels in the standard range (0-25 mg/dl). The enzyme and samples mixtures were incubated at 37° C. for 10 minutes. The absorbance (510 nm) was measured with a plate reader (SpectraMax M2). Glucose concentration was determined by comparison to a glucose standard curve. For the DPP4 assay, Gly-Pro-p-nitroanilide hydrochloride (Sigma, G0513) in PBS was added to an organoid pellet at a final concentration of 1.5 mM. The organoid tubes were incubated at 37° C. in a tissue culture incubator with the lip open for 30 minutes and were mixed every 10 minutes. The supernatants were collected and absorbance was measured at 410 nm with a plate reader (SpectraMax M2). Released nitroanilide concentration was determined by comparison to a 4-nitroanilide (Sigma, 185310) standard curve (0-200 μg/ml). The concentration was finally normalized to a total cell lysate protein amount of 1 mg.

Data Availability

The accession number for high-through sequencing raw and processed data reported in this paper are Gene Expression Omnibus (GEO): GSE148695. SubSeries information listed in Key Resources Table.

TABLE 2

| Organoid Culture Medium | | | | | | | |
|---|---|---|---|---|---|---|---|
| Mouse Large Intestine Culture Medium (Wnta3-EGF-Noggin-Rspondin1 medium(WENR) | | Mouse Small Intestine Culture Medium (EGF-Noggin-Rspondin1 medium (ENR)) | | Human 3D Organoid Culture Medium (HCM) | | Human 3D Organoid Differentiation Medium (HDM) | |
| Reagents | Final Concentration | Reagents | Final Concentration | Reagents | Final Concentrations | Reagents | Final Concentration |
| Glutamax | 2 mM | Glutamax | 2 mM | Glutamax | 2 mM | Glutamax | 2 mM |
| HEPES | 10 mM | HEPES | 10 mM | HEPES | 10 mM | HEPES | 10 mM |
| Primocin | 100 μg/ml | Primocin | 100 μg/ml | Primocin | 100 μg/ml | Primocin | 100 μg/ml |
| EGF | 50 ng/ml | EGF | 50 ng/ml | EGF | 50 ng/ml | Y-27632 | 10 μM |
| N2 supplement | 1X | N2 supplement | 1X | N2 supplement | 1X | A83-01 | 500 nM |
| B27 supplement | 1X | B27 supplement | 1X | B27 supplement | 1X | B27 supplement | 1X |
| N-acetyl-L-cysteine | 1 mM | N-acetyl-L-cysteine | 1 mM | N-acetyl-L-cysteine | 1 mM | N-acetyl-L-cysteine | 1 mM |
| L-WRN Condition | 50% V/V | Noggin | 100 ng/ml | L-WRN Condition | 50% V/V | L-WRN Condition | 25% V/V |

TABLE 2-continued

| Organoid Culture Medium | | | | | | | |
|---|---|---|---|---|---|---|---|
| Mouse Large Intestine Culture Medium (Wnta3-EGF-Noggin-Rspondin1 medium(WENR) | | Mouse Small Intestine Culture Medium (EGF-Noggin-Rspondin1 medium (ENR)) | | Human 3D Organoid Culture Medium (HCM) | | Human 3D Organoid Differentiation Medium (HDM) | |
| Reagents | Final Concentration | Reagents | Final Concentration | Reagents | Final Concentrations | Reagents | Final Concentration |
| Medium & | | | | Medium & | | Medium & | |
| A83-01* | 500 n/M | Respondin1 | 1 μg/ml | SB202190 | 100 μM | Gastrin | 10 nM |
| Y-27632* | 10 μM | Y-27632* | 10 μM | A83-01 | 500 nM | FGF-2 | 50 ng/ml |
| In Advanced DMEM/F12 | | In Advanced DMEM/F12 | | Y-27632* | 10 μM | IGF-1 | 100 ng/ml |
| & L-WRN cells was originally made in Thaddeus Stappenbeck Lab which secrete Wnt3a, R spondin and Noggin, collected in culture with 20% FBS in Advanced DMEM/F12 for 4 days, filtered and stored in −80° C. | | | | Gastrin | 10 nM | DAPT# | 5 μM |
| | | | | Nicotinamide | 10 mM | In Advanced DMEM/F12 | |
| *To avoid anoikis, supplement the culture medium with Y-27632 for the first two days. Supplement A83-01 in WENR for first two passaging. | | | | CHIR99021 | 2.5 μM | # DAPT was added for secretion cells niche differentiation (Goblet cells et. al.) | |
| | | | | In Advanced DMEM/F12 | | | |

TABLE 3

| Quantitative PCR (qPCR) Primer Sequence | |
|---|---|
| Gene Name (Mouse) | Primer Sequence |
| Gapdh | F: GGGTGTGAACCACGAGAAATA (SEQ ID NO: 16) |
| | R: GTCATGAGCCCTTCCACAAT (SEQ ID NO: 17) |
| Satb2 | F: GGGGCGTCTGTCACATAACT(SEQ ID NO: 18) |
| | R: TTTAGCCAGCTGGTGGAGAC(SEQ ID NO: 19) |
| Olfm4 | F CAGCCACTTTCCAATTTCACTG (SEQ ID NO: 20) |
| | R: GCTGGACATACTCCTTCACCTTA (SEQ ID NO: 21) |
| Bcl2l15 | F: CTGCTAACCGGAACCTATCGG (SEQ ID NO: 22) |
| | R: TCCAGCTCTCCATTGAACTGA (SEQ ID NO: 23) |
| Fabp1 | F: CAGAGCCAGGAGAACTTTGAG (SEQ ID NO: 24) |
| | R: GTCCATAGGTGATGGTGAGTTT (SEQ ID NO: 25) |
| Fabp6 | F: GTTCAAGGCTACCGTGAAGAT (SEQ ID NO: 26) |
| | R: TCTTGCTTACGCGCTCATAG (SEQ ID NO: 27) |

TABLE 3-continued

| Quantitative PCR (qPCR) Primer Sequence | |
|---|---|
| Gene Name (Mouse) | Primer Sequence |
| Gpd1 | F: ATGGCTGGCAAGAAAGTCTG (SEQ ID NO: 28) |
| | R: CGTGCTGAGTGTTGATGATCT (SEQ ID NO: 29) |
| Lgals2 | F: AACATGAAACCAGGGATGTCC (SEQ ID NO: 30) |
| | R: CGAGGGTTAAAATGCAGGTTGAG (SEQ ID NO: 31) |
| Sult1a1 | F: CAACATGGAGCCCTTGCGTAA (SEQ ID NO: 32) |
| | R: ATGAGCACATCATCAGGCCAG (SEQ ID NO: 33) |
| Myrf | F: CTCCCATCAAAGCAGAGCCA (SEQ ID NO: 34) |
| | R: CCACGTGGCATAGAGTCTCC (SEQ ID NO: 35) |
| Sis | F: GCTATCGCTCTTGTTGTGGTT (SEQ ID NO: 36) |
| | R: TTCCAGGACTAGGGGTTGAAG (SEQ ID NO: 37) |
| Tm4sf4 | F: AAGCCACCTTTCGGATGAGG (SEQ ID NO: 38) |
| | R: CGCAGCAGTCGTTGTTCTG (SEQ ID NO: 39) |

TABLE 3-continued

Quantitative PCR (qPCR) Primer Sequence

| Gene Name (Mouse) | Primer Sequence |
|---|---|
| B3galt5 | F: AGGCTAGTTTACGCCTCCATT (SEQ ID NO: 40)<br>R: AGGAACTTCCCGTGACTTTTC T (SEQ ID NO: 41) |
| Car1 | F: AACCCAAGCCTGCAGAAA (SEQ ID NO: 42)<br>R: GAGCCAAAGTAGGTCCAGTA ATC (SEQ ID NO: 43) |
| Car2 | F: GAATGTGTGACCTGGATCGT (SEQ ID NO: 44)<br>R: TGTCCACCATCGCTTCTTC (SEQ ID NO: 45) |
| Papss2 | F: AGGCCCATCATGTGAGCAG (SEQ ID NO: 46)<br>R: CACACGGTACATCCTCGGAAT (SEQ ID NO: 47) |
| Selenbp1 | F: ATGGCTACAAAATGCACAAA GTG (SEQ ID NO: 48)<br>R: CCTGTGTTCCGGTAAATGCAG (SEQ ID NO: 49) |
| Slc6a14 | F: GACAGCTTCATCCGAGAACTT C (SEQ ID NO: 50)<br>R: ATTGCCCAATCCCACTGCAT (SEQ ID NO: 51) |
| St6galna c6 | F: AACAGTGCCAACGAGGTCTT C (SEQ ID NO: 52)<br>R: CTTGTTGCCGAGGATAGGGA A (SEQ ID NO: 53) |

TABLE 4

Crispr Knockout sgRNA sequence

| Gene Name | SgRNA Sequence |
|---|---|
| Mouse Satb 2 | 1: CAGGAATAATCAAGCTAGG G (SEQ ID NO: 54)<br>2: TCACATAACTGAGGGGGAG G (SEQ ID NO: 55)<br>3: GGGCGTCTGTCACATAACTG (SEQ ID NO: 56) |

TABLE 4-continued

Crispr Knockout sgRNA sequence

| Gene Name | SgRNA Sequence |
|---|---|
| Mouse Foxd2 | 1: GGCGGCGGCACCATGACCC T (SEQ ID NO: 57)<br>2: CTCGCAGCAGCAGCTGCCCA (SEQ ID NO: 58)<br>3: CGCGGCCGGGGAGCTCTCG G (SEQ ID NO: 59) |
| Human SATB2 | 1: TGCTCCACGACACAAAAGAC (SEQ ID NO: 60)<br>2: GATTCCTGTCTTTTGTGTCG (SEQ ID NO: 61)<br>3: CTTTTGTGTCGGGAGCAGT (SEQ ID NO: 62)<br>4: TGTGTCGTGGAGCAGTTGGA (SEQ ID NO: 63) |

Example 12: SATB2 is Enriched and Required in Colonic Epithelium

Figure 8C:
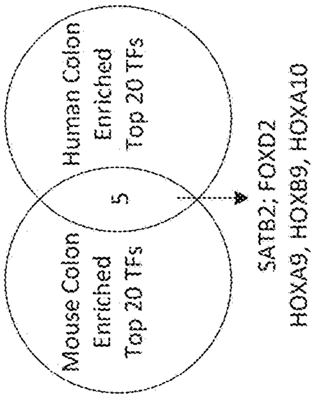
FIGS. 8A-8E illustrate identification of SATB2 as a transcription factor enriched in large intestine stem cells that regulates large intestine gene expression. Related to FIG. 1.
Figure 8A:
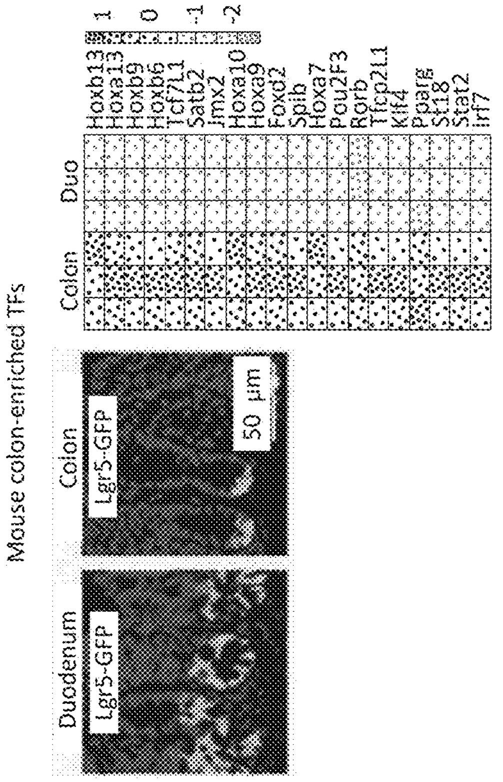
Figure 8B:
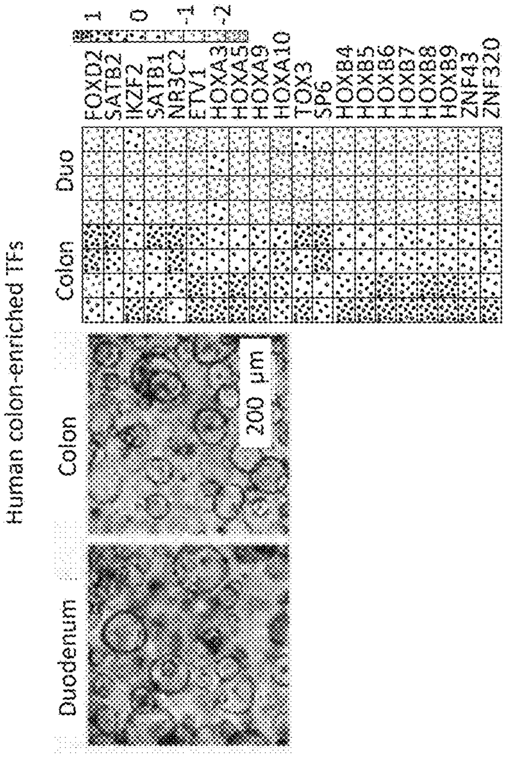
Figure 8D:
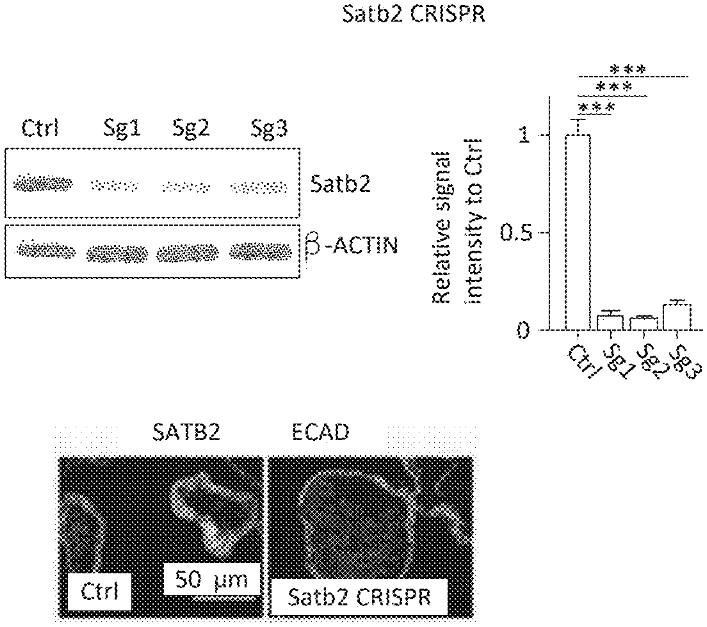
Figure 8E:
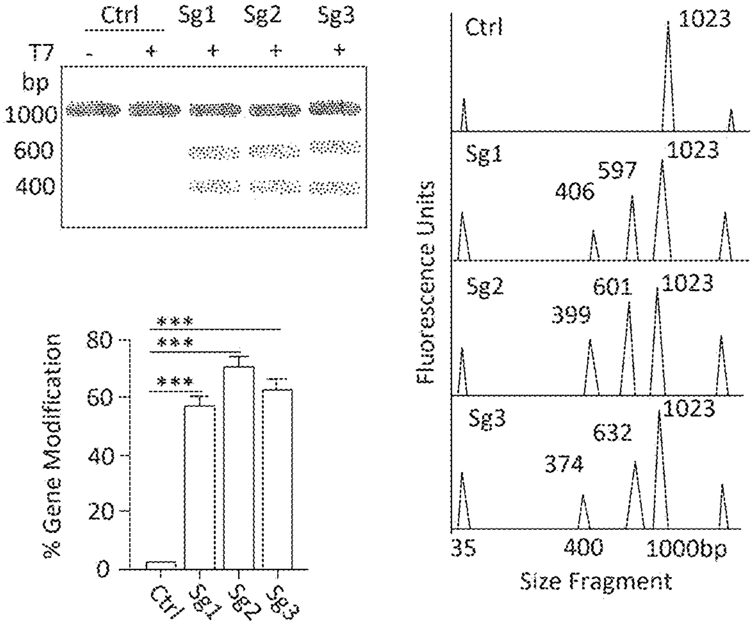
Figure 8F:
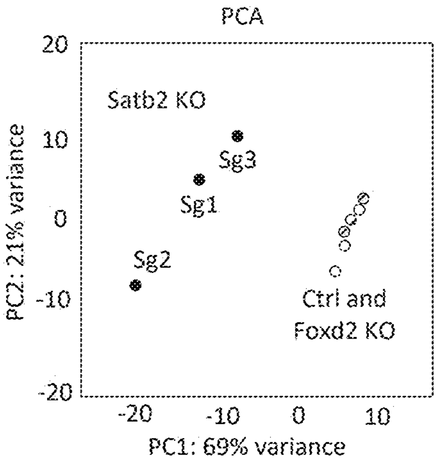
FIGS. 8F-I show RNA-seq of murine colonic organoids revealed significant transcriptomic changes in Satb2 CRISPR organoids (Satb2 KO), but not Foxd2 KO organoids. (F) Principal component analysis. 229 genes were up-regulated and 86 genes down-regulated in SATB2 CRISPR organoids vs control colonic organoids (LFC>2, Padj<0.05) as shown in the heatmap (FIG. 8G) and the volcano plots
Figure 8G:
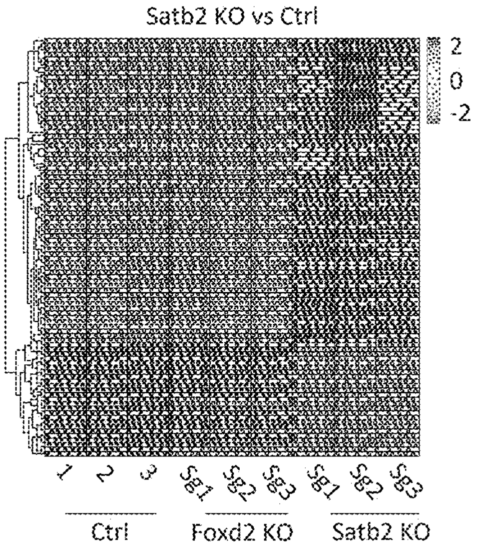
Figure 8H:
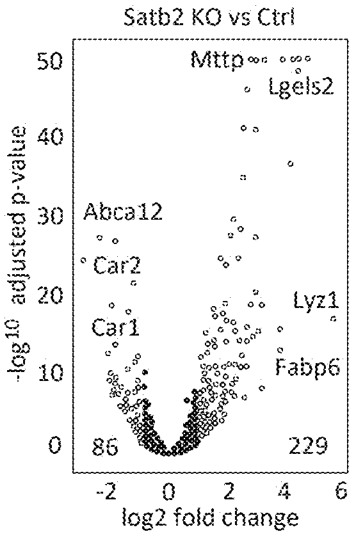
Figure 8I:
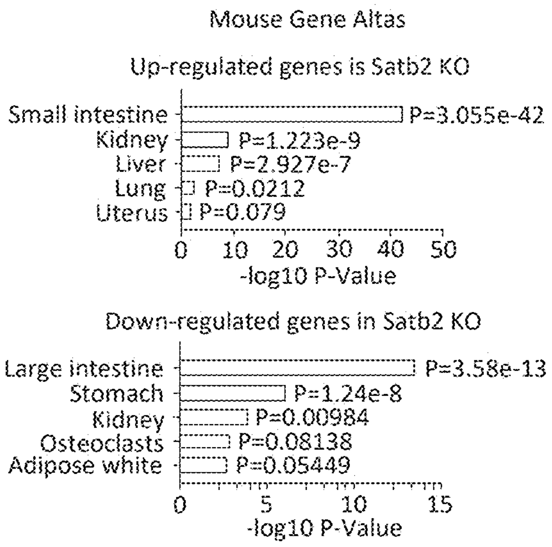

To identify genes that may be involved in maintaining colonic stem cell fate in adult mice and humans, RNA-seq data of purified $LGR5^+$ stem cells from the duodenum and the colon was interrogated for transcription factors (TFs) enriched in colonic stem cells (FIG. 8A) (Jadhav et al., 2016; Murata et al., 2020). Primary duodenal and colonic organoids from human biopsy samples were cultured under high Wnt conditions, which 10 favor stem cell growth (VanDussen et al., 2019), and used RNA-seq to identify TF transcripts enriched in human colonic organoids (FIG. 8B). Besides posterior Hox genes, which confer positional identity during development, only two TF genes, SATB2 and FOXD2, were enriched in both murine and human colon (FIG. 8C). To assess these TFs' requirements in regulating colonic identity, CRISPR (Clustered regularly interspaced short palindromic repeats), CAS9, and 3 different guide RNAs were used to disrupt expression of Satb2 or Foxd2 in murine colonic organoids, achieving deletion efficiencies of 55% to 95% in independent experiments (FIG. 8D and FIG. 8E). Disrupting Foxd2 had little impact on the colonic transcriptome, whereas Satb2 loss altered the mRNA profile significantly, with reduced expression of colonic genes and increased expression of small intestine genes (FIG. 8F-1), indicating a requirement for Satb2 in maintaining adult colonic identity.

Figure 9A:
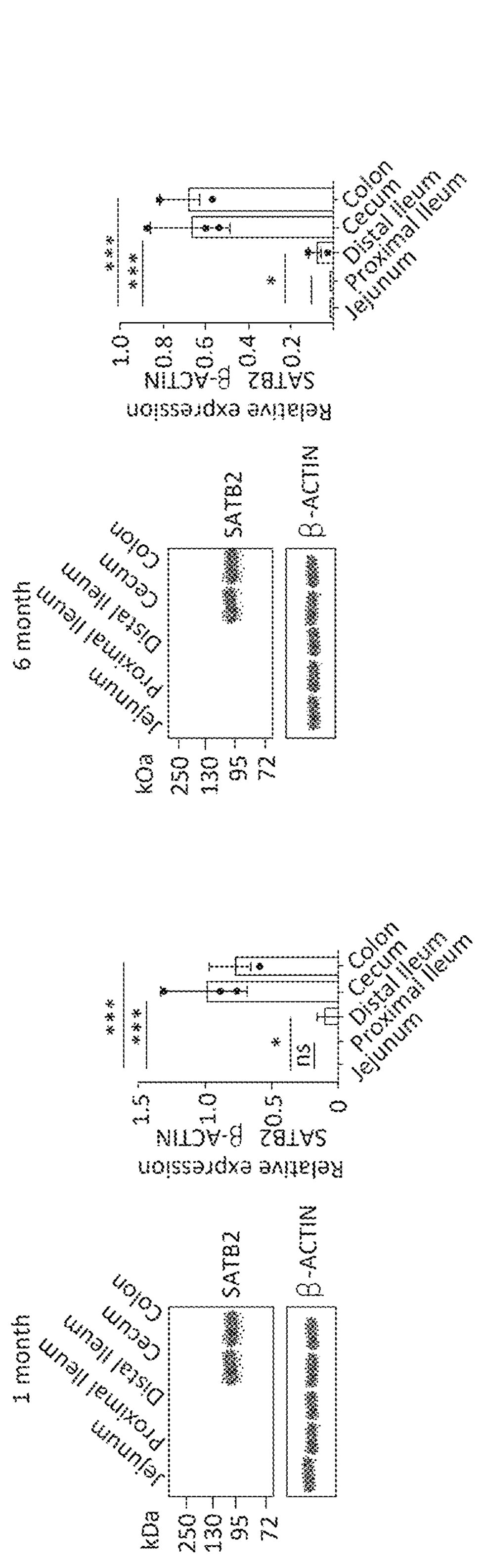
FIGS. 9A-9L illustrate colonic epithelium in $Vil\text{-}Cre^{ER}$; $Satb2^{f/ff}$, ($Satb2^{cKO}$) mice resembles that of ileal small intestine. Related to FIG. 1.

Example 13: Replacement of Colonic Mucosa by Ileal-Like Mucosa in Adult Mice after SATB2 Loss SATB2 is a homeodomain-containing chromatin factor expressed in developing craniofacial tissues and cortical neurons (Alcamo et al., 2008; Britanova et al., 2008; Britanova et al., 2006; Dobreva et al., 2006). Human SATB2 mutations produce a syndrome characterized by craniofacial anomalies and cognitive impairment (Zarate and Fish, 2017). SATB2 is also expressed in fetal and adult murine and human hindgut and may be used as a diagnostic marker for colorectal cancer (Munera and Wells, 2017; Perez Montiel et al., 2015), but its intestinal functions are largely unknown. Immunoblots (FIG. S2A) and immunohistochemistry revealed prominent SATB2 expression in adult mouse cecal and colonic epithelia, including in LGR5$^+$ stem cells at the crypt base. Scattered villus cells in the terminal ileum also showed SATB2 staining but the small intestine is otherwise devoid of SATB2 (FIG. 9A).

Figure 9B:
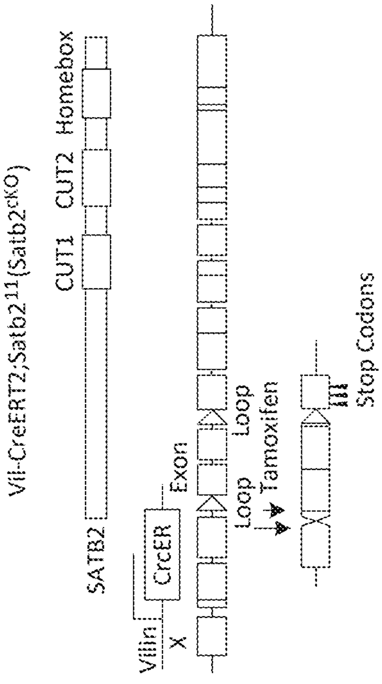
Figure 9C:
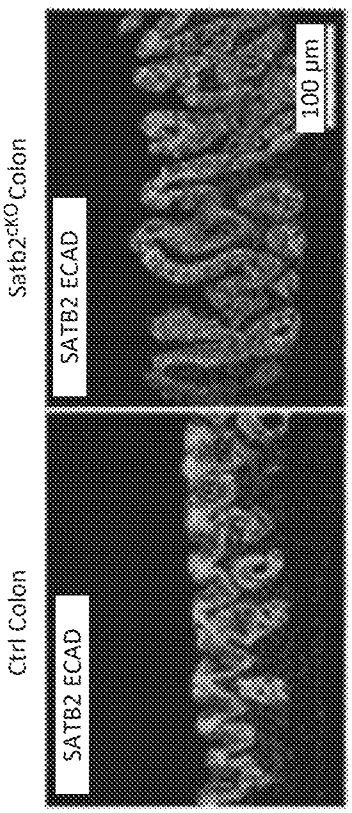
Figures 9D, 9E, 9F, 9G:
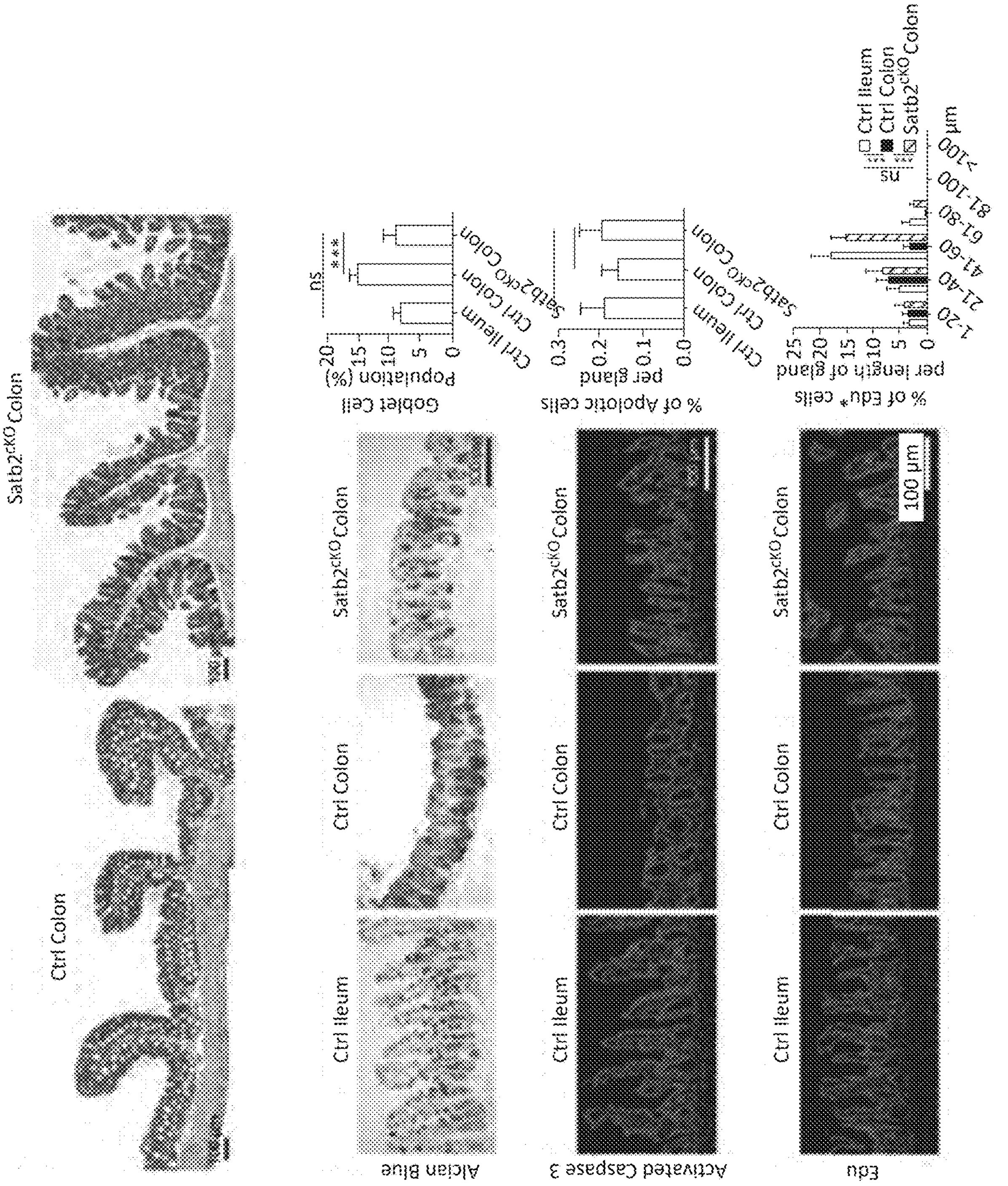

To evaluate intestinal Satb2 function in vivo, Satb2 was deleted in 2-month old Satb2$^{f/f}$ mice using the Villin1-Cre$^{ER}$ $_{(T2)}$ strain specifically in intestinal mucosa (FIG. 9B), leading to near complete absence of SATB2 (FIG. 9C). One month after Tamoxifen (TAM) treatment, the large intestine mucosae of Vil-Cre$^{ER}$; Satb2$^{f/f}$ mice (referred thereafter as Satb2$^{cKO}$) were significantly remodeled, with the characteristic flat epithelium replaced by villus structures (mucosal depth 208±24 μm vs. 92±18 μm in control Satb2$^{f/f}$ littermates) and presence of Paneth cells at the crypt base (FIGS. 9C-9D), resembling the small intestine instead of colon. Goblet cells stained with Alcian blue were significantly decreased (9%±2% of all epithelial cells), to a level comparable to the ileum (8%±1%) rather than that of the normal colon (15%±1.5%; FIG. 9E). Apoptosis rates were similar in mutant and control colonic cells (FIG. 9F). 5-ethynyl-2-deoxyuridine (EdU) pulse-chase revealed accelerated movement of epithelial cells away from the crypt base (mutant vs control colon, P<0.0001, Tukey's multiple comparison test, FIG. 9G). This rate is similar to that of the normal ileum (mutant colon vs. control ileum, P>9.99, Tukey's multiple comparison test) and may account for the architectural remodeling in Satb2$^{cKO}$ colon.

Figure 9H:
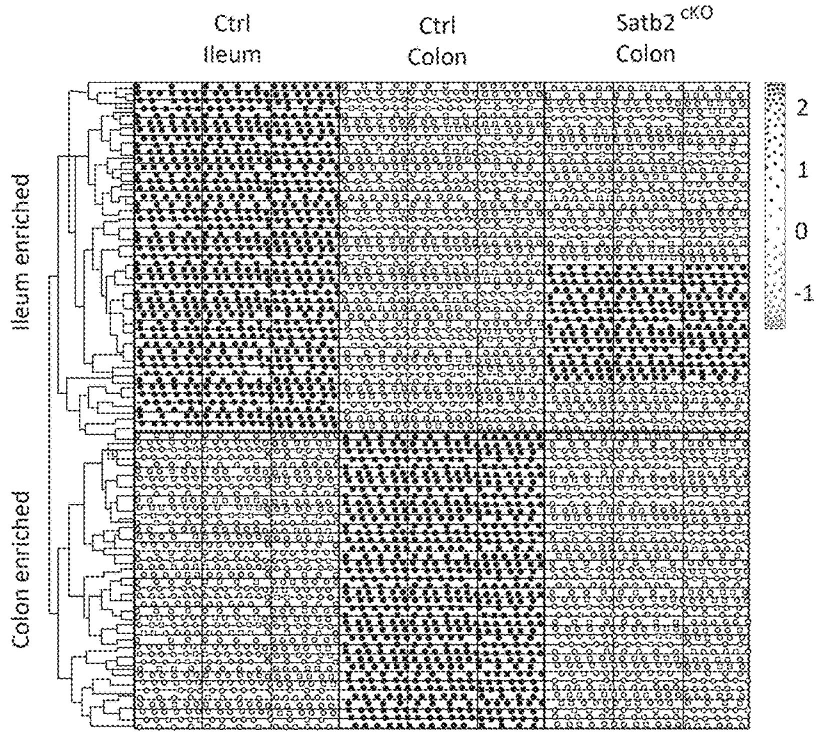
Figure 9I:
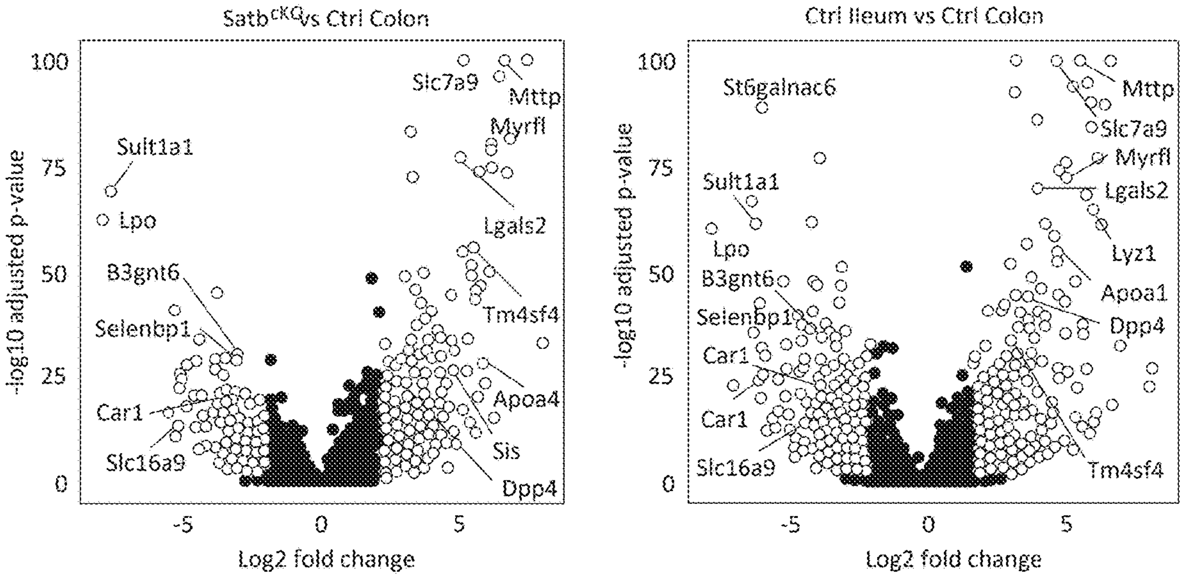
Figure 9J:
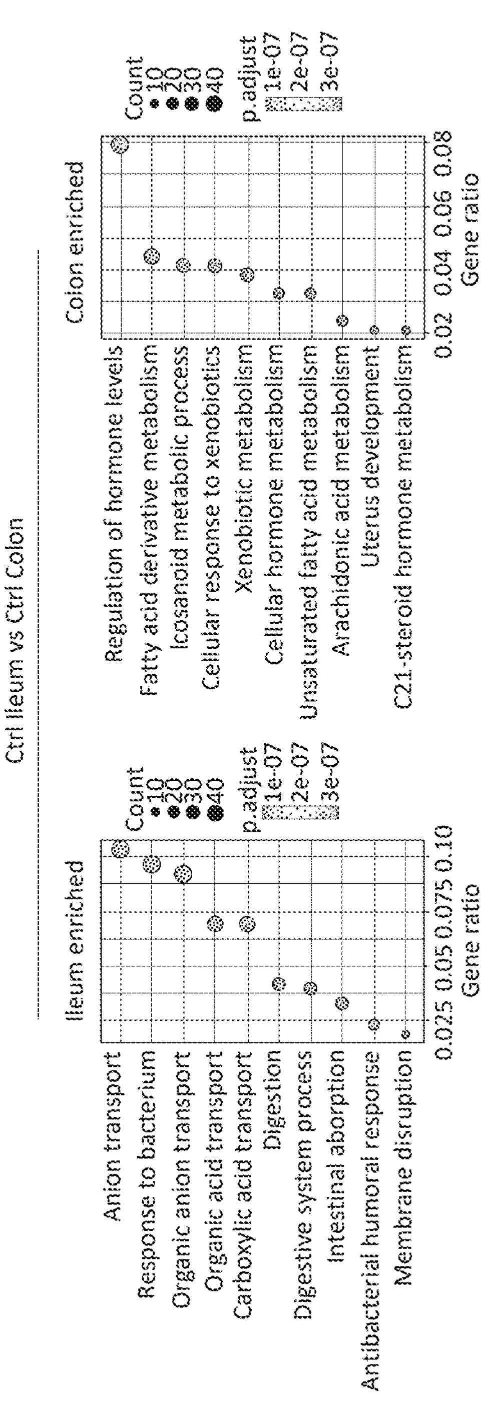
Figure 9K:
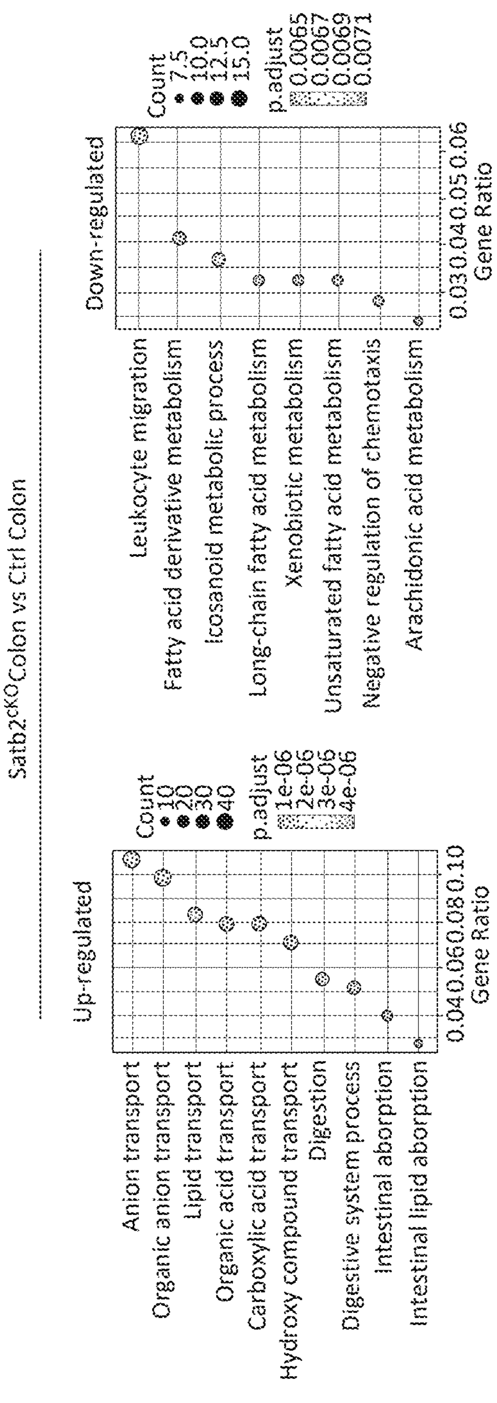
Figure 9L:
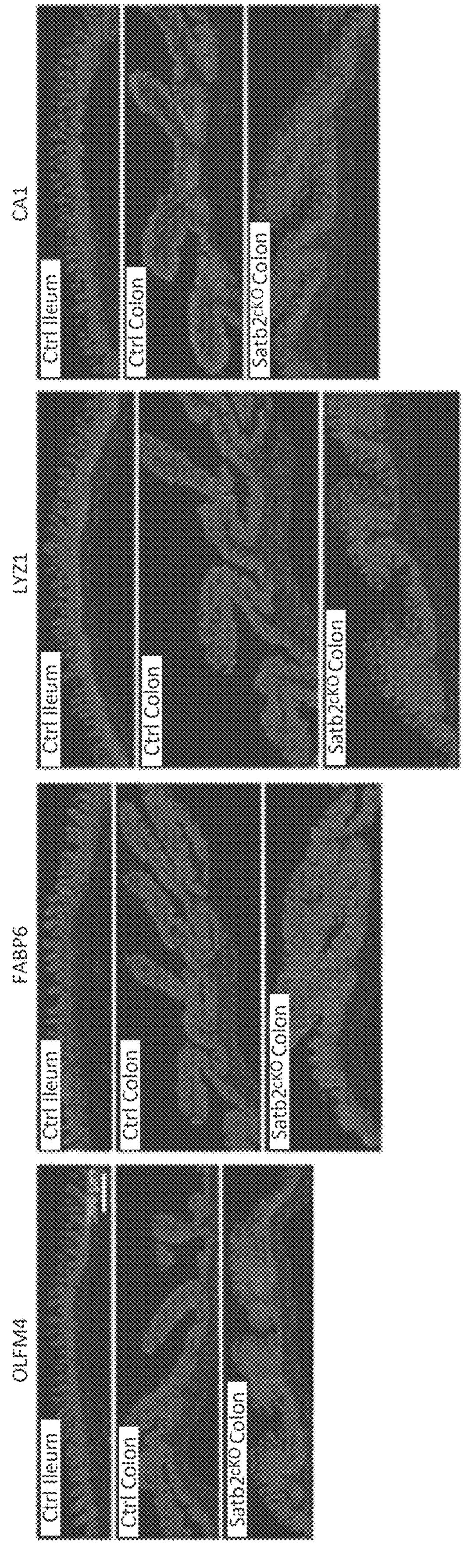

Whole epithelium RNA-seq analysis revealed little difference between SATB2-null and control jejunum or ileum, whereas the mutant cecal and colonic transcriptomes resemble that of normal ileum. Of the 362 ileal enriched genes (control ileal vs colonic transcriptome, $Log_2$ fold change (LFC)>2, adjusted P value (Padj)<0.05), 309 (85.4%) were up-regulated in SATB2 mutant colon whereas 238 out of 302 colon-enriched genes (78.8%) were down-regulated (FIG. 9H). Accordingly, molecular pathways that control digestion, absorption, and solute transport, reflecting ileal functions, were activated at the expense of colonic functions such as fatty acid and xenobiotic metabolism (FIGS. 9I-9K). In agreement with these findings, immunohistochemistry revealed loss of colonic markers such as CA 1 and AQP4 and gain of ileum-restricted markers such as OLFM4 (stem cells), FABP6 and FGF15 (enterocytes), and the Paneth cell product LYZ. Six months after TAM treatment, SATB2-null colon was still wholly lined by a villous ileum-like mucosa with widespread expression of ileal genes, indicating a stable mucosal conversion (FIG. 9L).

Example 14: Conversion of LGR5+ Colonic Stem Cells to Ileal-Like Stem Cells

Given the stable and long-lasting remodeling of colonic mucosa to ileal-like mucosa in adult mice after SATB2 loss, it was reasoned that the colonic stem cells may have been converted to ileal-like stem cells. To evaluate this hypothesis, three different approaches were used: single-cell transcriptome profiling of LGR5+ stem cells, organoid cultures, and SATB2 deletion from LGR5$^+$ stem cells.

Figures 10A, 10B:
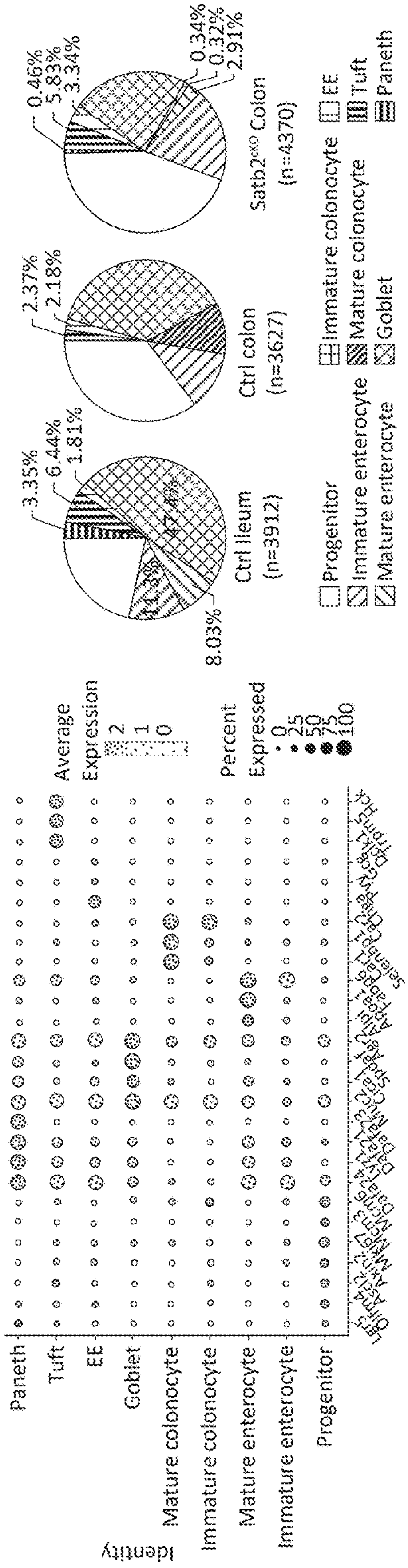
FIGS. 10A-10G illustrate single cell RNA sequencing reveals stem cell conversion and rerouting of cell lineage differentiation in Satb2cKO colon to ileum. Related to FIG. 2.
Figures 10C, 10D, 10E, 10F:
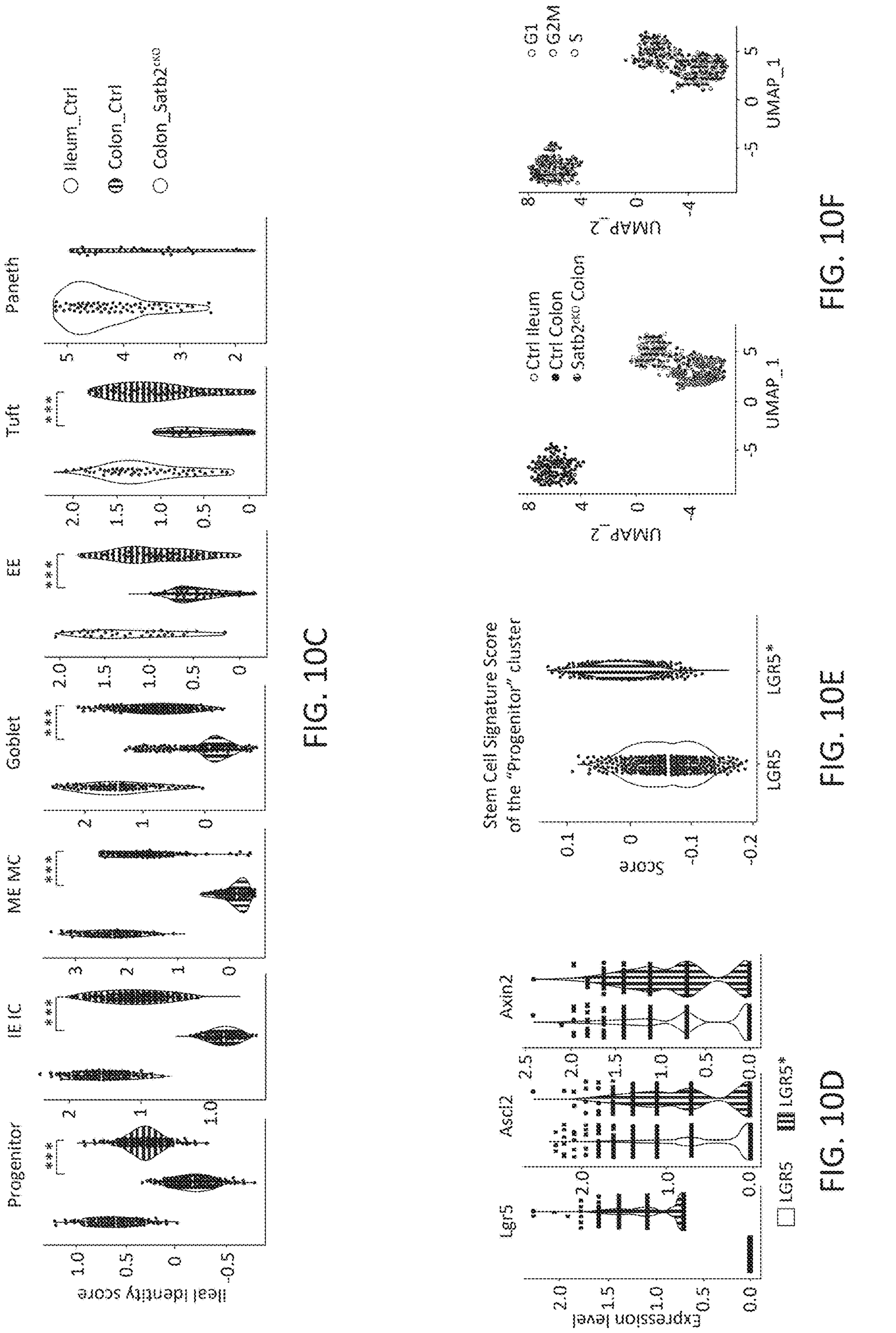

First, epithelial cells (FACS-purified EPCAM$^+$ CD45$^-$ CD3$^-$ cells) were profiled using single-cell RNA sequencing (scRNA-seq). The transcriptomes from 3,912 control ileal, 3,627 control colonic, and 4,370 Satb2$^{cKO}$ colonic cells (30 days post-TAM) passed quality controls and were integrated and partitioned into 7 broad intestinal populations including goblet, enterocyte, colonocyte, Paneth, tuft, and enteroendocrine (EE) cells, and annotated with lineage-specific marker genes (Haber et al., 2017) (FIG. 10A; Table 2). Cells bearing low or no distinct lineage markers but high levels of proliferating genes Mki67 or Mcm3/6 were collectively classified as progenitors, which include LGR5$^+$ stem cells as a subset (FIG. 10A). A majority of differentiated cells from the Satb2$^{cKO}$ colon clustered with control ileal cells and expressed canonical ileal markers. The similarity between control ileal and Satb2$^{cKO}$ colonic transcriptomes was assessed using cohorts of genes enriched in each ileal cell type (ileal identity scores), which similarly showed a broad adoption of ileal identity by cells in Satb2cKo colon (FIG. 10C). For instance, colonocytes, representing 22.4% of the control colon population, were replaced by enterocytes in Satb2$^{cKO}$ mice (21.5% of the total population) (FIGS. 10B-10C; Table 3). Paneth cells expressing Lysozyme and dozens of Defensin genes were also readily detected in Satb2cKo colon but not present in control colon (FIGS. 10B-10C).

Figure 10G:
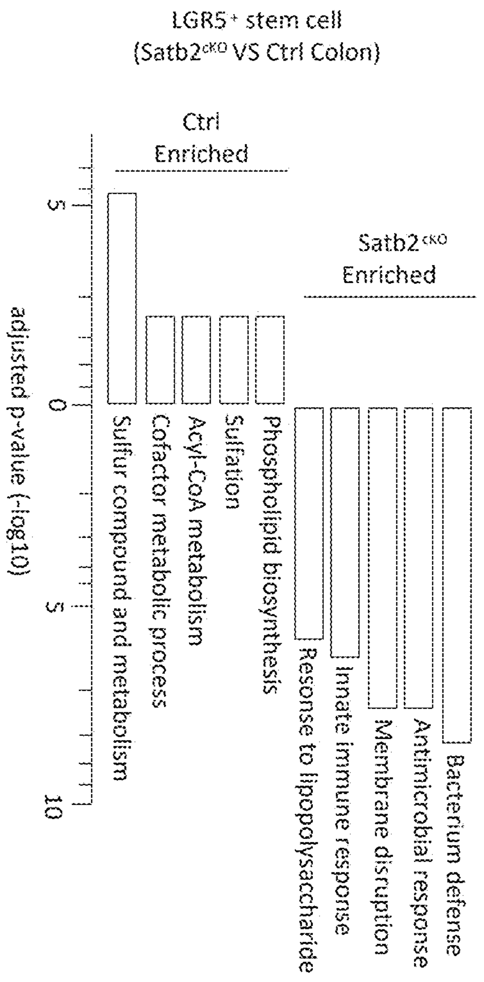

Lgr5$^+$ stem cells were identified from the "progenitor" groups (FIG. 10D). The Lgr5$^+$ cells expressed high levels of the ISC markers Ascl2 and Axin2 and scored significantly higher than Lgr5$^-$ progenitors using a stem-cell scorecard (Munoz et al., 2012) (Wilcoxon rank sum test continuity correction p-value<2.2 $e^{-16}$) (FIG. 10D and FIG. 10E). Focusing on the subsets of stem cells at the G1/S cell cycle phase (control ileum, 209 cells; control colon, 230 cells; mutant colon, 155 cells), which have been proposed as basal stem cells (Biton et al., 2018), Satb2$^{cKO}$ colonic stem cells clustered with ileal, not with colonic stem cells (FIG. 10F). Compared with control colon, the ileuml-like stem cells in Satb2$^{cKO}$ colon were enriched for GeneOntology pathways of antimicrobial response and innate immune response while depleted of sulfur and phospholipid metabolism pathways (FIG. 10G).

Figure 11B:
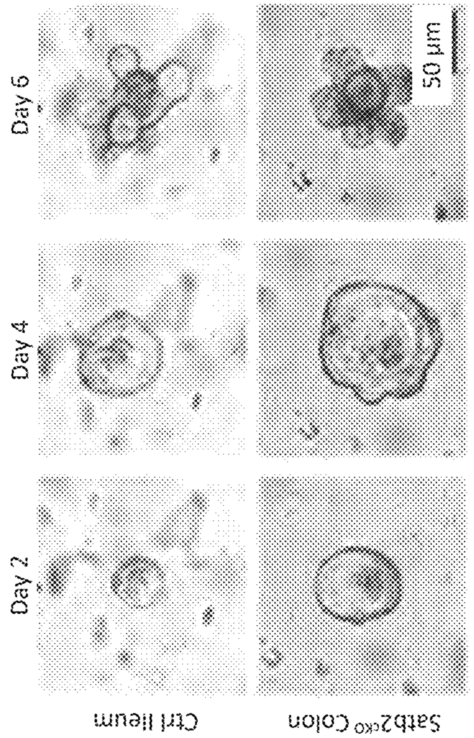
FIGS. 11A-11K illustrate characterization of SATB2 loss in colon and SATB2 gain in jejunum. Related to FIGS. 2 & 3 & 4.
Figure 11A:
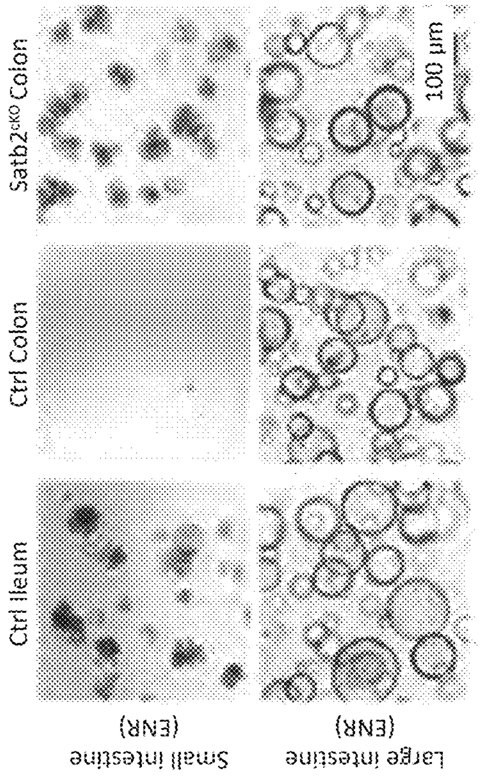

Next, stem cell properties in organoid cultures were evaluated. ISCs derived from the large and small intestines differ in their ability to form organoids in 3D Matrigel cultures. In particular, colonic crypts fail to generate organoids in medium lacking WNT3A (Sato et al., 2011). Crypts isolated from control ileum, control colon and Satb2$^{cKO}$ colon all produced spheroids in culture media containing high WNT3A (FIG. 11A). However, when grown in WNT3A-poor medium conducive to the expansion of small intestine organoids, control colonic crypts yielded only few non-branching spheroids (0.015±0.013 structures per crypt) and most of these could not be passaged. In contrast, both control ileal (0.25±0.06 primary and 1.4±0.6 secondary structures per crypt) and Satb2-null colonic crypts (0.19±0.03 primary and 1.8±0.5 secondary structures per crypt) formed branching organoids that could be perpetuated (FIG. 11A and FIG. 11B).

Lastly, SATB2 was deleted directly from LGR5$^+$ stem cells in Lgr5$^{GFP\text{-}cre(ER)}$; Satb2$^{f/f}$ mice. Lgr5$^{GFP\text{-}cre(ER)}$ expression is known to be mosaic and restricted to the ISC compartment. TAM injection into Lgr5$^{GFP\text{-}cre(ER)}$; Satb2$^{f/f}$ mice accordingly yielded mosaic SATB2-null colonic crypts carrying GFP$^+$ stem cells. One week after treatment, SATB2 disappeared from the lower parts of GFP$^+$ crypts, where new cells reside, but persisted in higher cell tiers, which house older cells originating in ISCs with intact Satb2. Activation of ileal markers OLFM4 and FABP6 and suppression of CA1 were partial in GFP$^+$ glands and LYZ1$^+$ cells were absent, suggesting incomplete epithelial remodeling at this early time point. Stem cell and epithelial remodeling were complete by 36 days, with OLFM4 present in most $GFP^+$ cells, $LYZ1^+$ cells present in GFP glands and replacement of $CA1^+$ colonocytes by $FABP6^+$ enterocytes. These observations indicate a time-dependent conversion of colonic stem cells and subsequent resetting of the differentiation pattern. In aggregate, findings from single-cell profiling, organoid culture, and stem cell-specific deletion are consistent with a fundamental conversion of colonic into ileum-like stem cells in the absence of SATB2.

Figure 11C:
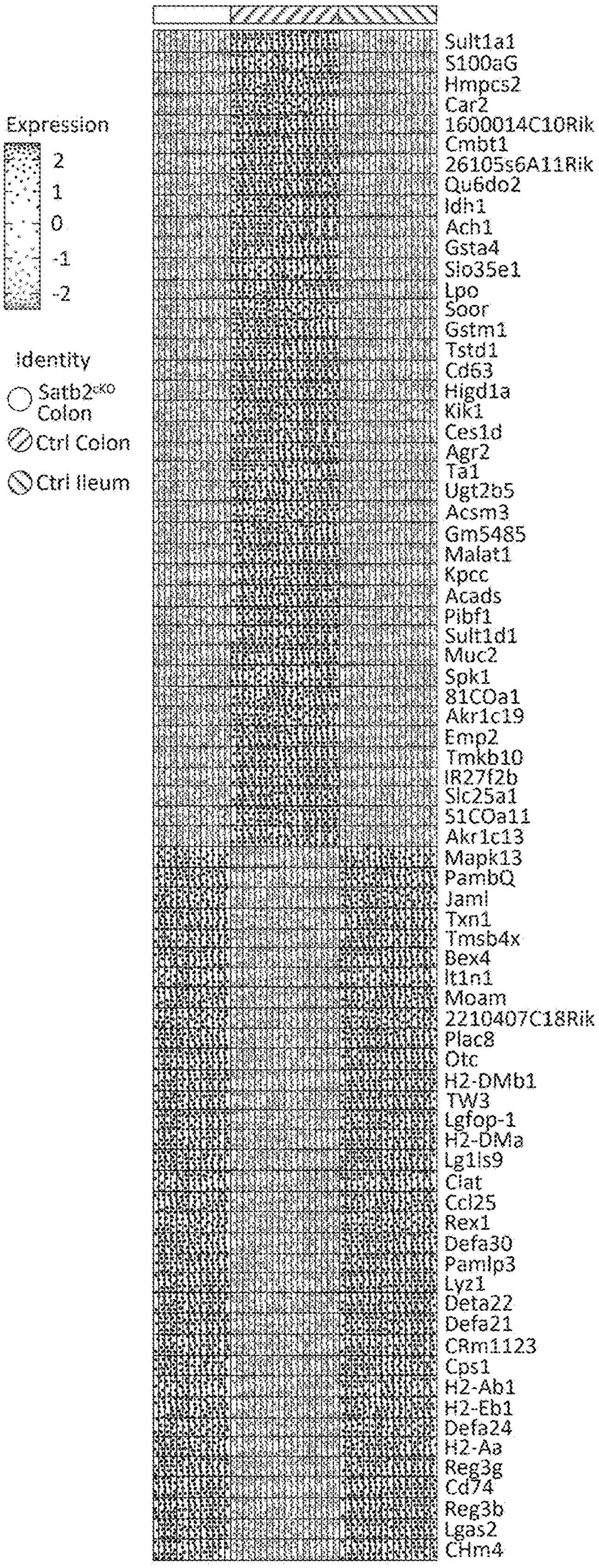
Figure 11E:
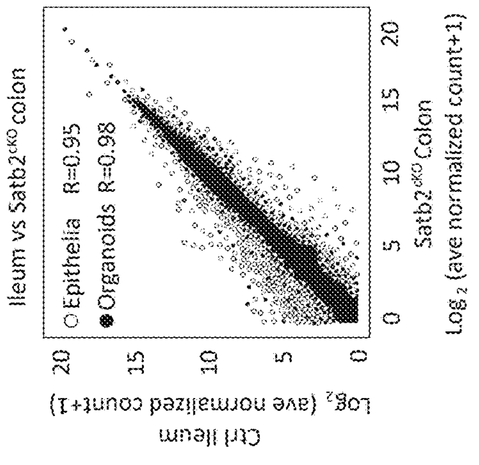
Figure 11D:
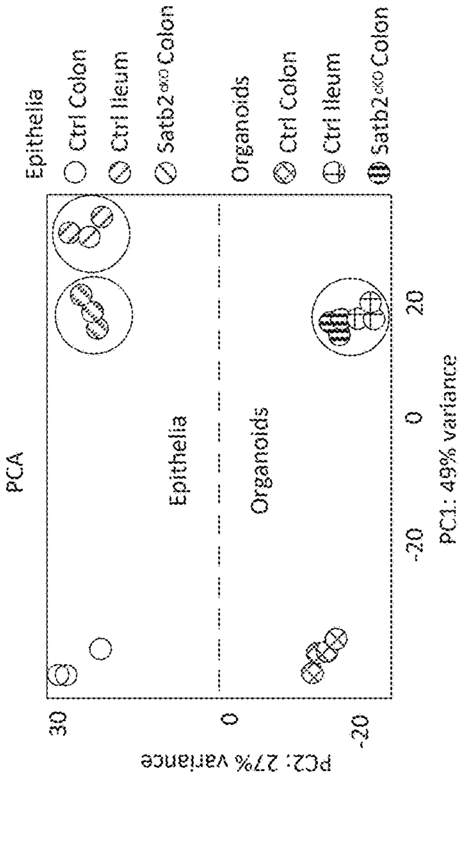

Example 15: Environmental Factors Influence Gene Expression of the Ileal-Like Epithelium in the SATB2-Null Colon Whereas the majority of $Satb2^{cKO}$ colonic cells resembled ileum, a minority were more colon-like (FIG. 10C). To understand this heterogeneous response to SATB2 loss, it was postulated that the colonic microenvironment may have influenced gene expression of the ileal-like mucosa in $Satb2^{cKO}$ colon. Indeed, many studies illustrated the importance of microbial factors and niche signals in regulating intestinal epithelial gene expression and transcription factor binding (Chen et al., 2019; Davison et al., 2017; Nichols and Davenport, 2020; Thaiss et al., 2016). For instance, the microbiota is necessary and sufficient to induce expression of the major histocompatibility complex class II (MHCII) genes in the small intestine (but not colon) stem cells (Biton et al., 2018; Umesaki et al., 1995). Consistently, MHCII genes were high in ileal stem cells and low in both control colonic and the ileum-like stem cells in $Satb2^{cKO}$ colon (FIG. 11C). To mitigate the environmental influence, we cultured control ileal and $Satb2^{cKO}$ colonic organoids in identical medium and performed RNA-Seq after one passage. Principal Component Analysis (PCA) and Pearson correlation showed that the transcriptomes of the two cultured samples were highly similar (Pearson r=0.98), more so than the ileal and $Satb2^{cKO}$ colonic epithelia harvested in vivo (r=0.95) (FIG. 11C and FIG. 11D). These data suggest that in vivo environmental factors likely altered epithelial gene expression and contributed to the heterogeneity in the conversion of a subset of colonic cells to ileal identity in $Satb2^{cKO}$ colon.

Figure 11F:
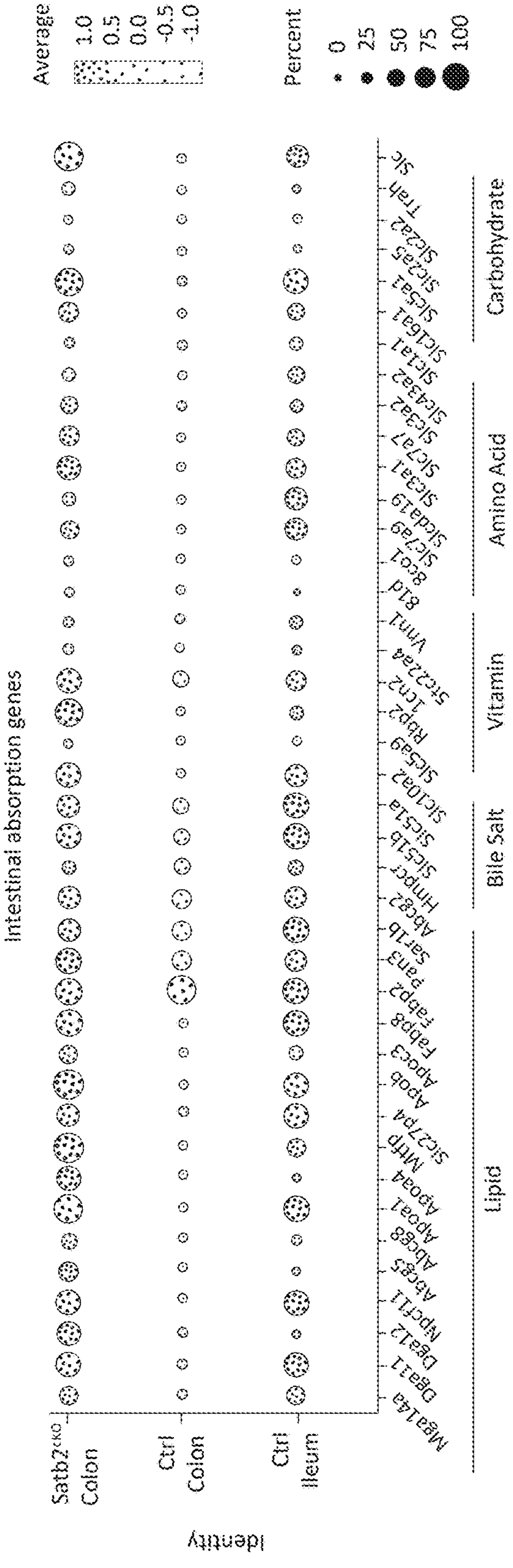
Figures 11G, 11H, 11I, 11J, 11K:
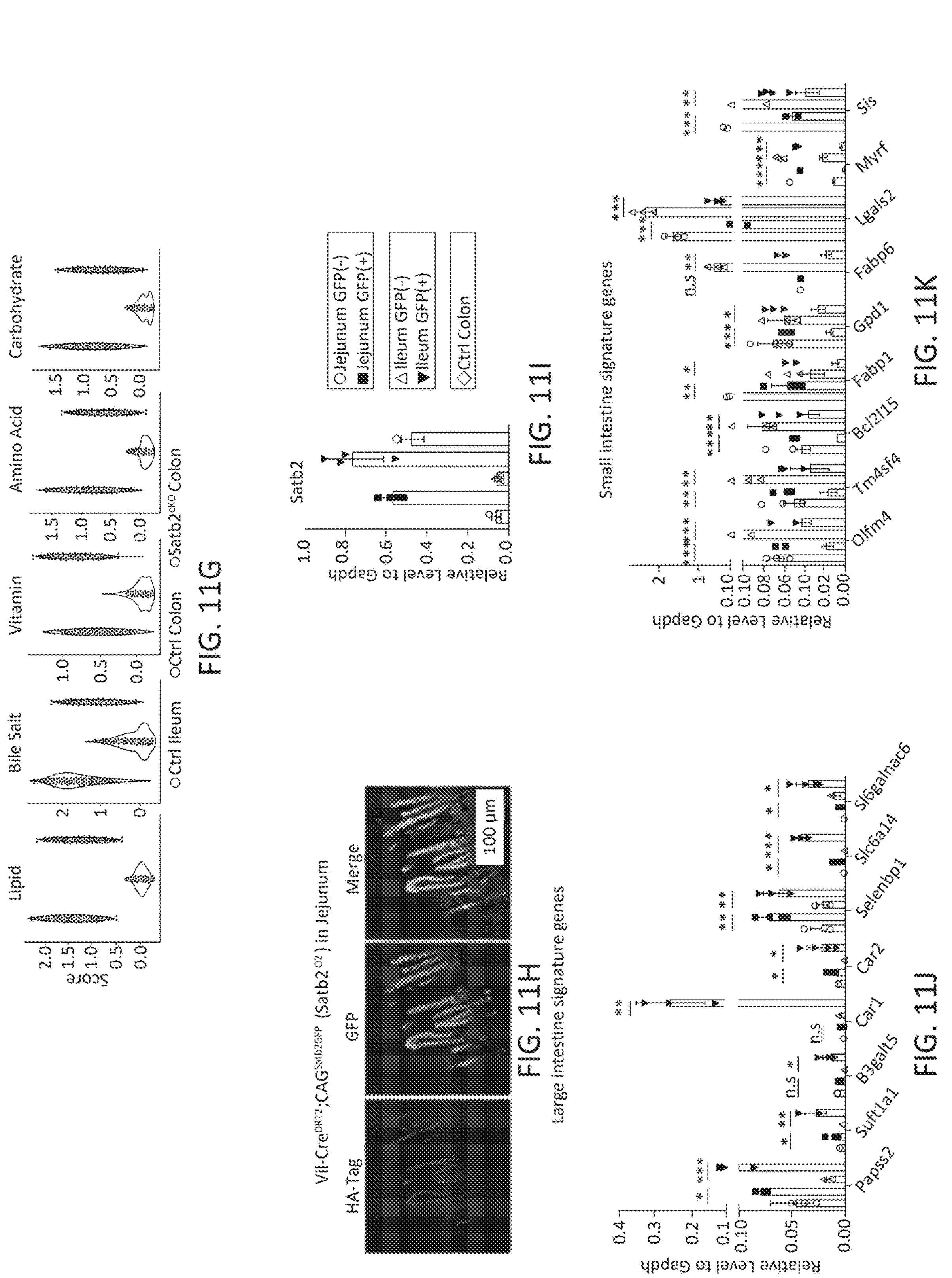

Example 16: Generation of Bona Fide Nutrient-Absorbing Enterocytes in the Ileal-Like Colon Ileal enterocytes absorb nutrients as well as bile salts and vitamins. The data revealed a general replacement of colonocytes by ileal enterocytes in $Satb2^{cKO}$ colon. To evaluate the properties of these absorptive cells, the single-cell transcriptomes of ileal and $Satb2^{cKO}$ colonic enterocytes were compared. Both populations expressed a large number of transporters for lipids, carbohydrates, amino acids, bile salts and vitamins that were absent or low in colonocytes (FIG. 11F and FIG. 11G). $Satb2^{cKO}$ colonic enterocytes were enriched for expression of functional pathways in nutrient absorption and digestion, and interestingly, also in genes relating to “microvillus organization”. Enterocytes are well known to spoil longer microvilli than colonocytes as a means to increase their absorptive surface. Using electron microscopy, it was determined that $Satb2^{cKO}$ colonic enterocyte microvilli were substantially longer than colonocyte microvilli, and comparable to those of ileal enterocytes.

To evaluate whether the ileum-like mucosa in $Satb2^{cKO}$ colon can more readily absorb nutrients and bile salts, an in vivo absorption assay was employed by tying both ends of a segment of the ileum or colon to create a pouch, followed by injection of [$^3$H]glucose and [$^{14}$C] taurocholic acid into this pouch enabling detection of trans-epithelial transport of radiolabeled materials into the portal circulation and its subsequent incorporation in the liver tissue. Both portal plasma and the liver parenchyma from $Satb2^{cKO}$ mice showed significantly higher radiotracer levels compared to controls. These findings together indicate generation of bona fide enterocytes in $Satb2^{cKO}$ colon.

Example 17: SATB2 Confers Colonic Characteristics on the Mature Ileum

To evaluate whether SATB2 is not only necessary to maintain adult colonic identity, but also sufficient to confer colonic fate to the small intestine mucosa, a transgenic mouse line was generated, $CAGs^{SATB2\text{-}GFP}$, in which CRE excision of a stop cassette activates HA epitope-tagged SATB2 and GFP fluorescence. TAM treatment of 2-month old $Vil\text{-}Cre^{ER}$; $CAG^{SATB2\text{-}GFP}$ mice (referred to as $Satb2^{OE}$) led to mosaic expression of the HA epitope tag and GFP throughout the intestine, relatively low in ileum (approximately 10-15% of the glands), and higher in jejunum (>50% of the glands; FIG. 11H). RNA-seq of FAGS-purified $GFP^+$ cells from the ileum (5.6%±1.9% of total EPCAM+ cells) showed Satb2 mRNA levels comparable to the colon. Compared with the transcriptome of $GFP^-$ ileal cells, 225 genes were down-regulated and 131 genes were up-regulated in $GFP^+$ cells (LFC>1.5, Padj<0.1); these genes were enriched for colonic and ileal tissue signatures, respectively. Among the down-regulated genes were large numbers of enterocyte nutrient transporters and Defensins characteristic of Paneth cells.

The primary function of colonic epithelium is to absorb electrocytes, some of which generate osmotic gradients to enable water uptake; additionally, colon synthesizes many glycoproteins, including specific MUCINs for anti-microbial defense. $GFP^+$ ileal cells expressed an array of key transporters for electrocytes and principal enzymes involved in protein glycosylation. Thus, they acquired the molecular machineries necessary to perform colonic functions. In ileal villi marked with GFP, immunohistochemistry 30 days after TAM showed suppression of ileal marker FABP6 and activation of colonic marker CA1. OLFM4 and LYZ1 also disappeared from GFP crypts, consistent with the transcriptomic data. Ileal villus structures remained unchanged in $Satb2^{OE}$ mice, possibly reflecting lack of continuous SATB2 expression across the ileal mucosal surface due to high mosaicism. In contrast to $Satb2^{OE}$ ileum, qRT-PCR analysis indicated that jejunal GFP+ cells down-regulated small intestine genes but showed less activation of colonic genes (FIGS. 11H-11K). Taken together, SATB2 is sufficient to confer colon-like characteristics to the adult ileum.

Example 18: SATB2 Regulates Enhancer Dynamics and Transcription Factor Binding in Colon There is limited understanding of SATB2 mechanisms of action in the tissues that express it, including craniofacial and neuronal cells. SATB1, a close homolog expressed primarily in thymocytes, binds both DNA and nuclear matrix and regulates transcription partly by modulating genomic binding of TFs and chromatin remodeling complexes (Cai et al., 2003; Skowronska-Krawczyk et al., 2014; Yasui et al., 2002). To investigate how SATB2 might control colonic fate and tissue plasticity, the genomic binding sites of SATB2 in mature colonic epithelia were mapped using chromatin immunoprecipitation-sequencing (ChlP-seq). Duplicate SATB2 ChlP data from control colonic epithelia yielded highly concordant data with 25,576 high-quality peaks (peak call by MACS2, P $1\times10^{-9}$, using both input and Satb2$^{cKO}$ ChlP as controls) (FIG. 12A). These peaks were enriched for AT-rich sequences, consistent with SATB2 binding preference (Szemes et al., 2006), Among the top enriched DNA-binding motifs identified by HOMER were those for the intestinal TFs CDX2 and HNF4A, suggesting potential co-localization of the two TFs with SATB2. Indeed, CDX2 and HNF4A genomic binding sites were found to co-localize extensively with SATB2, with 54.1% (13,843 out of 25,576) of SAT132 peaks co-bound by both TFs (FIGS. 12C-12D). Moreover, CDX2 and HNF4A antibodies co-precipitated SATB2 from colonic tissue, suggesting interactions of SATB2 with CDX2/HNF4A at its genomic binding sites.

Colonic SATB2 binding occurred predominantly in intergenic regions and introns (39.1% and 53.2% of peaks, respectively) (FIG. 12B), and enriched for the motif of P300, the histone H3K27 acetyltransferase and a hallmark of active enhancers $P<1\times10^{-443}$). Cleavage Under Targets & Release Using Nuclease (CUT&RUN) was used to map putative (H3K4me1) and active (H3K27ac) enhancers in control ileum, colon, and SATB2$^{cKO}$ colon epithelia. Peaks were called with MACS2 using duplicate samples. Enhancers (H3K4me1, TSS-distal regions) were identified by MAnorm. Assay for Transposase-Accessible Chromatin (AT AC-seq) was employed to further chart the chromatin landscapes in these tissues. Analysis of all H3K4me1$^{+}$ enhancers defined 7,375 colon-specific and 5,784 ileum-specific sites (MAnorm; P<0.01), with the nearby genes (<50 kb) enriched for colonic or ileal expression, respectively. In the normal colon, a majority of SATB2 binding (59.5%) occurred within H3K27ac$^{+}$ active enhancers (FIGS. 12E-12F).

Figure 12G:
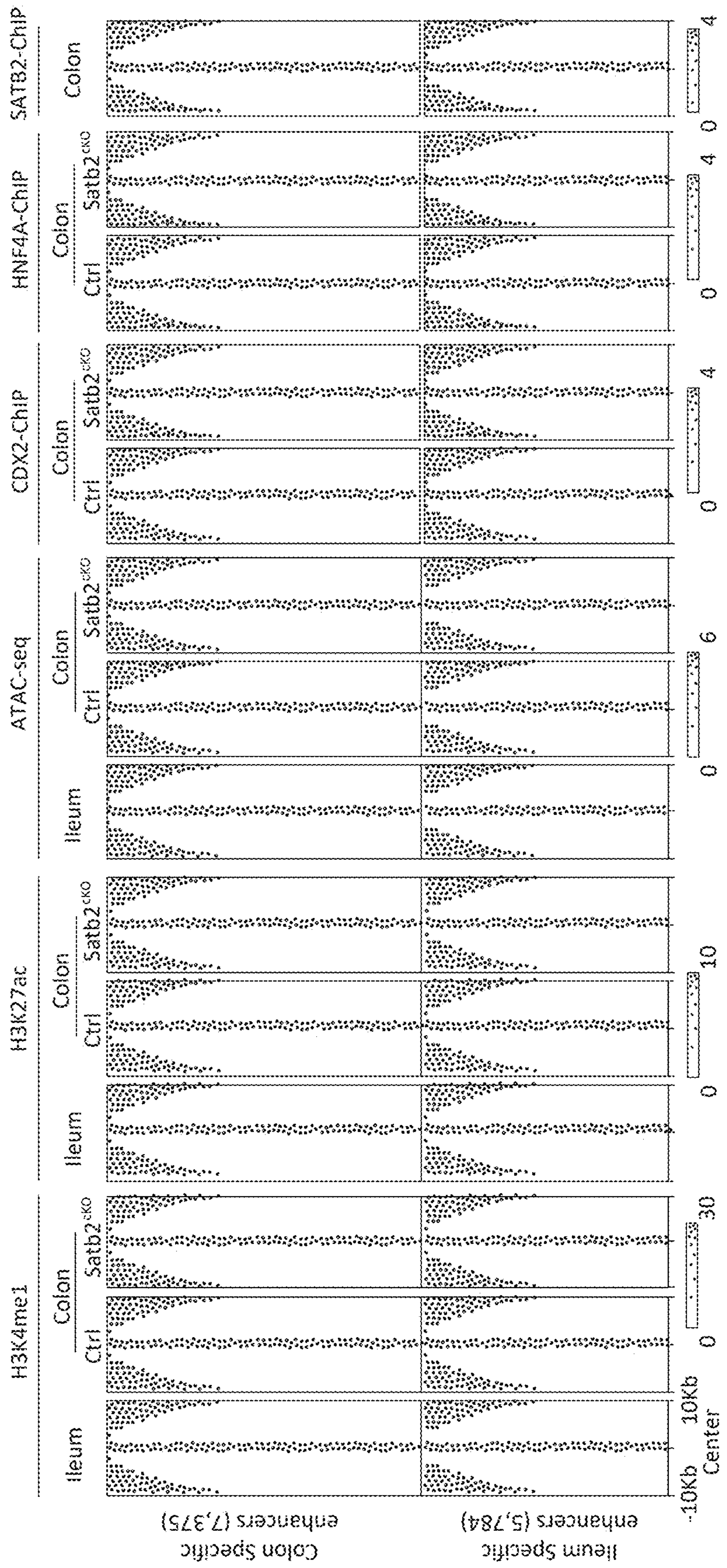

In control colon, the colon-specific enhancers had high levels of H3K4me1 and H3K27ac, strong ATAC signals, and robust binding by CDX2 and HNF4A, all hallmarks of active enhancers (FIG. 12G). These enhancers were deactivated in Satb2$^{cKO}$ colon and displayed low levels of H3K4me1, H3K27ac, open chromatin, and CDX2 or HNF4A occupancy, indicating a critical role for SATB2 in maintaining active colonic enhancers. Notably, ileal-specific enhancers in normal colon retained low but detectable signals of ATAC, H3K4me1, H3K27ac, CDX2 and HNF4A; after SATB2 loss they acquired high levels of H3K4me1 and H3K27ac, strong A TAC signals, and robust CDX2 and HNF4A binding (FIG. 12G). Thus, ileal enhancers are not permanently inactivated at the baseline in mature colon, but retain weak enhancer features and provide the necessary chromatin substrate for ileal gene activation and tissue fate plasticity.

Figure 12H:
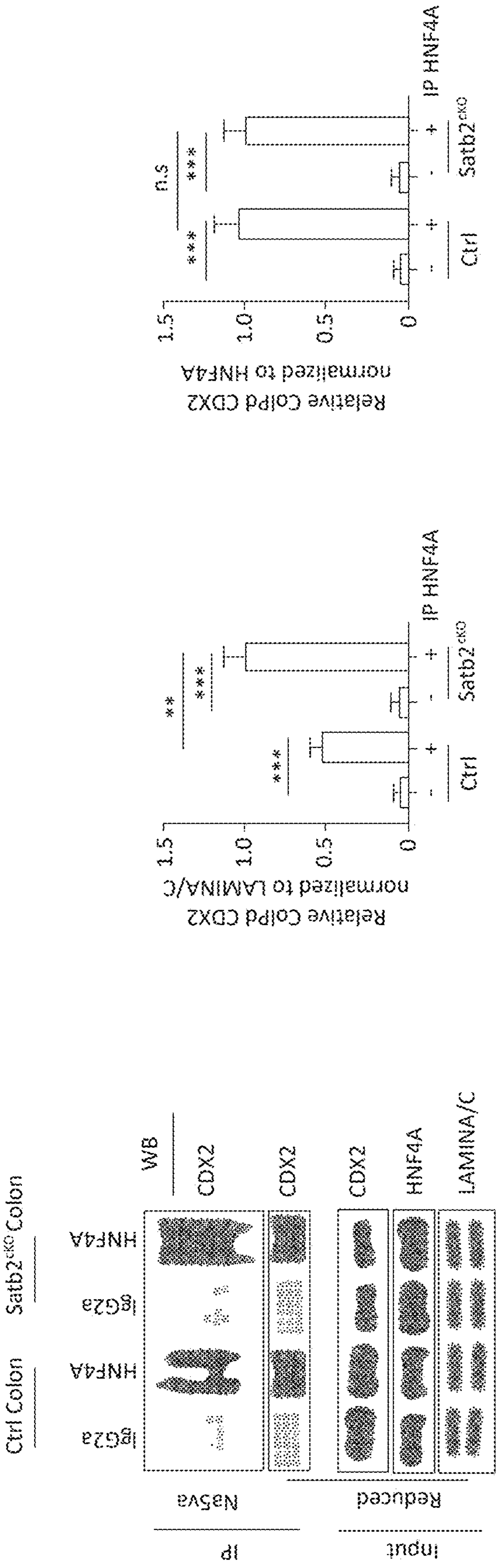

Prior studies of CDX2 and HNF4A in adult intestine indicate that they function primarily as transcriptional activators (Verzi et al., 2011; Verzi et al, 2013). The two TFs closely associate with each other in both normal and Satb2 knockout colon (FIG. 12H) and their co-binding switched from colonic to ileal enhancers after SATB2 loss (FIG. 12G), closely correlating with down-regulation of colonic genes and activation of ileal genes. These data together indicate that SATB2 regulates colonic gene expression and tissue plasticity in part by modulating the enhancer binding of critical intestinal transcription factors.

Figure 13A:
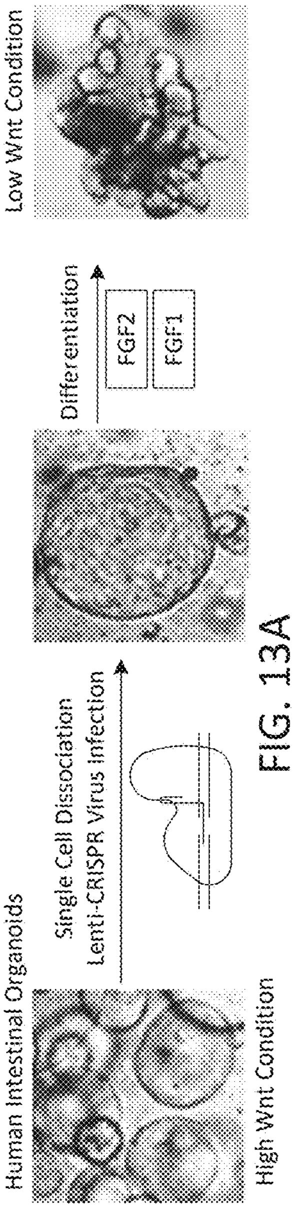
FIGS. 13A-13J illustrate human colonic organoids became ileal-like after CRISPR-mediated SATB2 deletion. Related to FIG. 6.
Figure 13B:
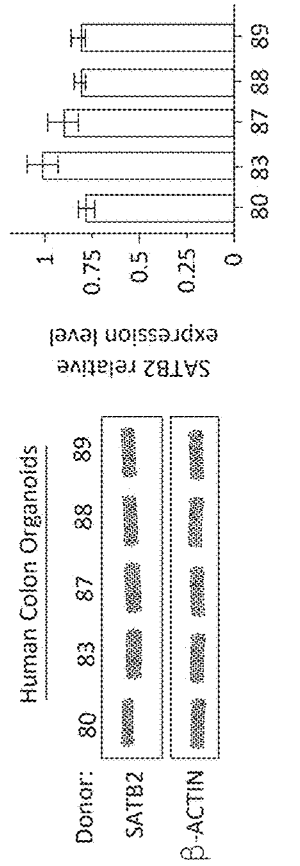
Figure 13C:
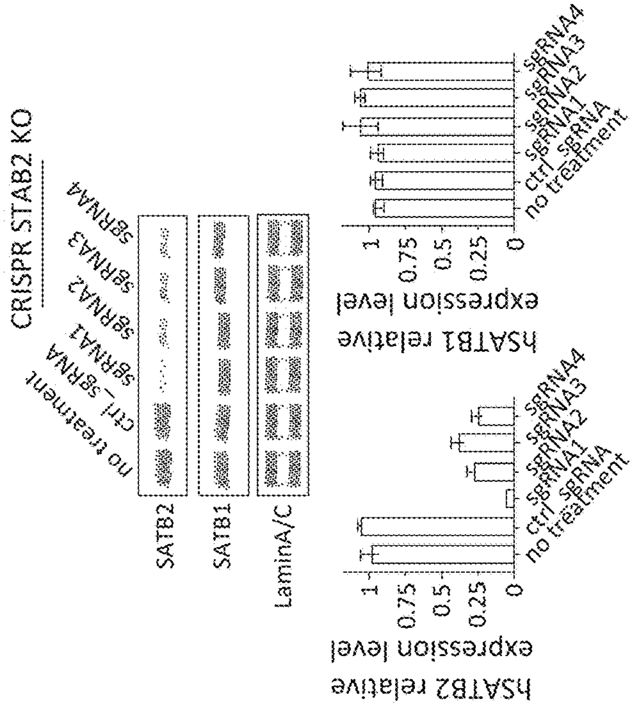
Figure 13E:
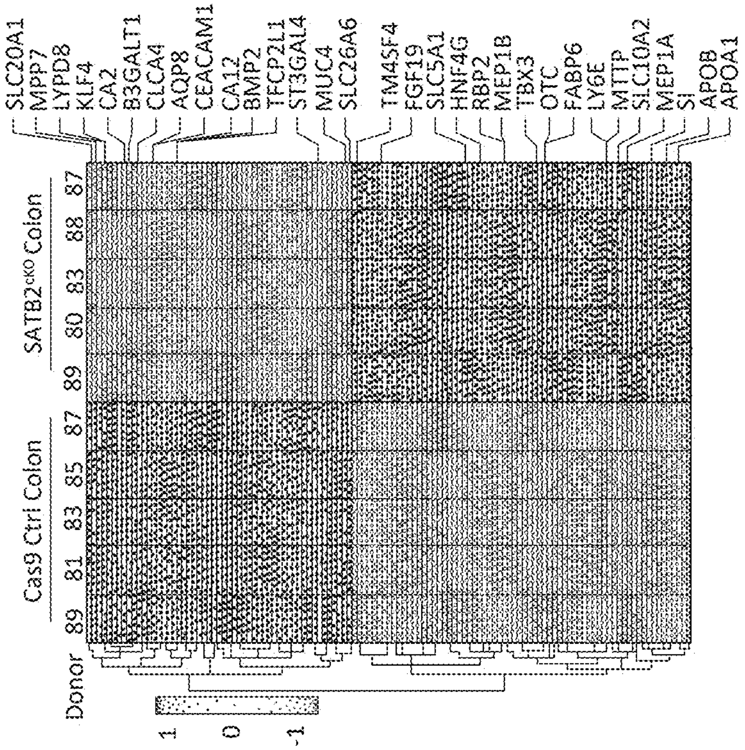
Figure 13D:
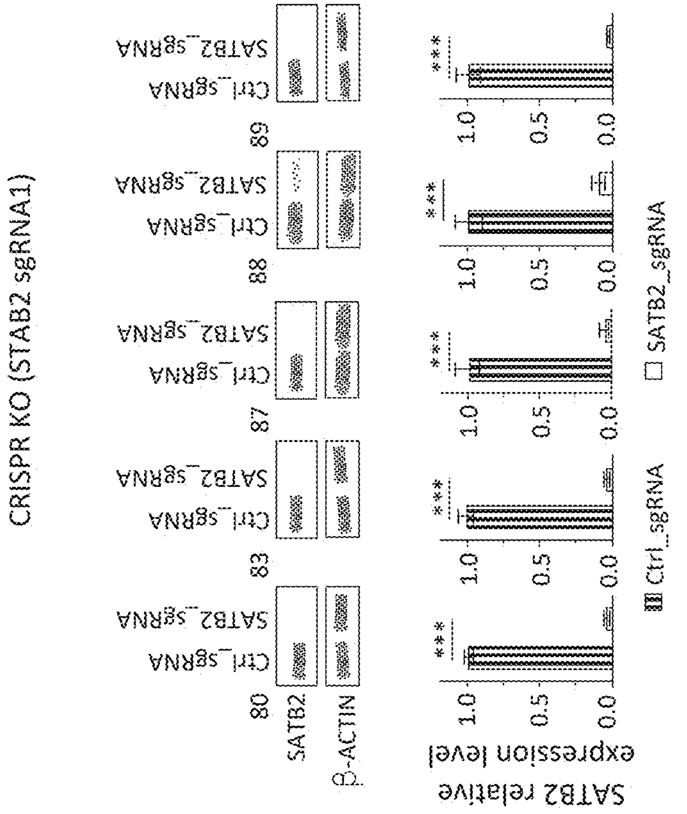

Example 19: Human Colonic Organoids Adopt Ileal Characteristics after SATB2 Loss Similar to mice, SATB2 expression is restricted to the colonic mucosa in adult human intestine. To evaluate whether SATB2 function is conserved in human colon, CRISPR-CAS9 was used to delete SATB2 from 5 normal human colonic organoid lines, which expressed SATB2 at comparable levels (FIGS. 13A and FIG. 13B). Of the four guide RNAs (gRNAs) assessed, one efficiently reduced SATB2 expression by 95-98% (FIGS. 13B-D). RNA-seq analysis of the 5 isogenic control (CAS9 alone) and SATB2 knockout (SATB2hKo) organoid lines showed significant suppression of colonic genes and activation of small intestinal genes (FIG. 13E). The top activated KEGG pathways included nutrient and vitamin absorption and retinol metabolism.

Figures 13F, 13G, 13H:
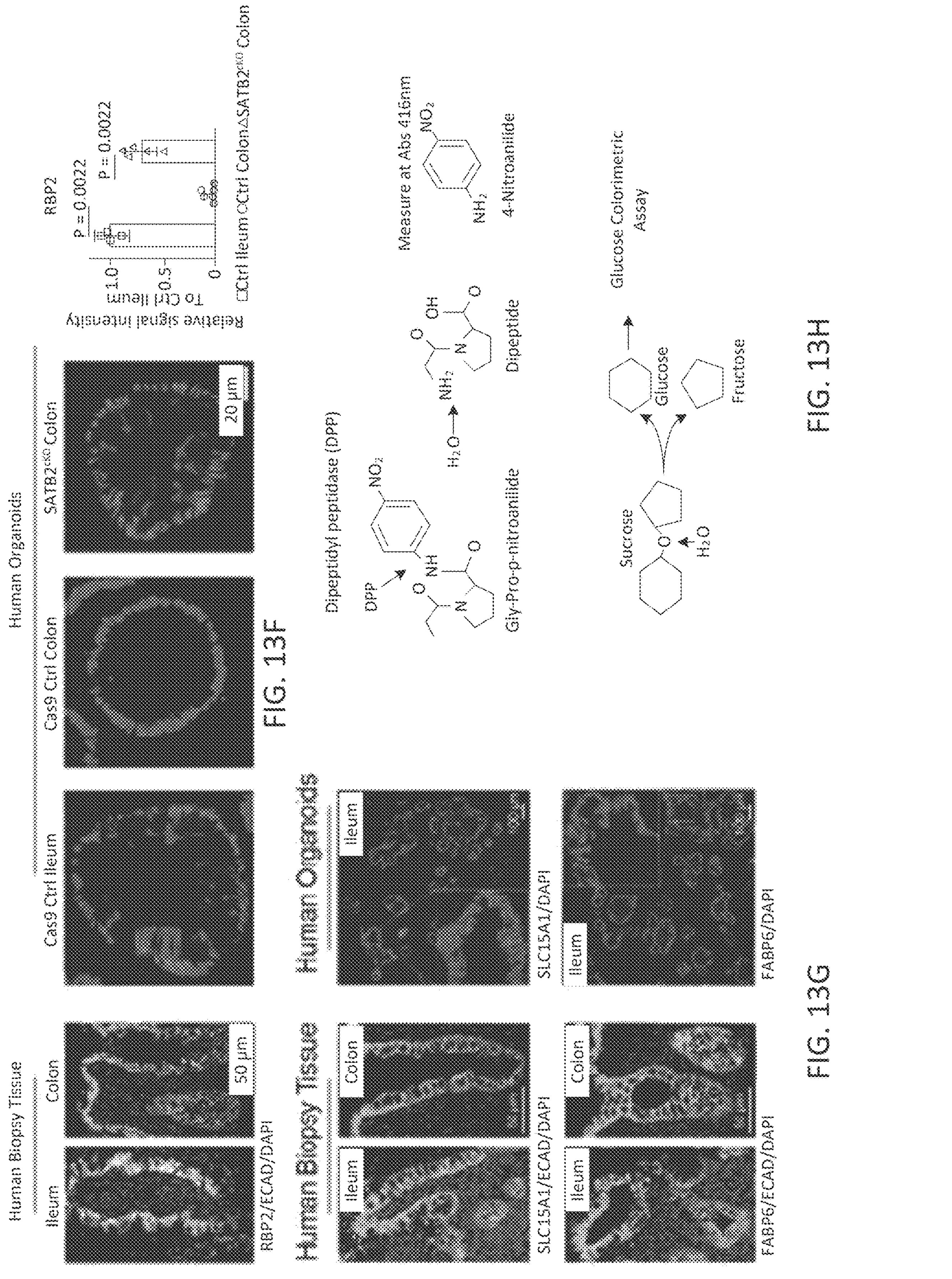
Figure 13I:
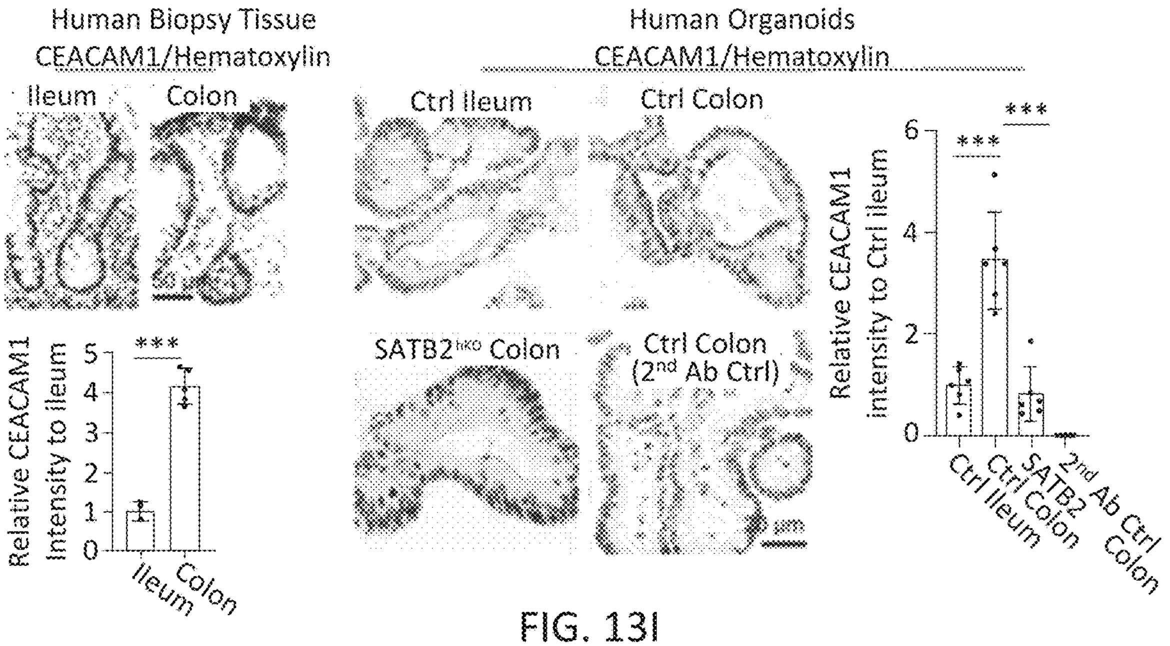
Figure 13J:
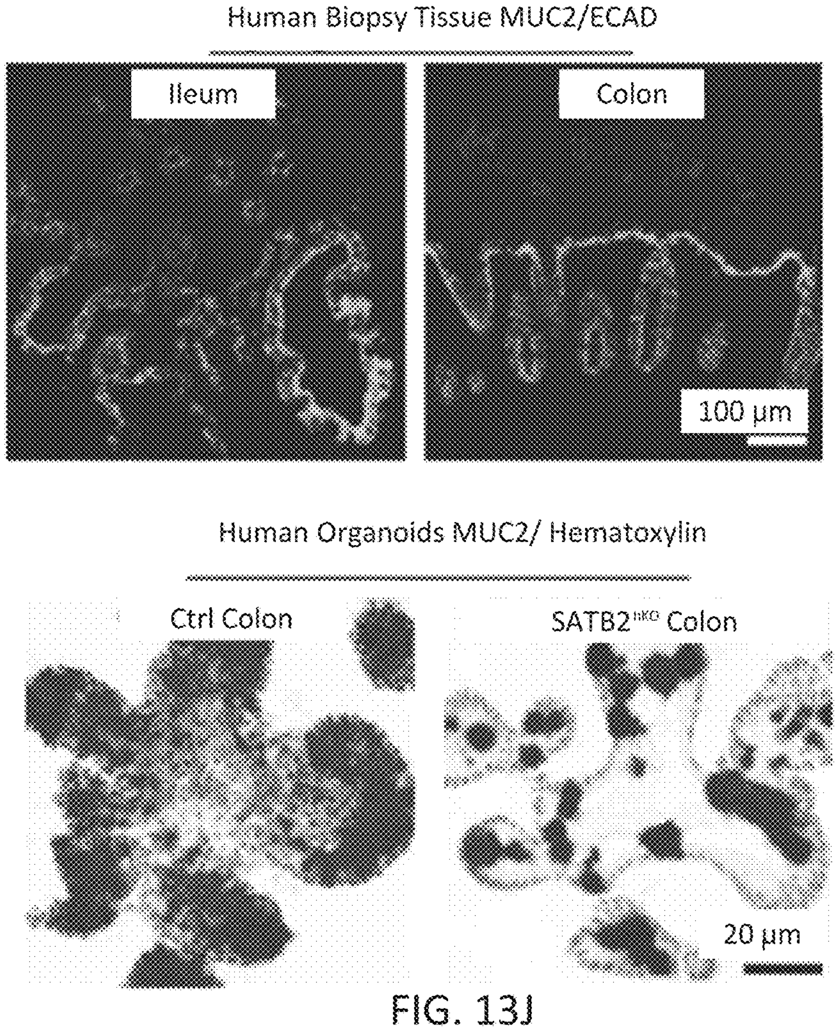
Figure 14A:
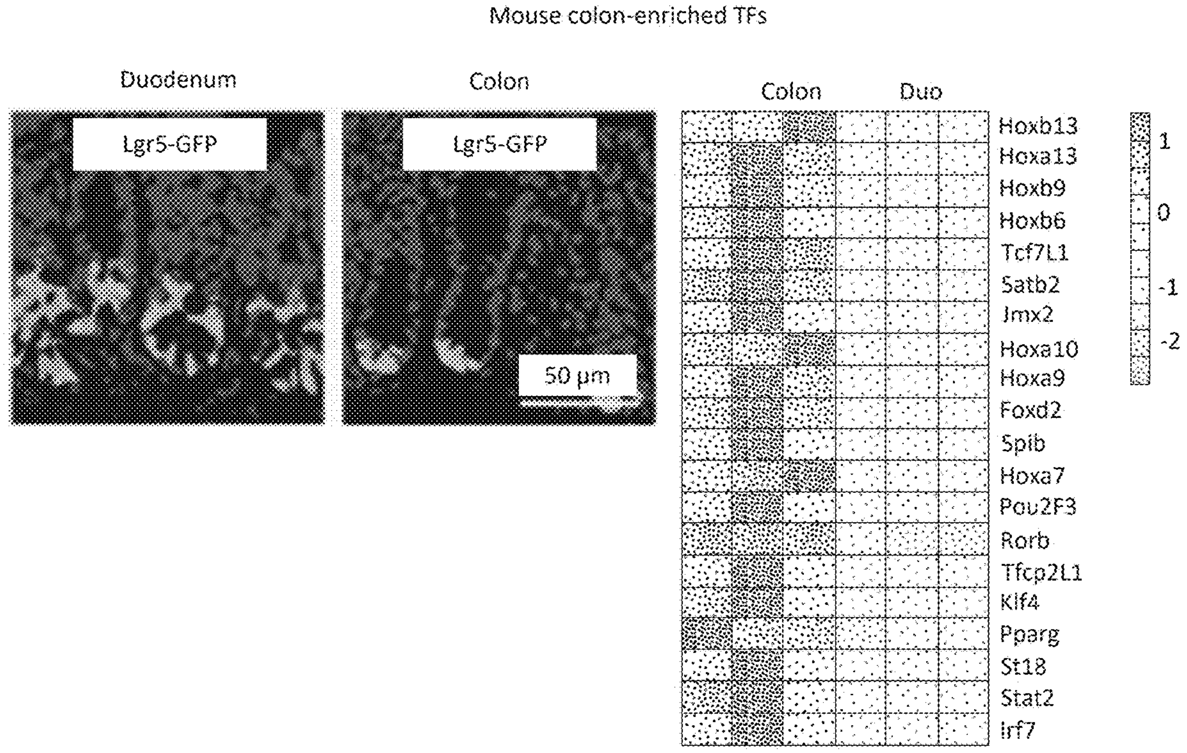
FIGS. 14A-14I illustrate identification of SATB2 as a transcription factor enriched in large intestine stem cells that regulates large intestine gene expression.
Figure 14B:
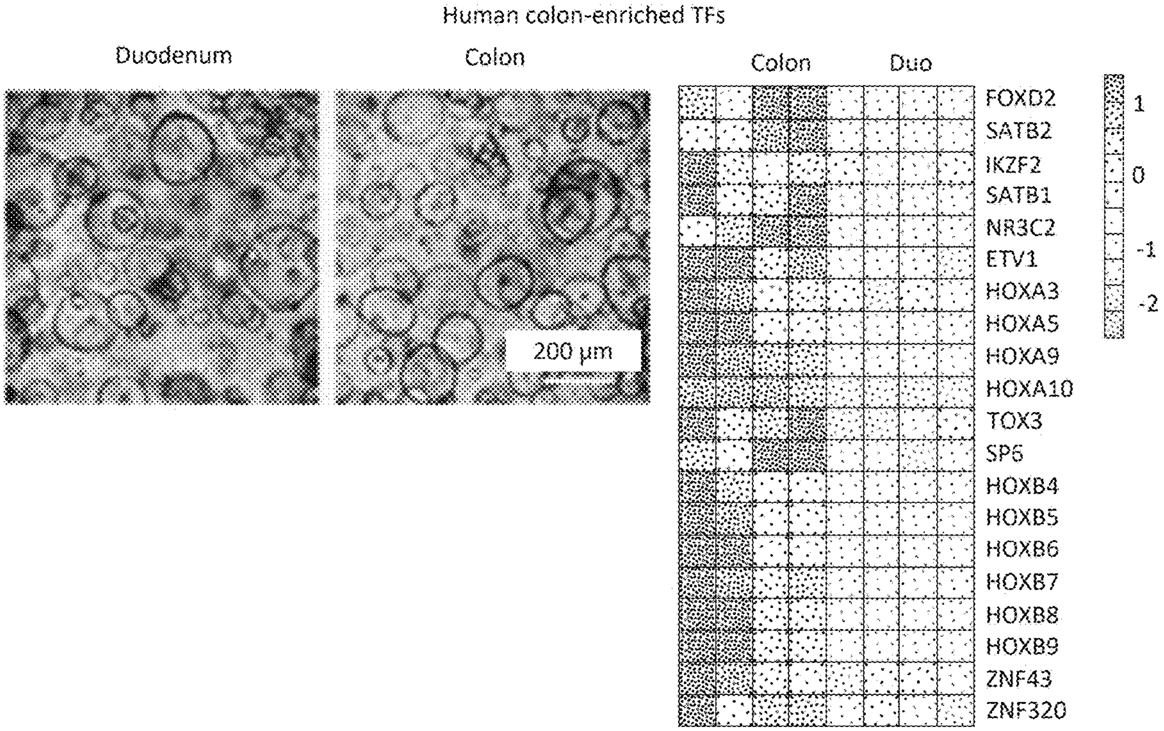
Figure 14E:
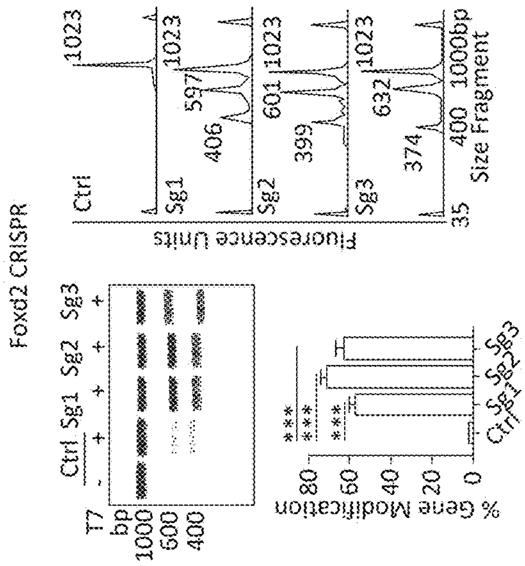
Figure 14D:
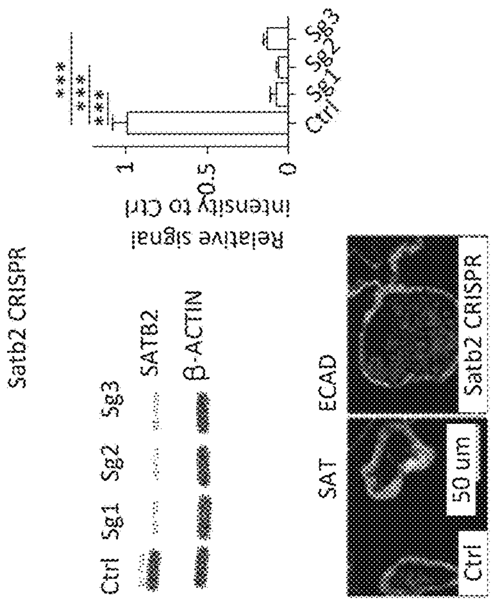
Figure 14C:
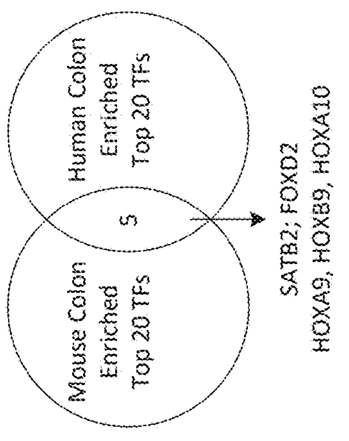
Figure 14H:
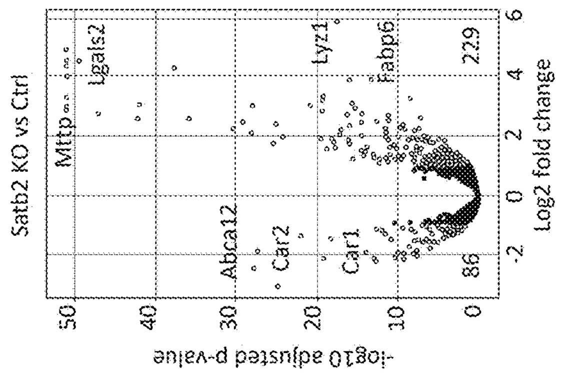
Figure 14G:
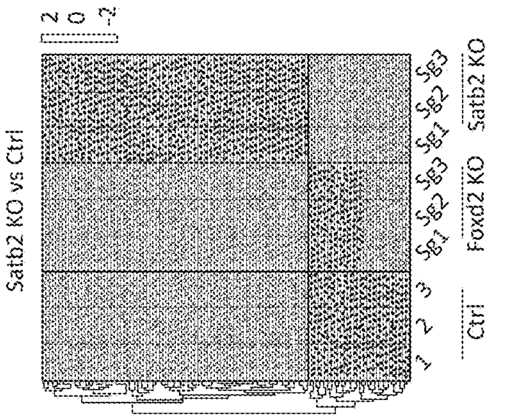
Figure 14F:
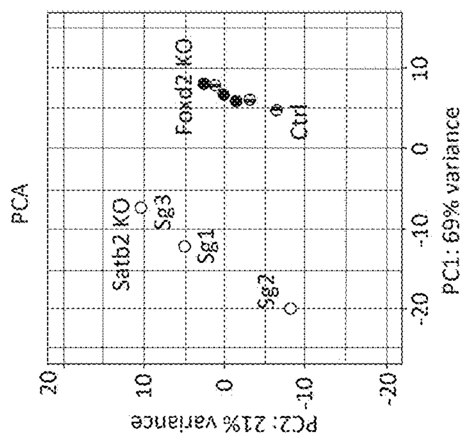
Figure 14I:
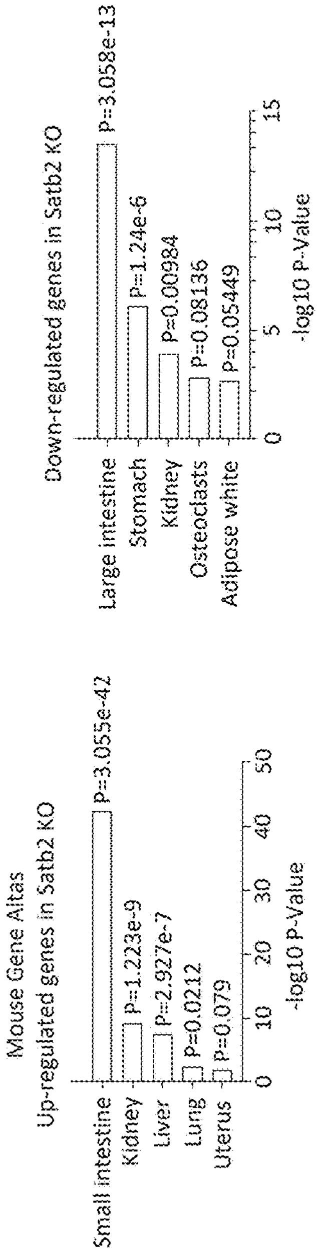
Figure 15A:
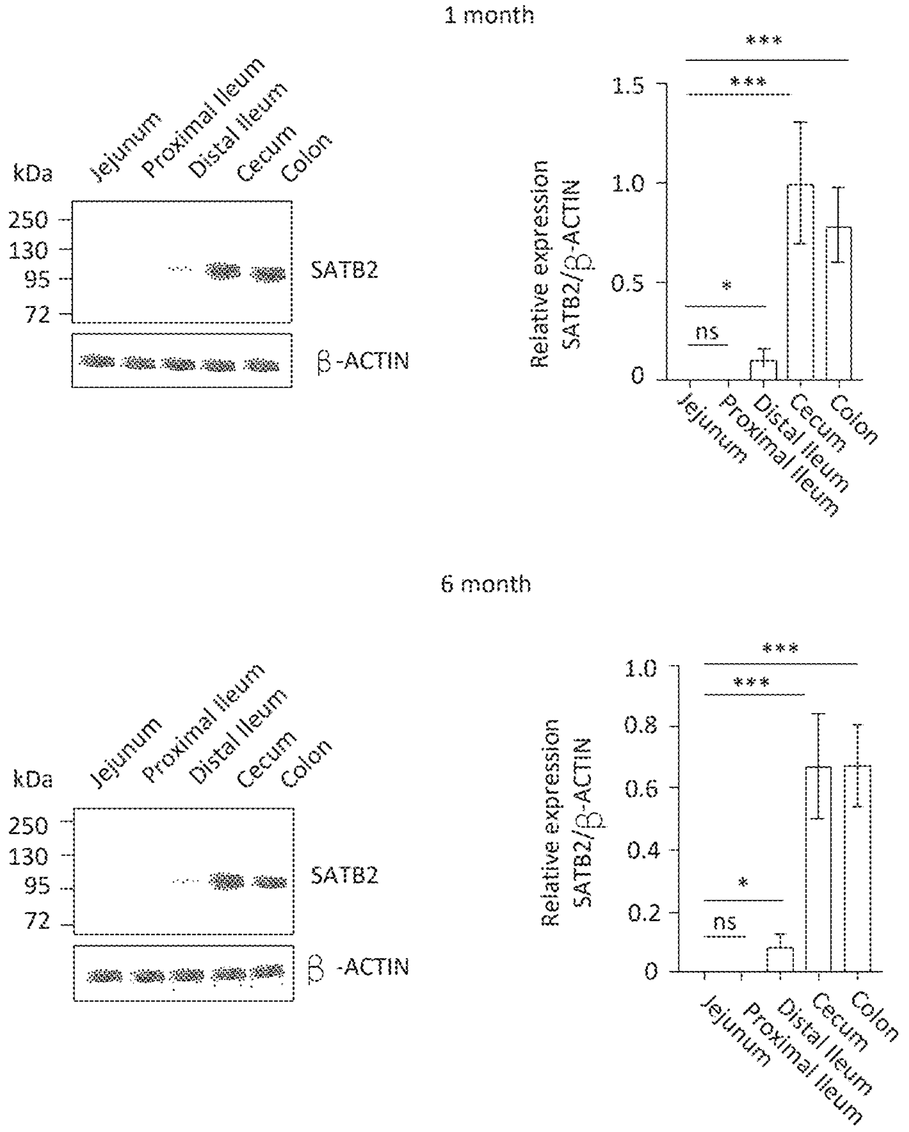
FIGS. 15A-15M. illustrate colonic epithelium in Vil-CreER; Satb2f/f (Satb2cKO) mice resembles that of ileal small intestine.
Figures 15B, 15C:
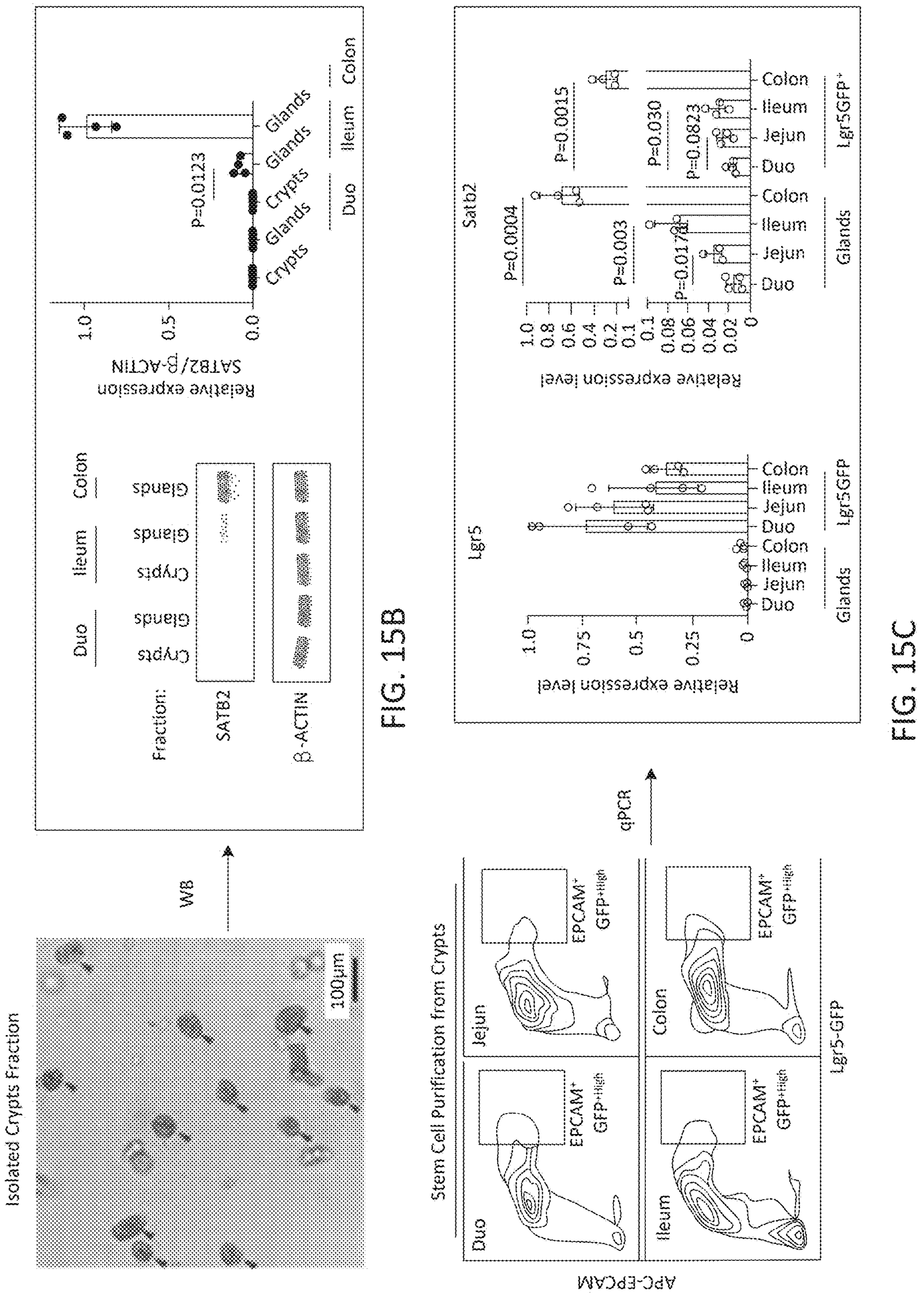
Figure 15D:
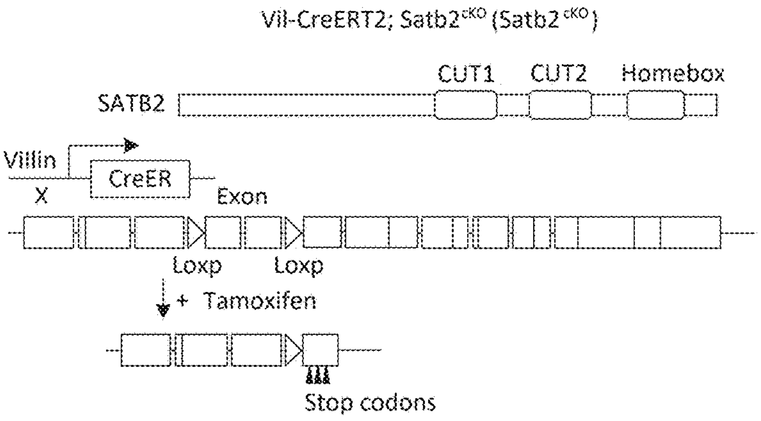
Figure 15E:
Figure 15F:
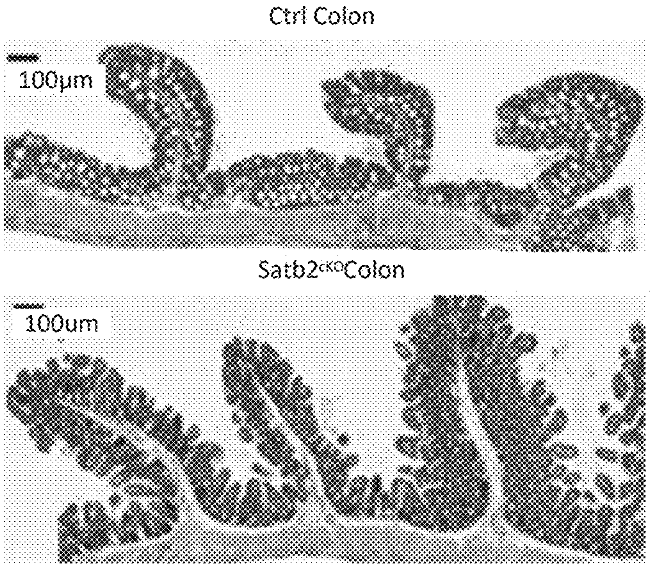
Figures 15G, 15H, 15I:
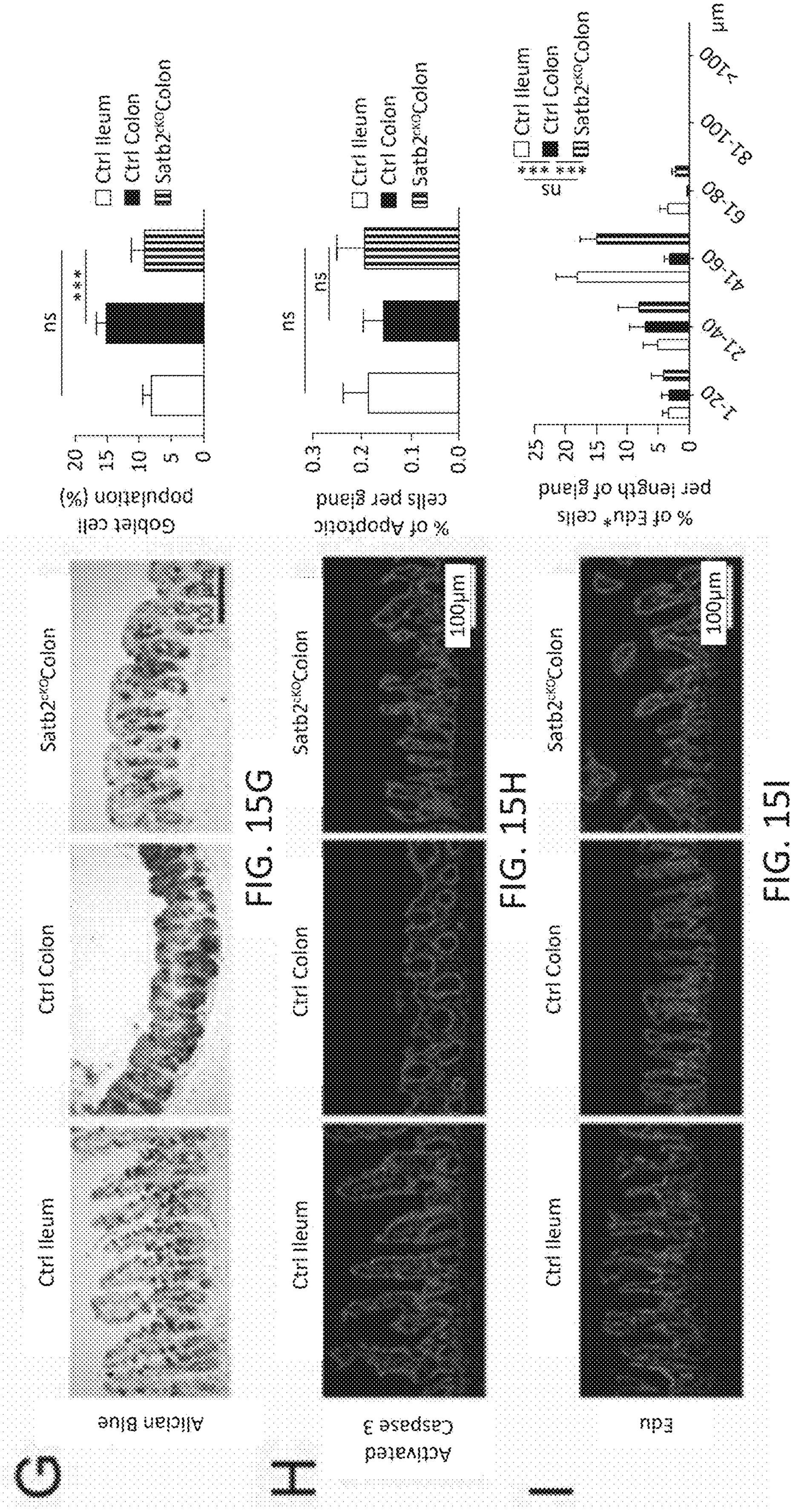
Figure 15J:
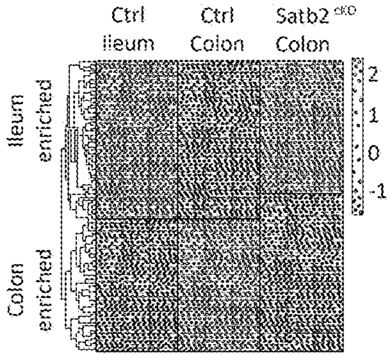
Figure 15K:
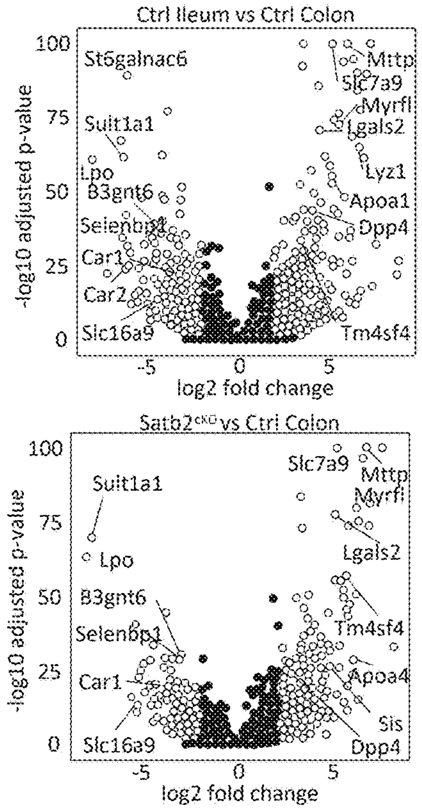
Figure 15L:
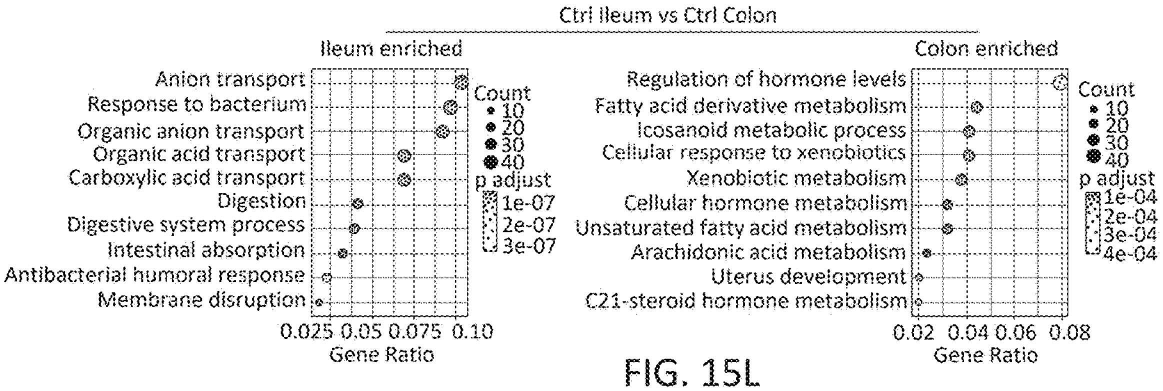
Figure 15M:
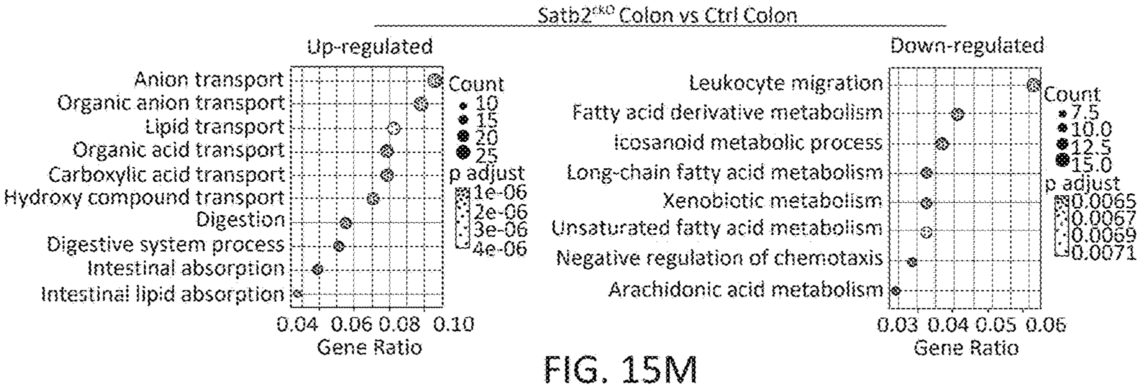
Figure 16A:
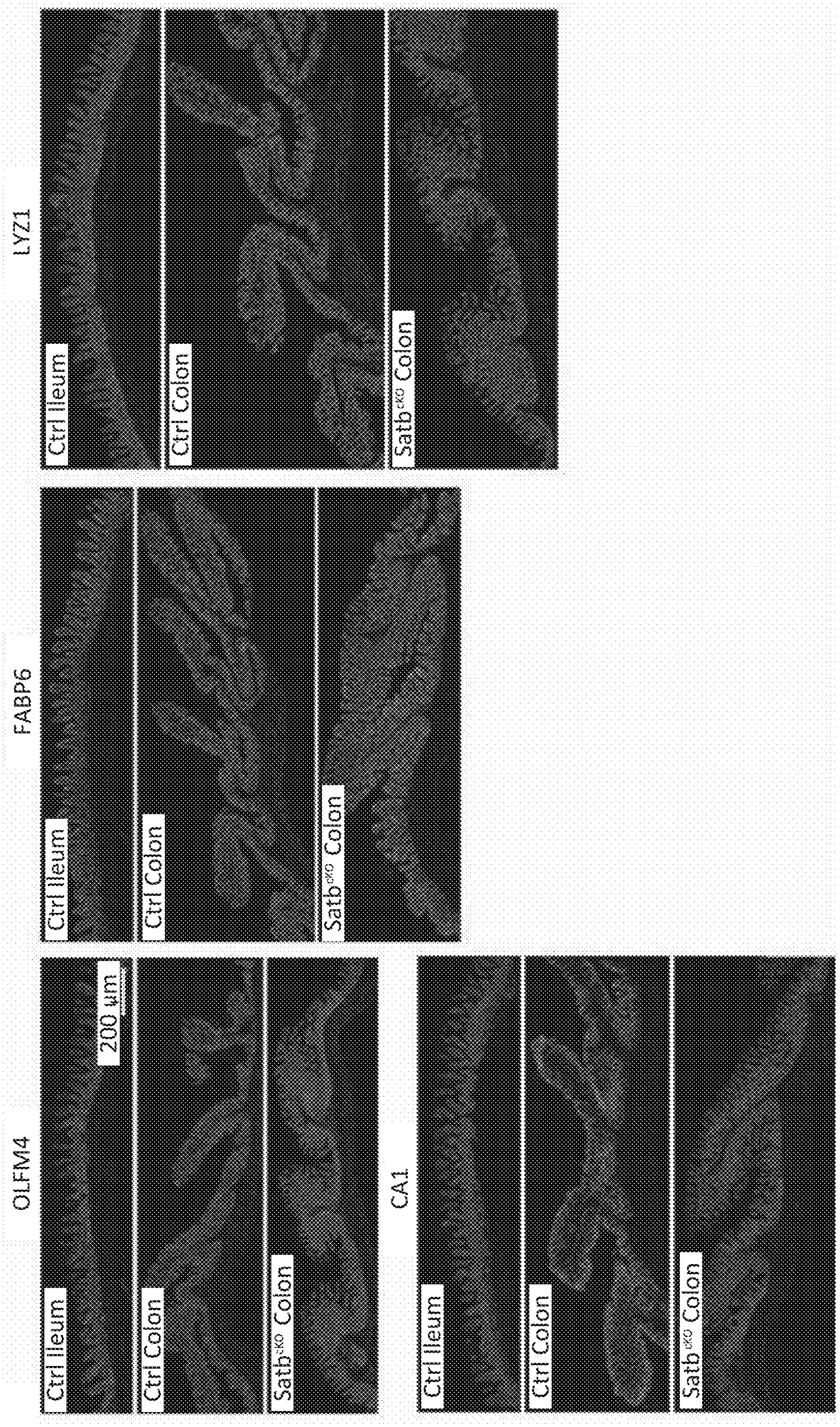
FIGS. 16A-16C illustrate the ileal to colonic mucosal conversion in Satb2cKO mice is stable.
Figures 16B, 16C:
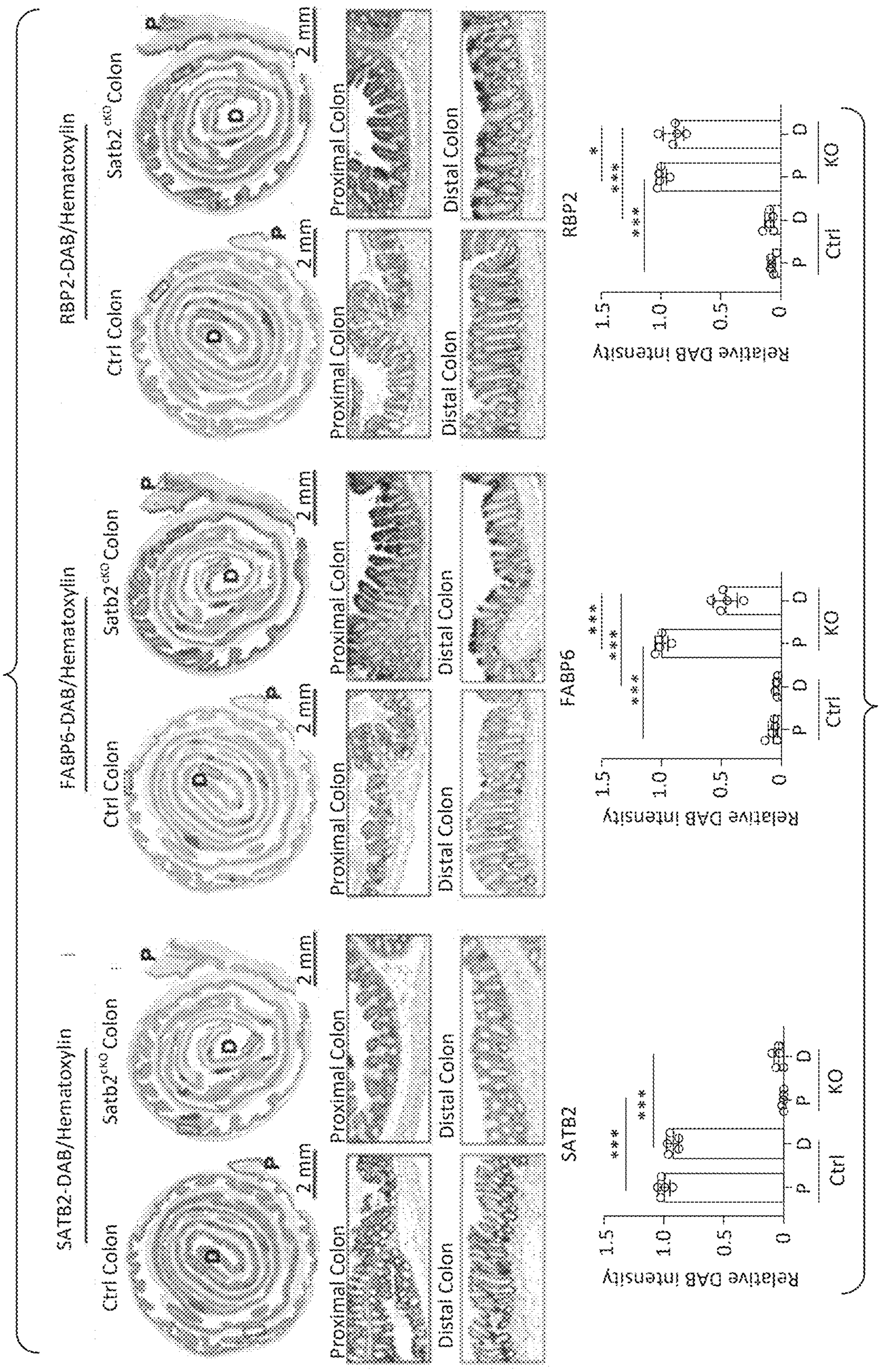
Figure 17A:
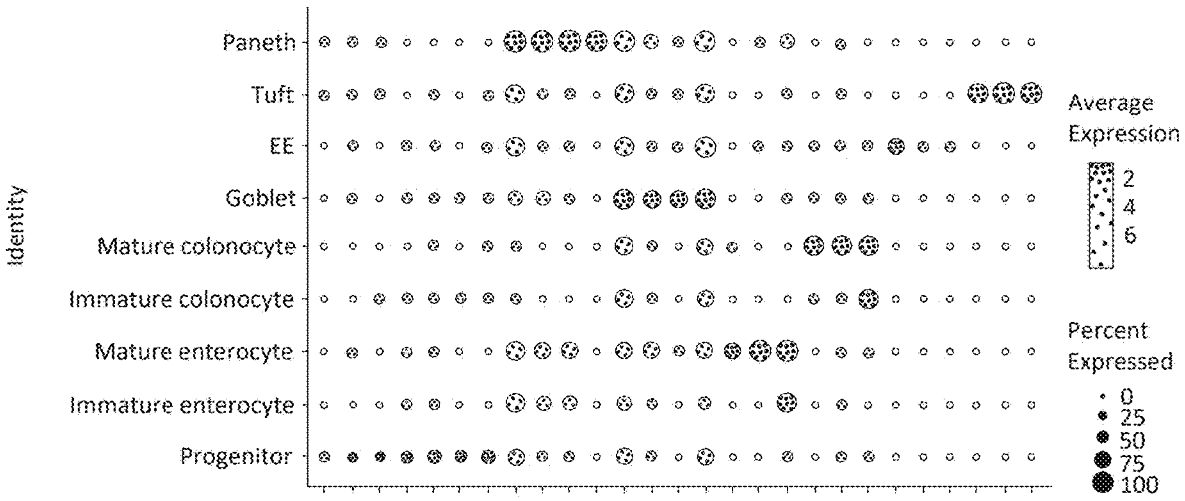
Figure 17B:
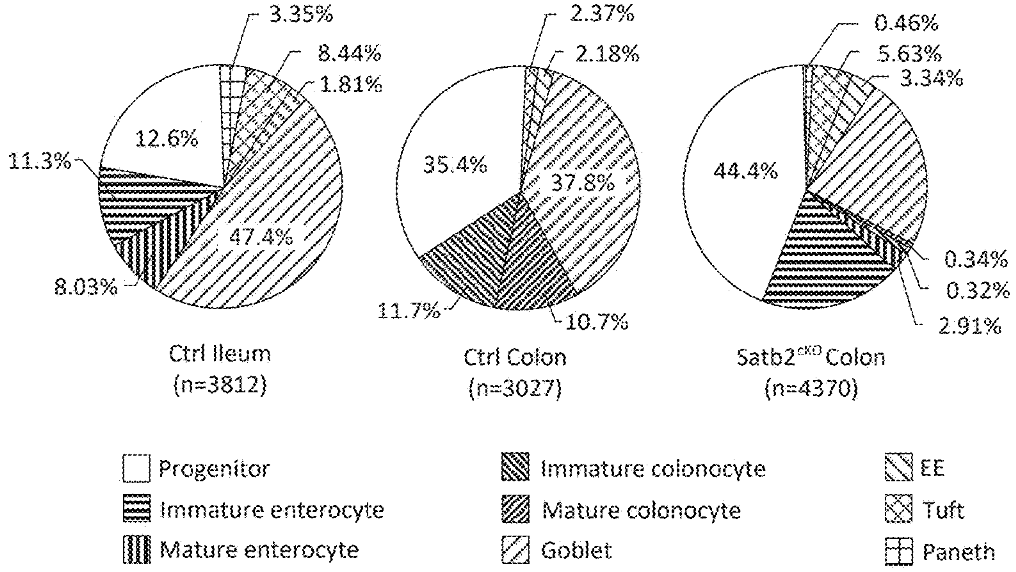
Figure 17C:
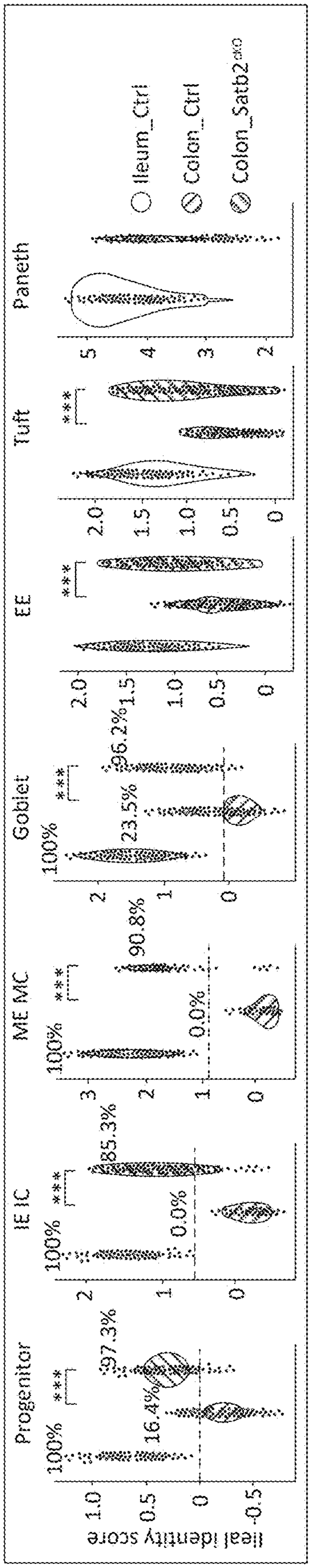
Figure 17D:
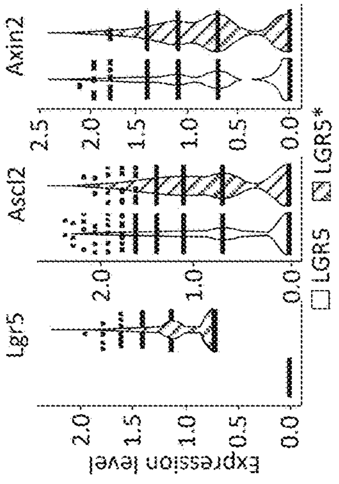
Figure 17E:
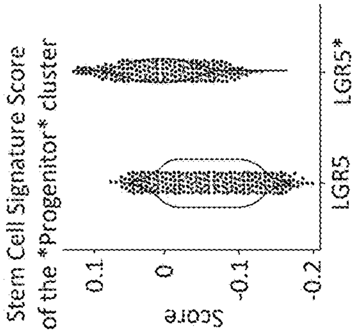
Figure 17F:
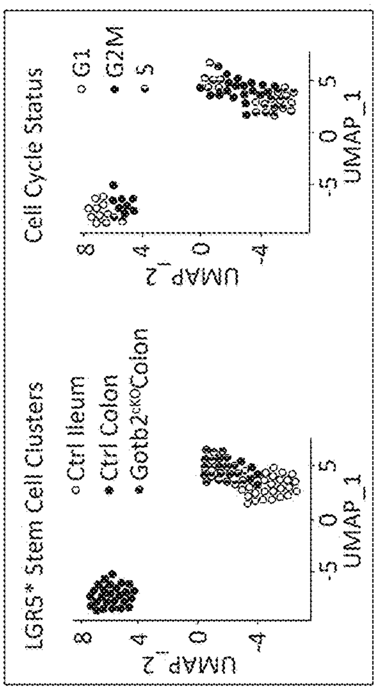
Figure 17G:
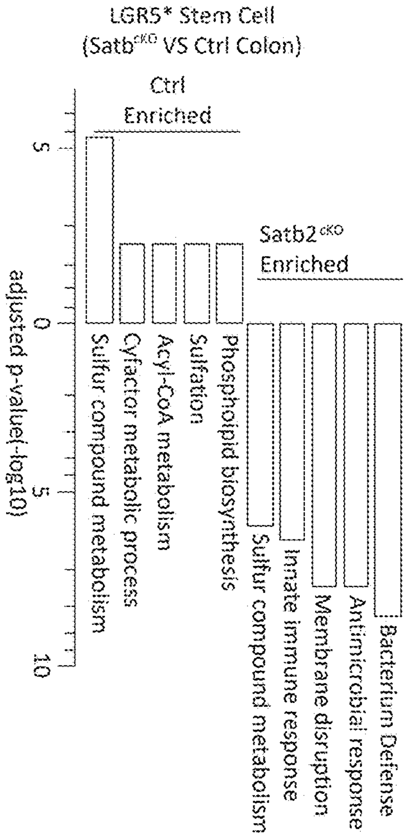
Figure 17H:
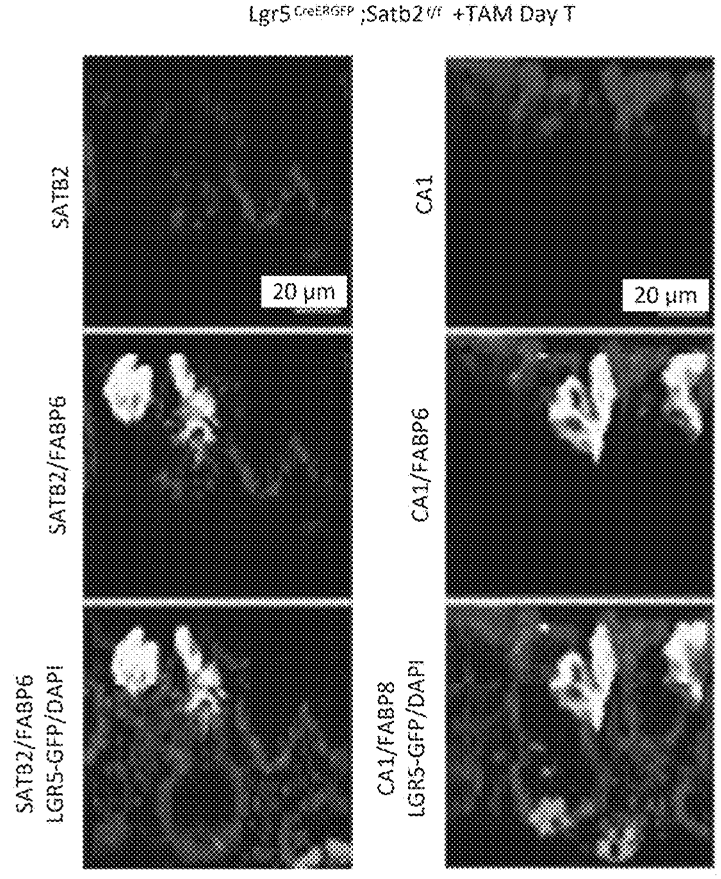
Figure 18A:
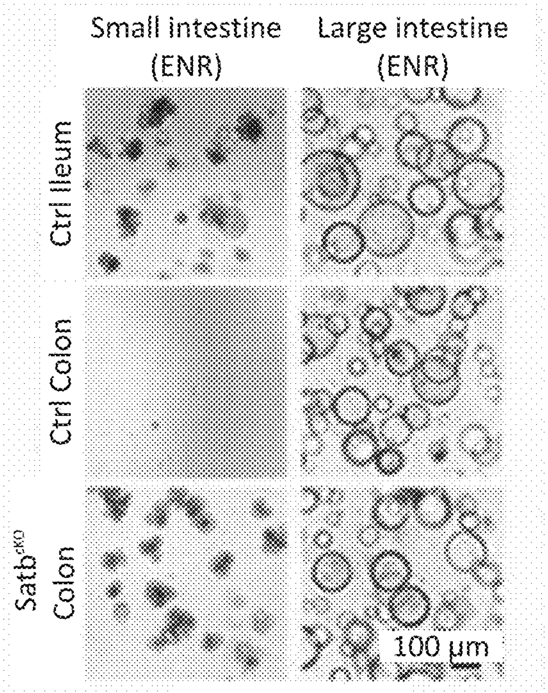
FIGS. 18A-18M illustrate characterization of SATB2 loss in colon and SATB2 gain in jejunum.
Figure 18B:
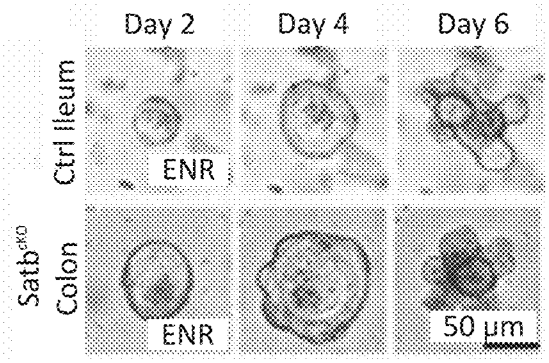
Figure 18C:
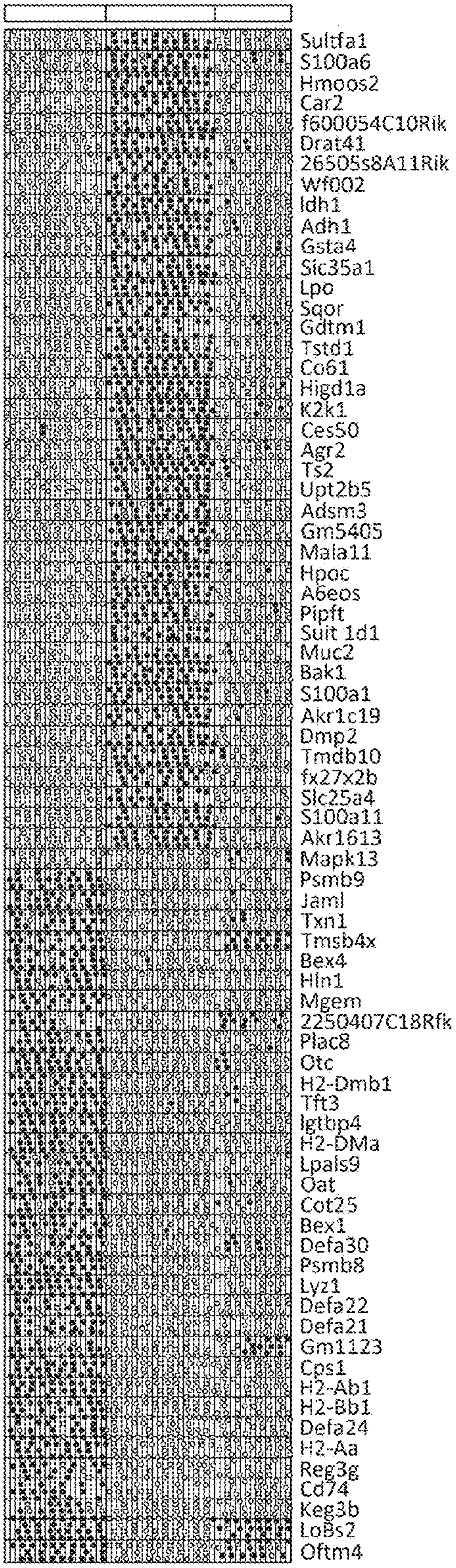
Figure 18D:
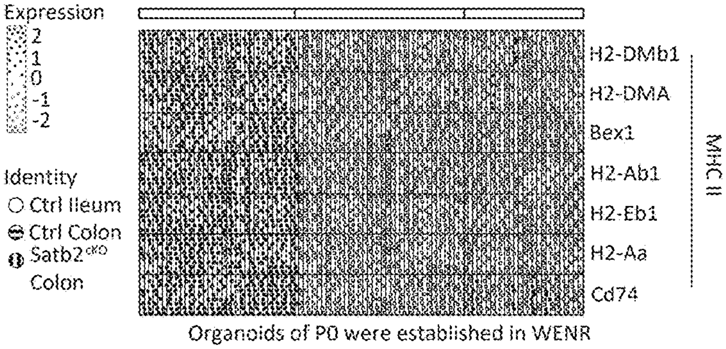
Figure 18F:
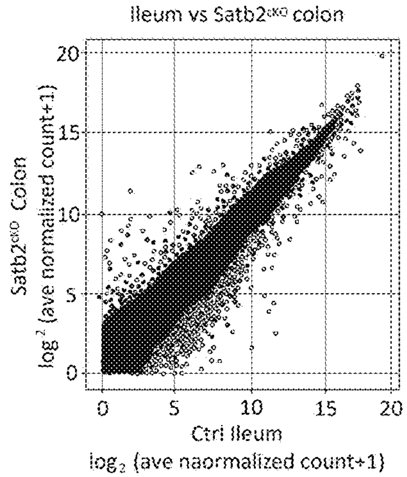
Figure 18E:
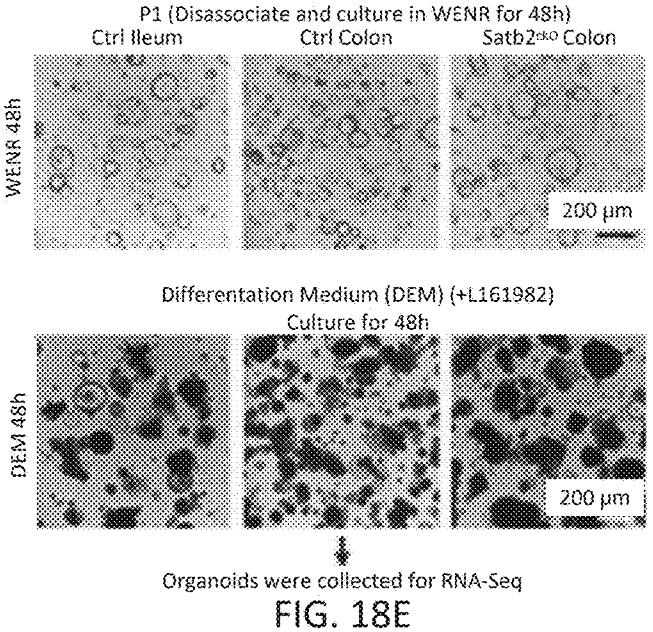
Figure 18G:
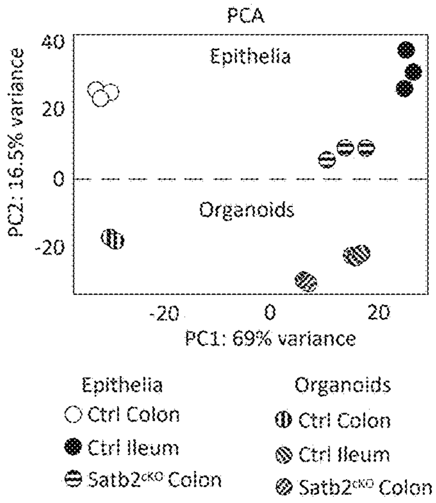
Figure 18H:
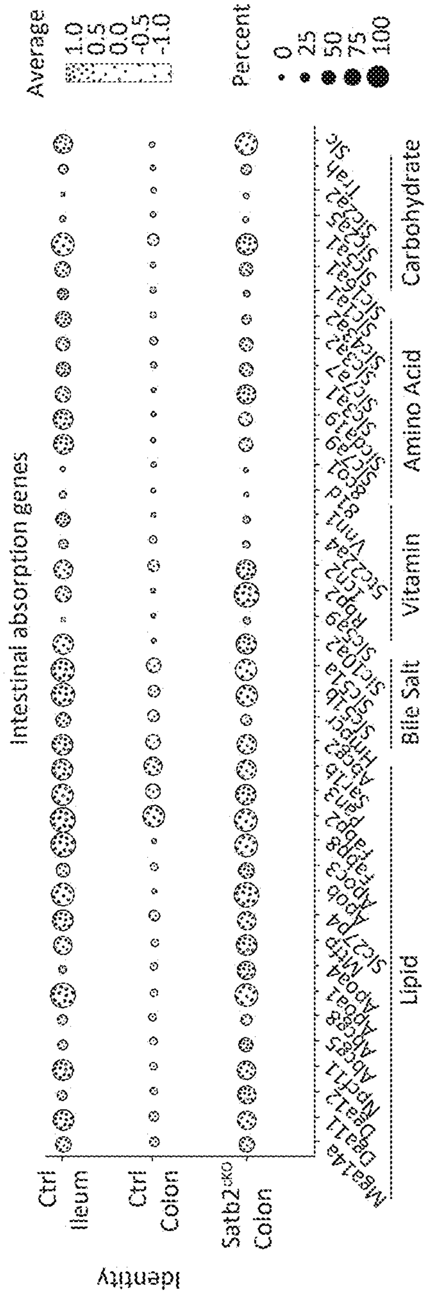
Figure 18I:
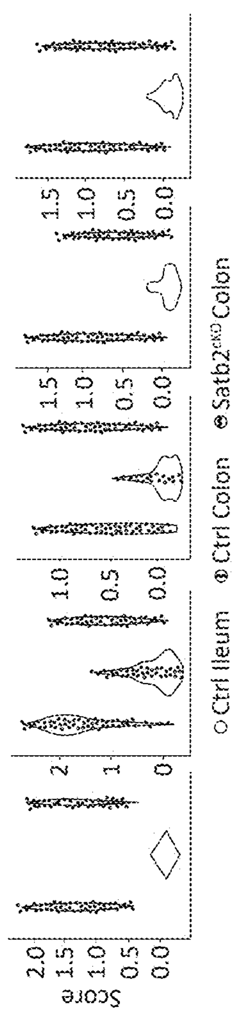
Figure 18J:
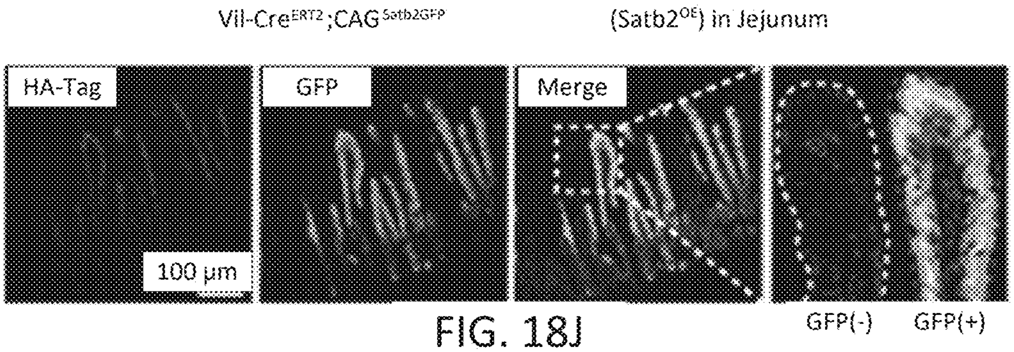
Figure 18K:
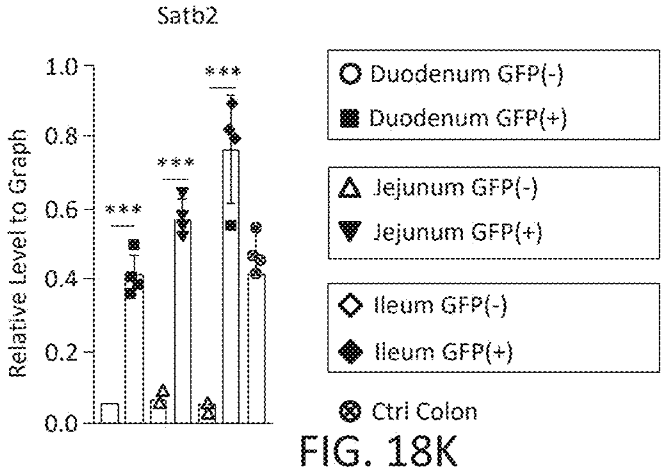
Figure 18L:
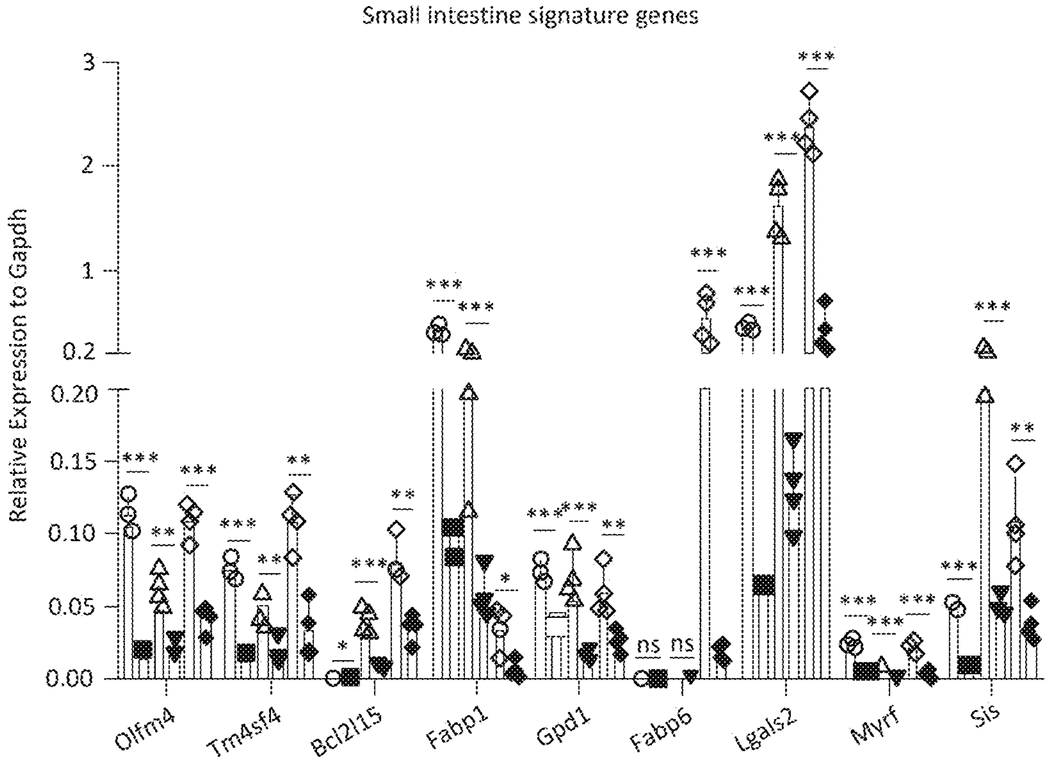
Figure 18M:
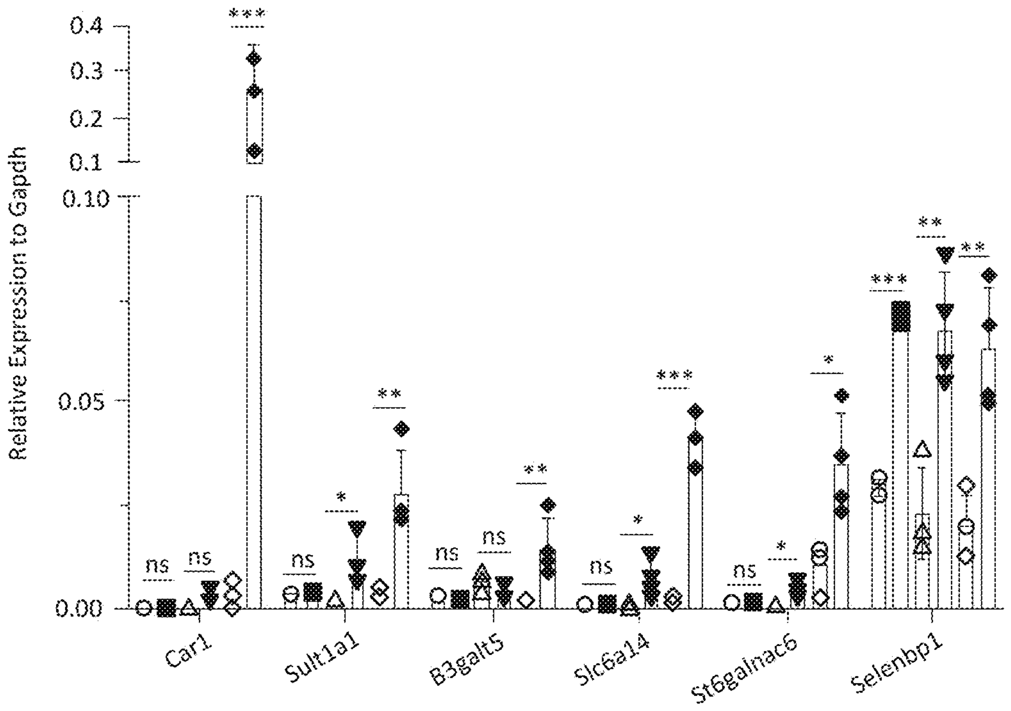
Figure 19A:
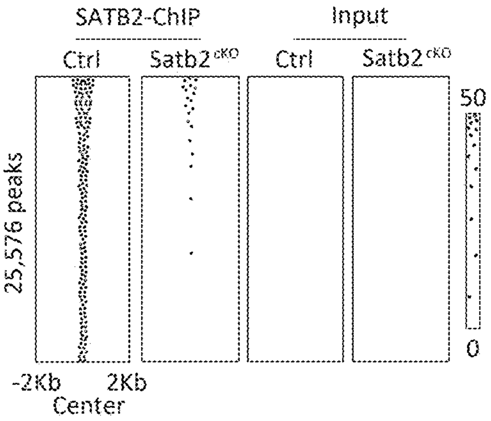
FIGS. 19A-19P show SATB2 regulates enhancer dynamics and transcription factor binding in the colon to ileum plasticity.
Figure 19B:
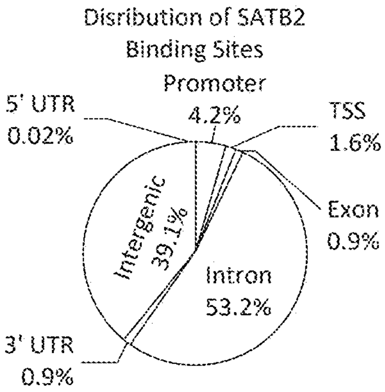
Figure 19C:
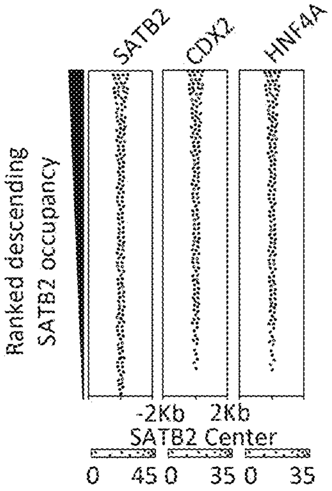
FIG. 19C and FIG. 19D show aligned genomic binding profiles of SATB2, CDX2 and HNF4a in control colon showed extensive co-localization.
Figure 19D:
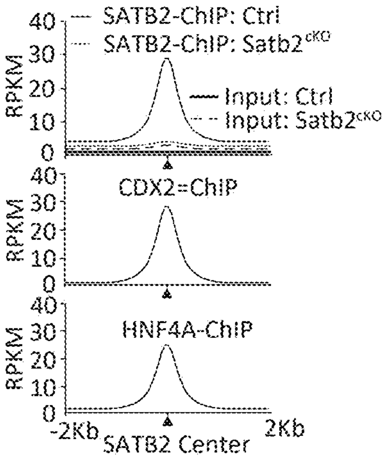
Figure 19E:
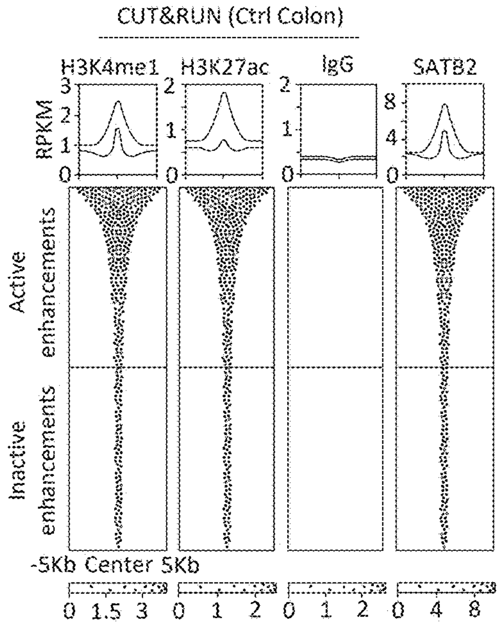
FIG. 19E and FIG. 19F show enrichments of H3K4me1, H3k27ac and IgG controls determined by CLT&RUN in control colon was aligned with SATB2 binding sites (FIG. 19E) and quantified (FIG. 19F). Enhancers were partitioned into active and inactive based on FH3K27ac enrichments.
Figure 19F:
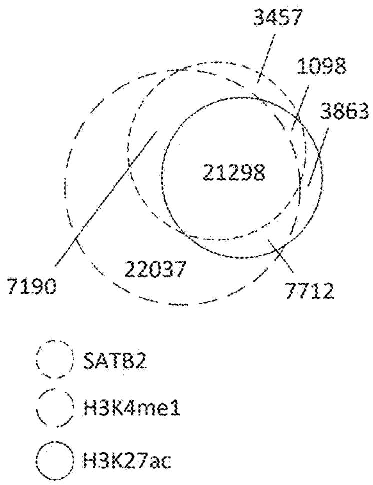
Figure 19G:
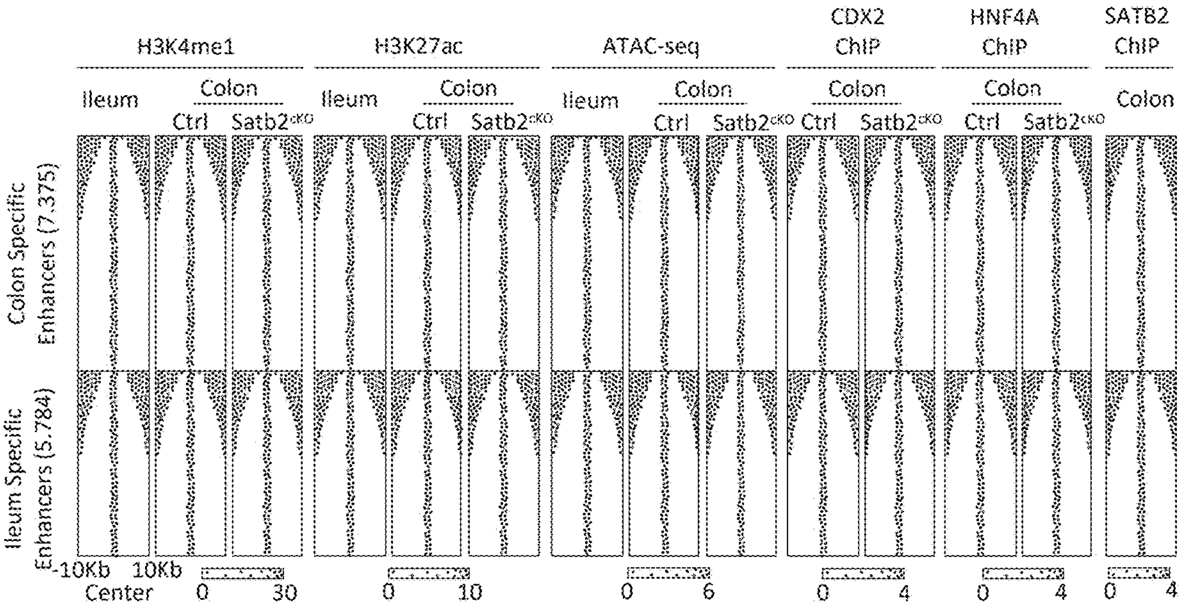
FIG. 19G and FIG. 19H show signals of histone marks, TFs, and ATAC around colon- and ileum-specific enhancers (identified by comparing the signal strength between all H3K4me1+ enhancers in control colon and ileum) in controls and Satb2cKO colon (KO), indicating activation of ileal enhancers and inactivation of colonic enhancers in SATB2 mutant colon. The two independent replicates of CDX2 binding profiles are shown in FIG. 19H.
Figure 19H:
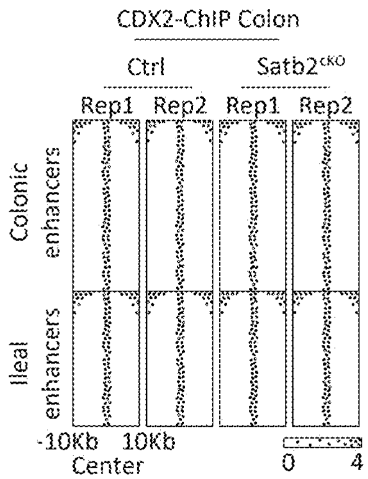
Figure 19I:
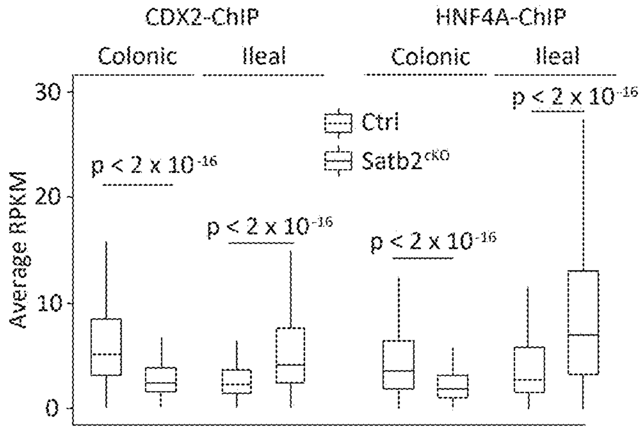
FIG. 19I shows box-and-whisker plots of HNF4A and CDX2 genomic binding signals in colon showing significant decreases of both TFs on colonic enhancers and increases on ileal enhancers after SATB2 loss.
Figure 19J:
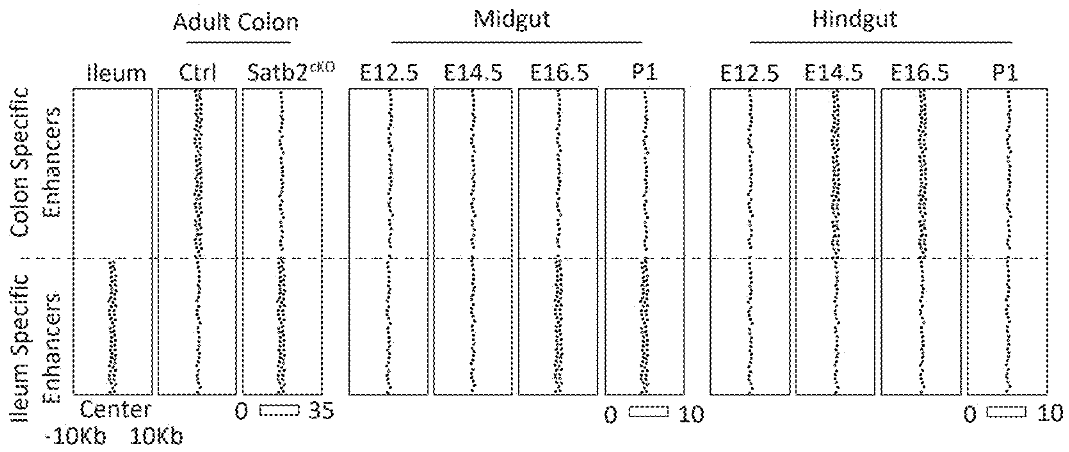
FIG. 19J shows ATAC profiles of colonic and ileal enhancers in developing murine midgut and hindgut EPCAM+ epithelial cells showed that ileal enhancers had low ATAC signals in hindgut and thus were not active enhancers. Similarly, colonic enhancers were not active in developing ileum.
Figure 19K:
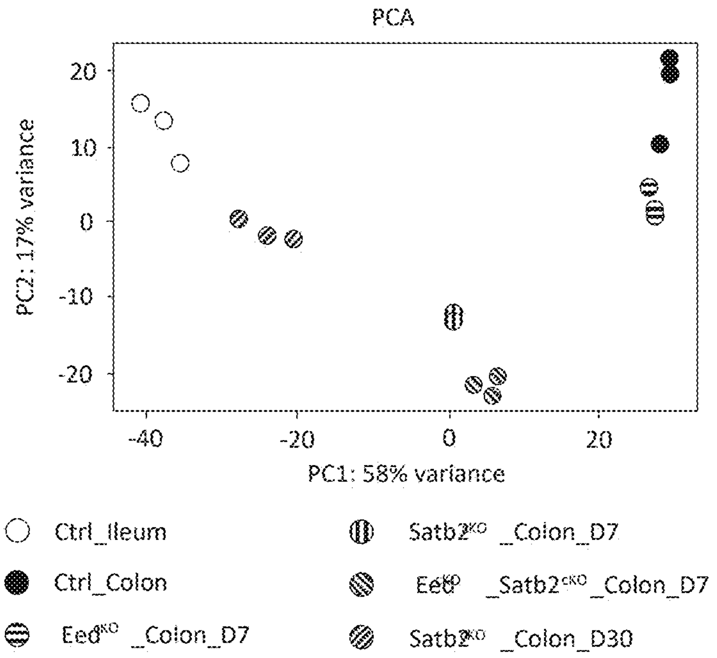
FIGS. 19K and 19L show PCA and heatmap representation of RNA-seq data showed Eed deletion alone (EedcKO) did not lead to colonic to ileal transcriptomic conversion whereas Eed removal in SATB2-null colon (double deletion; EedcKOSatb2cKO) also did not enhance transcriptomic shift further toward ileum.
Figure 19L:
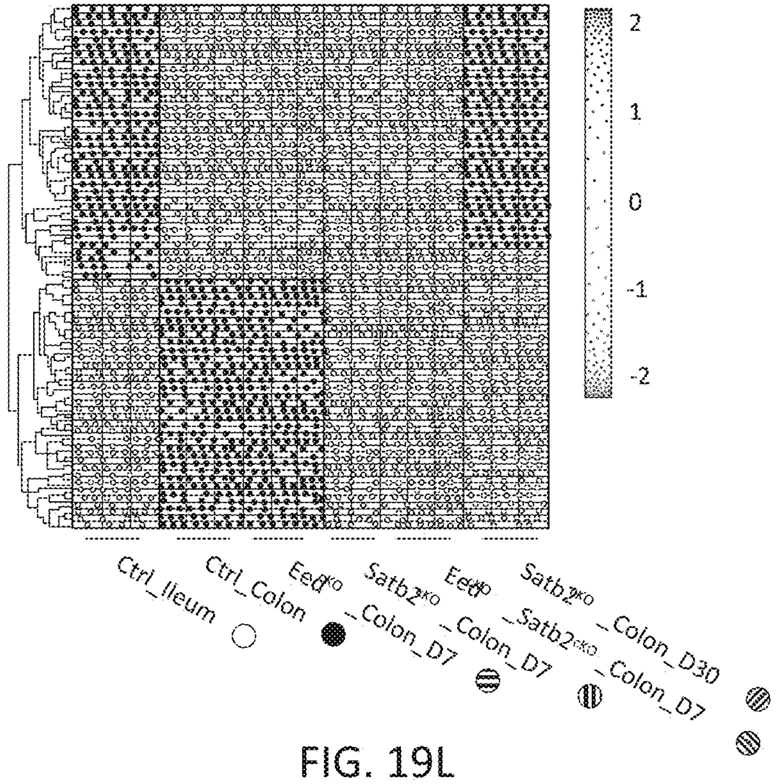
Figure 19M:
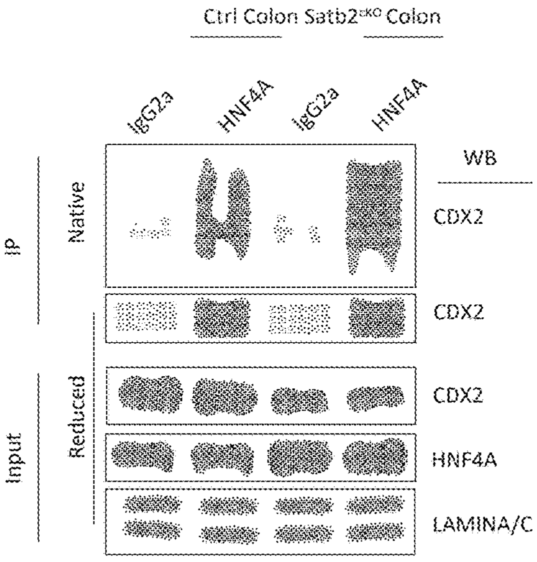
FIG. 19M shows Western blots and quantification of HNF4A and CDX2 co-IP from control and Satb2cKO colonic tissues. n=3 samples. Mean±S.D. P<0.01, *P<0.001. Unpaired t-test.
Figure 19N:
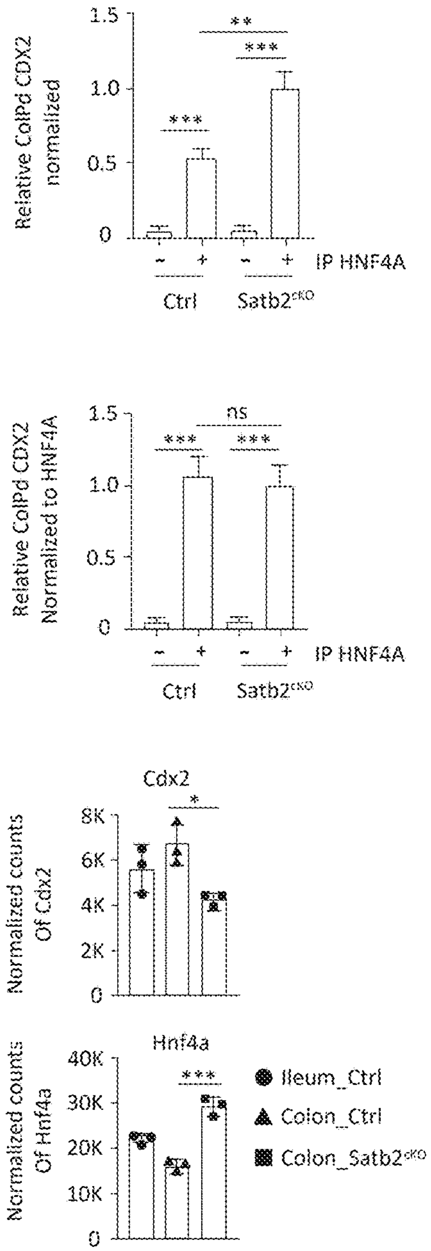
FIGS. 19N and 19O show CDX2 levels decreased whereas HNF4A levels increased after SATB2 loss (Normalized counts from Bulk RNA-Seq). N=3 mice in FIG. 19N and N=4 mice in FIG. 19O. Mean±SD. *P<005, P<0.01, *P<0.001. Unpaired t-test.
Figure 19O:
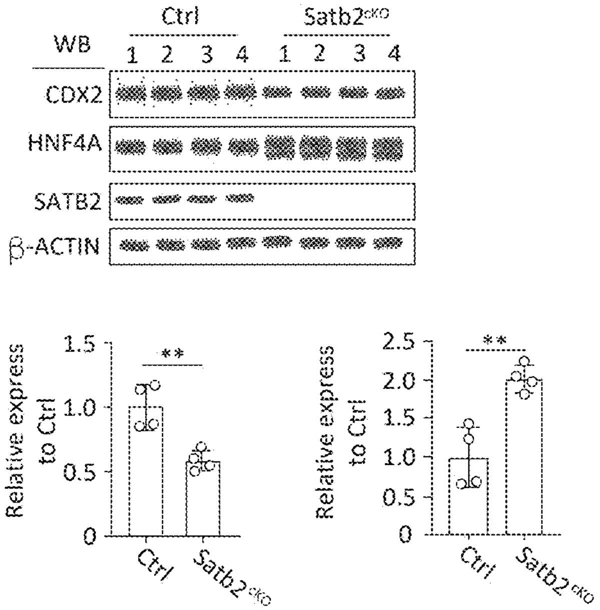
Figure 19P:
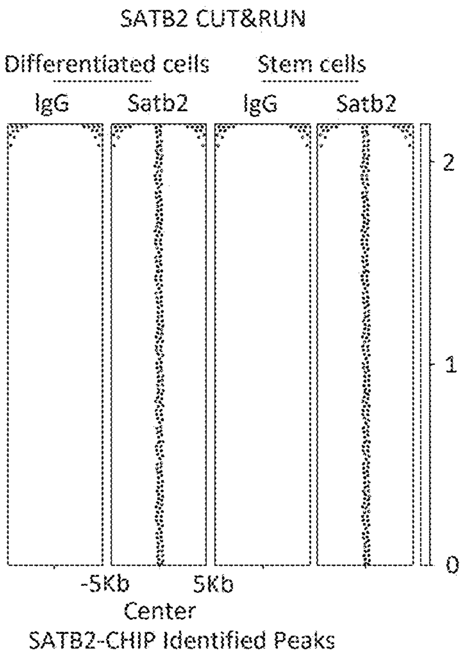
Figure 20A:
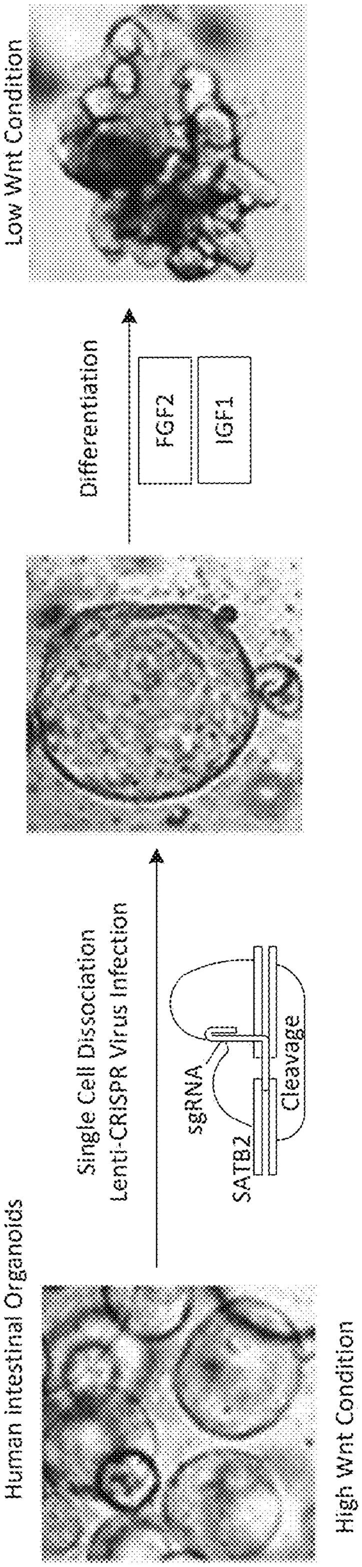
FIGS. 20A-20J illustrate human colonic organoids became ileal-like after CRISPR-mediated SATB2 deletion.
Figure 20B:
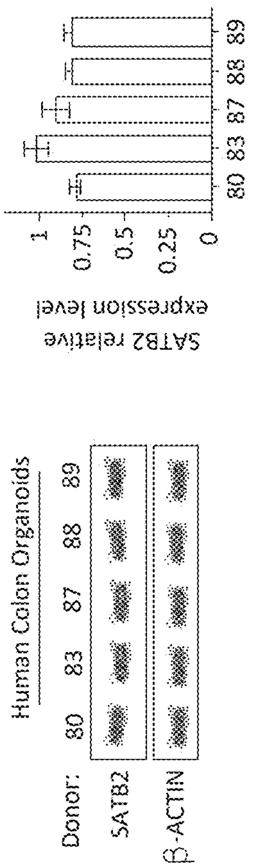
Figure 20C:
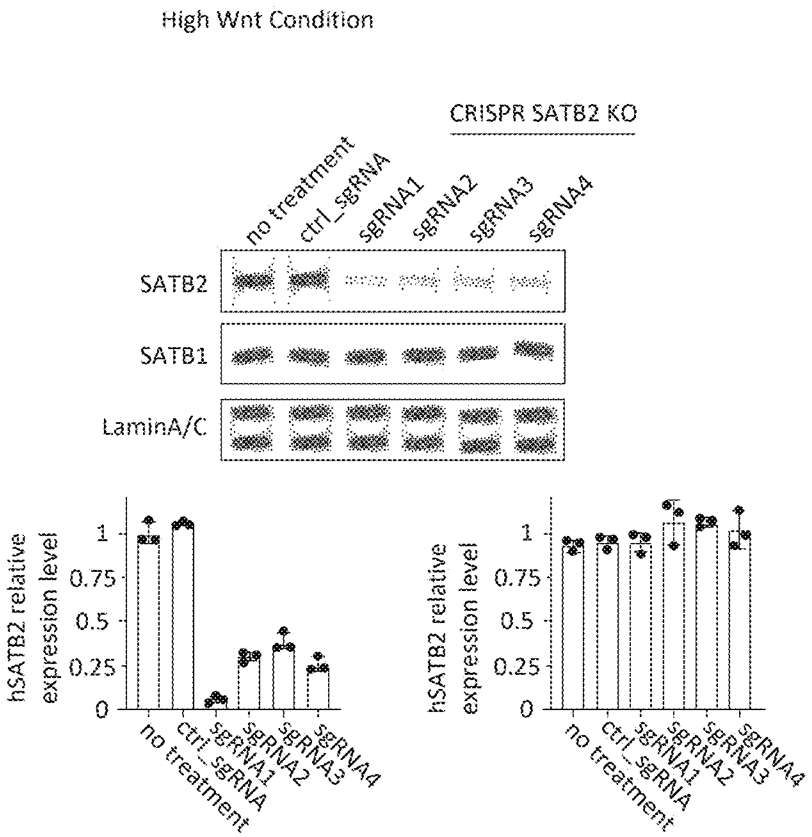
Figure 20D:
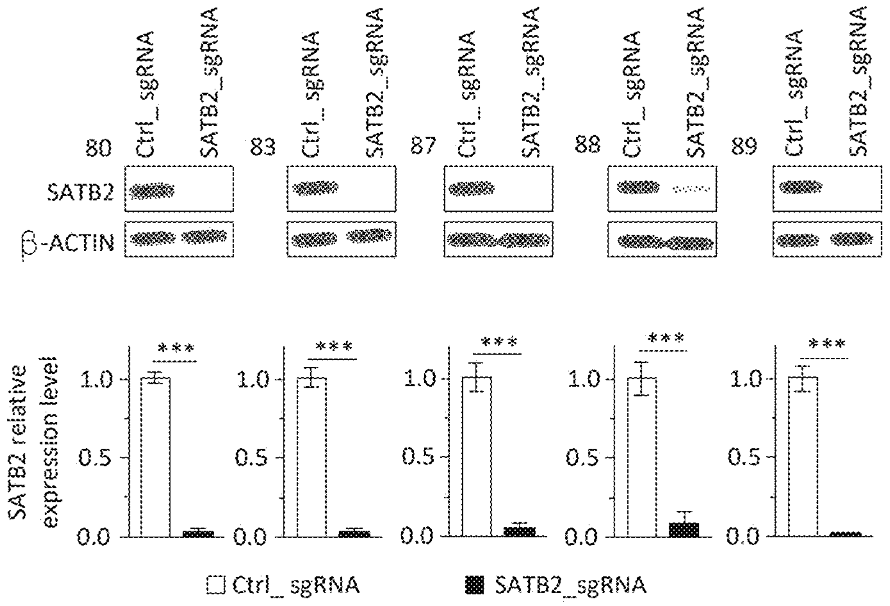
Figure 20E:
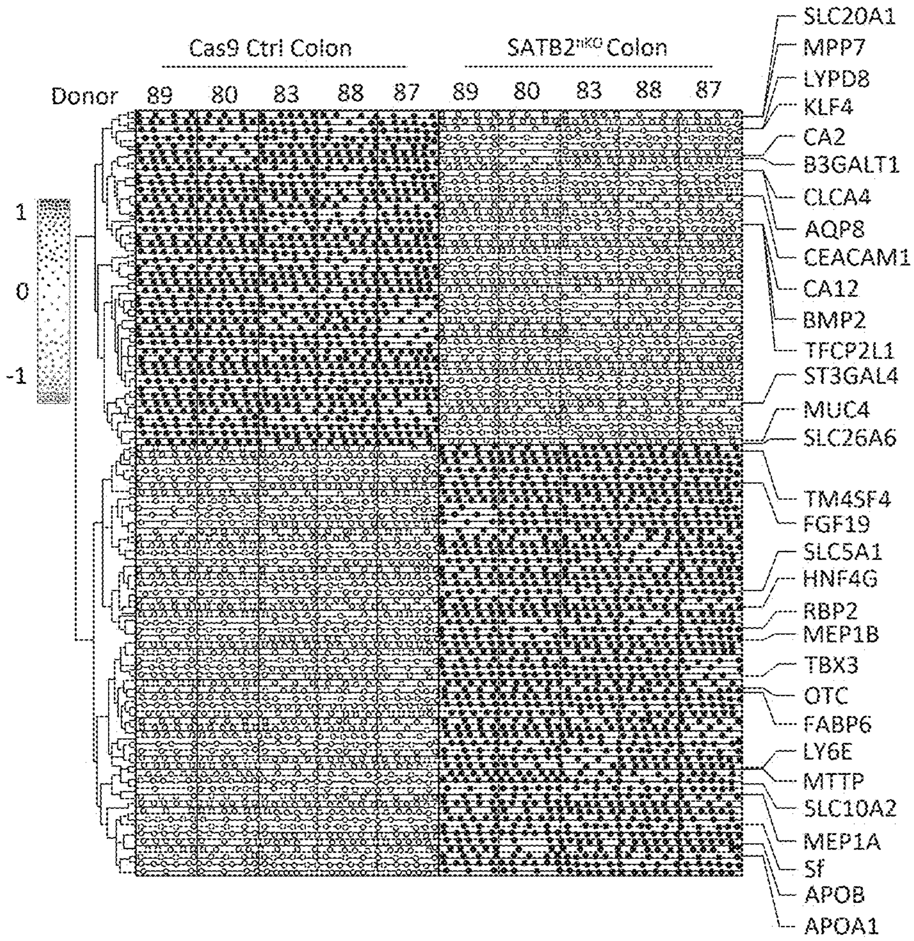
Figure 20F:
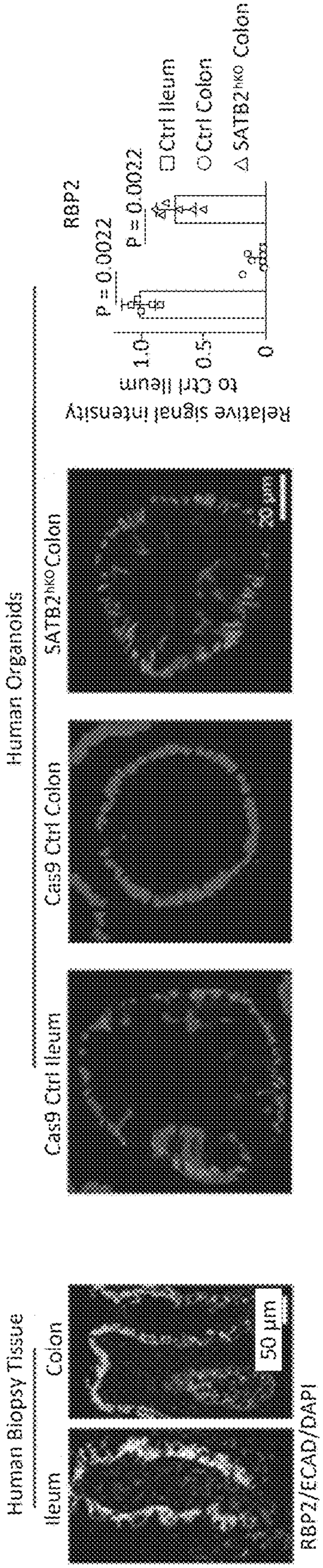
Figure 20G:
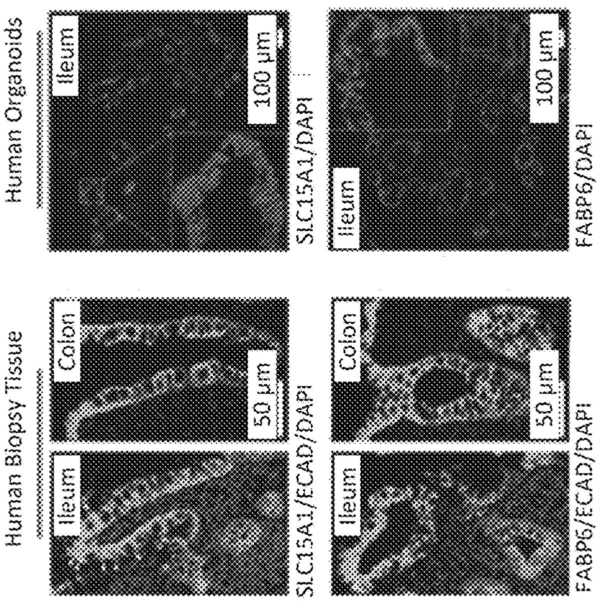
Figure 20H:
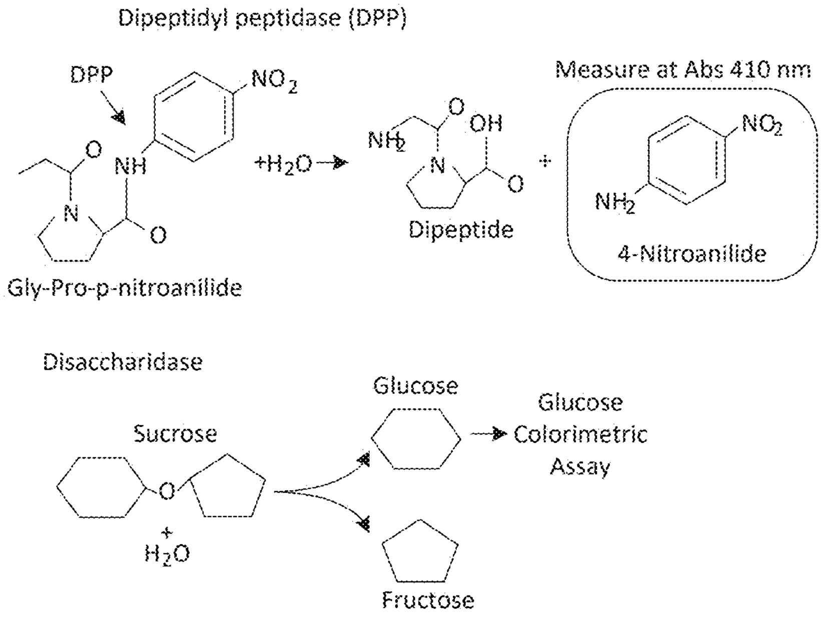
Figure 20I:
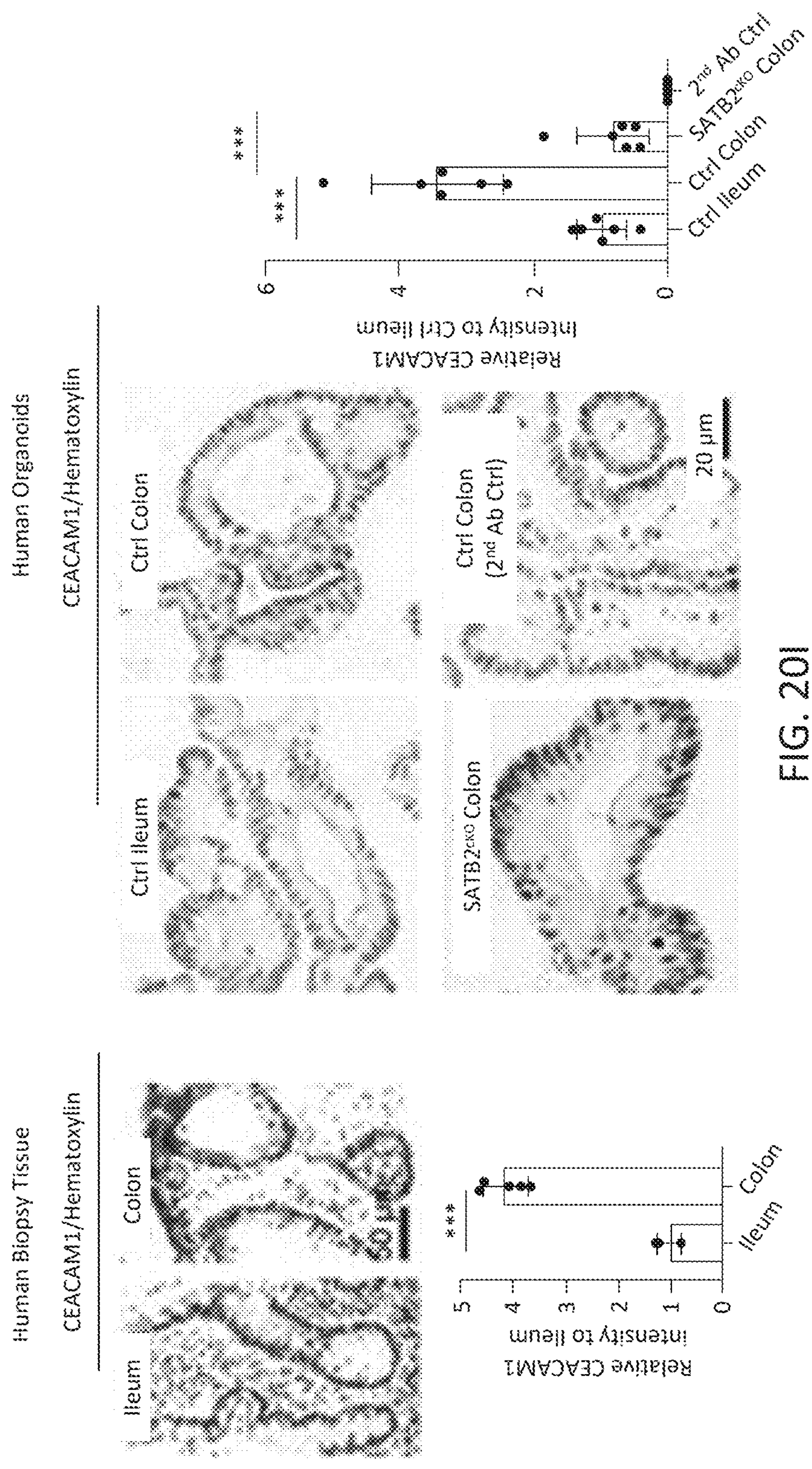
Figure 20J:
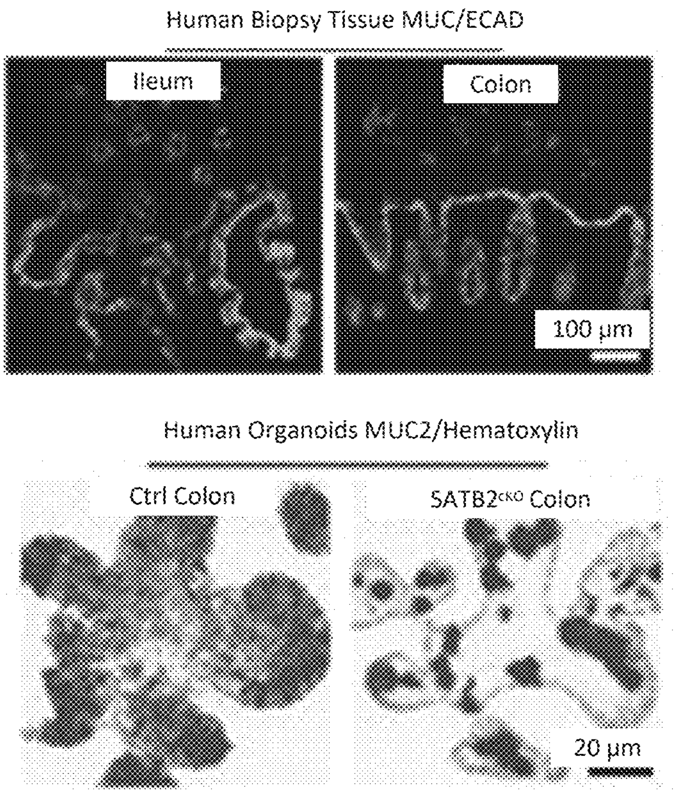

Immunohistochemistry of SATB2$^{hKO}$ colonic organoids confirmed expression of the ileal enterocyte markers FABP6 and RBP2, and the small intestine brush-border peptide transporter SLC15A1 (FIGS. 13F-13G). Digestive enzyme activities of the small intestine disaccharidase and dipeptidyl peptidase were also significantly elevated in SATB2$^{hKO}$ colonic organoids (FIG. 13H). In contrast, CEACAM1 and MUC2, highly expressed in human colon but substantially less in ileum, were down-regulated (FIGS. 13I-13J). These data indicate that SATB2 has a conserved function in human in preserving colonic epithelial identity and mediating colonic to ileal plasticity.

Example 20

Adult stein cells sustain structure and function of regenerative tissues in homeostasis and tissue repair. Significant phenotypic plasticity of adult stem cells have been observed after injury in many organs (Blanpain and Fuchs, 2014; Tetteh et al., 2015). This plasticity generally occurs along the differentiation hierarchy of the adult stem cells while their core tissue identities remain intact. In principle, adult tissue fate could be enforced by distributed actions of assemblies of intrinsic and extrinsic factors, with perturbation of each producing only a limited effect. Although master fate determination factors operate widely in embryogenesis to specify tissue identity, their abilities are often lost in adults, partly due to changing epigenetic landscapes across development (Banerjee et al., 2018; Spitz and Furlong, 2012; Stergachis et al., 2013; Zaret and Mango, 2016). Loss of the intestinal regulator CDX2, for example, has dramatic effects in embryos, including homeotic-like transformations to esophagus or stomach (Gao et al., 2009; Grainger et al., 2013), but CDX2 loss from the adult intestine leads to defects in adult tissue function without affecting tissue fate (Banerjee et al., 2018). In contrast, it is shown here that a tissue-restricted chromatin factor, SATB2, uniquely maintains mouse and human colonic stem cell and tissue fate. Similarly important fate regulators might also operate in other adult stem cell populations in the body.

Stable formation of ectopic tissues, known as metaplasia, is relatively rare, but does occur in several human organs such as the lung, esophagus and bladder, and is reported in animal studies (Giroux and Rustgi, 2017; Slack, 2007). Different mechanisms could account for metaplasia without necessarily involving stem cell plasticity. For instance, in Barret's esophagus, where the esophageal squamous epithelium is replaced by a stomach- and intestine-like columnar epithelium, possible mechanisms include stem cell conversion (Quante et al., 2012), migration of stomach cells (McDonald et al., 2015), persistence of embryonic cells (Wang et al., 2011), and transdifferentiation of mature epithelia (Minacapelli et al., 2017) or of esophageal submucosal glands (Owen et al., 2018). The single-cell analysis showed a genuine conversion of colonic stem cells to ileal-like stem cells after SatB2 loss, followed by differentiation of ileal cell types within the colon. In this context, the cross-tissue plasticity is mediated by direct stem cell conversion.

Studies of SATB1 in the thymus and other tissues suggest that SATB1 can engage nuclear matrix, bind DNA at base-unpaired regions, regulate genomic binding of chromatin remodeling complexes and signaling molecules, and influence chromatin looping (Cai et al., 2003; Skowronska-Krawczyk et al., 2014; Yasui et al., 2002). These complex, multi-faceted functions have led to the proposal that it acts as a hub for many kinds of protein-protein and protein-chromatin interactions. Our studies indicate that SATB2 regulates colonic transcription and colonic fate in part by modulating enhancer dynamics and appropriate targeting of the intestinal TFs CDX2 and HNF4A, consistent with the proposed properties of SATB1/2 proteins. Additional work will be needed to characterize more fully the chromatin mechanisms of SATB2 in regulating colonic stem cell fate.

In embryonic stem cells and developing tissues, a subset of inactive enhancers, some decorated with the repressive histone mark H3K27me3, exist in a "poised" or "primed" state, ready for timely activation (Creyghton et al., 2010; Rada-Iglesias et al., 2011). Adult intestine enhancers lack H3K27me3 (Saxena et alt, 2017; Zentner et al, 2011), but enhancers used during fetal development retain hypomethylated DNA and traces of the active histone mark H3K4me1 (Jadhav et al., 2019). We observed that ileal enhancers in the mature colon are not permanently inactivated but carry features of weak enhancers and are readily activated in the absence of SATB2. They thus could be considered as existing in a primed state, providing a necessary chromatin substrate for ileal gene activation and tissue fate plasticity in mature intestine.

The digestive tract is one of the most ancient and conserved organs across multicellular organisms. A distinct large intestine, separated from the small intestine by an ileocaecal valve, is however only well recognized in tetrapods (Schultz et al., 1989). Colon-like structures are postulated to exist in lower vertebrates but there are uncertainties (Brugman, 2016). The SATB2 gene is highly conserved across animal phyla.

REFERENCES

Alcamo et al.,. *Neuron,* 57:364 (2008).
Ariyachet et al., *Cell Stem Cell,* 18:410 (2016).
Banerjee et al.,. *Genes Dev.,* 32:1430 (2018).
Banerjee et al., *Genes Dev.,* 32:1430 (2018).
Barker et al., *Nature,* 449:1003 (2007).
Beumer & Clevers, *Nat. Rev. Mol. Cell Biol.,* 22:39 (2021).
Biton et al., *Cell,* 175:1307 (2018).
Blanpain & Fuchs, *Science,* 344:1242281 (2014).
Britanova et al., *Neuron,* 57:378 (2008).
Britanova et al., *Am. J. Hum. Genet.,* 79:668 (2006).
Brugman, *Dev. Comp. Immunol.,* 64:82 (2016)
Cai et al., *Nat. Genet.,* 34:42 (2003).
Chen et al., *Nat. Genet* 51:777 (2019).
Clevers & Watt, *Annu. Rev. Biochem.,* 87:1015 (2018).
Creyghton et al.,. *Proc. Natl. Acad. Sci. USA,* 107:21931 (2010).
Davison et al., *Genome Res.,* 27:1195 (2017).
Dobreva et al., *Cell.* 125:971 (2006).
Donati et al., *Nat. Cell Biol.,* 19:603 (2017).
Feng et al., *Nat. Protoc.* 7:1728 (2012).
Fuhrich et al.,. *Anal. Quant. Cytopathol. Histpathol.,* 35:210 (2013).
Gao et al., *Dev. Cell.,* 16:588 (2009).
Gehart & Clevers, *Nat. Rev. Gastroenterol. Hepatol.,* 16:19 (2019).
Giroux & Rustgi, *Nat. Rev. Cancer,* 17:594 (017).
Grainger et al., *PLoS One,* 8:e54757 (2013).
Haber et al.,. *Nature,* 551:333 (2017).
Haber et al., *Nature,* 551:333 (2017).
Heinz et al., *Mol. Cell.,* 38:576 (2010).
Jadhav et al.,. *Mol. Cell.,* 74:542 (2019).
Jadhav et al., *Cell,* 165:1389 (2016).
Jensen. *Anat. Rec.* (Hoboken), 296:378 (2013).
Kim et al., *Nature,* 506:511 (2014).
Langmead & Salzberg, *Nat. Methods,* 9:357 (2012).
Leushacke et al., *Nat. Cell Biol.,* 19:774 (2017).
Li et al., *Bioinformatics,* 25:2078 (2009).
McDonald et al., *Nat. Rev. Gastroenterol. Hepatol,* 12:50 (2015).
Minacapelli et al., *Am. J. Physiol. Gastrointest. Liver Physiol.,* 312:G615 (2017).
Munera & Wells, *Methods Mol. Biol.,* 1597:167 (2017).
Munoz et al., *EMBO J.,* 31:3079 (2012).
Murata et al., *Cell Stem Cell,* 26:377 (2020).
Mutch et al., *Biochem. Biophys. Res. Commun.,* 294:470 (2002).
Nichols & Davenport, *Hum. Genet.,* (2020).
Nusse et al., *Nature,* 559:109 (2018).
Owen et al., *Nat. Commun.,* 9:4261 (2018).
Page et al., *Cell Stem. Cell,* 13:471 (2013).
Perez Montiel et al., *Ann. Diagn. Pathol.,* 19:249 (2015).
Quante et al., *Cancer Cell,* 21:36 (2012).
Rada-Iglesias et al.,. *Nature,* 470:279 (2011).
Ramirez et al., *Nucleic Acids Res.,* 42:W187 (2014).
Ritchie et al., *Nucleic Acids Res,* 43:e47 (2015).
Santos et al., *Trends Cell Biol.,* 28:1062 (2018).
Sato et al., et al., *Gastroenterology,* 41:1762 (2011).
Sato et al.,. *Nature,* 459:262 (2009).
Saxena et al.,. *Genes Dev.,* 31:2391 (2017).
Saxena et al., *Genes Dev.,* 31:2391 (2017).
Schultz et al. and American Physiological Society (1887-). The Gastrointestinal system (Bethesda, Md. New York, N.Y.: American Physiological Society; Distributed by Oxford University Press) (1989).
Shao et al.,. *Genome Biol.,* 13:R16 (2012).
Skene et al., *Nat. Protoc.,* 0.1:1006 (2018).
Skowronska-Krawczyk et al., *Nature,* 514:257 (2014).
Slack, *Nat. Rev. Mol. Cell Biol.,* 8:369 (2007).
Spitz & Furlong, *Nat. Rev, Genet,* 13:613 (2012).
Stange et al., *Cell,* 155:357 (2013).
Stergachis et al., *Cell,* 154:888 (2013).
Sugimoto & Sato, *Methods Mol. Biol.,* 1612:97 (2017).
Sugimoto et al., *Cell Stem Cell,* 22:171 (2018).
Szemes et al., *Neurochem. Res.,* 31:237 (2006).
Tarasov et al., *Bioinformatics,* 31:2032 (2015).
Tata al., *Nature,* 503:218 (2013).
Tetteh et al., *Trends Cell Biol.,* 25:100 (2015).
Thaiss et al., *Cell,* 167:1495 (2016).
Thompson et al., *Dev. Biol.,* 435:97 (2018).
Umesaki et al.,. *Microbiol. Immunol.,* 39:555 (1995).
van Es et al., *Nat. Cell Biol.,* 14:1099 (2012).
VanDussen et al., *Stem Cell Res,* 37:101430 (2019).
Verzi et al., *Mol. Cell Biol.,* 3:2026 (2011).
Verzi et al., *Mol. Cell Biol.,* 33:281 (2013).

Wang et al., *Cell.* 145:1023 (2011).
Wang et al., *Cell,* 179:1144 (2019).
Wells& Spence, *Development,* 141:752 (2014).
Wells & Watt, *Nature,* 557:322 (2018).
Yasui et al., *Nature,* 419:641 (2002).
Yu et al., *OMICS,* 16:284 (2012).
Zarate & Fish, *Am. J. Med. Genet. A,* 173:327 (2017).
Zaret & Mango, *Curr. Opin. Genet. Dev.,* 37:76 (2016).
Zentner et al, *Genome Res.,* 21:1273 (2011).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following Statements summarize aspects and features of the invention.

Statements:

1. A method comprising deleting or inactivating least one Satb2 allele or inhibiting expression of a Satb2 gene in one or more starting cells of a subject, to thereby convert the starting cells into small intestine-like cells.

2. The method of statement 1, wherein the Satb2 gene encodes a SATB2 protein with at least 95% sequence identity to any one of SEQ ID NOs:1, 3, 4, or 5.

3. The method of statement 1 or 2, wherein the starting cells are within the subject.

4. The method of statement 1, 2, or 3, wherein deleting or inactivating least one Satb2 allele comprises administering genomic modifying agents to the subject that target one or both Satb2 alleles in the subject.

5. The method of statement 4, wherein the genomic modifying agents comprise expression vectors and/or targeting vectors for modifying endogenous Satb2 alleles.

6. The method of statement 5, wherein the expression vectors and/or targeting vectors can encode and express nucleases (e.g., cas nucleases), guide RNAs, donor DNAs, and/or any other components for genomic editing.

7. The method of any of statements 1-6, wherein the starting cells comprise colonic cells, colonic stem cells, or a combination thereof.

8. The method of statement 1 or 2, wherein the method is performed in vitro.

9. The method of any of statements 1, 2 or 8, wherein the starting cells comprise biopsy cells, autopsy cells, colonic organoids, colonic cells, colonic stem cells, colonic progenitor cells, embryonic stem cells (ESCs), induced pluripotent stem cells (iPSCs), or a combination thereof.

10. The method of any one of statements 1, 2, 8, or 9 wherein the starting cells are autologous or allogeneic to the subject.

11. The method of any one of statements 1-10, wherein deleting or inactivating least one Satb2 allele comprises one or more of Cre/lox-mediated, floxing (flox/flox)-mediated, CRISPR-mediated, TALENS-mediated, ZFN-mediated knockout, base-editing-mediated, knockout, or knockdown of at least one Satb2 allele in one or more starting cells.

12. The method of any one of statements 1, 2, 8-11, comprising isolating one or more cells from the subject and incubating the cells with one or more CRISPR, TALENS, Cre/lox, ZFN, or base-editing, reagents to generate a modified population of cells comprising cells having one or more modified Satb2 allele sequences.

13. The method of statement 12, wherein the one or more CRISPR, TALENS, ZFN, or base-editing reagents comprises one or more guide RNAs or a vector that can express one or more guide RNAs, where the one or more guide RNAs can specifically bind to a Satb2 genomic site.

14. The method of statement 12 or 13, wherein the one or more CRISPR reagents comprises a cas nuclease.

15. The method of statement 6, 13 or 14 wherein one or more of the guide RNAs can specifically bind to a Satb2 genomic site and guide a cas nuclease to efficiently cleave or modify the Satb2 genomic site.

16. The method of any one of statements 6, 8, 13, or 15, wherein one or more of the guide RNAs comprises an RNA sequence corresponding to SEQ ID NO:6.

17. The method of any one of statements 1, 2, 8-16, further comprising selecting at least one small intestine-like cell and expanding the at least one small intestine-like cell into a population of small intestine-like cells.

18. The method of any one of statements 1, 2, 8-17, further comprising administering a population of small intestine-like cells to the subject.

19. The method of statement 18, wherein the population of small intestine-like cells is administered intravenously to the subject.

20. The method of statement 18 or 19, wherein the population of small intestine-like cells is administered to the abdomen of the subject.

21. The method of statement 18, 19, or 20, wherein the population of small intestine-like cells is administered to the intestines of the subject.

22. The method of any one of statements 19-21, wherein the population of small intestine-like cells is seeded onto a hollow scaffold tube, a de-cellularized intestinal segment, a hollow scaffold tube comprising a polymer, or an artificial tube scaffold, to generate one or more transplantable gut segments.

23. The method of statement 22, wherein one or more of the transplantable gut segments is administered to the subject.

24. The method of statement 22 or 23, wherein one or more of the transplantable gut segments is spliced into a section of the subject's intestine.

25. The method of any one of statements 1-24, further comprising administering one or more CRISPR, TALENS, Cre/lox, ZFN, or base-editing-mediated reagents to the subject's intestines.

26. The method of statement 25, wherein the one or more CRISPR, TALENS, ZFN, or base-editing reagents comprises one or more guide RNAs or a vector that can express one or more guide RNAs, where the one or more of the guide RNAs can specifically bind to a Satb2 genomic site.

27. The method of statement 25 or 26, wherein the one or more CRISPR reagents comprises a cas nuclease.

28. The method of statement 26 or 27 wherein one or more of the guide RNAs can specifically bind to a Satb2 genomic site and guide a cas nuclease to efficiently cleave and/or modify the Satb2 genomic site.

29. The method of any one of statements 26-28, wherein one or more of the guide RNAs comprises an RNA sequence corresponding to SEQ ID NO:6.

30. The method of statement 1, wherein inhibiting expression of the Satb2 gene comprises contacting a nucleic acid encoding a SATB2 protein with at least 95% sequence identity to any one of SEQ ID NOs:1, 3, 4, or 5 with a small hairpin RNA, an siRNA, or a vector that can express a small hairpin RNA or an siRNA.

31. The method of statement 30, wherein the small hairpin RNA, the siRNA, or a combination thereof binds to an RNA with at least 95% sequence identity or complementarity to a segment of SEQ ID NO:2.

32. The method of statement 30 or 31, wherein the small hairpin RNA or the siRNA is about 13-50 nucleotides in length.

33. A method comprising administering to a subject one or more agents that delete or modify at least one Satb2 allele or administering to a subject one or more reagents that inhibit expression of a Satb2 gene in one or more intestinal cells of a subject, to thereby convert the intestinal cells into small intestine-like cells.

34. The method of statement 33, wherein the one or more agents that delete at least one Satb2 allele in the one or more intestinal cells of a subject comprise one or more CRISPR, TALENS, ZFN, or base-editing reagents.

35. The method of statement 34, wherein the CRISPR, TALENS, ZFN, or base-editing reagents comprise one or more guide RNAs or a vector that can express one or more guide RNAs, where the one or more of the guide RNAs can specifically bind to a Satb2 genomic site.

36. The method of statement 33, 35, or 36, wherein the one or more CRISPR reagents comprises a cas nuclease.

37. The method of statement 35 or 36, wherein one or more of the guide RNAs can specifically bind to a Satb2 genomic site and guide a cas nuclease to efficiently cleave the Satb2 genomic site.

38. The method of any one of statements 33-37, wherein one or more of the guide RNAs comprises an RNA sequence corresponding to SEQ ID NO:6.

39. The method of statement 38, wherein one or more reagents that inhibit expression of a Satb2 gene in one or more intestinal cells of a subject is a small hairpin RNA, an siRNA, or a vector that can express a small hairpin RNA or an siRNA.

40. The method of statement 39, wherein the small hairpin RNA, the siRNA, or a combination thereof binds to an RNA with at least 95% sequence identity or complementarity to a segment of SEQ ID NO:2.

41. The method of statement 39 or 40, wherein the small hairpin RNA or the siRNA is about 13-50 nucleotides in length.

42. The method of any one of statements 1-41, wherein the subject has an intestinal disease or condition.

43. The method of statement 36, wherein the intestinal disease or condition is short bowel disease, congenital short bowel syndrome, intestinal injury, intestinal atresia, intussusception, meconium ileus, midgut volvulus, omphalocele, irritable bowel syndrome, digestive failure, reduced nutritional absorption, fistula, Crohn's disease, necrotizing enterocolitis ulcerative colitis, or colorectal cancer.

The specific methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a" "an," and "the" include plural reference unless the context clearly dictates otherwise. Thus, for example, a reference to "a nucleic acid" or "a protein" or "a cell" includes a plurality of such nucleic acids, proteins, or cells (for example, a solution or dried preparation of nucleic acids or expression cassettes, a solution of proteins, or a population of cells), and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed:

1. A method comprising deleting or inactivating at least one Satb2 allele or inhibiting expression of a Satb2 gene in one or more starting cells of a subject, to thereby convert the starting cells into ileal-like cells, wherein the starting cells comprise colonic cells, colonic stem cells, colonic organoids, colonic progenitor cells or a combination thereof.

2. The method of claim 1, wherein the Satb2 gene encodes a SATB2 protein with at least 95% sequence identity to any one of SEQ ID NOs:1, 3, 4, or 5.

3. The method of claim 1, wherein the starting cells are within the subject.

4. The method of claim 1, wherein deleting or inactivating at least one Satb2 allele comprises administering genomic modifying agents to the subject that target one or both Satb2 alleles in the subject.

5. The method of claim 1, wherein the starting cells are obtained from a biopsy, autopsy or a combination thereof.

6. The method of claim 1, wherein the method is performed in vitro.

7. The method of claim 6, wherein the starting cells are autologous or allogeneic to the subject.

8. The method of claim 1, wherein deleting or inactivating at least one Satb2 allele comprises one or more of Cre/lox-mediated, floxing (flox/flox)-mediated, CRISPR-mediated, TALENS-mediated, ZFN-mediated knockout, base-editing-mediated, knockout, or knockdown of at least one Satb2 allele in one or more starting cells.

9. The method of claim 8, wherein the one or more CRISPR, TALENS, ZFN, or base-editing reagents comprises one or more guide RNAs or a vector that can express one or more guide RNAs, where the one or more guide RNAs can specifically bind to a Satb2 genomic site.

10. The method of claim 9, wherein one or more of the guide RNAs comprises an RNA sequence corresponding to SEQ ID NO:6.

11. The method of claim 6, further comprising selecting at least one ileal-like cell and expanding the at least one ileal-like cell into a population of ileal-like cells.

12. The method of claim 11, further comprising administering a population of ileal-like cells to the subject.

13. The method of claim 12, wherein the population of ileal-like cells is administered to the abdomen or intestines of the subject.

14. The method of claim 11, wherein the population of ileal-like cells is seeded onto a hollow scaffold tube, a de-cellularized intestinal segment, a hollow scaffold tube comprising a polymer, or an artificial tube scaffold, to generate one or more transplantable gut segments.

15. The method of claim 14, wherein one or more of the transplantable gut segments is administered to the subject's intestines, and/or spliced into a section of the subject's intestine.

16. The method of claim 1, wherein inhibiting expression of the Satb2 gene comprises contacting a nucleic acid encoding a SATB2 protein with at least 95% sequence identity to any one of SEQ ID NOs:1, 3, 4, or 5 with a small hairpin RNA, an siRNA, or a vector that can express a small hairpin RNA or an siRNA.

17. The method of claim 16, wherein the small hairpin RNA, the siRNA, or a combination thereof binds to an RNA with at least 95% sequence identity or complementarity to a segment of SEQ ID NO:2.

18. A method comprising administering to a subject one or more agents that delete or modify at least one Satb2 allele or administering to a subject one or more reagents that inhibit expression of a Satb2 gene in one or more intestinal cells of a subject, to thereby convert the intestinal cells into ileal-like cells.

19. The method of claim 1, wherein the subject has an intestinal disease or condition.

20. The method of claim 18, wherein the subject has short bowel disease, congenital short bowel syndrome, intestinal injury, intestinal atresia, intussusception, meconium ileus, midgut volvulus, omphalocele, irritable bowel syndrome, digestive failure, reduced nutritional absorption, fistula, Crohn's disease, necrotizing enterocolitis ulcerative colitis, or colorectal cancer.

* * * * *